(12) United States Patent
Adams et al.

(10) Patent No.: US 7,795,249 B2
(45) Date of Patent: Sep. 14, 2010

(54) CERTAIN PYRAZOLINE DERIVATIVES WITH KINASE INHIBITORY ACTIVITY

(75) Inventors: Ruth S. Adams, Medford, MA (US); Matthew Duffey, Somerville, MA (US); Alexandra E. Gould, Cambridge, MA (US); Paul D. Greenspan, Acton, MA (US); Bheemashankar A. Kulkarni, Newton, MA (US); Tricia J. Vos, Medford, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 106 days.

(21) Appl. No.: 12/002,883

(22) Filed: Dec. 19, 2007

(65) Prior Publication Data

US 2008/0171754 A1 Jul. 17, 2008

Related U.S. Application Data

(60) Provisional application No. 60/876,688, filed on Dec. 22, 2006.

(51) Int. Cl.
*C07D 401/04* (2006.01)
*C07D 413/14* (2006.01)
*C07D 409/14* (2006.01)
*A61K 31/4155* (2006.01)
*A61P 35/00* (2006.01)

(52) U.S. Cl. .............. 514/222.2; 514/230.5; 514/236.5; 514/253.01; 514/255.05; 514/269; 514/272; 514/278; 514/307; 514/313; 514/318; 514/333; 514/337; 514/338; 514/341; 544/3; 544/105; 544/124; 544/131; 544/297; 544/333; 544/364; 546/15; 546/148; 546/162; 546/256; 546/268.7; 546/270.7; 546/272.1; 546/274.7; 546/275.4

(58) Field of Classification Search ................ None
See application file for complete search history.

(56) References Cited

U.S. PATENT DOCUMENTS 5,389,648 A 2/1995 Tsuboi et al.

FOREIGN PATENT DOCUMENTS

| EP | 00537580 A2 | 4/1993 |
| WO | WO 01/32173 A1 | 5/2001 |
| WO | WO 03/079973 A2 | 10/2003 |
| WO | WO 2006/007496 A2 | 1/2006 |
| WO | WO 2006/007501 A2 | 1/2006 |

OTHER PUBLICATIONS

Golub, T.R. et al., "Molecular classification of cancer: class discovery and class prediction by gene expression monitoring," Science (1999), vol. 286, pp. 31-537.*
Babu, V. et al., "Synthesis and Biological Evaluation of 1,3,5-Trisubstituted Pyrazolines Bearing Benzofuran", Indian Journal of Heterocyclic Chemistry, 13(3), 253-256, 2004.*
International Search Report and Written Opinion dated Apr. 4, 2008 in International Application No. PCT/US07/026034 which corresponds to U.S. Appl. No. 12/002,883.
Structures from CAS Registry Database for which there are no corresponding references.
Babu, V. Harinadha, et al., "Synthesis and biological evaluation of 1,3,5-trisubstituted pyrazolines bearing benzofuran," *Indian Journal of Heterocyclic Chemistry*, vol. 13 (Jan.-Mar. 2004) pp. 253-256.
Mehta, K. H., et al., "Synthesis of new heterocyclic dibromo chalcone and quinoxaline compounds and their antibacterial activity," *Oriental Journal of Chemistry*, vol. 18, No. 3 (2002) pp. 539-542.

\* cited by examiner

*Primary Examiner*—Fiona T Powers

(57) ABSTRACT

The present invention provides certain pyrazoline compounds useful as inhibitors of protein kinases. The invention also provides pharmaceutical compositions and methods of using the compositions in the treatment of various diseases.

37 Claims, No Drawings

CERTAIN PYRAZOLINE DERIVATIVES WITH KINASE INHIBITORY ACTIVITY

The present invention relates to certain protein kinase inhibitors, particularly inhibitors of Raf-kinase. The invention also provides pharmaceutical compositions and methods of using the compositions in the treatment of various diseases.

Protein kinases constitute a large family of structurally related enzymes that effect the transfer of a phosphate group from a nucleoside triphosphate to a Ser, Thr or Tyr residue on a protein acceptor. A vast array of cellular functions, including DNA replication, cell cycle progression, energy metabolism, and cell growth and differentiation, are regulated by reversible protein phosphorylation events mediated by protein kinases. Additionally, protein kinase activity has been implicated in a number of disease states, including cancers. Of the >100 dominant oncogenes known to date, many encode receptor and cytoplasmic protein kinases known to be mutated and/or over expressed in human cancers (Blume-Jensen and Hunter, Nature, 411:355-365 (2001)). Accordingly, protein kinase targets have attracted substantial drug discovery efforts in recent years, with several protein kinase inhibitors achieving regulatory approval (reviewed in Fischer, Curr. Med. Chem., 11:1563 (2004); Dancey and Sausville, Nature Rev. Drug Disc., 2:296 (2003)).

Intracellular signaling pathways activated in response to growth factor/cytokine stimulation are known to control functions such as proliferation, differentiation and cell death (Chiloeches and Marais, In Targets for Cancer Therapy; Transcription Factors and Other Nuclear Proteins, 179-206 (La Thangue and Bandara, eds., Totowa, Humana Press 2002)). One example is the Ras-Raf-MEK-ERK pathway which is controlled by receptor tyrosine kinase activation. Activation of Ras proteins at the cell membrane leads to phosphorylation and recruitment of accessory factors and Raf which is then activated by phosphorylation. Activation of Raf leads to downstream activation of MEK and ERK. ERK has several cytoplasmic and nuclear substrates, including ELK and Ets-family transcription factor, which regulates genes involved in cell growth, survival and migration (Marais et al., J. Biol. Chem., 272:4378-4383 (1997); Peyssonnaux and Eychene, Biol. Cell, 93-53-62 (2001)). As a result, this pathway is an important mediator of tumor cell proliferation and angiogenesis. For instance, overexpression of constitutively active B-Raf can induce an oncogenic event in untransformed cells (Wellbrock et al., Cancer Res., 64:2338-2342 (2004)). Aberrant activation of the pathway, such as by activating Ras and/or Raf mutations, is known to be associated with a malignant phenotype in a variety of tumor types (Bos, Hematol. Pathol., 2:55-63 (1988); Downward, Nature Rev. Cancer, 3:11-22 (2003); Karasarides et al., Oncogene, 23:6292-6298 (2004); Tuveson, Cancer Cell, 4:95-98 (2003); Bos, Cancer Res, 49:4682-4689 (1989)). Activating mutations in B-Raf are found in 60-70% of melanomas. Melanoma cells that carry mutated B-Raf-V599E are transformed, and cell growth, ERK signaling and cell viability are dependent on mutant B-Raf function (Karasarides et al., Oncogene, 23:6292-6298 (2004)). Although this mutation historically has been referred to in the literature as V599E, the mutated valine actually is located at position 600 (Wellbrock et al., Cancer Res., 64:2338-2342 (2004)).

There are three Raf isoforms, A-Raf, B-Raf and C-Raf (Raf-1), all of which can act as downstream effectors of Ras. Although they show significant sequence similarities, they also exhibit distinct roles in development, in addition to significant biochemical and functional differences. In particular, the high basal kinase activity of B-Raf may explain why mutated forms of only this isoform have been found in human cancers. Nevertheless, the isoforms show redundant functions in facilitating oncogenic Ras-induced activation of the MEK-ERK signaling cascade (Wellbrock, Cancer Res, 64:2338-2342 (2004)). In addition to Raf signaling via the MEK-ERK pathway, there is some evidence that C-Raf (and possibly B-Raf and A-Raf) may signal via alternative pathways directly involved in cell survival by interaction with the BH3 family of anti-apoptotic proteins (Wellbrock et al., Nature Rev.: Mol. Cell. Biol., 5:875 (2004)).

Inhibitors of the Raf kinases may be expected to interrupt the Ras-Raf signaling cascade and thereby provide new methods for the treatment of proliferative disorders, such as cancer. There is thus a need for new inhibitors of Raf kinase activity.

Provided is at least one chemical entity selected from compounds of formula (I):

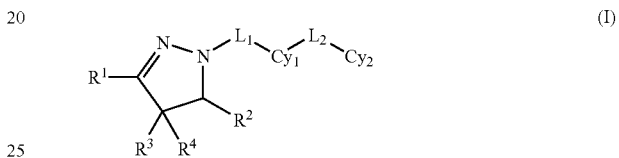

and pharmaceutically acceptable salts thereof, wherein $R^1$ is a substituted or unsubstituted 5- or 6-membered nitrogen-containing heteroaryl ring, which ring optionally is fused to an aryl, heteroaryl, heterocyclyl, or cycloaliphatic ring, each of which is optionally substituted;

$R^2$ is a substituted or unsubstituted 5- or 6-membered aryl or heteroaryl ring, which ring optionally is fused to an aryl, heteroaryl, heterocyclyl, or cycloaliphatic ring, each of which is optionally substituted;

$R^3$ is selected from hydrogen, fluoro, $C_{1-4}$ aliphatic, and $C_{1-4}$ fluoroaliphatic;

$R^4$ is hydrogen, fluoro, or a $C_{1-4}$ aliphatic or $C_{1-4}$ fluoroaliphatic optionally substituted with one or two substituents independently selected from —OH, —O($C_{1-4}$ aliphatic), —N($R^a$)($R^{a'}$), —N($R^a$)C(O)($C_{1-4}$ aliphatic), —N($R^a$)C(O)N($R^a$)$_2$, —C(O)($C_{1-4}$ aliphatic), —CO$_2$H, —CO$_2$($C_{1-4}$ aliphatic), and —C(O)N($R^a$)$_2$; or $R^3$ and $R^4$, taken together with the carbon to which they are bound, form an optionally substituted 3- to 6-membered cycloaliphatic or 4- to 7-membered heterocyclic ring;

$L_1$ is selected from —C(O)NR$^a$—(CR$^b$R$^c$)$_m$—, —C(O)C(R$^b$)=C(R$^b$)—(CR$^b$R$^c$)$_m$—, —C(O)—(CR$^b$R$^c$)$_m$—, and —SO$_2$—(CR$^b$R$^c$)$_m$—, wherein the C(O) or SO$_2$ functionality, respectively, is bound to the nitrogen of the pyrazoline ring;

$Cy_1$ is a bivalent radical derived from a ring system selected from optionally substituted 5- or 6-membered aromatic rings having zero to four ring nitrogen atoms and optionally one or two additional ring heteroatoms selected from oxygen and sulfur, which 5- or 6-membered aromatic ring optionally is fused to an aryl, heteroaryl, heterocyclyl, or cycloaliphatic ring, each of which is optionally substituted;

optionally substituted 4- to 7-membered heterocyclic rings, which 4- to 7-membered heterocyclic ring optionally is fused to an aryl, heteroaryl, heterocyclyl, or cycloaliphatic ring, each of which is optionally substituted; and optionally substituted 3- to 7-membered cycloaliphatic rings, which 3- to 7-membered cycloaliphatic ring optionally is fused to an aryl, heteroaryl, heterocyclyl, or cycloaliphatic ring, each of which is optionally substituted;

$L_2$ is —$(CR^bR^c)_n$— or —$(CR^bR^c)_n$—X—$(CR^bR^c)_n$—,

X is chosen from —O—, —C(O)—, —S—, —SO—, —SO$_2$—, —NR$^a$—, —C(R$^f$)=C(R$^f$)—, —C≡C—, —NR$^a$C(O)—, —C(O)NR$^a$—, —SO$_2$—NR$^a$, —NR$^a$SO$_2$—, and —NR$^a$C(O)NR$^a$—;

Cy$_2$ is a radical derived from a ring system selected from optionally substituted 5- or 6-membered aromatic rings having zero to four ring nitrogen atoms and optionally one or two additional ring heteroatoms selected from oxygen and sulfur, which 5- or 6-membered aromatic ring optionally is fused to an aryl, heteroaryl, heterocyclyl, or cycloaliphatic ring, each of which is optionally substituted; and optionally substituted 4- to 7-membered heterocyclic rings, which 4- to 7-membered heterocyclic ring optionally is fused to an aryl, heteroaryl, heterocyclyl, or cycloaliphatic ring, each of which is optionally substituted; and optionally substituted 3- to 7-membered cycloaliphatic rings, which 3- to 7-membered cycloaliphatic ring optionally is fused to an aryl, heteroaryl, heterocyclyl, or cycloaliphatic ring, each of which is optionally substituted;

m is selected from 0, 1 and 2;

each n is independently selected from 0, 1, and 2;

each R$^a$ independently is hydrogen or optionally substituted aliphatic; or R$^a$ and R$^{a'}$, taken together with the nitrogen atom to which they are attached, form an optionally substituted 4 to 8-membered heterocyclyl ring having, in addition to the nitrogen atom, 0-2 ring heteroatoms independently selected from N, O, and S;

R$^{a'}$ is selected from hydrogen, optionally substituted aliphatic, optionally substituted aryl, optionally substituted heteroaryl, and optionally substituted heterocyclyl; or R$^{a'}$ and R$^a$, taken together with the nitrogen atom to which they are attached, form an optionally substituted 4 to 8-membered heterocyclyl ring having, in addition to the nitrogen atom, 0-2 ring heteroatoms independently selected from N, O, and S;

each R$^b$ independently is selected from hydrogen, fluoro, $C_{1-4}$ aliphatic, and $C_{1-4}$ fluoroaliphatic, and each R$^c$ independently is selected from hydrogen, fluoro, $C_{1-4}$ aliphatic, $C_{1-4}$ fluoroaliphatic, —OH, —O($C_{1-4}$ aliphatic), —N(R$^a$)$_2$, —N(R$^a$)C(O)($C_{1-4}$ aliphatic), —C(O)($C_{1-4}$ aliphatic), —CO$_2$H, —CO$_2$($C_{1-4}$ aliphatic), and —C(O)N(R$^a$)$_2$; or R$^b$ and R$^c$, taken together with the carbon atom to which they are attached, form a 3- to 6-membered cycloaliphatic ring;

each R$^f$ independently is hydrogen, fluoro, or a $C_{1-3}$ aliphatic or $C_{1-3}$ fluoroaliphatic group optionally substituted with a substituent selected from the group consisting of —OH, —O($C_{1-3}$ aliphatic), —O($C_{1-3}$ fluoroaliphatic), —NH$_2$, —NH($C_{1-3}$ aliphatic), and —N($C_{1-3}$ aliphatic)$_2$;

provided that

R$^1$ is not 6-bromo-1,2-dihydro-2-oxo-4-phenyl-3-quinolinyl.

Also provided is a pharmaceutical composition comprising at least one chemical entity described herein and a pharmaceutically acceptable carrier.

Also provided is use of at least one chemical entity described herein for the treatment or prophylaxis of a human disorder.

Also provided is a method for the treatment or prophylaxis of cancer in a patient in need thereof, comprising administering to the patient at least one chemical entity described herein.

Chemical entities of the invention include those described generally above, and are further illustrated by the classes, subclasses, and species disclosed herein. Terms used herein shall be accorded the following defined meanings, unless otherwise indicated.

The terms "Raf" and "Raf kinase" are used interchangeably, and unless otherwise specified refer to any member of the Raf family of kinase enzymes, including without limitation, the isoforms A-Raf, B-Raf, and C-Raf. These enzymes, and the corresponding genes, also may be referred to in the literature by variants of these terms, e.g., RAF, raf; BRAF, B-raf, b-raf; CRAF, C-raf, c-raf, Raf-1 and C-Raf-1.

The term "aliphatic" or "aliphatic group", as used herein, means a substituted or unsubstituted straight-chain, branched, or cyclic $C_{1-12}$ hydrocarbon, which is completely saturated or which contains one or more units of unsaturation, but which is not aromatic. For example, suitable aliphatic groups include substituted or unsubstituted linear, branched or cyclic alkyl, alkenyl, or alkynyl groups and hybrids thereof, such as (cycloalkyl)alkyl, (cycloalkenyl)alkyl or (cycloalkyl)alkenyl. In various embodiments, the aliphatic group has 1 to 12, 1 to 8, 1 to 6, 1 to 4, or 1 to 3 carbons.

The terms "alkyl", "alkenyl", and "alkynyl", used alone or as part of a larger moiety, refer to a straight or branched chain aliphatic group having from 1 to 12 carbon atoms. For purposes of the present invention, the term "alkyl" will be used when the carbon atom attaching the aliphatic group to the rest of the molecule is a saturated carbon atom. However, an alkyl group may include unsaturation at other carbon atoms. Thus, alkyl groups include, without limitation, methyl, ethyl, propyl, allyl, propargyl, butyl, pentyl, and hexyl.

For purposes of the present invention, the term "alkenyl" will be used when the carbon atom attaching the aliphatic group to the rest of the molecule forms part of a carbon-carbon double bond. Alkenyl groups include, without limitation, vinyl, 1-propenyl, 1-butenyl, 1-pentenyl, and 1-hexenyl.

For purposes of the present invention, the term "alkynyl" will be used when the carbon atom attaching the aliphatic group to the rest of the molecule forms part of a carbon-carbon triple bond. Alkynyl groups include, without limitation, ethynyl, 1-propynyl, 1-butynyl, 1-pentynyl, and 1-hexynyl.

The term "cycloaliphatic", used alone or as part of a larger moiety, refers to a saturated or partially unsaturated cyclic aliphatic ring system having from 3 to about 14 members, wherein the aliphatic ring system is optionally substituted. In some embodiments, the cycloaliphatic is a monocyclic hydrocarbon having 3-8 or 3-6 ring carbon atoms. Nonlimiting examples include cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloaliphatic is a bridged or fused bicyclic hydrocarbon having 6-12, 6-10, or 6-8 ring carbon atoms, wherein any individual ring in the bicyclic ring system has 3-8 members.

In some embodiments, two adjacent substituents on the cycloaliphatic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the term "cycloaliphatic" includes aliphatic rings that are fused to one or more aryl, heteroaryl, or heterocyclyl rings. Nonlimiting examples include indanyl, 5,6,7,8-tetrahydroquinoxalinyl, decahydronaphthyl, or tetrahydronaphthyl, where the radical or point of attachment is on the aliphatic ring.

The terms "aryl" and "ar-", used alone or as part of a larger moiety, e.g., "aralkyl", "aralkoxy", or "aryloxyalkyl", refer to a $C_6$ to $C_{14}$ aromatic hydrocarbon, comprising one to three rings, each of which is optionally substituted. Preferably, the aryl group is a $C_{6-10}$ aryl group. Aryl groups include, without limitation, phenyl, naphthyl, and anthracenyl. In some embodiments, two adjacent substituents on the aryl ring, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the term "aryl", as used herein, includes groups in which an aryl ring is fused to one or more heteroaryl, cycloaliphatic, or heterocyclyl rings, where the radical or point of attachment is on the aromatic ring. Nonlimiting examples of such fused ring systems include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl. An aryl group may be mono-, bi-, tri-, or polycyclic, preferably mono-, bi-, or tricyclic, more preferably mono- or bicyclic. The term "aryl" may be used interchangeably with the terms "aryl group", "aryl moiety", and "aryl ring".

Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from a ring carbon atom are named by adding "-ene" to the name of the corresponding univalent radical, e.g., a naphthyl group with two points of attachment is termed naphthylene.

An "aralkyl" or "arylalkyl" group comprises an aryl group covalently attached to an alkyl group, either of which independently is optionally substituted. Preferably, the aralkyl group is $C_{6-10}$ aryl($C_{1-6}$)alkyl, $C_{6-10}$ aryl($C_{1-4}$)alkyl, or $C_{6-10}$ aryl($C_{1-3}$)alkyl, including, without limitation, benzyl, phenethyl, and naphthylmethyl.

The terms "heteroaryl" and "heteroar-", used alone or as part of a larger moiety, e.g., heteroaralkyl, or "heteroaralkoxy", refer to groups having 5 to 14 ring atoms, preferably 5, 6, 9, or 10 ring atoms; having 6, 10, or 14 .pi. electrons shared in a cyclic array; and having, in addition to carbon atoms, from one to four heteroatoms. The term "heteroatom" refers to nitrogen, oxygen, or sulfur, and includes any oxidized form of nitrogen or sulfur, and any quaternized form of a basic nitrogen. Thus, when used in reference to a ring atom of a heteroaryl, the term "nitrogen" includes an oxidized nitrogen (as in pyridine N-oxide). Certain nitrogen atoms of 5-membered heteroaryl groups also are substitutable, as further defined below. Heteroaryl groups include, without limitation, radicals derived from thiophene, furan, pyrrole, imidazole, pyrazole, triazole, tetrazole, oxazole, isoxazole, oxadiazole, thiazole, isothiazole, thiadiazole, pyridine, pyridazine, pyrimidine, pyrazine, indolizine, naphthyridine, pteridine, pyrrolopyridine, imidazopyridine, oxazolopyridine, thiazolopyridine, triazolopyridine, pyrrolopyrimidine, purine, and triazolopyrimidine. As used herein, the phrase "radical derived from" means a monovalent radical produced by removal of a hydrogen radical from the parent heteroaromatic ring system. The radical (i.e., the point of attachment of the heteroaryl to the rest of the molecule) may be created at any substitutable position on any ring of the parent heteroaryl ring system.

In some embodiments, two adjacent substituents on the heteroaryl, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, benzoxazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono-, bi-, tri-, or polycyclic, preferably mono-, bi-, or tricyclic, more preferably mono- or bicyclic. The term "heteroaryl" may be used interchangeably with the terms "heteroaryl ring", or "heteroaryl group", any of which terms include rings that are optionally substituted. The term "heteroaralkyl" refers to an alkyl group substituted by a heteroaryl, wherein the alkyl and heteroaryl portions independently are optionally substituted.

As used herein, the terms "aromatic ring" and "aromatic ring system" refer to an optionally substituted mono-, bi-, or tricyclic group having 0-6, preferably 0-4 ring heteroatoms, and having 6, 10, or 14 .pi. electrons shared in a cyclic array. Thus, the terms "aromatic ring" and "aromatic ring system" encompass both aryl and heteroaryl groups.

As used herein, the terms "heterocycle", "heterocyclyl", "heterocyclic radical", and "heterocyclic ring" are used interchangeably and refer to a stable 3- to 7-membered monocyclic, or to a fused 7- to 10-membered or bridged 6- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a heterocyclyl ring having 1-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). A heterocyclic ring can be attached to its pendant group at any heteroatom or carbon atom that results in a stable structure, and any of the ring atoms can be optionally substituted. For example, a heterocyclic ring having at least one nitrogen atom can be attached by that nitrogen atom. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

In some embodiments, two adjacent substituents on a heterocyclic ring, taken together with the intervening ring atoms, form an optionally substituted fused 5- to 6 membered aromatic or 3- to 8-membered non-aromatic ring having 0-3 ring heteroatoms selected from the group consisting of O, N, and S. Thus, the terms "heterocycle", "heterocyclyl", "heterocyclyl ring", "heterocyclic group", "heterocyclic moiety", and "heterocyclic radical", are used interchangeably herein, and include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted.

Bivalent radicals derived from univalent heteroaryl radicals whose names end in "-yl" by removal of one hydrogen atom from a ring atom are named by adding "-ene" to the name of the corresponding univalent radical, e.g., a pyridyl group with two points of attachment is a pyridylene.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "linker group" or "linker" means an organic moiety that connects two parts of a compound. Linkers typically comprise an atom such as oxygen or sulfur, a unit such as —NH—, —CH$_2$—, —C(O)—, —C(O)NH—, or a chain of atoms, such as an alkylene chain. The molecular mass of a linker is typically in the range of about 14 to 200, preferably in the range of 14 to 96 with a length of up to about six atoms. In some embodiments, the linker is a C$_{1-6}$ alkylene chain.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

An alkylene chain also can be optionally interrupted by a functional group. An alkylene chain is "interrupted" by a functional group when an internal methylene unit is replaced with the functional group. Examples of suitable "interrupting functional groups" include —C(R*)=C(R*)—, —C≡C—, —S—, —S(O)—, —S(O)$_2$—, —S(O)$_2$N(R$^+$)—, —N(R*)—, —N(R$^+$)CO—, —N(R$^+$)C(O)N(R$^+$)—, —N(R$^+$)C(=NR$^+$)—N(R$^+$)—, —N(R$^+$)—C(=NR$^+$)—, —N(R$^+$)CO$_2$—, —N(R$^+$)SO$_2$—, —N(R$^+$)SO$_2$N(R$^+$)—, —OC(O)—, —OC(O)O—, —OC(O)N(R$^+$)—, —C(O)—, —CO$_2$—, —C(O)N(R$^+$)—, —C(O)—C(O)—, —C(=NR$^+$)—N(R$^+$)—, —C(NR$^+$)=N—, —C(=NR$^+$)—O—, —C(OR*)=N—, —C(R$^o$)=N—O—, or —N(R$^+$)—N(R$^+$)—. Each R$^+$, independently, is hydrogen or an optionally substituted aliphatic, aryl, heteroaryl, or heterocyclyl group, or two R$^+$ on the same nitrogen atom, taken together with the nitrogen atom, form a 4-8 membered aromatic or non-aromatic ring having, in addition to the nitrogen atom, 0-2 ring heteroatoms selected from N, O, and S. Each R* independently is hydrogen or an optionally substituted aliphatic, aryl, heteroaryl, or heterocyclyl group.

Examples of C$_{3-6}$ alkylene chains that have been "interrupted" with —O— include —CH$_2$OCH$_2$—, —CH$_2$O(CH$_2$)$_2$—, —CH$_2$O(CH$_2$)$_3$—, —CH$_2$O—(CH$_2$)$_4$—, —(CH$_2$)$_2$OCH$_2$, —(CH$_2$)$_2$O(CH$_2$)$_2$—, —(CH$_2$)$_2$O(CH$_2$)$_3$—, —(CH$_2$)$_3$O(CH$_2$)—, —(CH$_2$)$_3$O(CH$_2$)$_2$—, and —(CH$_2$)$_4$O(CH$_2$)—. Other examples of alkylene chains that are "interrupted" with functional groups include —CH$_2$ZCH$_2$—, —CH$_2$Z(CH$_2$)$_2$—, —CH$_2$Z(CH$_2$)$_3$—, —CH$_2$Z(CH$_2$)$_4$—, —(CH$_2$)$_2$ZCH$_2$—, —(CH$_2$)$_2$Z(CH$_2$)$_2$—, —(CH$_2$)$_2$Z(CH$_2$)$_3$—, —(CH$_2$)$_3$Z(CH$_2$)—, —(CH$_2$)$_3$Z(CH$_2$)$_2$—, and —(CH$_2$)$_4$Z(CH$_2$)—, wherein Z is one of the "interrupting functional groups" listed above.

For purposes of clarity, all bivalent groups described herein, including, e.g., the alkylene chain linkers described above and the variables L$_1$, L$_2$, and X, are intended to be read from left to right, with a corresponding left-to-right reading of the formula or structure in which the variable appears.

One of ordinary skill in the art will recognize that when an alkylene chain having an interruption is attached to a functional group, certain combinations are not sufficiently stable for pharmaceutical use. Only stable or chemically feasible compounds are within the scope of the present invention. A stable or chemically feasible compound is one in which the chemical structure is not substantially altered when kept at a temperature from about −80° C. to about +40° C., preferably −20° C. to about +40° C. in the absence of moisture or other chemically reactive conditions, for at least a week, or a compound which maintains its integrity long enough to be useful for therapeutic or prophylactic administration to a patient.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different.

As used herein, the term "independently selected" means that the same or different values may be selected for multiple instances of a given variable in a single compound. By way of example, in a compound of formula (I), if R$^1$ is substituted with two substituents, each substituent is selected from the group of defined values for that substituent, and the two values selected may be the same or different.

An aryl (including the aryl moiety in aralkyl, aralkoxy, aryloxyalkyl and the like) or heteroaryl (including the heteroaryl moiety in heteroaralkyl and heteroaralkoxy and the like) group may contain one or more substituents. Examples of suitable substituents on the unsaturated carbon atom of an aryl or heteroaryl group include -halo, —NO$_2$, —CN, —R*, —C(R*)=C(R*)$_2$, —C≡C—R*, —OR*, —SR$^o$, —S(O)R$^o$, —SO$_2$R$^o$, —SO$_3$R*, —SO$_2$N(R$^+$)$_2$, —N(R$^+$)$_2$, —NR$^+$C(O)R*, —NR$^+$C(O)N(R$^+$)$_2$, —N(R$^+$)C(=NR$^+$)—N(R$^+$)$_2$, —N(R$^+$)C(=NR$^+$)—R$^o$, —NR$^+$CO$_2$R$^o$, —NR$^+$SO$_2$R$^o$, —NR$^+$SO$_2$N(R$^+$)$_2$, —O—C(O)R*, —O—CO$_2$R*, —OC(O)N(R$^+$)$_2$, —C(O)R*, —CO$_2$R*, —C(O)—C(O)R*, —C(O)N(R$^+$)$_2$, —C(O)N(R$^+$)—OR*, —C(O)N(R$^+$)C(=NR$^+$)—N(R$^+$)$_2$, —N(R$^+$)C(=NR$^+$)—N(R$^+$)—C(O)R*, —C(=NR$^+$)—N(R$^+$)$_2$, —C(=NR$^+$)—OR*, —N(R$^+$)—N(R$^+$)$_2$, —N(R$^+$)—OR*, —C(=NR$^+$)—N(R$^+$)—OR*, —C(R$^o$)=N—OR*, —P(O)(R*)$_2$, —P(O)(OR*)$_2$, —O—P(O)—OR*, and —P(O)(NR$^+$)—N(R$^+$)$_2$, wherein R$^o$ is an optionally substituted aliphatic, aryl, or heteroaryl group, and R$^+$ and R* are as defined above, or two adjacent substituents, taken together with their intervening atoms, form a 5-6 membered unsaturated or partially unsaturated ring having 0-3 ring atoms selected from the group consisting of N, O, and S.

An aliphatic group or a non-aromatic heterocyclic ring may be substituted with one or more substituents. Examples of suitable substituents on the saturated carbon of an aliphatic group or of a non-aromatic heterocyclic ring include, without limitation, those listed above for the unsaturated carbon of an aryl or heteroaryl group and the following: =O, =S, =C(R*)$_2$, =N—N(R*)$_2$, =N—OR*, =N—NHC(O)R*, =N—NHCO$_2$R$^o$, =N—NHSO$_2$R$^o$, or =N—R*, where each R* and R$^o$ is as defined above. Additionally, two substituents on the same carbon atom, taken together with the carbon atom to which they are attached may form an optionally substituted spirocyclic 3- to 6-membered cycloaliphatic ring.

Suitable substituents on a substitutable nitrogen atom of a heteroaryl or non-aromatic heterocyclic ring include —R*, —N(R*)$_2$, —C(O)R*, —CO$_2$R*, —C(O)—C(O)R* —C(O) CH$_2$C(O)R*, —SO$_2$R*, —SO$_2$N(R*)$_2$, —C(=S)N(R*)$_2$, —C(=NH)—N(R*)$_2$, and —NR*SO$_2$R*; wherein each R* is as defined above. A ring nitrogen atom of a heteroaryl or non-aromatic heterocyclic ring also may be oxidized to form the corresponding N-hydroxy or N-oxide compound. A non-limiting example of such a heteroaryl having an oxidized ring nitrogen atom is N-oxidopyridyl.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, the term "comprises" means "includes, but is not limited to."

It will be apparent to one skilled in the art that certain compounds of this invention may exist in tautomeric forms, all such tautomeric forms of the compounds being within the scope of the invention. Unless otherwise stated, structures depicted herein are also meant to include all geometric (or conformational) isomers, i.e., (Z) and (E) double bond isomers and (Z) and (E) conformational isomers, as well as all stereochemical forms of the structure; i.e., the R and S configurations for each asymmetric center. Therefore, single stereochemical isomers as well as enantiomeric and diastereomeric mixtures of the present compounds are within the scope of the invention. When a mixture is enriched in one stereoisomer relative to another stereoisomer, the mixture may contain, for example, an enantiomeric excess of at least 50%, 75%, 90%, 99%, or 99.5%.

Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

Provided is at least one chemical entity selected from compounds of formula (I):

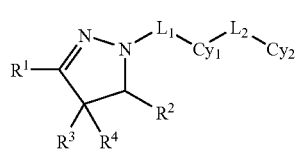

(I)

and pharmaceutically acceptable salts thereof, wherein $R^1$ is a substituted or unsubstituted 5- or 6-membered nitrogen-containing heteroaryl ring, which ring optionally is fused to an aryl, heteroaryl, heterocyclyl, or cycloaliphatic ring, each of which is optionally substituted;

$R^2$ is a substituted or unsubstituted 5- or 6-membered aryl or heteroaryl ring, which ring optionally is fused to an aryl, heteroaryl, heterocyclyl, or cycloaliphatic ring, each of which is optionally substituted;

$R^3$ is selected from hydrogen, fluoro, $C_{1-4}$ aliphatic, and $C_{1-4}$ fluoroaliphatic;

$R^4$ is hydrogen, fluoro, or a $C_{1-4}$ aliphatic or $C_{1-4}$ fluoroaliphatic optionally substituted with one or two substituents independently selected from —OH, —O($C_{1-4}$ aliphatic), —N($R^a$)($R^{a'}$), —N($R^a$)C(O)($C_{1-4}$ aliphatic), —N($R^a$)C(O)N ($R^a$)$_2$, —C(O)($C_{1-4}$ aliphatic), —CO$_2$H, —CO$_2$($C_{1-4}$ aliphatic), and —C(O)N($R^a$)$_2$; or $R^3$ and $R^4$, taken together with the carbon to which they are bound, form an optionally substituted 3- to 6-membered cycloaliphatic or 4- to 7-membered heterocyclic ring;

$L_1$ is selected from —C(O)NR$^a$—(CR$^b$R$^c$)$_m$—, —C(O)C (R$^b$)=C(R$^b$)—(CR$^b$R$^c$)$_m$—, —C(O)—(CR$^b$R$^c$)$_m$—, and —SO$_2$—(CR$^b$R$^c$)$_m$—, wherein the C(O) or SO$_2$ functionality, respectively, is bound to the nitrogen of the pyrazoline ring;

$Cy_1$ is a bivalent radical derived from a ring system selected from optionally substituted 5- or 6-membered aromatic rings having zero to four ring nitrogen atoms and optionally one or two additional ring heteroatoms selected from oxygen and sulfur, which 5- or 6-membered aromatic ring optionally is fused to an aryl, heteroaryl, heterocyclyl, or cycloaliphatic ring, each of which is optionally substituted;

optionally substituted 4- to 7-membered heterocyclic rings, which 4- to 7-membered heterocyclic ring optionally is fused to an aryl, heteroaryl, heterocyclyl, or cycloaliphatic ring, each of which is optionally substituted; and optionally substituted 3- to 7-membered cycloaliphatic rings, which 3- to 7-membered cycloaliphatic ring optionally is fused to an aryl, heteroaryl, heterocyclyl, or cycloaliphatic ring, each of which is optionally substituted;

$L_2$ is —(CR$^b$R$^c$)$_n$— or —(CR$^b$R$^c$)$_n$—X—(CR$^b$R$^c$)$_n$—, X is chosen from —O—, —C(O)—, —S—, —SO—, —SO$_2$—, —NR$^a$—, —C(R$^f$)=C(R$^f$)—, —C≡C—, —NR$^a$C(O)—, —C(O)NR$^a$—, —SO$_2$—NR$^a$, —NR$^a$SO$_2$—, and —NR$^a$C(O)NR$^a$—;

$Cy_2$ is a radical derived from a ring system selected from optionally substituted 5- or 6-membered aromatic rings having zero to four ring nitrogen atoms and optionally one or two additional ring heteroatoms selected from oxygen and sulfur, which 5- or 6-membered aromatic ring optionally is fused to an aryl, heteroaryl, heterocyclyl, or cycloaliphatic ring, each of which is optionally substituted; and optionally substituted 4- to 7-membered heterocyclic rings, which 4- to 7-membered heterocyclic ring optionally is fused to an aryl, heteroaryl, heterocyclyl, or cycloaliphatic ring, each of which is optionally substituted; and optionally substituted 3- to 7-membered cycloaliphatic rings, which 3- to 7-membered cycloaliphatic ring optionally is fused to an aryl, heteroaryl, heterocyclyl, or cycloaliphatic ring, each of which is optionally substituted;

m is selected from 0, 1 and 2;

each n is independently selected from 0, 1, and 2;

each $R^a$ independently is hydrogen or optionally substituted aliphatic; or $R^a$ and $R^{a'}$, taken together with the nitrogen atom to which they are attached, form an optionally substituted 4 to 8-membered heterocyclyl ring having, in addition to the nitrogen atom, 0-2 ring heteroatoms independently selected from N, O, and S;

$R^{a'}$ is selected from hydrogen, optionally substituted aliphatic, optionally substituted aryl, optionally substituted heteroaryl, and optionally substituted heterocyclyl; or $R^{a'}$ and $R^a$, taken together with the nitrogen atom to which they are attached, form an optionally substituted 4 to 8-membered heterocyclyl ring having, in addition to the nitrogen atom, 0-2 ring heteroatoms independently selected from N, O, and S;

each $R^b$ b independently is selected from hydrogen, fluoro, $C_{1-4}$ aliphatic, and $C_{1-4}$ fluoroaliphatic, and each $R^c$ independently is selected from hydrogen, fluoro, $C_{1-4}$ aliphatic, $C_{1-4}$ fluoroaliphatic, —OH, —O($C_{1-4}$ aliphatic), —N($R^a$)$_2$, —N($R^a$)C(O)($C_{1-4}$ aliphatic), —C(O)($C_{1-4}$ aliphatic), —CO$_2$H, —CO$_2$($C_{1-4}$ aliphatic), and —C(O)N($R^a$)$_2$; or $R^b$ and $R^c$, taken together with the carbon atom to which they are attached, form a 3- to 6-membered cycloahpatic ring;

each $R^f$ independently is hydrogen, fluoro, or a $C_{1-3}$ aliphatic or $C_{1-3}$ fluoroaliphatic group optionally substituted with a substituent selected from the group consisting of —OH, —O($C_{1-3}$ aliphatic), —O($C_{1-3}$ fluoroaliphatic), —NH$_2$, —NH($C_{1-3}$ aliphatic), and —N($C_{1-3}$ aliphatic)$_2$;

provided that $R^1$ is not 6-bromo-1,2-dihydro-2-oxo-4-phenyl-3-quinolinyl.

In some embodiments, $R^1$ is an optionally substituted 6-membered heteroaryl ring with 1 or 2 ring nitrogen atoms, which ring optionally is fused to an aryl, heteroaryl, heterocyclyl, or cycloaliphatic ring, any of which is optionally substituted.

In some embodiments, each of the substitutable ring carbon atoms in $R^1$ independently is unsubstituted or is substituted with halo, —NO$_2$, —CN, —R*, —C(R*)=C(R*)$_2$, —C≡C—R*, —OR*, —SR*, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$—NR$^+$CO$_2$R$^o$, —OC(O)N(R$^+$)$_2$, —CO$_2$R*, —C(O)R*, —C(O)N(R$^+$)$_2$, —N(R$^+$)C(=NR$^+$)—N(R$^+$)—C(O)R*, —C(=NR$^+$)—N(R$^+$)$_2$, —N(R$^+$)C(=NR$^+$)—N(R$^+$)$_2$, —NR$^+$SO$_2$R$^o$, and —NR$^+$SO$_2$N(R$^+$)$_2$; wherein $R^o$ is an optionally substituted aliphatic, aryl, or heteroaryl group;

each R* independently is hydrogen or an optionally substituted aliphatic, aryl, heteroaryl, or heterocyclyl group;

each R$^+$ independently is hydrogen or an optionally substituted aliphatic, aryl, heteroaryl, or heterocyclyl group, or two R$^+$ on the same nitrogen atom, taken together with the nitrogen atom, form a 4-8 membered aromatic or non-aromatic ring having, in addition to the nitrogen atom, 0-2 ring heteroatoms selected from N, O, and S; and one ring nitrogen atom in $R^1$ optionally is oxidized.

In some embodiments, $R^1$ is an optionally substituted monocyclic 6-membered heteroaryl ring with 1 or 2 ring nitrogen atoms. In some embodiments, $R^1$ is pyridinyl, wherein the pyridinyl ring optionally is substituted on any substitutable ring carbon atom and the ring nitrogen atom optionally is oxidized. In some embodiments, $R^1$ is pyrid-3-yl optionally substituted on any substitutable ring carbon atom.

In some embodiments, $R^1$ is pyrid-3-yl optionally substituted with one or more substituents independently selected from —F, —Cl, —CN, —OR$^{1*}$, —SR$^{1*}$, —SO$_2$R$^{1o}$, —N(R$^{1+}$)$_2$, N(R$^{1+}$)C(O)R$^{1*}$, —CO$_2$R$^{1*}$, —C(O)N(R$^{1+}$)$_2$, $C_{6-10}$ ar($C_{1-4}$ alkyl), the aryl portion of which is optionally substituted, an optionally substituted 5- or 6-membered aryl, heteroaryl, or heterocyclyl ring, an optionally substituted 3- to 6-membered cycloaliphatic ring, and a $C_{1-4}$ aliphatic or $C_{1-4}$ fluoroaliphatic group optionally substituted with one or two substituents independently selected from the group consisting of —OR$^{1*}$, —SR$^{1*}$, —SO$_2$R$^{1o}$, —N(R$^{1+}$)$_2$, —N(R$^{1+}$)C(O)R$^{1*}$, —CO$_2$R$^{1*}$, and —C(O)N(R$^{1+}$)$_2$; wherein R$^{1*}$ is hydrogen, $C_{1-4}$ aliphatic, $C_{1-4}$ fluoroaliphatic, or $C_{6-10}$ ar($C_{1-4}$ alkyl), the aryl portion of which is optionally substituted;

R$^{1o}$ is $C_{1-4}$ aliphatic, $C_{1-4}$ fluoroaliphatic, $C_{6-10}$ ar($C_{1-4}$ alkyl), the aryl portion of which is optionally substituted, or an optionally substituted 5- or 6-membered aryl or heteroaryl ring; and each R$^{1+}$ independently is hydrogen, $C_{1-4}$ aliphatic, $C_{1-4}$ fluoroaliphatic, or $C_{6-10}$ ar($C_{1-4}$ alkyl), the aryl portion of which is optionally substituted; or two R$^{1+}$ on the same nitrogen atom, taken together with the nitrogen atom form an optionally substituted pyrrolidinyl, piperidinyl, piperazinyl, or morpholinyl ring.

In some embodiments, $R^1$ is pyrid-3-yl.

In some embodiments, $R^2$ is a 6-membered aryl ring, optionally fused to an aryl, heteroaryl, heterocyclyl, or cycloaliphatic ring, wherein the ring system optionally is substituted on any substitutable ring carbon atom.

In some embodiments, $R^2$ is optionally substituted phenyl, which ring optionally is fused to an aryl, heteroaryl, heterocyclyl, or cycloaliphatic ring, any of which is optionally substituted. In some embodiments, each of the substitutable ring carbon atoms in $R^2$ independently is unsubstituted or is substituted with halo, —NO$_2$, —CN, —R*, —C(R*)=C(R*)$_2$, —C≡C—R*, —OR*, —SR*, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$—NR$^+$CO$_2$R$^o$, —OC(O)N(R$^+$)$_2$, —CO$_2$R*, —C(O)R*, —C(O)N(R$^+$)$_2$, —N(R$^+$)C(=NR$^+$)—N(R$^+$)—C(O)R*, —C(=NR$^+$)—N(R$^+$)$_2$, —N(R$^+$)C(=NR$^+$)—N(R$^+$)$_2$, —NR$^+$SO$_2$R$^o$, and —NR$^+$SO$_2$N(R$^+$)$_2$;

$R^o$ is an optionally substituted aliphatic, aryl, or heteroaryl group;

each R* independently is hydrogen or an optionally substituted aliphatic, aryl, heteroaryl, or heterocyclyl group; and each R$^+$ independently is hydrogen or an optionally substituted aliphatic, aryl, heteroaryl, or heterocyclyl group, or two R$^+$ on the same nitrogen atom, taken together with the nitrogen atom, form a 4-8 membered aromatic or non-aromatic ring having, in addition to the nitrogen atom, 0-2 ring heteroatoms selected from N, O, and S.

In some embodiments, $R^2$ is phenyl substituted with one hydroxy group and optionally substituted with one or two additional groups independently selected from —F, —Cl, —CN, —OR$^{2*}$, —SR$^{2*}$, —SO$_2$R$^{2o}$, —N(R$^{2+}$)$_2$, —N(R$^{2+}$)C(O)R$^{2*}$, —CO$_2$R$^{2*}$, —C(O)N(R$^{2+}$)$_2$, $C_{6-10}$ ar($C_{1-4}$ alkyl), the aryl portion of which is optionally substituted, an optionally substituted 5- or 6-membered aryl, heteroaryl, or heterocyclyl ring, an optionally substituted 3- to 6-membered cycloaliphatic ring, and a $C_{1-4}$ aliphatic or $C_{1-4}$ fluoroaliphatic group optionally substituted with one or two substituents independently selected from the group consisting of —OR$^{2*}$, —SR$^{2*}$, —SO$_2$R$^{2o}$, —N(R$^{2+}$)$_2$, —N(R$^{2+}$)C(O)R$^{2*}$, —CO$_2$R$^{2*}$, and —C(O)N(R$^{2+}$)$_2$; wherein R$^{2*}$ is hydrogen, $C_{1-4}$ aliphatic, $C_{1-4}$ fluoroaliphatic, or $C_{6-10}$ ar($C_{1-4}$ alkyl), the aryl portion of which is optionally substituted;

R$^{2o}$ is $C_{1-4}$ aliphatic, $C_{1-4}$-fluoroaliphatic, $C_{6-10}$ ar($C_{1-4}$ alkyl), the aryl portion of which is optionally substituted, or an optionally substituted 5- or 6-membered aryl or heteroaryl ring; and each R$^{2+}$ independently is hydrogen, $C_{1-4}$ aliphatic, $C_{1-4}$ fluoroaliphatic, or $C_{6-10}$ ar($C_{1-4}$ alkyl), the aryl portion of which is optionally substituted; or two R$^{2+}$ on the same nitrogen atom, taken together with the nitrogen atom form an optionally substituted pyrrolidinyl, piperidinyl, piperazinyl, or morpholinyl ring.

In some embodiments, $R^2$ is 2-hydroxyphenyl or 3-hydroxyphenyl, either of which groups optionally is additionally substituted with one or two substituents selected from —F, —Cl, $C_{1-4}$ aliphatic, $C_{1-4}$ fluoroaliphatic, —O($C_{1-4}$ aliphatic), and —O($C_{1-4}$ fluoroaliphatic). In certain embodiments, $R^2$ is 2-hydroxyphenyl, which group optionally is additionally substituted with one or two substituents selected from —F, —Cl, $C_{1-4}$ aliphatic, $C_{1-4}$ fluoroaliphatic, —O($C_{1-4}$ aliphatic), and —O($C_{1-4}$ fluoroaliphatic).

In some embodiments, $R^3$ is hydrogen.

In some embodiments, $R^4$ is hydrogen.

In some embodiments, $L_1$ is —C(O)—. In some other embodiments, $L_1$ is —SO$_2$—. In some other embodiments, $L_1$ is —C(O)NH—.

In some embodiments, $L_2$ is selected from the group consisting of —C($R^b$)($R^c$)$_n$—, —O—, —C($R^b$)($R^c$)—O—, —O—C($R^b$)($R^c$)—, —N($R^a$)—, —C($R^b$)($R^c$)—N($R^a$)—, —N($R^a$)—C($R^b$)($R^c$), —SO$_2$—, —SO$_2$—N($R^a$)—C($R^b$)($R^c$)—, —N($R^a$)—SO$_2$—C($R^b$)($R^c$)—, —C≡C—, —C($R^b$)($R^c$)—N($R^a$)—C(O)—, and —C($R^b$)($R^c$)—S—C($R^b$)($R^c$)—. In some such embodiments, $L_2$ is selected from the group consisting of —(CH$_2$)$_n$—, —O—, —CH$_2$—O—, —O—CH$_2$—, —NH—, —CH$_2$—NH—, —NH—CH$_2$—, —SO$_2$—, —SO$_2$NHCH$_2$—, —NH—SO$_2$—CH$_2$—, —C≡C—, —CH$_2$—NH—C(O)—, and —CH$_2$—S—CH$_2$—. In certain embodiments, $L_2$ is selected from the group consisting of —(CH$_2$)$_n$—, —O—, —NH—CH$_2$—, —CH$_2$—NH—, and —SO$_2$—. In certain particular embodiments, $L_2$ is —(CH$_2$)$_n$— and n is 0.

In some embodiments, Cy$_1$ is a bivalent radical derived from a ring system selected from benzene, benzimidazole, benzoxazole, benzthiazole, cinnoline, cyclopropane, cyclopentane, cyclohexane, furan, imidazole, imidazolidine, imidazoline, imidazopyridine, indole, indolizine, isoindole, isoquinoline, isothiazole, isoxazole, morpholine, naphthyridine, oxadiazole, oxazolidine, oxazole, oxazolopyridine, 1,3-oxathiolane, phthalazine, piperazine, piperidine, pteridine, purine, pyrazine, pyrazole, pyrazolidine, pyrazoline, pyridazine, pyridine, pyrimidine, pyrrole, pyrrolidine, pyrrolopyridine, pyrrolopyrimidine, quinazoline, quinoline, quinoxaline, tetrahydrofuran, tetrahydro-2H-pyran, tetrahydrothiophene, thiadiazole, thiazole, thiazolopyridine, thiophene, triazine, triazole, triazolopyridine, and triazolopyrimidine, wherein the ring system optionally is substituted on any substitutable ring carbon atom and any substitutable ring nitrogen atom; and one ring nitrogen atom in the ring system optionally is oxidized.

In some embodiments, Cy$_1$ is a bivalent radical derived from a monocyclic 5-membered aryl, heteroaryl, cycloaliphatic, or heterocyclyl ring, wherein the ring optionally is substituted on any substitutable ring carbon atom and on any substitutable ring nitrogen atom, and one ring nitrogen atom optionally is oxidized.

In some embodiments, Cy$_1$ is a bivalent radical derived from a ring system selected from thiophene, thiazole, pyrazole, imidazole, oxazole, isoxazole, furan, cyclopropane, pyrrole, indole, pyridine, benzene, and pyrrolidine, wherein the ring system optionally is substituted on any substitutable ring carbon atom and any ring nitrogen atom, and one ring nitrogen atom in the ring system optionally is oxidized.

In some embodiments, each substitutable ring nitrogen atom in Cy$_1$ is unsubstituted or is substituted with —C(O)$R^{5*}$, —C(O)N($R^{5+}$)$_2$, —CO$_2$$R^{5o}$, —SO$_2$$R^{5o}$, —SO$_2$N($R^{5+}$)$_2$, $C_{1-4}$ aliphatic, or a $C_{6-10}$ ar($C_{1-4}$)alkyl, the aryl portion of which is optionally substituted;

each substitutable saturated ring carbon atom in Cy$_1$ is unsubstituted or is substituted with =O, =S, =C($R^{5*}$)$_2$, or —$R^5$;

each substitutable unsaturated ring carbon atom in Cy$_1$ is unsubstituted or is substituted with $R^5$;

$R^5$ is —F, —Cl, —CN, —O$R^{5*}$, —S$R^{5*}$, —SO$_2$$R^{5o}$, —N($R^{5+}$)$_2$, —N($R^{5+}$)C(O)—, —CO$_2$$R^{5*}$, —C(O)N($R^{5+}$)$_2$, $C_{6-10}$ ar($C_{1-4}$ alkyl), the aryl portion of which is optionally substituted, an optionally substituted 5- or 6-membered aryl, heteroaryl, or heterocyclyl ring, an optionally substituted 3- to 6-membered cycloaliphatic ring, or a $C_{1-4}$ aliphatic or $C_{1-4}$ fluoroaliphatic group optionally substituted with one or two substituents independently selected from the group consisting of —O$R^{5*}$, —N($R^{5+}$)$_2$, —N($R^{5+}$)C(O)—, —SO$_2$N($R^{5+}$)$_2$, —CO$_2$$R^{5*}$, and —C(O)N($R^{5+}$)$_2$; wherein $R^{5*}$ is hydrogen, $C_{1-4}$ aliphatic, $C_{1-4}$ fluoroaliphatic, or $C_{6-10}$ ar($C_{1-4}$ alkyl), the aryl portion of which is optionally substituted;

$R^{5o}$ is $C_{1-4}$ aliphatic, $C_{1-4}$ fluoroaliphatic, $C_{6-10}$ ar($C_{1-4}$ alkyl), the aryl portion of which is optionally substituted, or an optionally substituted 5- or 6-membered aryl or heteroaryl ring;

each $R^{5+}$ independently is hydrogen, $C_{1-4}$ aliphatic, $C_{1-4}$ fluoroaliphatic, or $C_{6-10}$ ar($C_{1-4}$ alkyl), the aryl portion of which is optionally substituted; or two $R^{5+}$ on the same nitrogen atom, taken together with the nitrogen atom form an optionally substituted pyrrolidinyl, piperidinyl, piperazinyl, or morpholinyl ring.

In some embodiments, Cy$_2$ is a radical derived from a ring system selected from benzene, benzimidazole, benzodioxine, benzodioxole, benzoxazole, benzthiazole, cinnoline, cyclohexane, cyclopentane, dihydrobenzofuran, furan, imidazole, imidazolidine, imidazopyridine, indole, indolizine, isoindole, isoquinoline, isothiazole, isoxazole, morpholine, naphthyridine, oxadiazole, oxazole, oxazolopyridine, phthalazine, piperazine, piperidine, pteridine, purine, pyrazine, pyrazole, pyridazine, pyridine, pyrimidine, pyrrole, pyrrolidine, pyrrolopyridine, pyrrolopyrimidine, quinazoline, quinoline, quinoxaline, tetrazole, thiadiazole, thiazole, thiazolopyridine, thiophene, triazine, triazole, triazolopyridine, and triazolopyrimidine, wherein the ring system optionally is substituted on any substitutable ring carbon atom and any substitutable ring nitrogen atom; and one ring nitrogen atom in the ring system optionally is oxidized.

In some embodiments, Cy$_2$ is a radical derived from a ring system selected from benzene, benzodioxine, benzodioxole, benzoxazole, dihydrobenzofuran, furan, morpholine, piperazine, piperidine, pyrazine, pyrazole, pyridine, pyrimidine, pyrrole, pyrrolidine, tetrazole, thiazole, and thiophene, wherein the ring system optionally is substituted on any substitutable ring carbon atom and any substitutable ring nitrogen atom; and one ring nitrogen atom in the ring system optionally is oxidized.

In some embodiments, each substitutable ring nitrogen atom in Cy$_2$ is unsubstituted or is substituted with —C(O)$R^*$, —C(O)N($R^+$)$_2$, —CO$_2$$R^o$, —SO$_2$$R^o$, —SO$_2$N($R^+$)$_2$, $C_{1-4}$ aliphatic, —$R^r$, -T-$R^r$, or -T-$R^s$;

each substitutable saturated ring carbon atom in Cy$_2$ is unsubstituted or is substituted with =O, =S, =C($R^*$)$_2$, or —$R^6$;

each substitutable unsaturated ring carbon atom in Cy$_2$ is unsubstituted or is substituted with $R^6$;

$R^6$ is selected from $C_{1-4}$ aliphatic, $C_{1-4}$ fluoroaliphatic, halo, —$R^r$, —$R^s$, -T-$R^s$, -T-$R^r$, —V-T-$R^s$, —V-T-$R^r$, and —V—$R^r$;

each T independently is a $C_{1-4}$ alkylene chain optionally substituted with one or two substituents independently selected from $C_{1-3}$ aliphatic, $C_{1-3}$ fluoroaliphatic, —F, —OH, —O($C_{1-4}$ alkyl), —CO$_2$H, —CO$_2$($C_{1-4}$ alkyl), —C(O)NH$_2$, and —C(O)NH($C_{1-4}$ alkyl), wherein the alkylene chain optionally is interrupted with —N($R^a$)—, —C(=N$R^a$)—N (R$^a$)—, —C(NR$^a$)=N(R$^a$)—, —N(R$^a$)—C(=NR$^a$)—, —N(R$^a$)—C(O)—, or —C(O)N(R$^a$)—;

V is selected from —C(R$^f$)=C(R$^f$)—, —C≡C—, —O—, —N(R$^a$)—, —N(R$^a$)C(O)—, —C(O)N(R$^a$)—, —C(=NR$^a$)—N(R$^a$)—, —C(NR$^a$)=N(R$^a$)—, and —N(R$^a$)C(=NR$^a$)—;

each R$^r$ independently is selected from an optionally substituted aryl, optionally substituted heteroaryl, optionally substituted heterocyclyl, and optionally substituted cycloaliphatic ring;

each R$^s$ independently is selected from —NO$_2$, —CN, —R*, —C(R*)=C(R*)$_2$, —C≡C—R*, —OR*, —SR*, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —OC(O)N(R$^+$)$_2$, —CO$_2$R*, —C(O)R*, —C(O)N(R$^+$)$_2$, —N(R$^+$)C(=NR$^+$)—N(R$^+$)—C(O)R*, —C(=NR$^+$)—N(R$^+$)$_2$, —N(R$^+$)C(=NR$^+$)—N(R$^+$)$_2$, —NR$^+$SO$_2$R$^o$, and —NR$^+$SO$_2$N(R$^+$)$_2$; wherein R$^o$ is an optionally substituted aliphatic, aryl, or heteroaryl group;

each R* independently is hydrogen or an optionally substituted aliphatic, aryl, heteroaryl, or heterocyclyl group; and each R$^+$ independently is hydrogen or an optionally substituted aliphatic, aryl, heteroaryl, or heterocyclyl group, or two R$^+$ on the same nitrogen atom, taken together with the nitrogen atom, form a 4-8 membered aromatic or non-aromatic ring having, in addition to the nitrogen atom, 0-2 ring heteroatoms selected from N, O, and S.

In some embodiments, the substitutable ring carbon atoms of Cy$_2$ are substituted with 0-2 R$^6$ wherein R$^6$ is selected from halo, C$_{1-4}$ aliphatic, C$_{1-4}$ fluoroaliphatic, —R$^s$, -T-R$^s$, —R$^r$, and -T-R$^r$. In some embodiments, R$^6$ is halo, C$_{1-4}$ aliphatic, C$_{1-4}$ fluoroaliphatic, —R$^s$, wherein R$^s$ is —NO$_2$, —CN, morpholin-4-yl, —OH, —O(C$_{1-4}$ aliphatic), —O(C$_{1-4}$ fluoroaliphatic), —CO$_2$H, —CO$_2$(C$_{1-4}$ aliphatic), —C(O)NH$_2$, —C(O)NH(C$_{1-4}$ aliphatic), or —C(O)N(C$_{1-4}$ aliphatic), or -T-R$^s$ wherein R$^s$ is —OH, —O(C$_{1-4}$ aliphatic), —O(C$_{1-4}$ fluoroaliphatic), —NH$_2$, —NH(C$_{1-4}$ aliphatic), or —N(C$_{1-4}$ aliphatic)$_2$.

Specific examples of compounds of formula (I) are shown below in Table 1.

TABLE 1

Raf Kinase Inhibitors

I-1

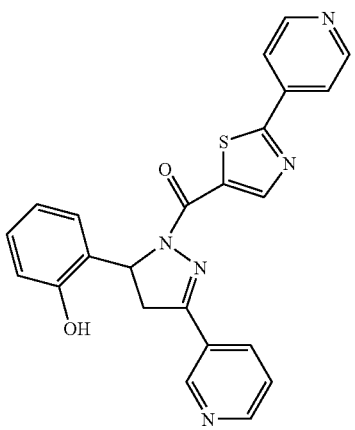

TABLE 1-continued

Raf Kinase Inhibitors

I-2

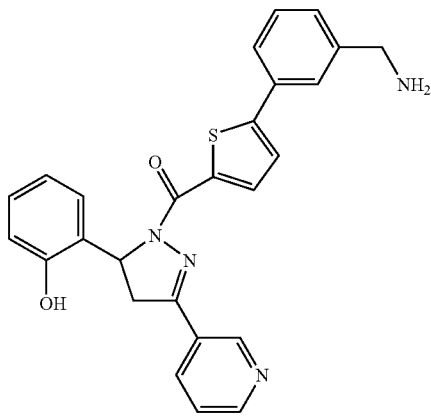

I-3

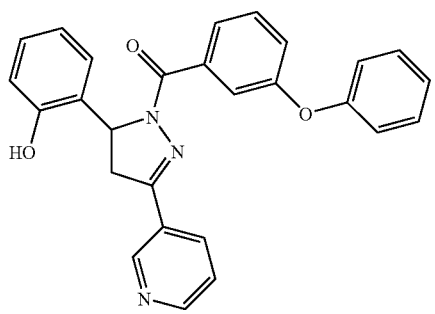

I-4

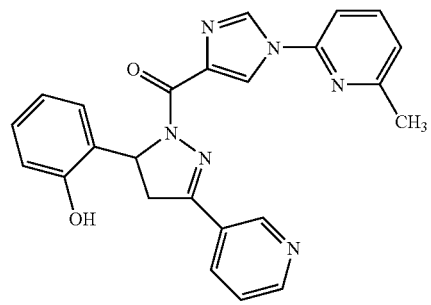

I-5

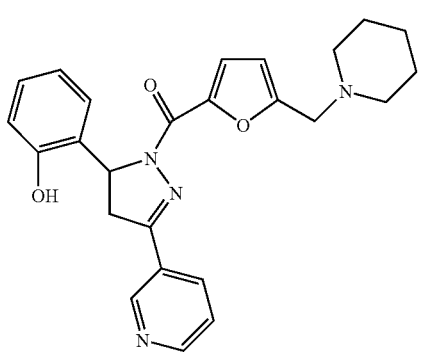

TABLE 1-continued
Raf Kinase Inhibitors
I-6
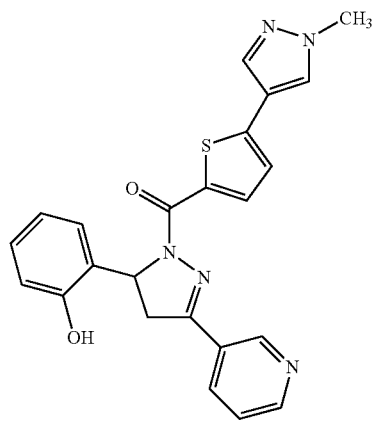
I-7
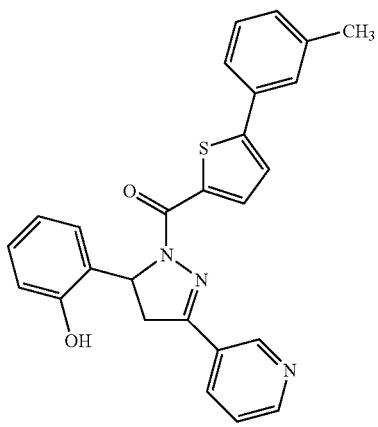
I-8
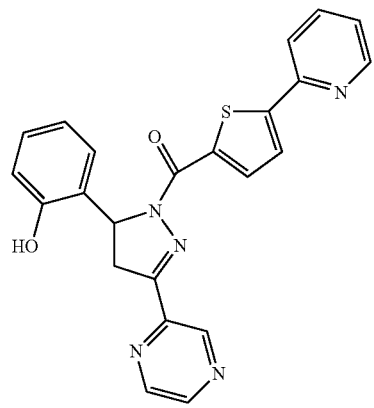
TABLE 1-continued
Raf Kinase Inhibitors
I-9
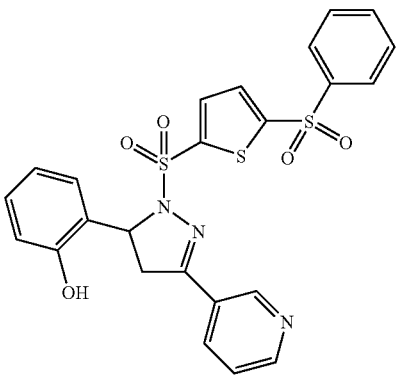
I-10
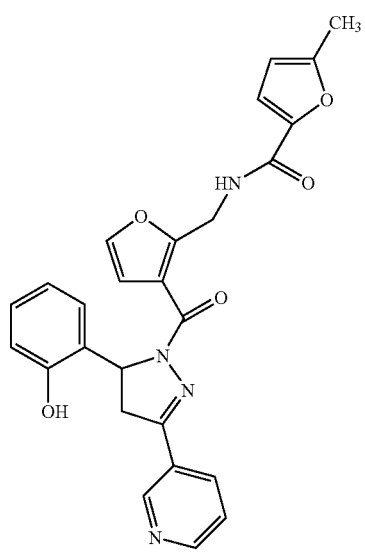
I-11
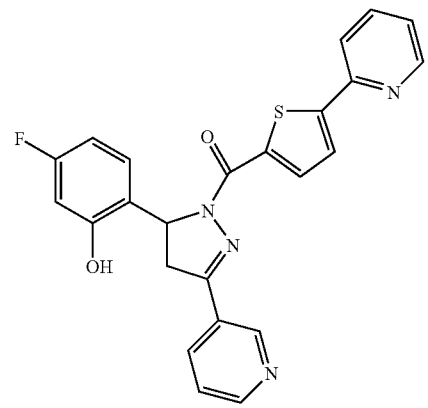

TABLE 1-continued
Raf Kinase Inhibitors
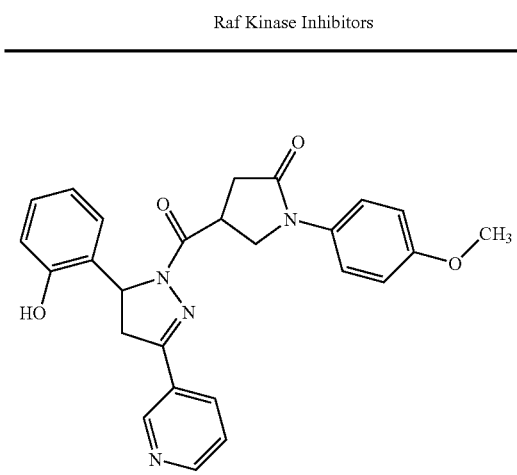
I-12
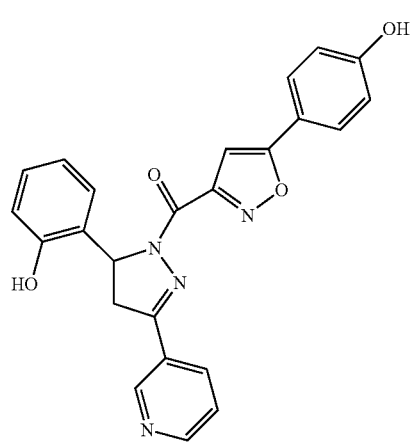
I-13
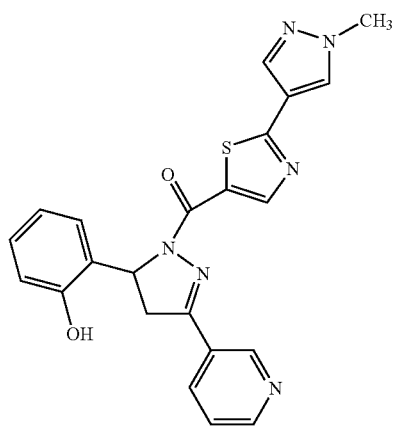
I-14
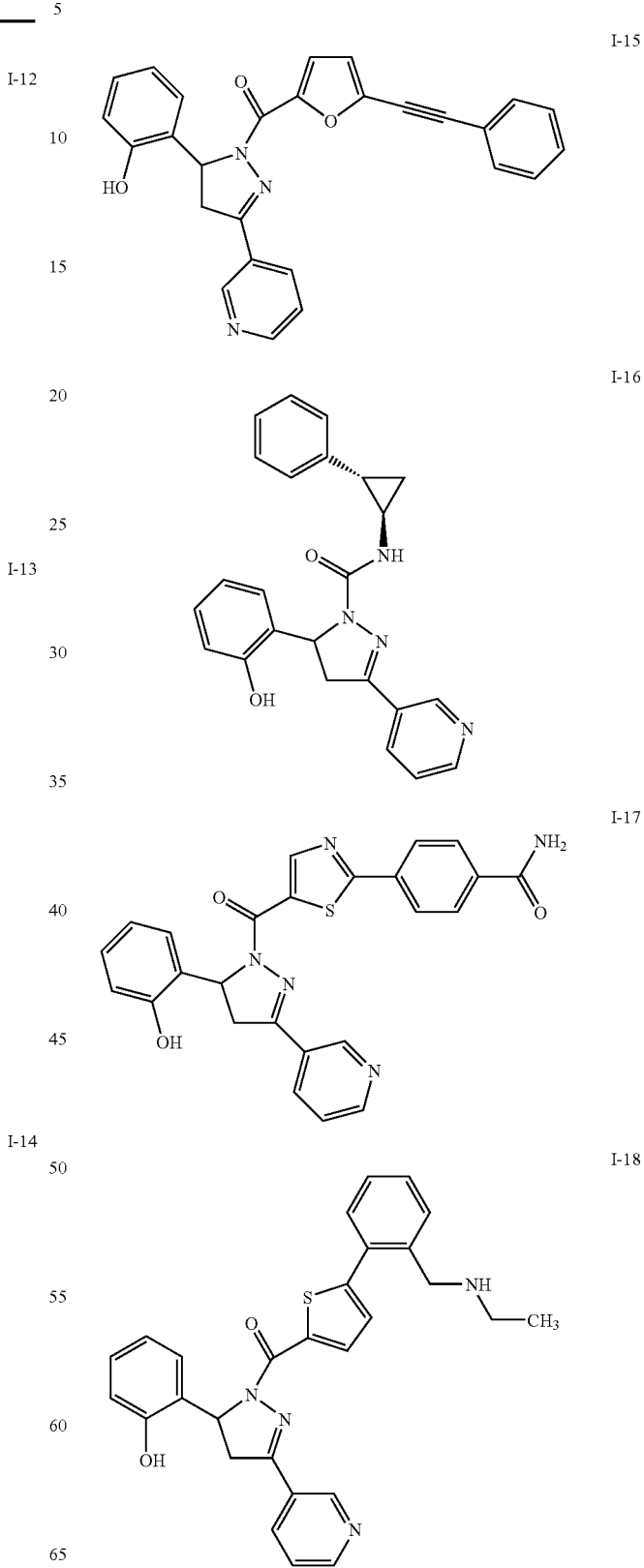

TABLE 1-continued
Raf Kinase Inhibitors
I-19
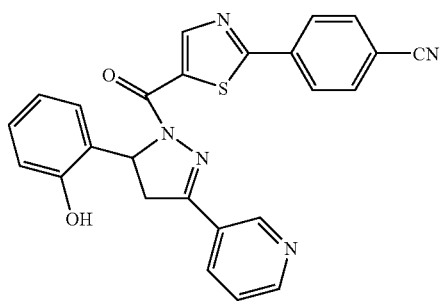
I-20
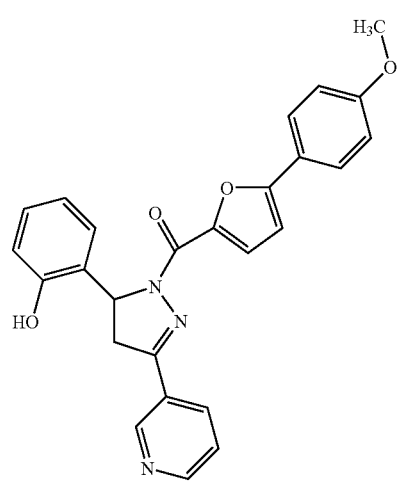
I-21
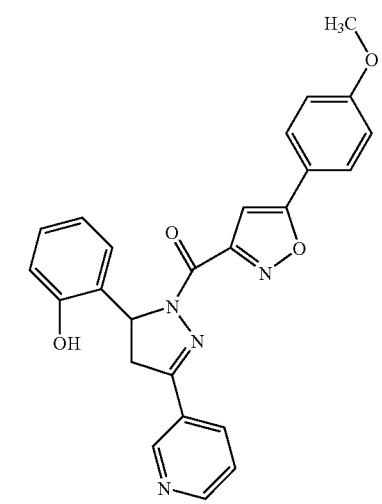
TABLE 1-continued
Raf Kinase Inhibitors
I-22
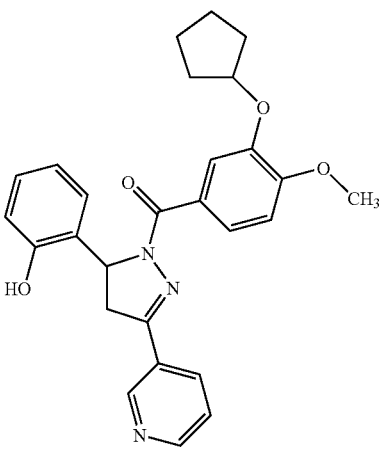
I-23
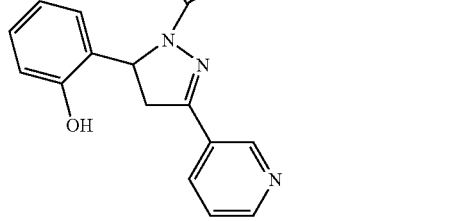
I-24
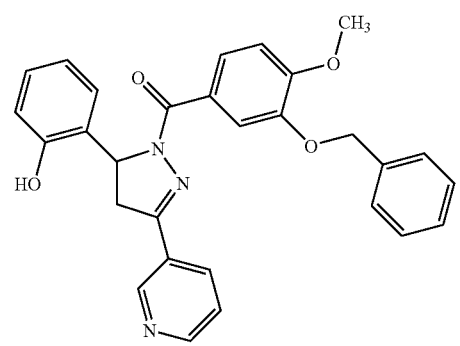

TABLE 1-continued
Raf Kinase Inhibitors
I-25
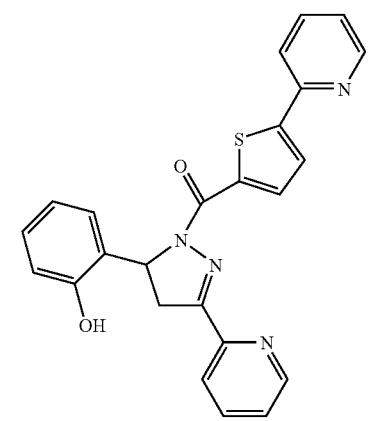
I-26
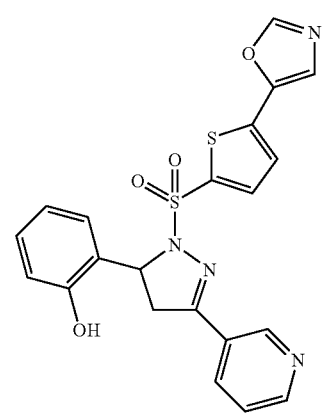
I-27
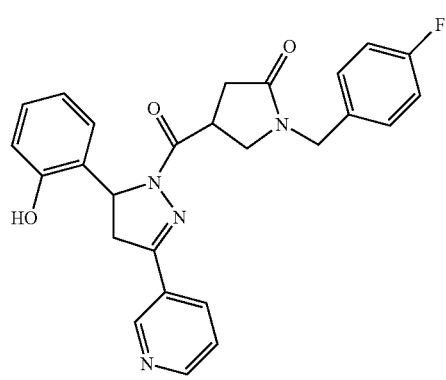
TABLE 1-continued
Raf Kinase Inhibitors
I-28
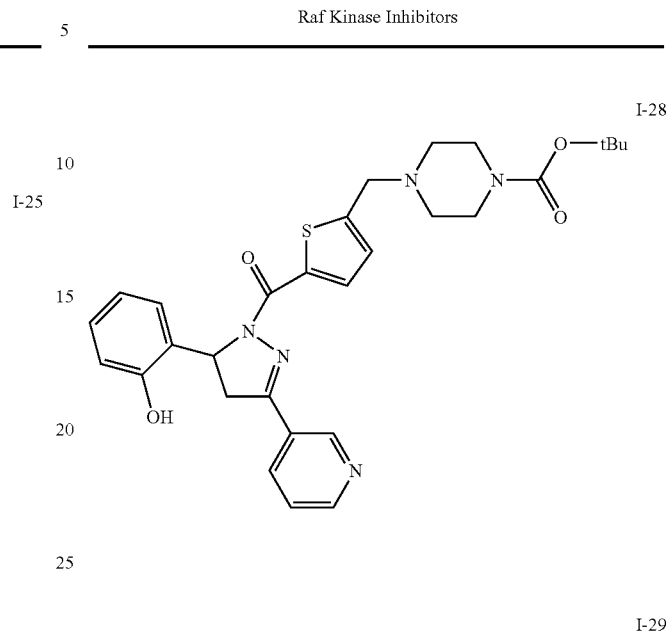
I-29
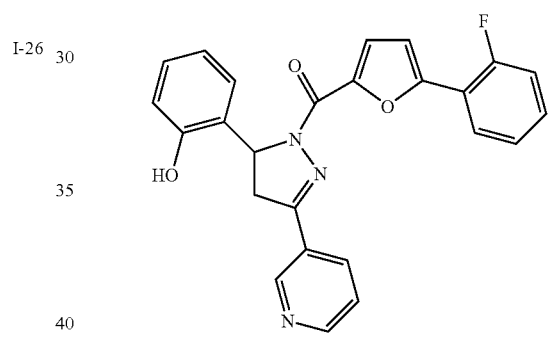
I-30
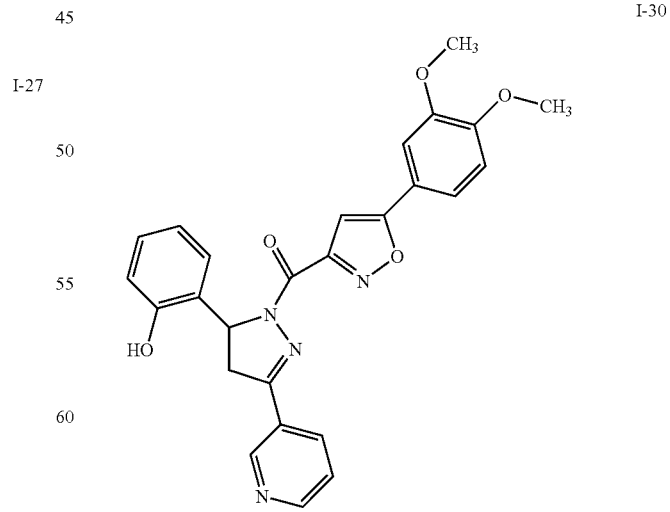

TABLE 1-continued
Raf Kinase Inhibitors
I-31
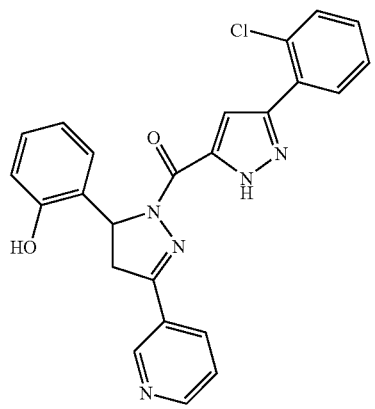
I-32
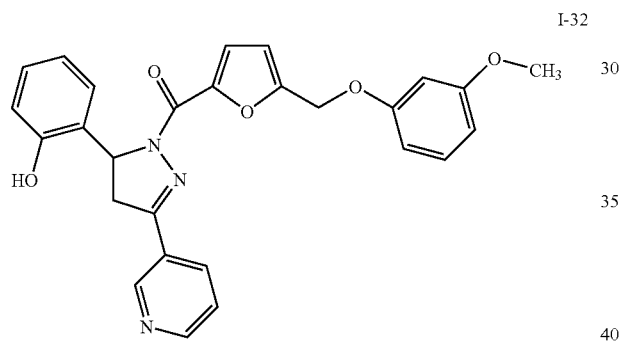
I-33
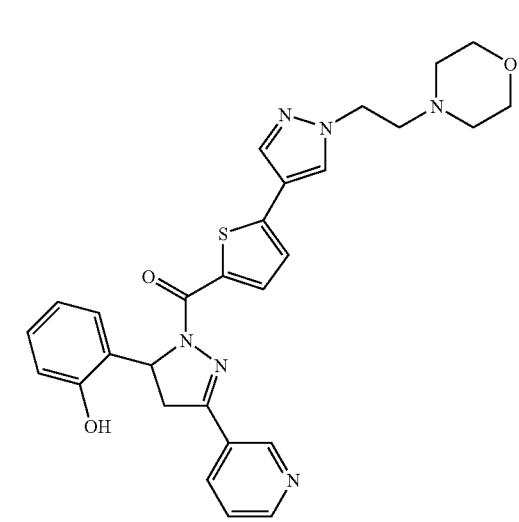
TABLE 1-continued
Raf Kinase Inhibitors
I-34
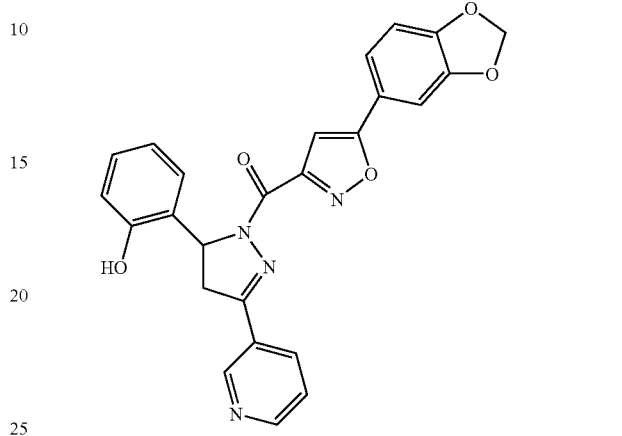
I-35
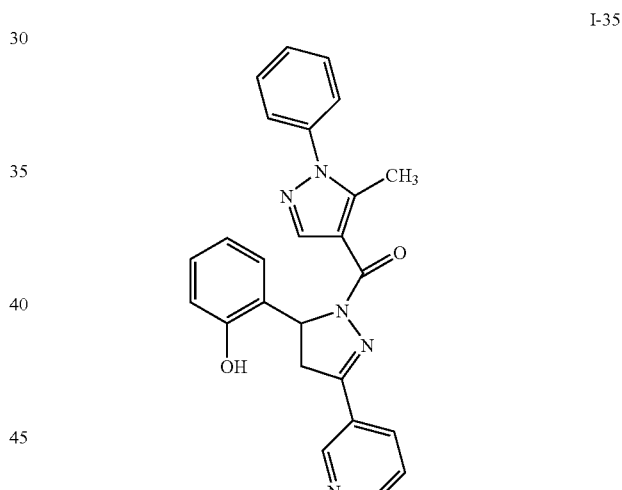
I-36
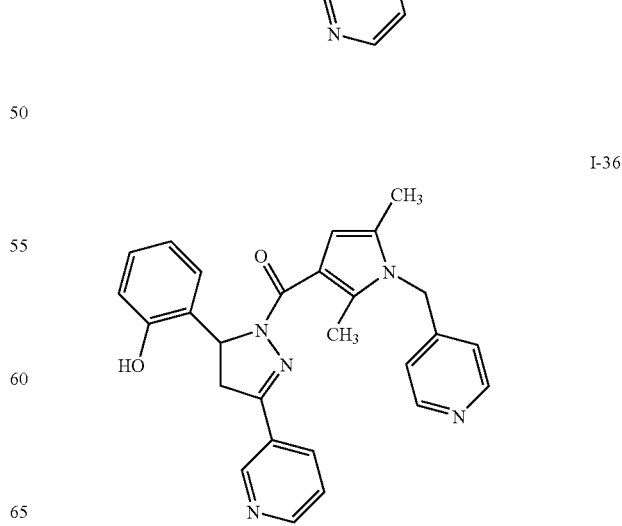

TABLE 1-continued

Raf Kinase Inhibitors

I-37

I-39

I-40

I-41

I-42

I-43

I-44

TABLE 1-continued
Raf Kinase Inhibitors
I-45
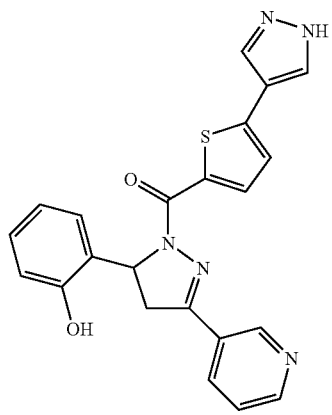
I-46
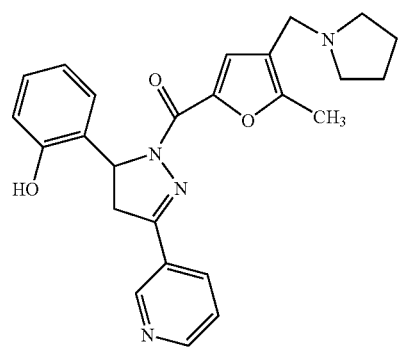
I-47
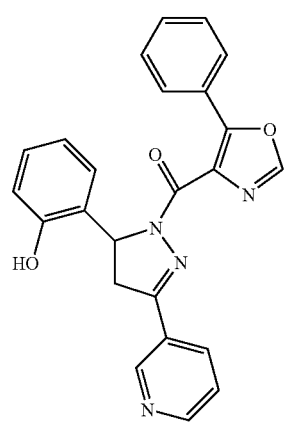
TABLE 1-continued
Raf Kinase Inhibitors
I-48
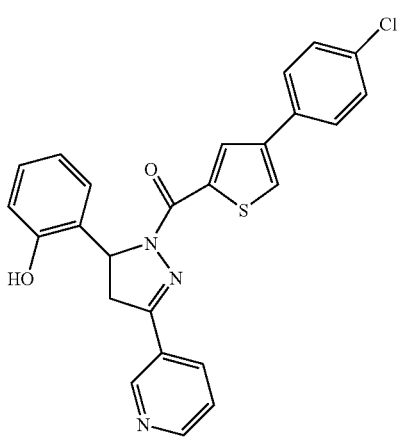
I-49
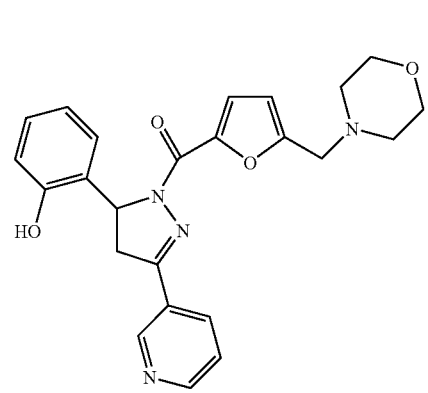
I-50
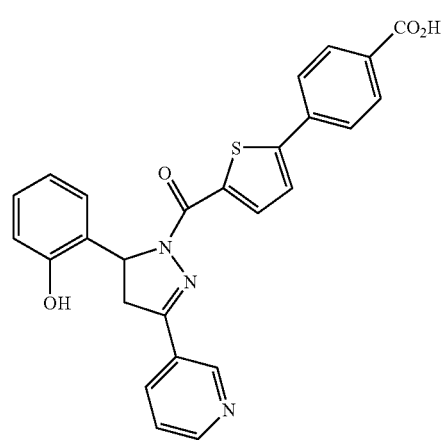

TABLE 1-continued
Raf Kinase Inhibitors
I-51
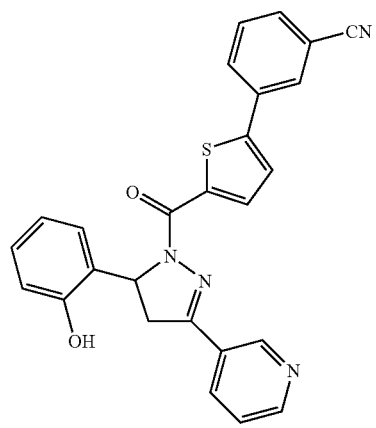
I-52
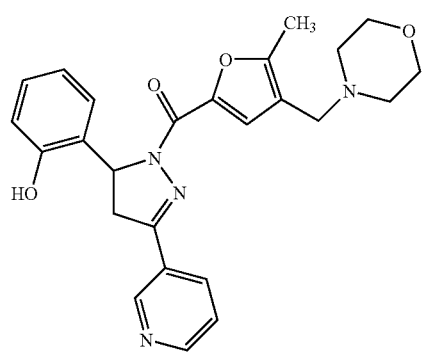
I-53
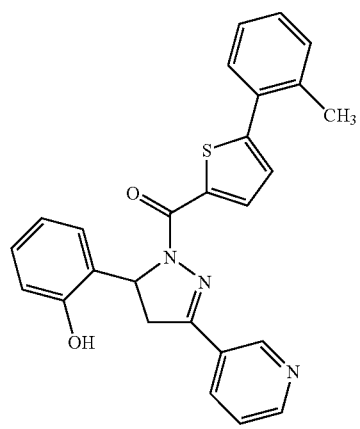
TABLE 1-continued
Raf Kinase Inhibitors
I-54
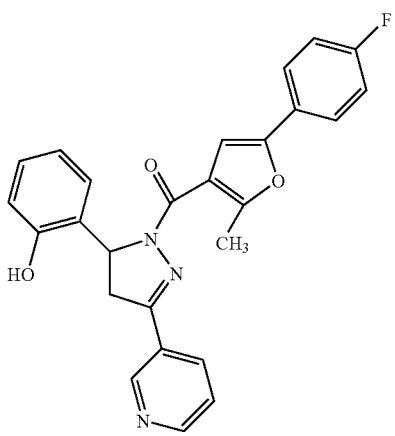
I-56
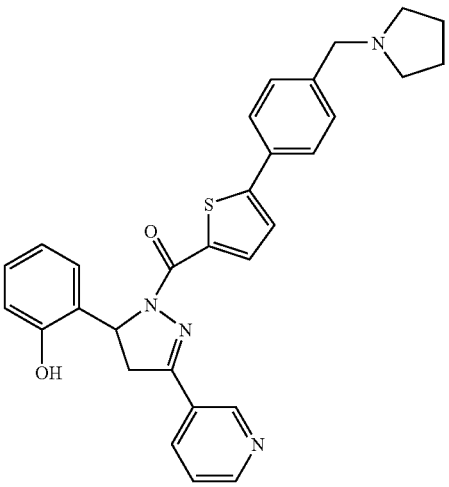
I-57
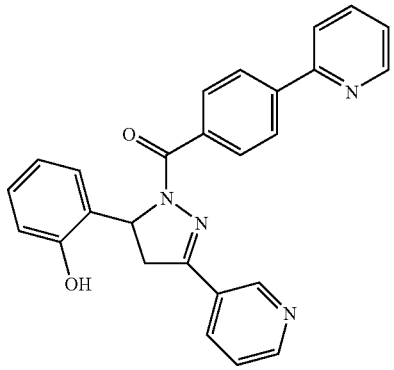

TABLE 1-continued
Raf Kinase Inhibitors
I-58
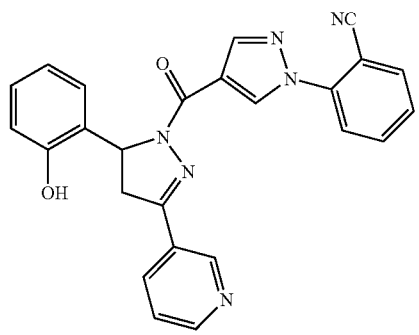
I-59
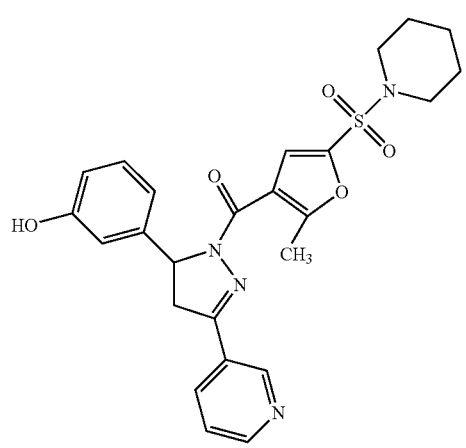
I-60
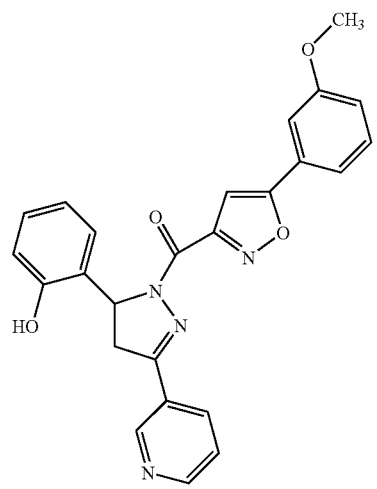
TABLE 1-continued
Raf Kinase Inhibitors
I-61
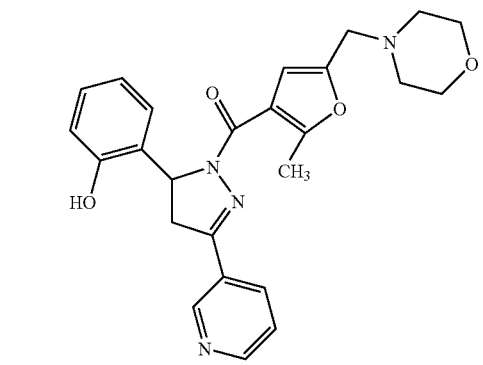
I-62
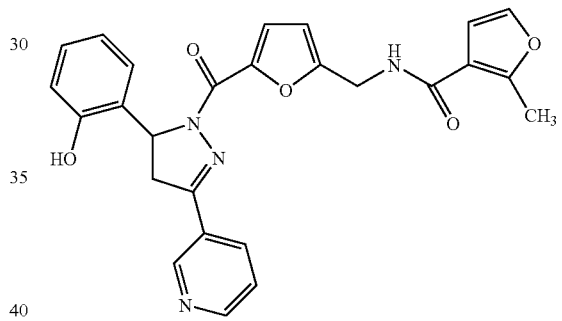
I-63
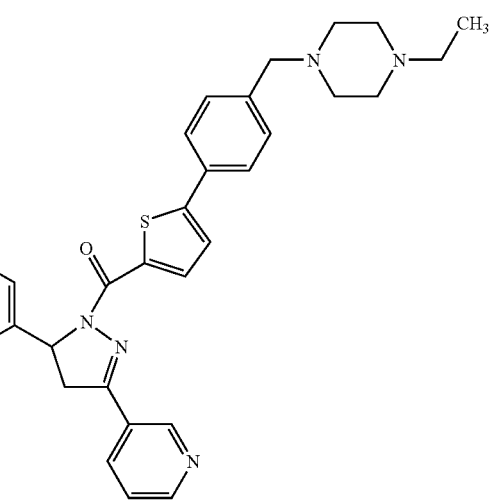

TABLE 1-continued
Raf Kinase Inhibitors
I-64
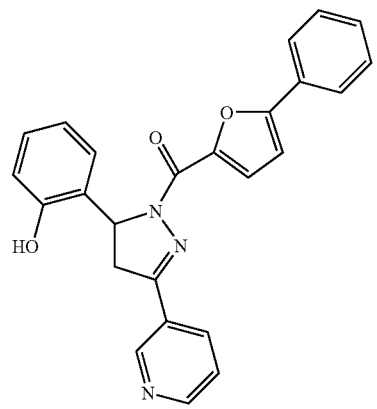
I-65
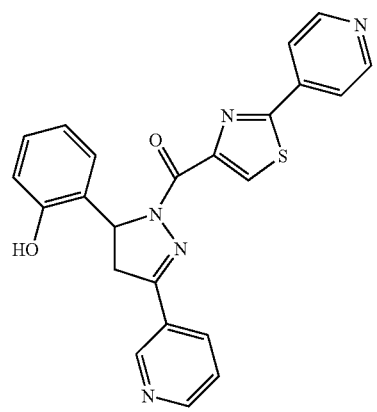
I-66
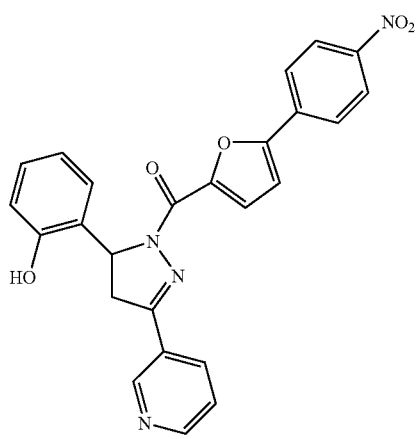
TABLE 1-continued
Raf Kinase Inhibitors
I-67
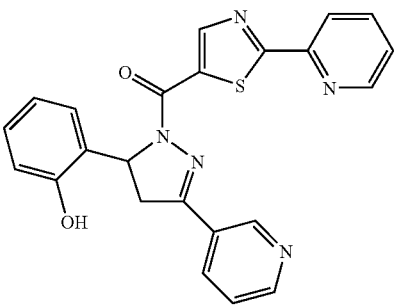
I-68
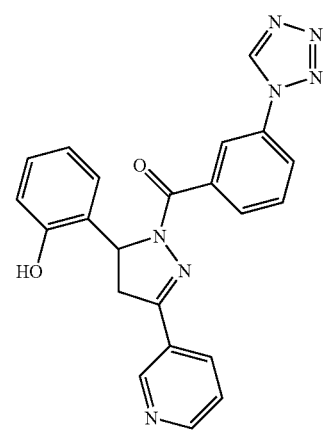
I-69
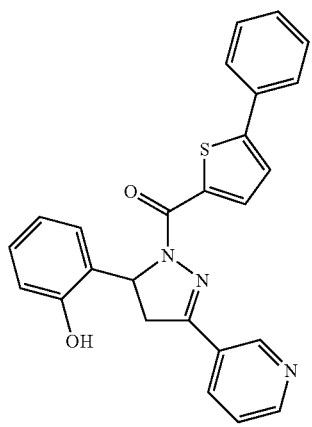

TABLE 1-continued
Raf Kinase Inhibitors
I-70
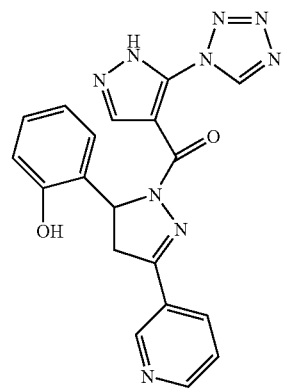
I-71
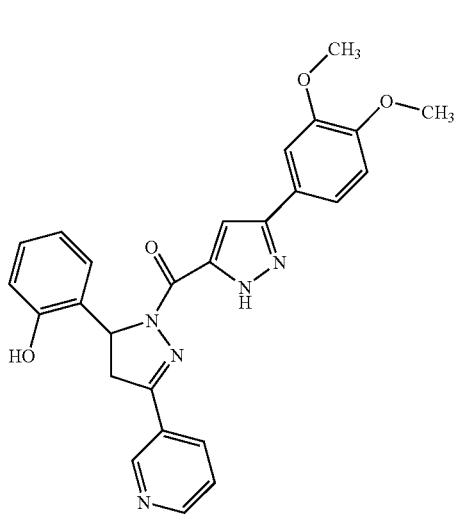
I-72
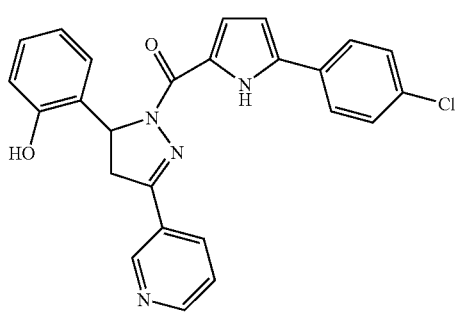
TABLE 1-continued
Raf Kinase Inhibitors
I-73
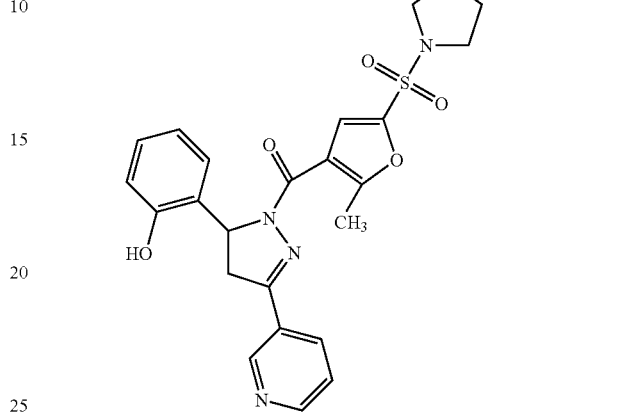
I-74
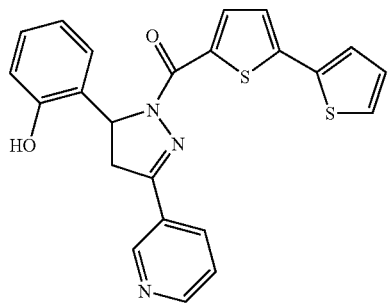
I-75
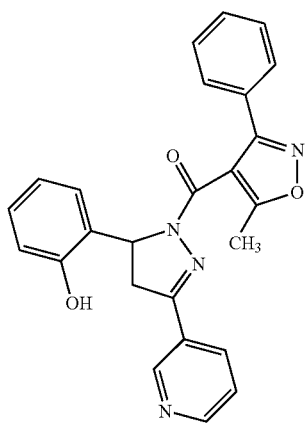

TABLE 1-continued
Raf Kinase Inhibitors
I-76
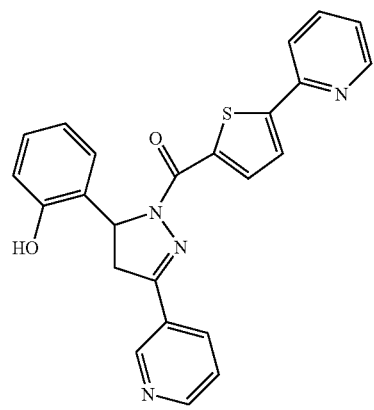
I-77
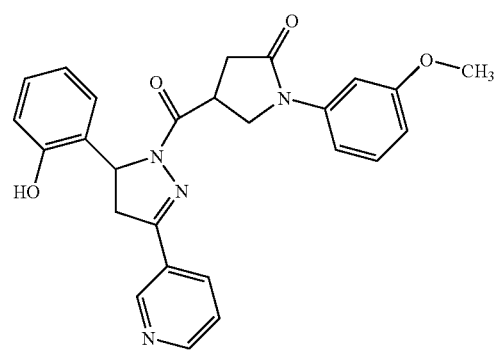
I-78
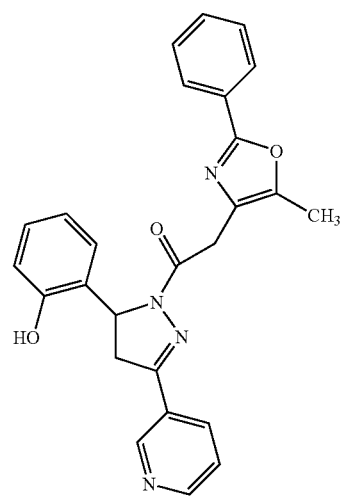
TABLE 1-continued
Raf Kinase Inhibitors
I-79
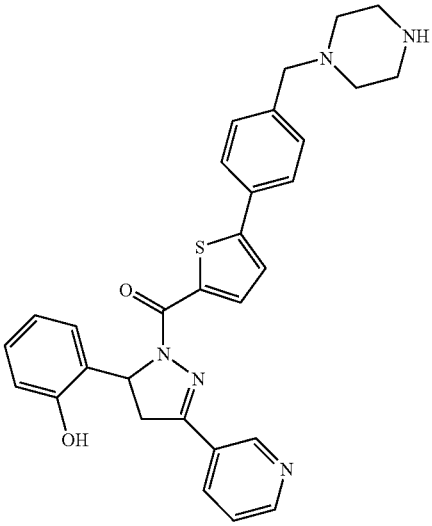
I-80
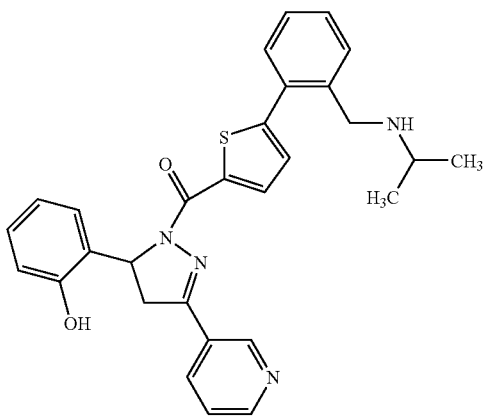
I-81
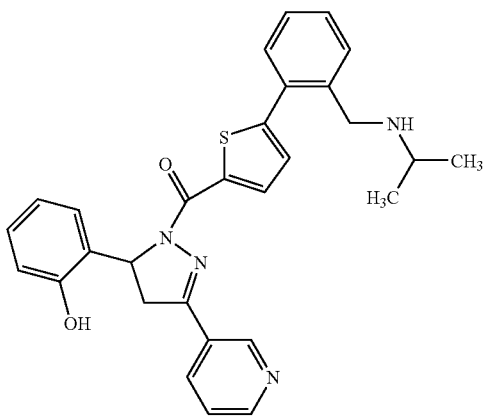

TABLE 1-continued
Raf Kinase Inhibitors
I-82
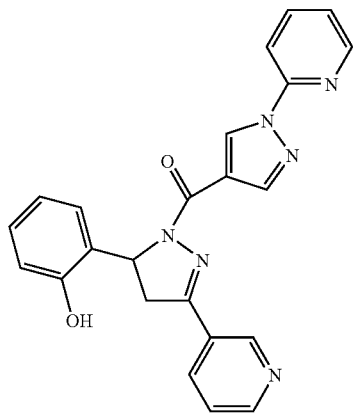
I-83
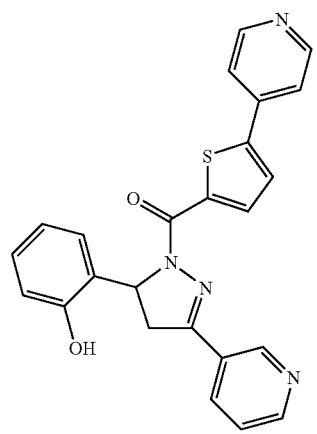
I-84
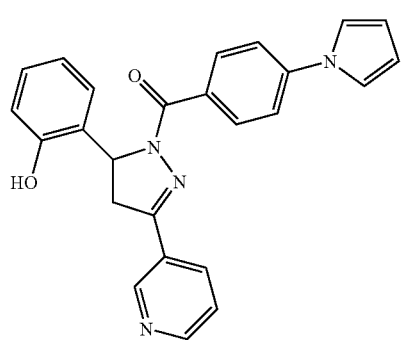
TABLE 1-continued
Raf Kinase Inhibitors
I-85
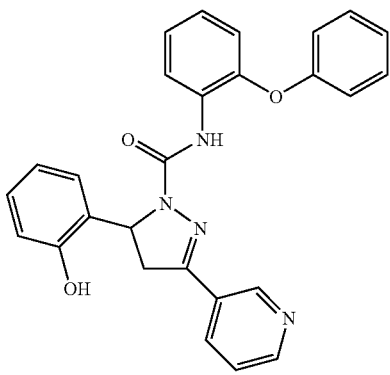
I-86
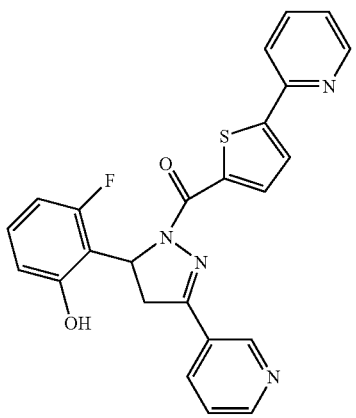
I-87
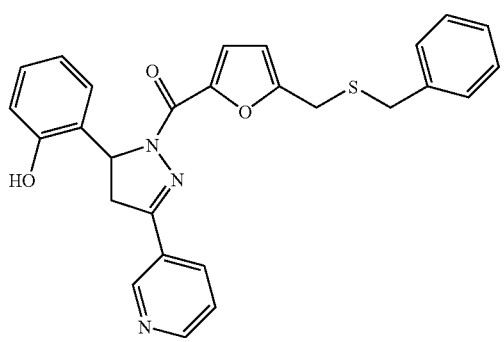

TABLE 1-continued
Raf Kinase Inhibitors
I-88
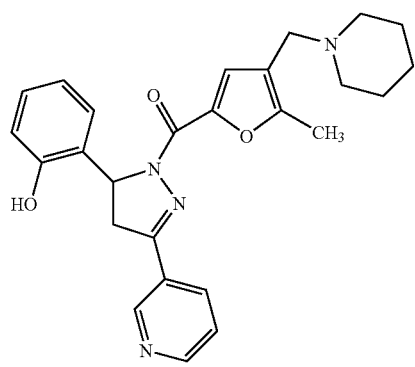
I-89
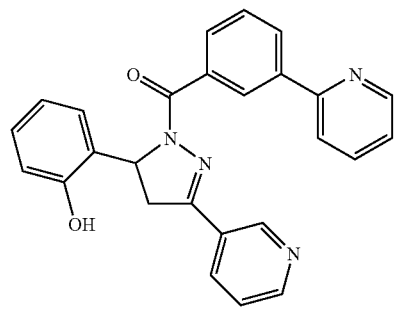
I-90
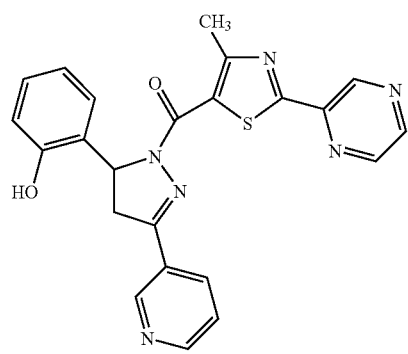
I-91
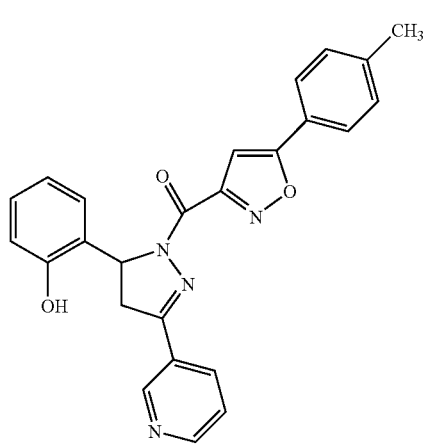
TABLE 1-continued
Raf Kinase Inhibitors
I-92
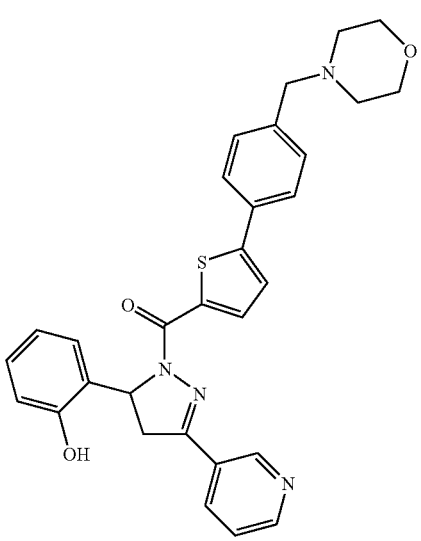
I-93
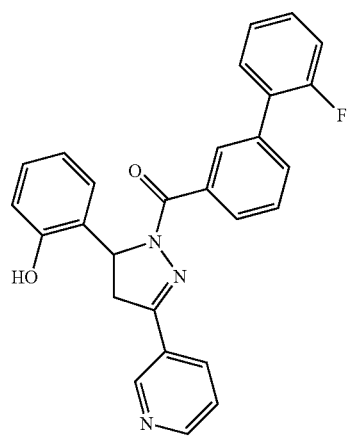
I-94
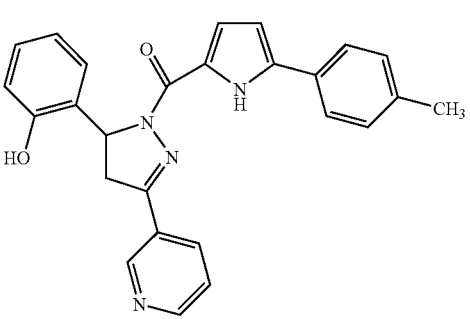

TABLE 1-continued
Raf Kinase Inhibitors
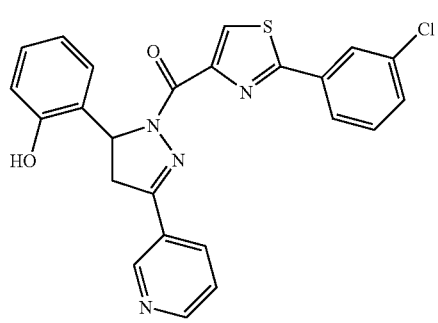
I-95
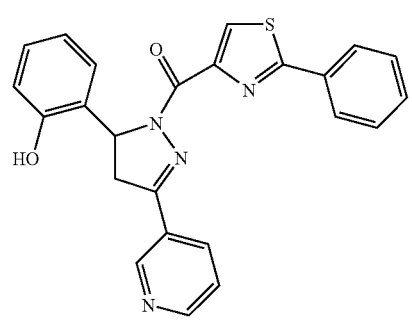
I-96
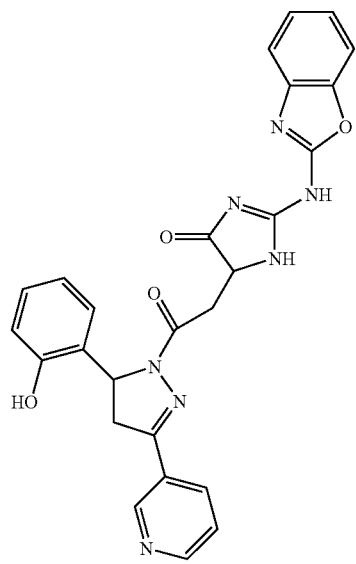
I-97
TABLE 1-continued
Raf Kinase Inhibitors
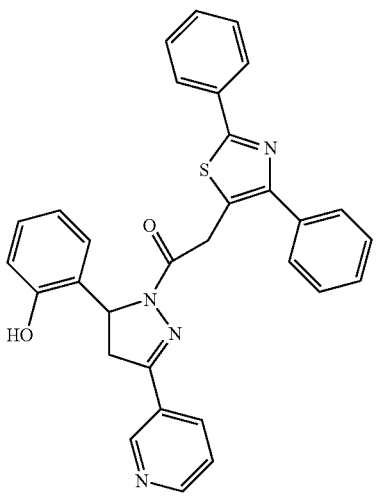
I-98
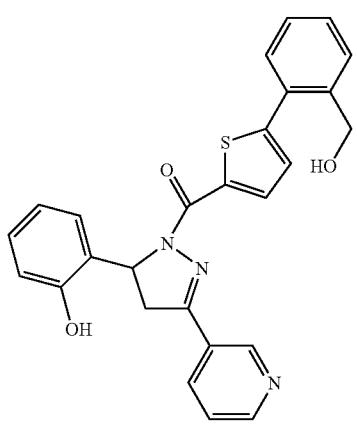
I-99
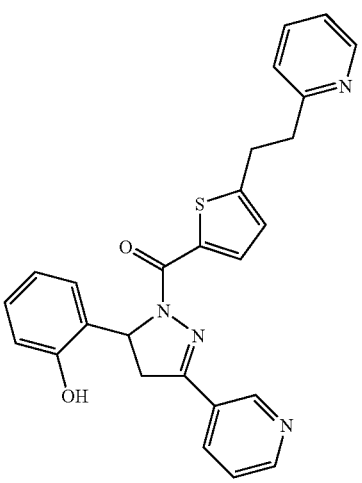
I-100

TABLE 1-continued
Raf Kinase Inhibitors
I-101
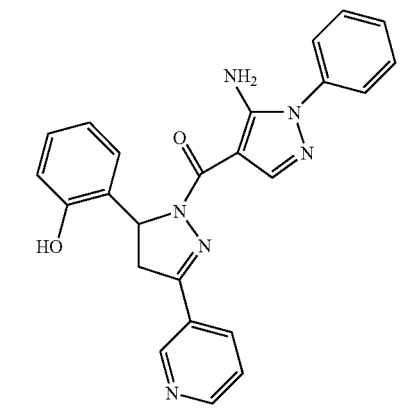
I-102
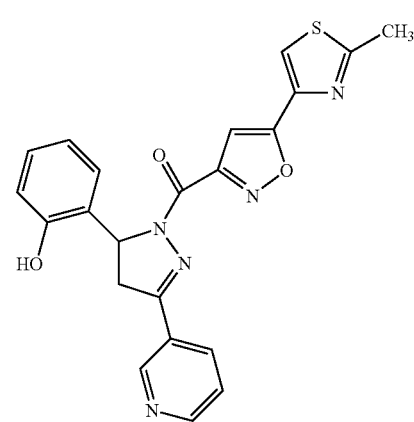
I-103
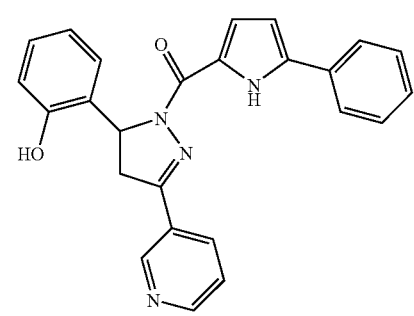
I-104
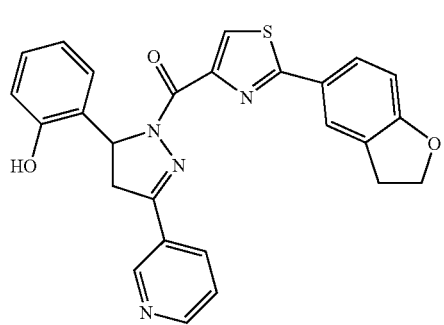
TABLE 1-continued
Raf Kinase Inhibitors
I-105
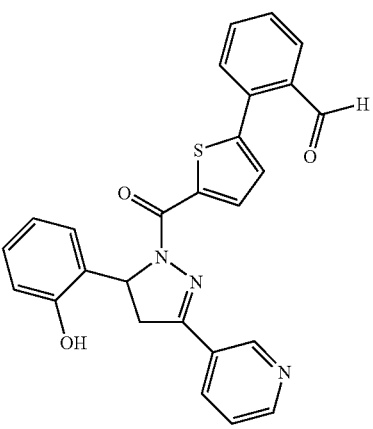
I-106
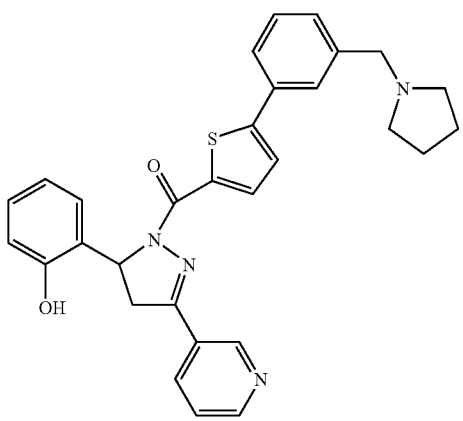
I-107
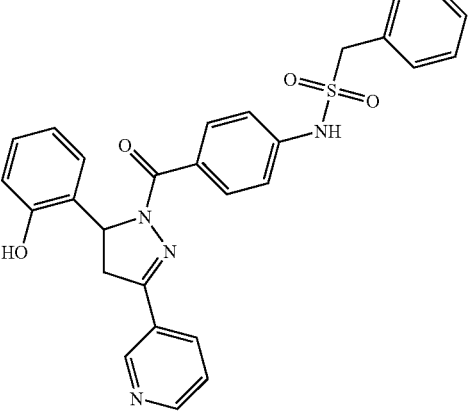

TABLE 1-continued
Raf Kinase Inhibitors
I-108
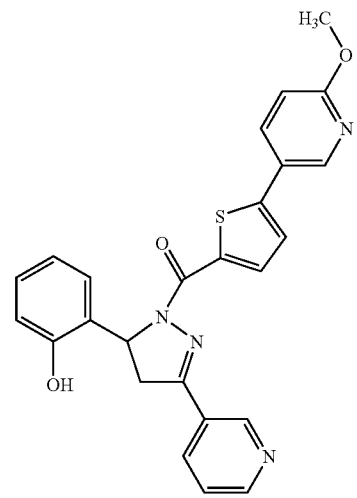
I-109
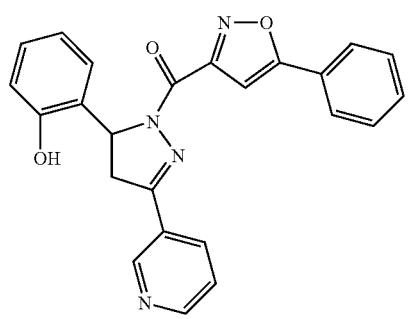
I-110
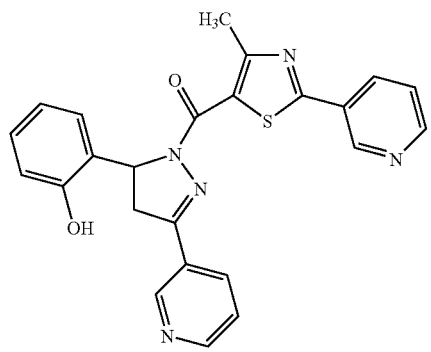
TABLE 1-continued
Raf Kinase Inhibitors
I-111
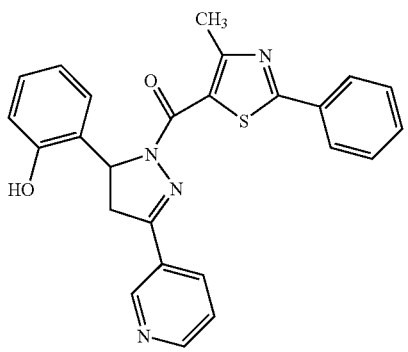
I-112
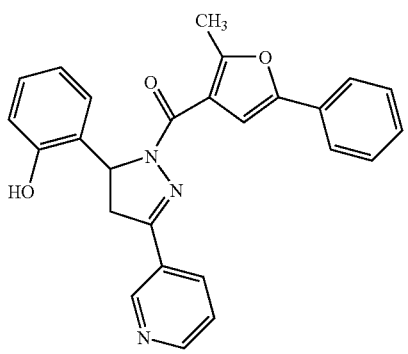
I-113
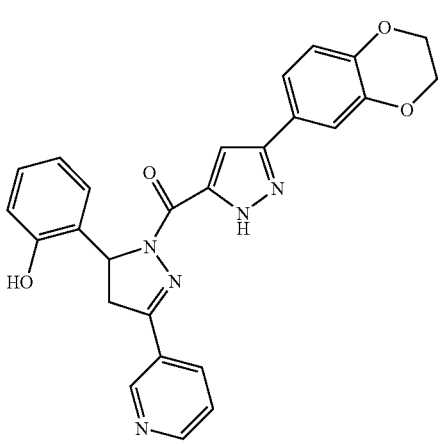

TABLE 1-continued
Raf Kinase Inhibitors
I-114
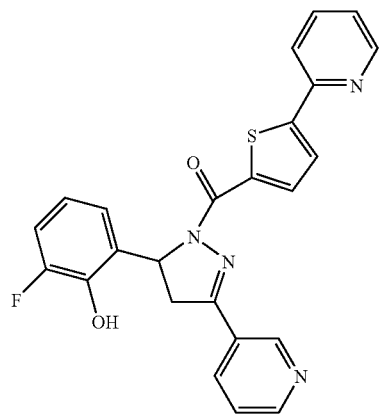
I-115
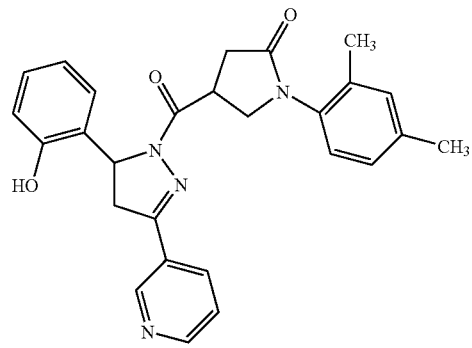
I-116
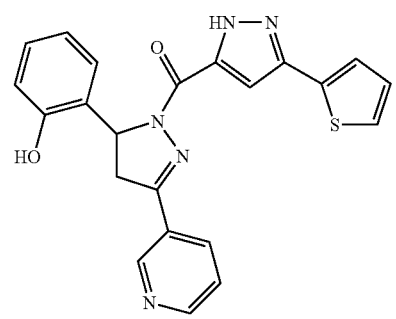
TABLE 1-continued
Raf Kinase Inhibitors
I-117
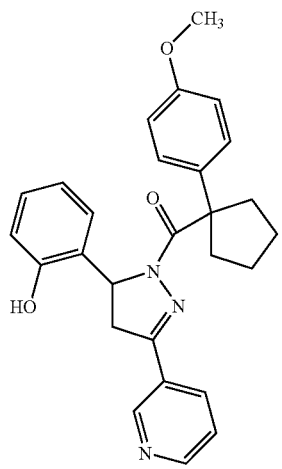
I-118
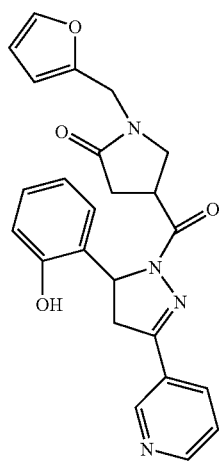
I-119
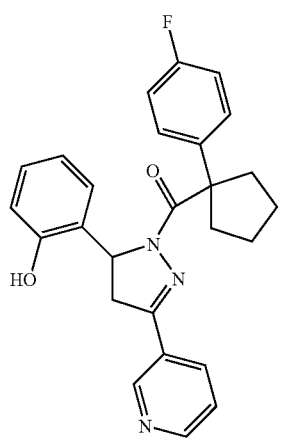

TABLE 1-continued
Raf Kinase Inhibitors
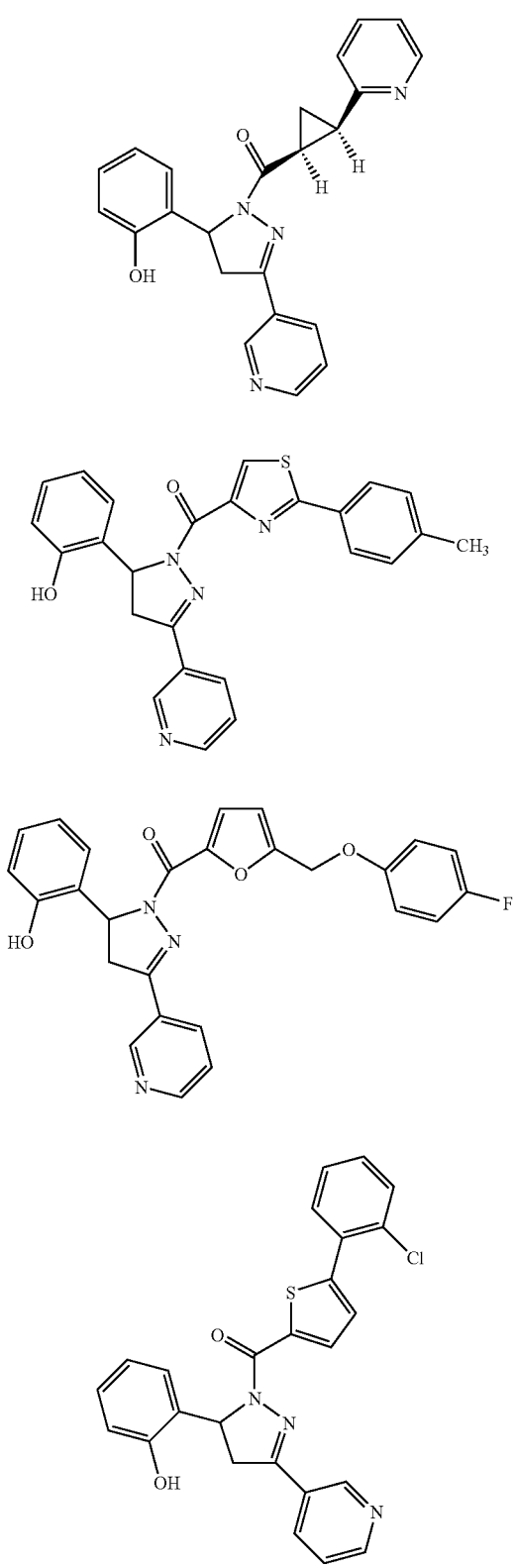
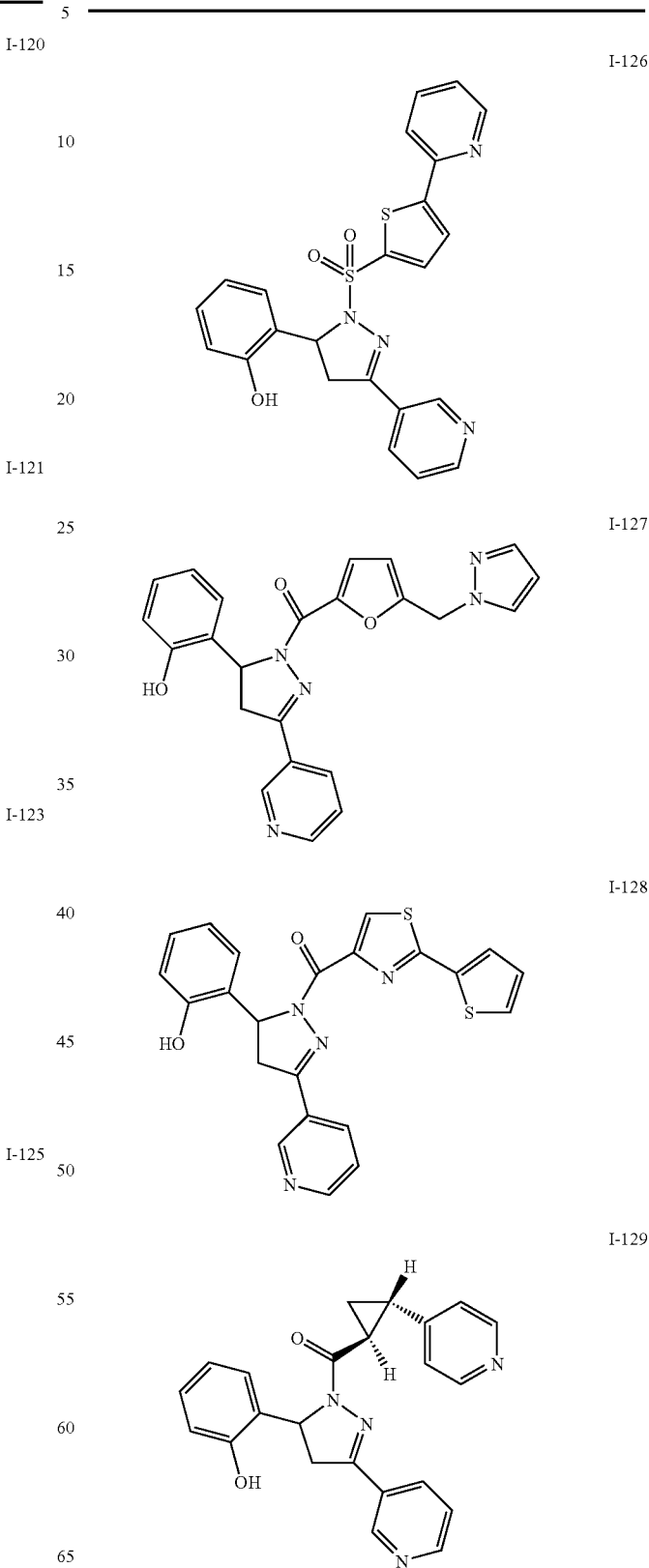

TABLE 1-continued
Raf Kinase Inhibitors
I-130
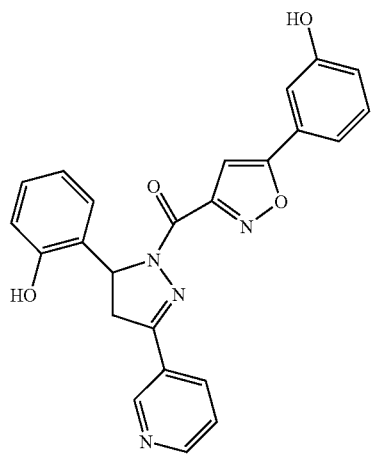
I-132
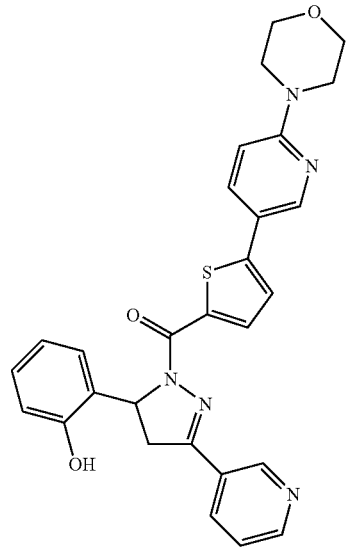
I-133
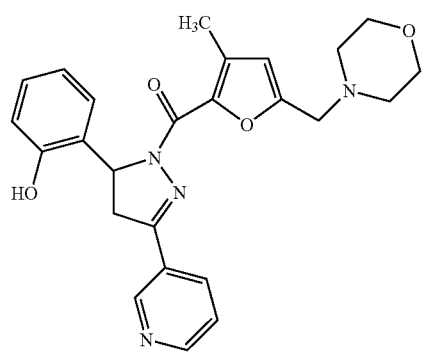
TABLE 1-continued
Raf Kinase Inhibitors
I-134
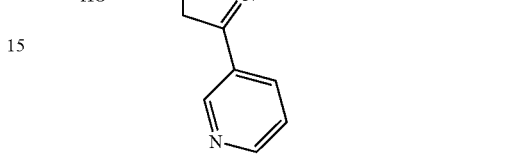
I-135
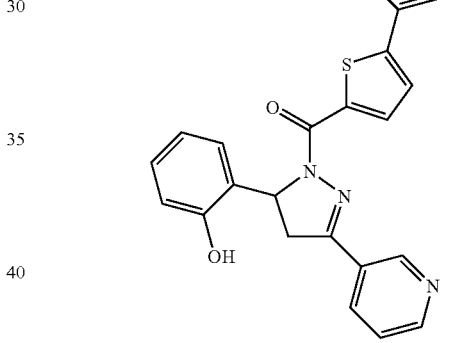
I-136
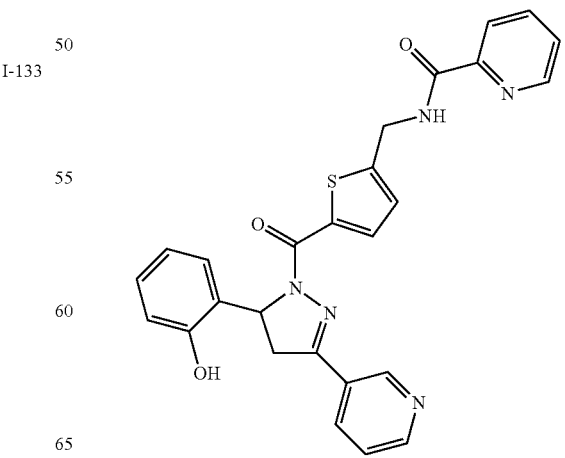

TABLE 1-continued
Raf Kinase Inhibitors
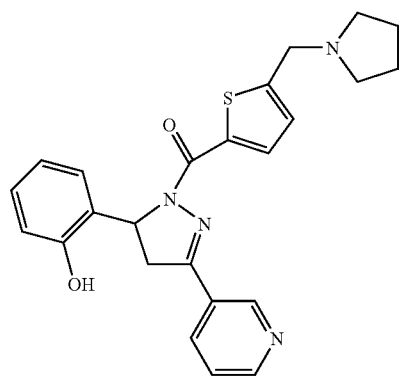
I-137
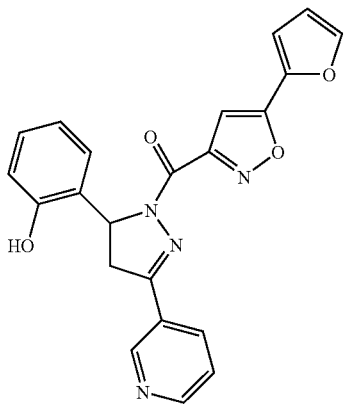
I-140
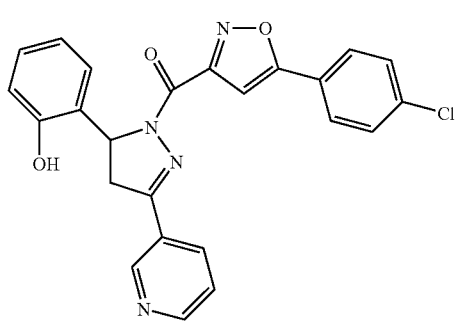
I-138
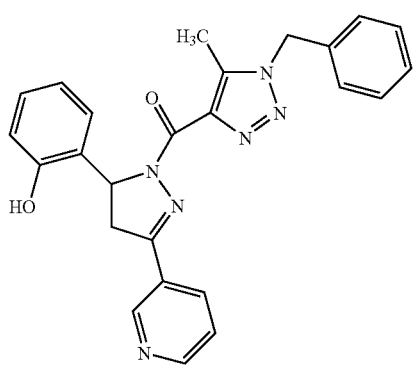
I-142
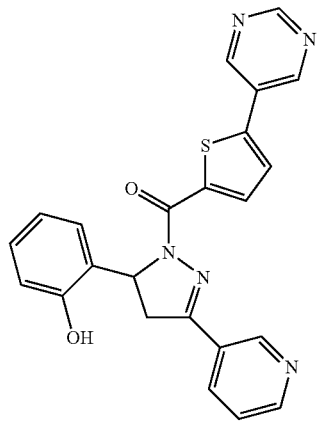
I-139
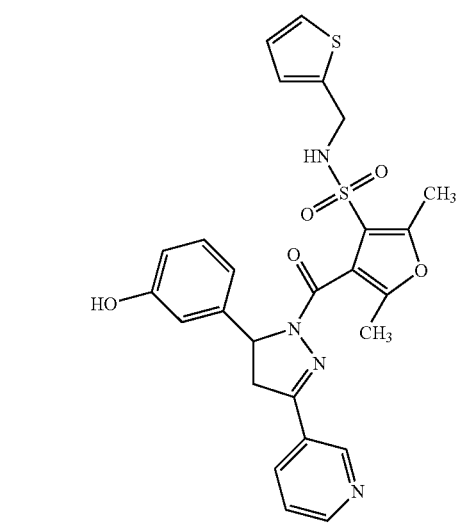
I-143

TABLE 1-continued
Raf Kinase Inhibitors
I-144
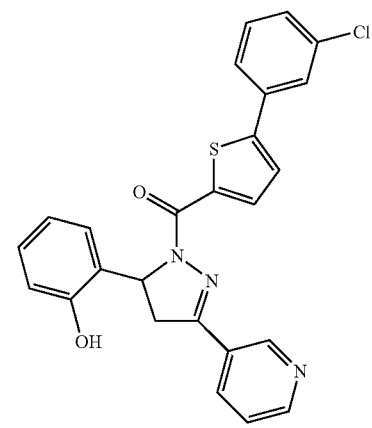
I-145
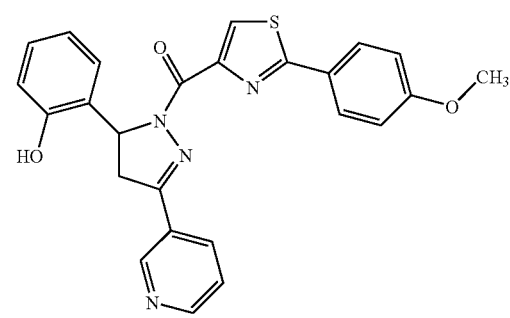
I-146
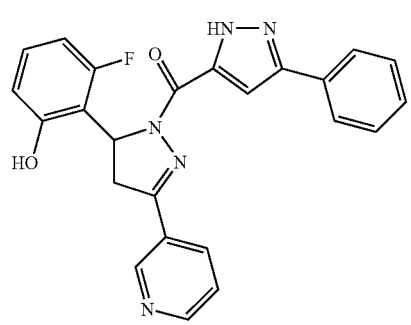
I-147
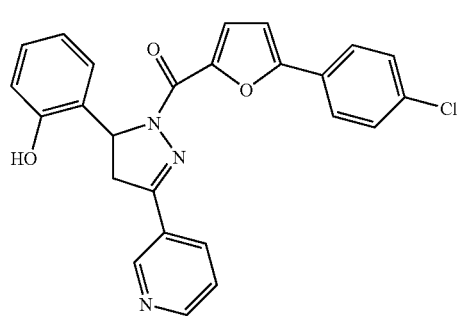
TABLE 1-continued
Raf Kinase Inhibitors
I-148
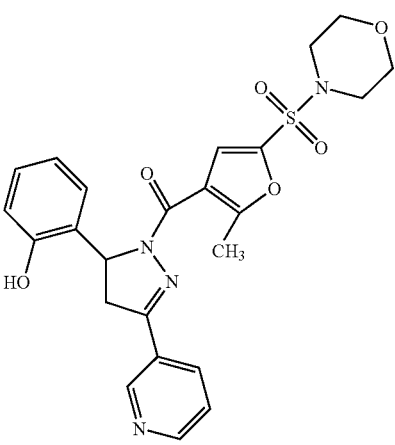
I-149
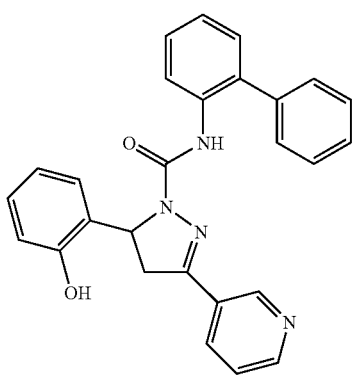
I-150
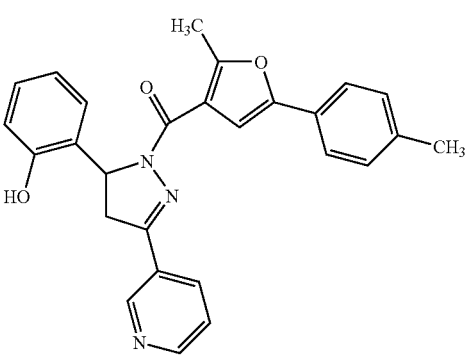

TABLE 1-continued
Raf Kinase Inhibitors
I-151
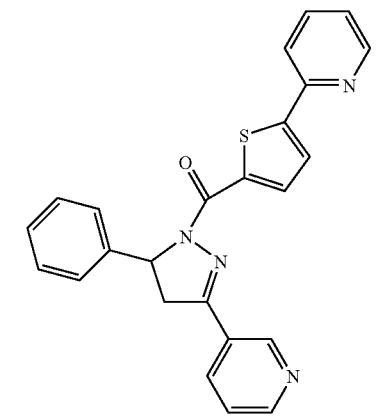
I-152
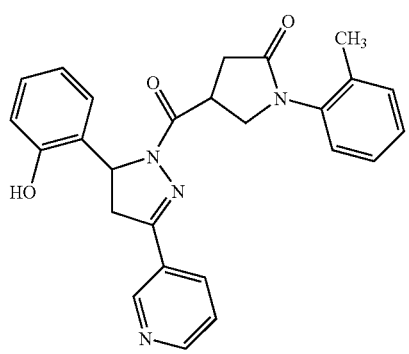
I-153
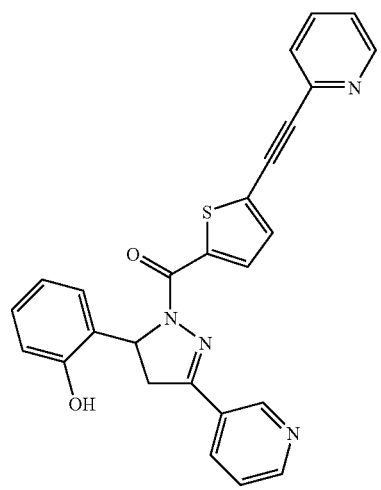
TABLE 1-continued
Raf Kinase Inhibitors
I-154
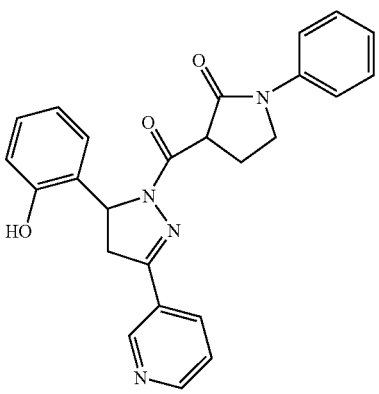
I-155
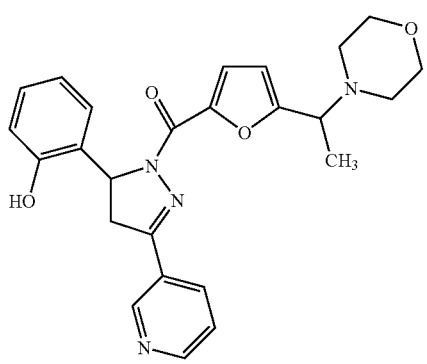
I-156
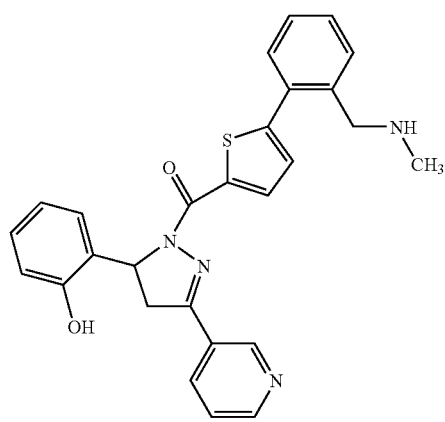
I-158
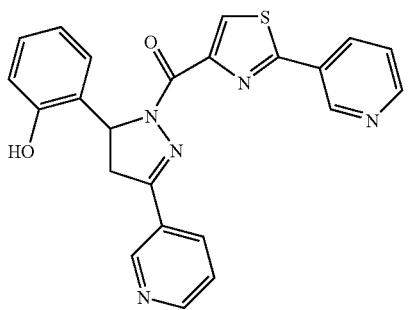

TABLE 1-continued
Raf Kinase Inhibitors
I-160
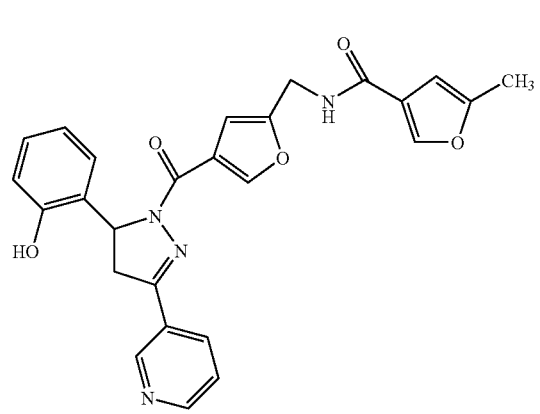
I-161
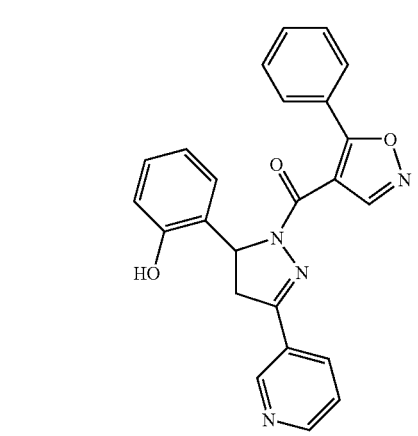
I-162
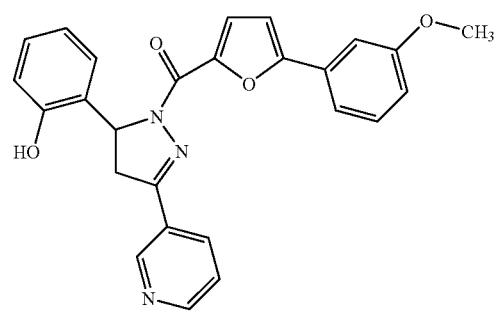
TABLE 1-continued
Raf Kinase Inhibitors
I-163
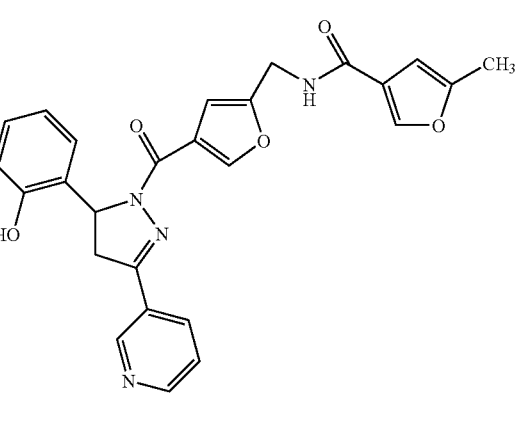
I-164
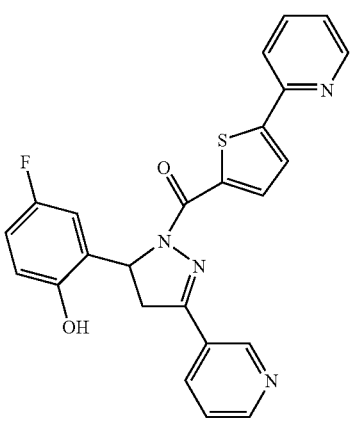
I-165
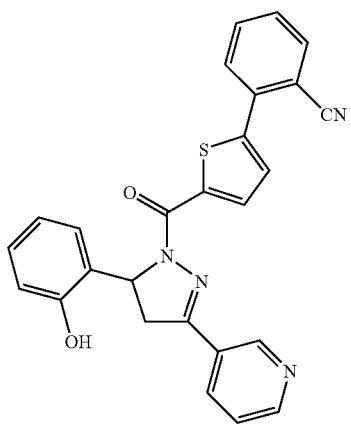

TABLE 1-continued
Raf Kinase Inhibitors
I-166
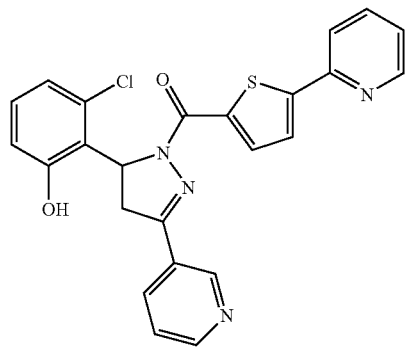
I-167
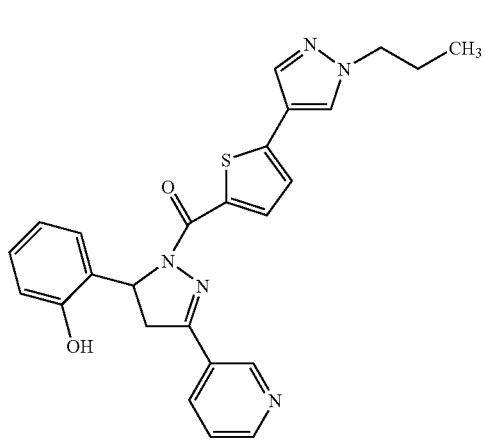
I-168
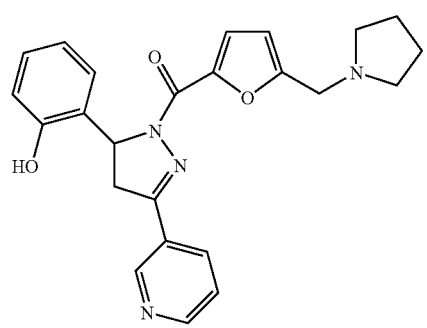
TABLE 1-continued
Raf Kinase Inhibitors
I-169
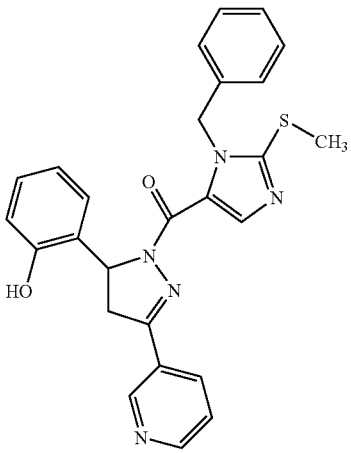
I-170
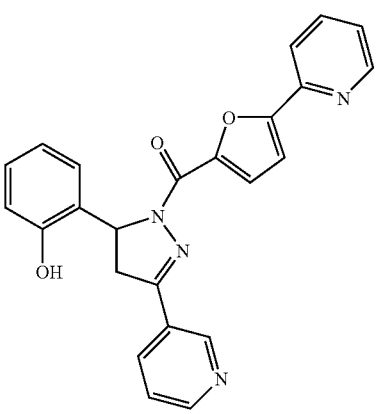
I-171
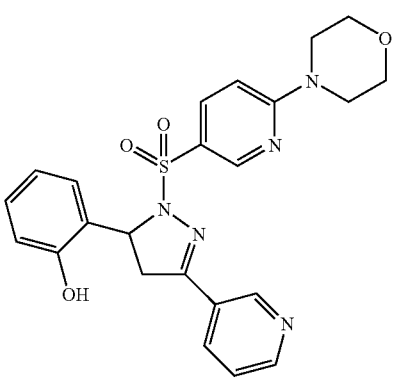

TABLE 1-continued
Raf Kinase Inhibitors
I-172
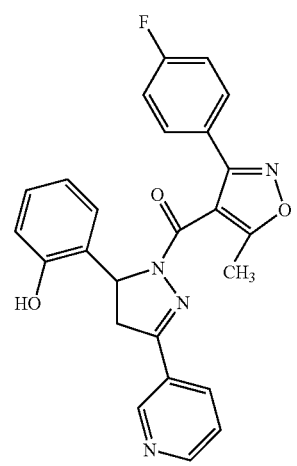
I-173
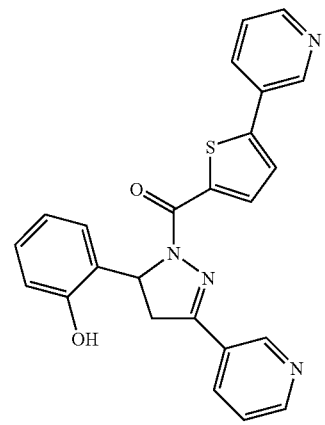
I-174
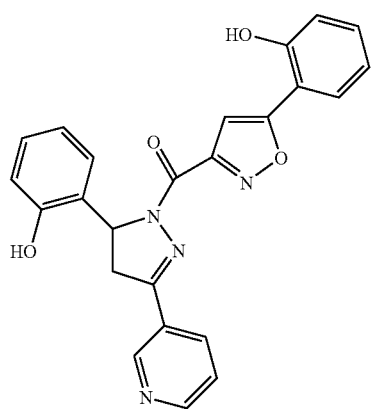
TABLE 1-continued
Raf Kinase Inhibitors
I-175
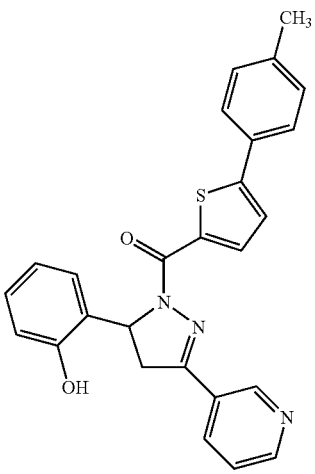
I-176
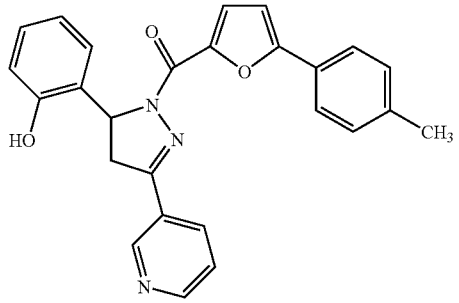
I-177
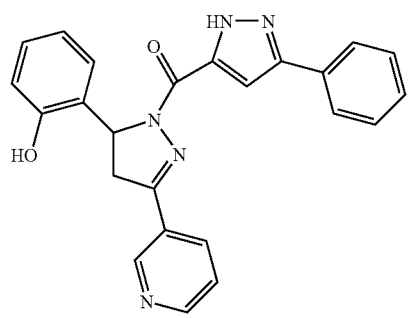
I-178
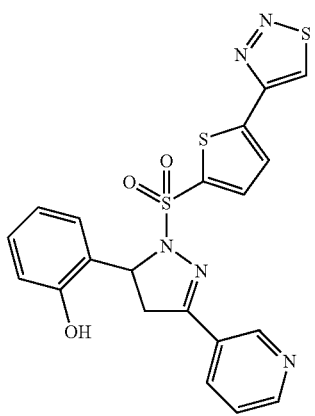

TABLE 1-continued
Raf Kinase Inhibitors
I-179
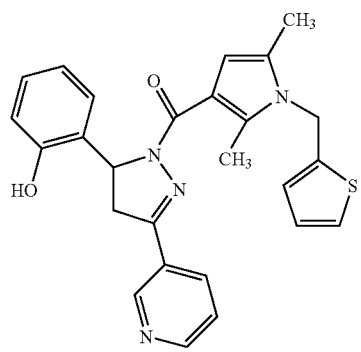
I-180
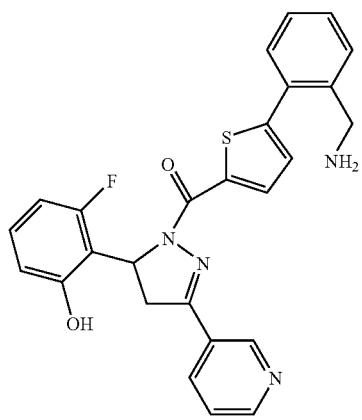
I-181
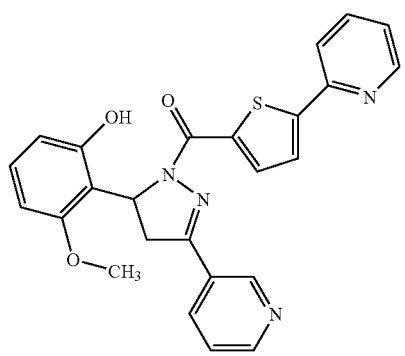
TABLE 1-continued
Raf Kinase Inhibitors
I-182
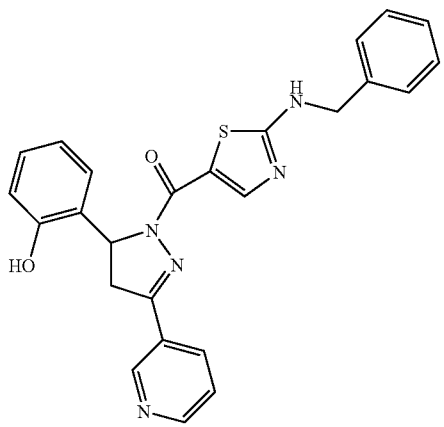
I-183
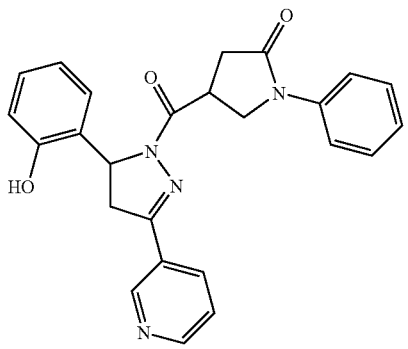
I-184
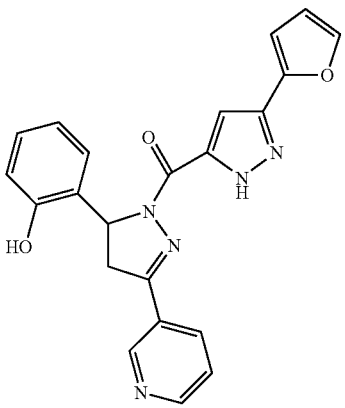

TABLE 1-continued
Raf Kinase Inhibitors
I-185
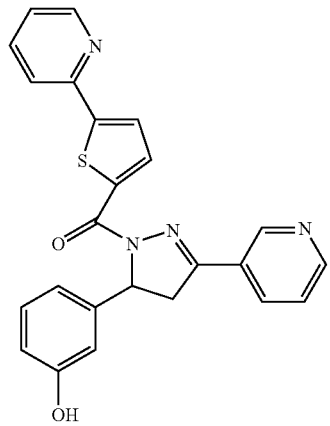
I-186
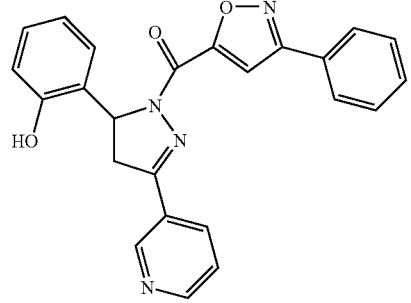
I-188
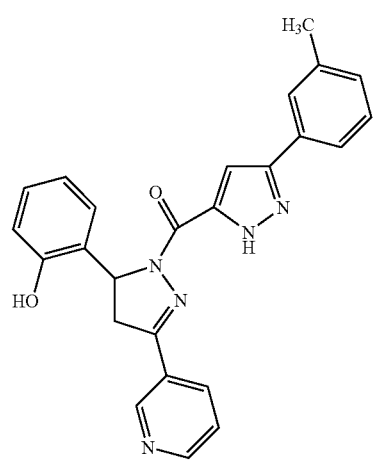
TABLE 1-continued
Raf Kinase Inhibitors
I-190
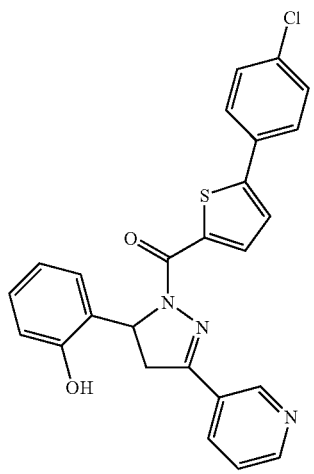
I-191
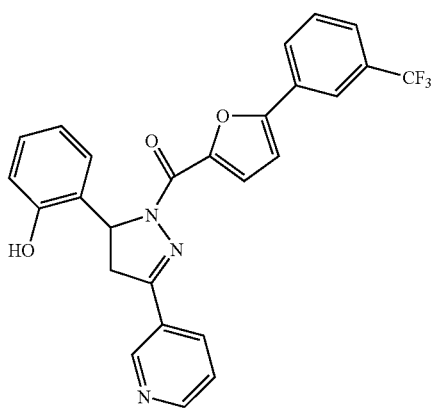
I-192
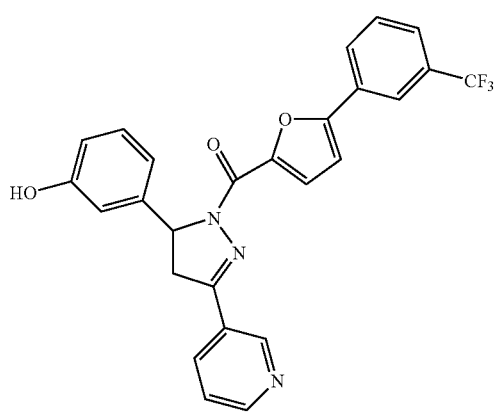

TABLE 1-continued
Raf Kinase Inhibitors
I-193
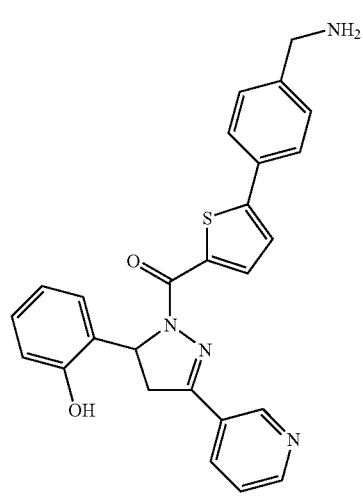
I-194
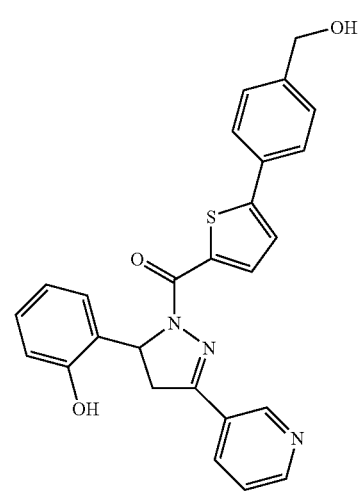
I-195
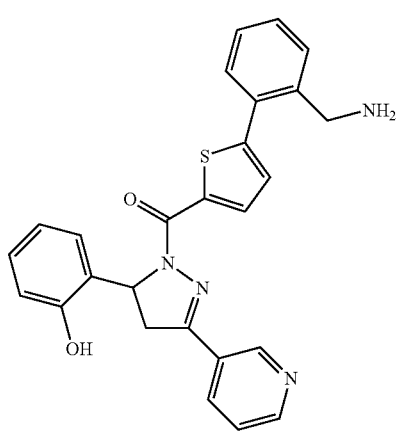
TABLE 1-continued
Raf Kinase Inhibitors
I-196
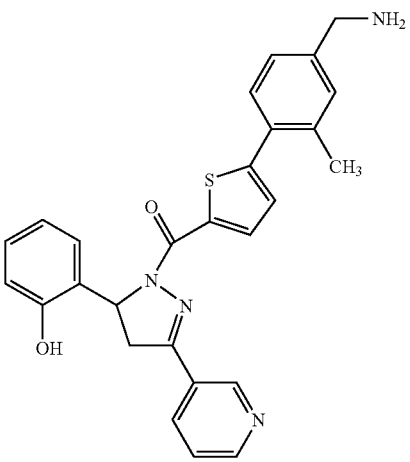
I-197
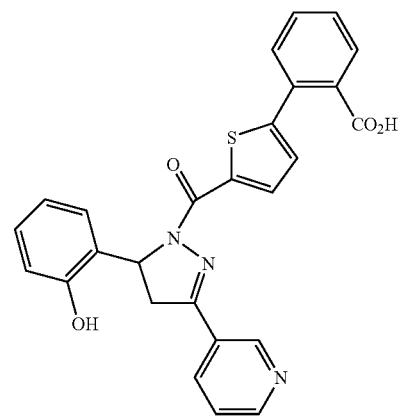
I-198
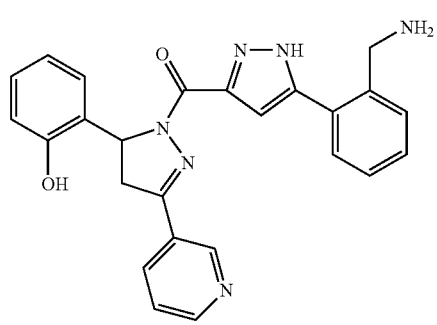

TABLE 1-continued
Raf Kinase Inhibitors
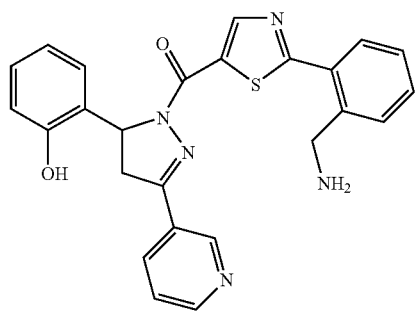
I-200
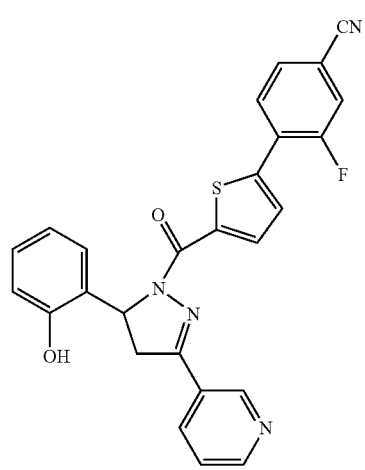
I-201
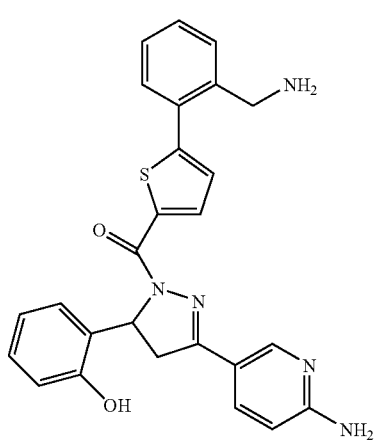
I-202
TABLE 1-continued
Raf Kinase Inhibitors
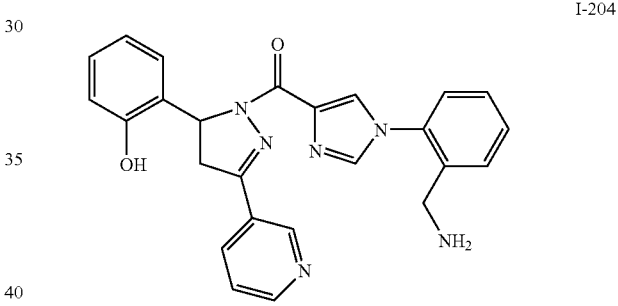
I-203
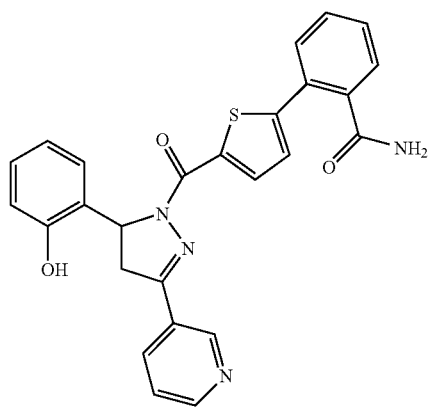
I-204
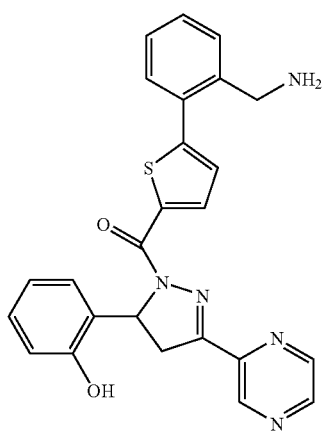
I-205

TABLE 1-continued
Raf Kinase Inhibitors
I-207
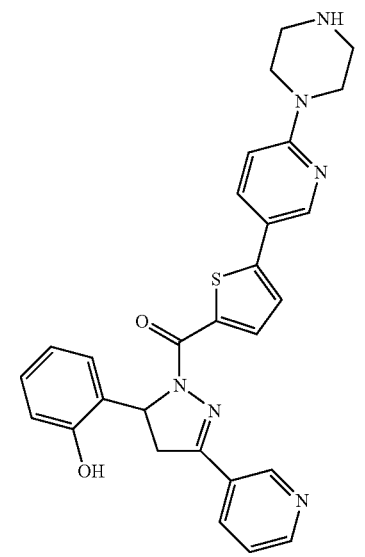
I-208
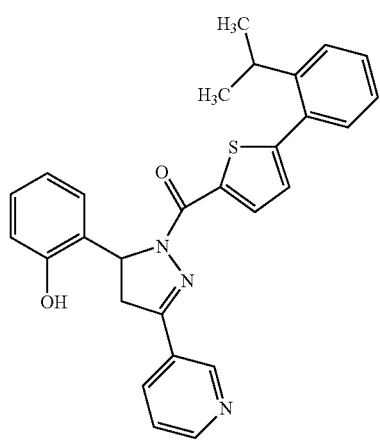
I-209
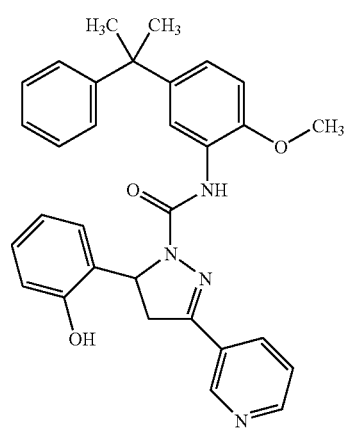
TABLE 1-continued
Raf Kinase Inhibitors
I-211
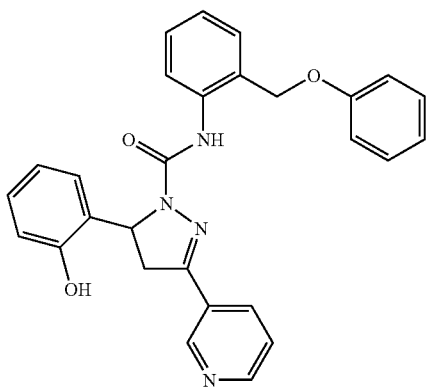
I-212
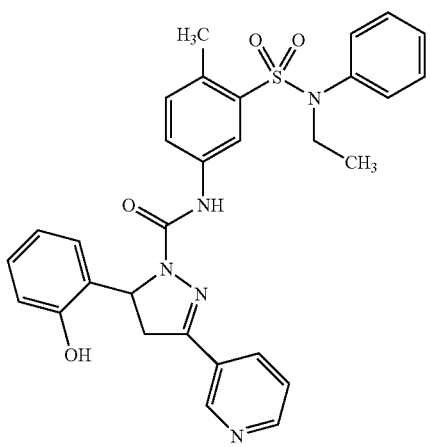
I-213
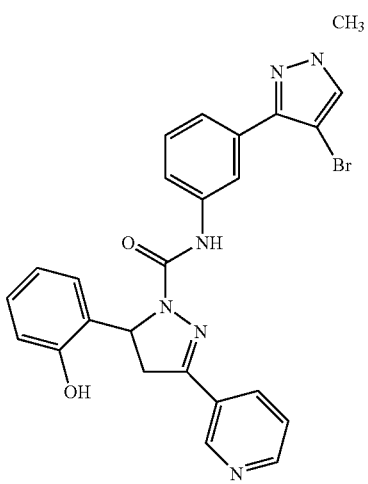

TABLE 1-continued
Raf Kinase Inhibitors
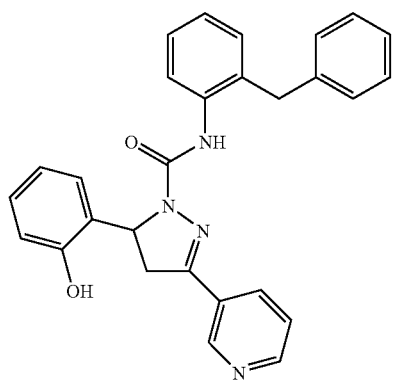
I-214
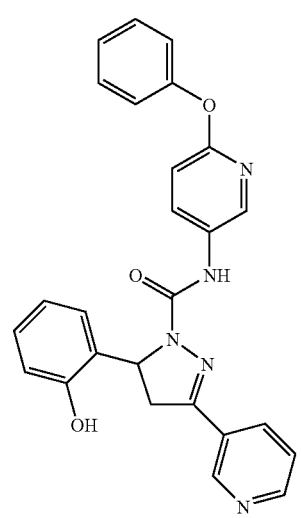
I-215
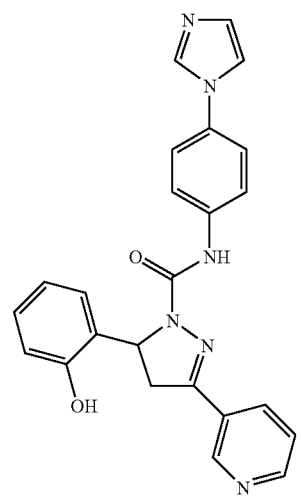
I-216
TABLE 1-continued
Raf Kinase Inhibitors
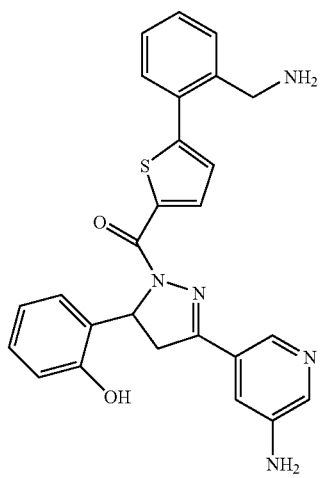
I-217
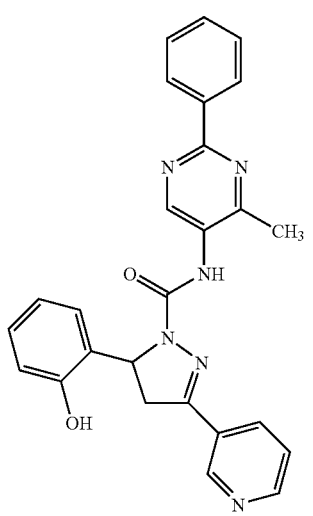
I-218
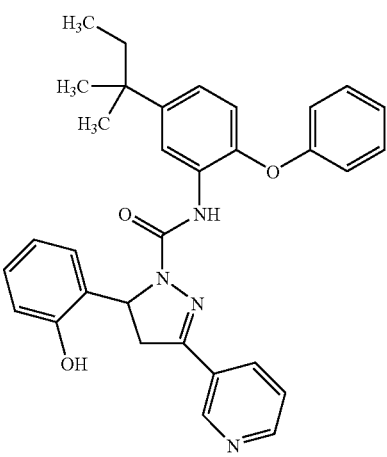
I-219

TABLE 1-continued
Raf Kinase Inhibitors
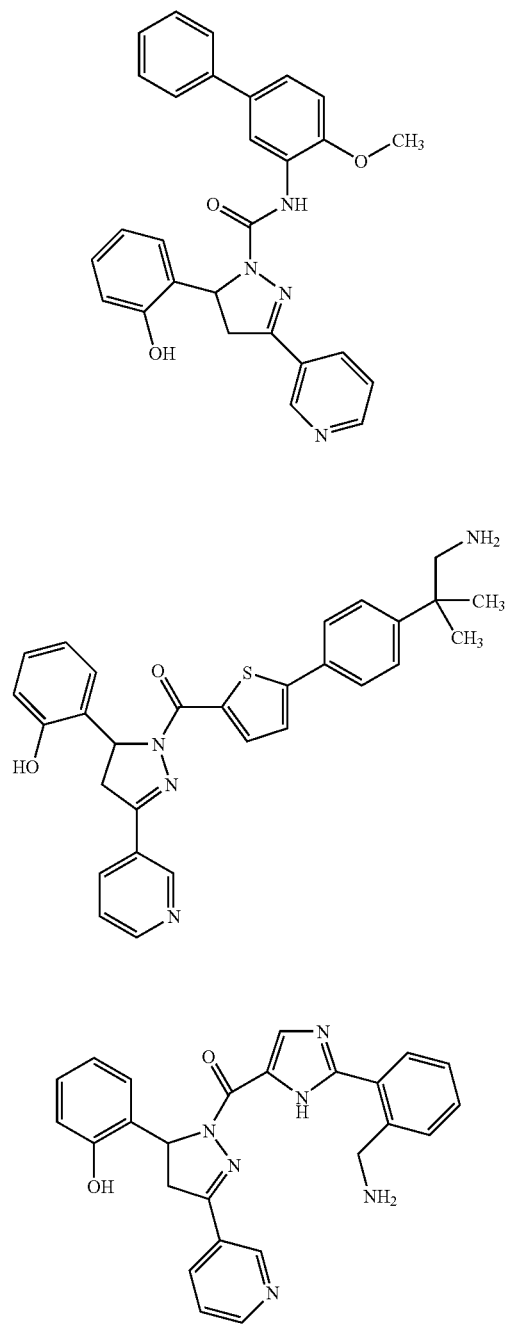
I-220
I-221
I-222
TABLE 1-continued
Raf Kinase Inhibitors
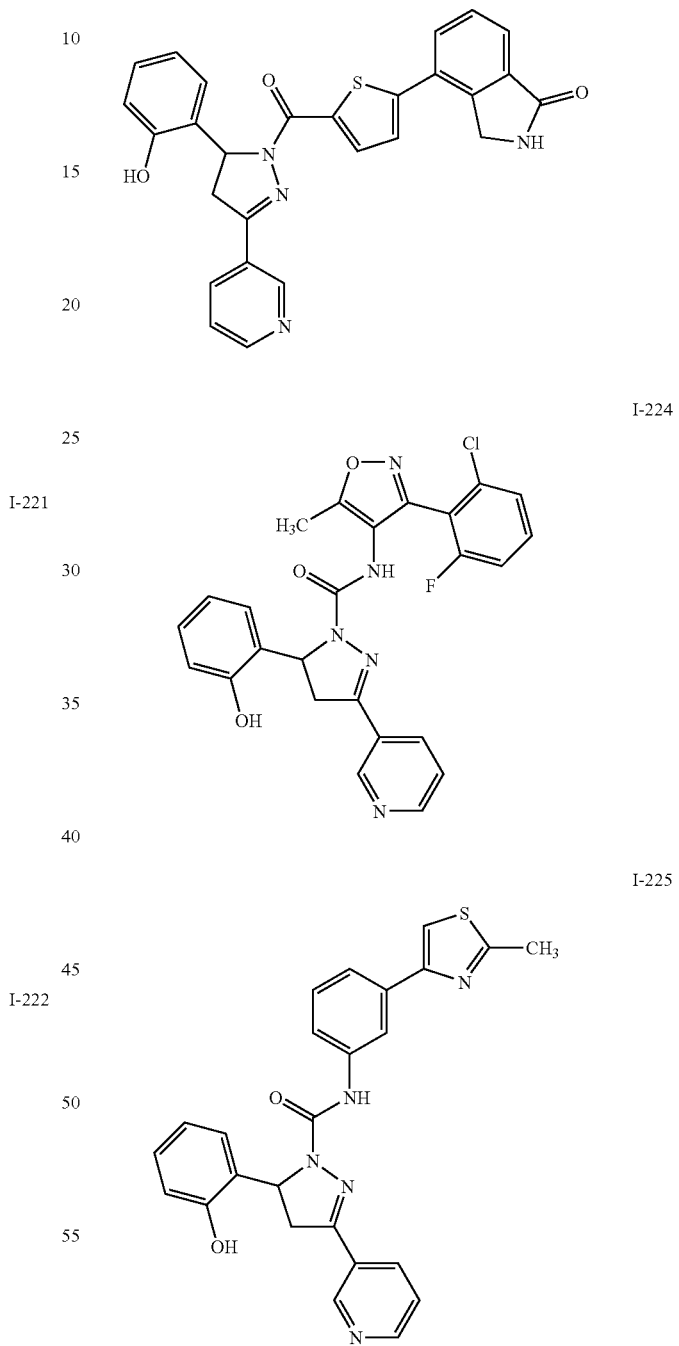
I-223
I-224
I-225

TABLE 1-continued
Raf Kinase Inhibitors
I-226
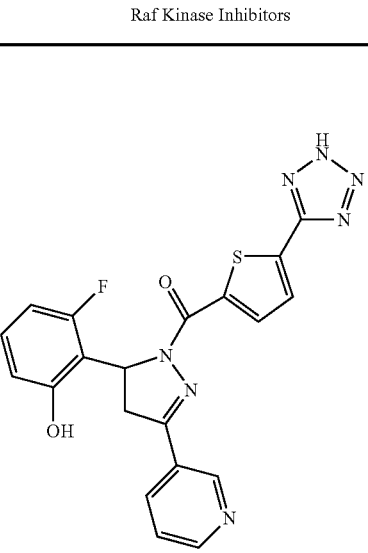
I-227
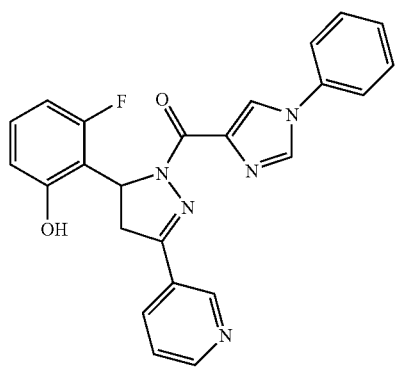
I-228
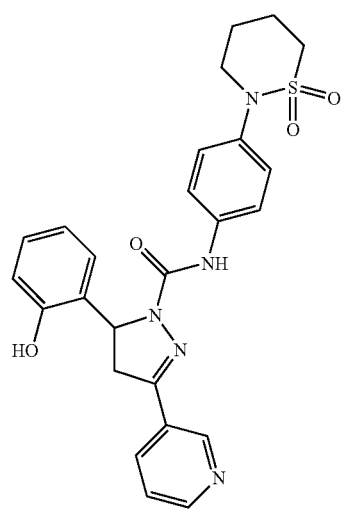
TABLE 1-continued
Raf Kinase Inhibitors
I-229
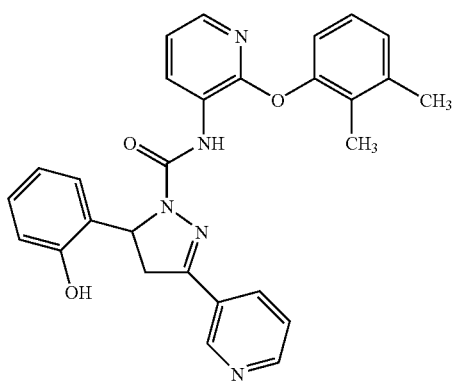
I-230
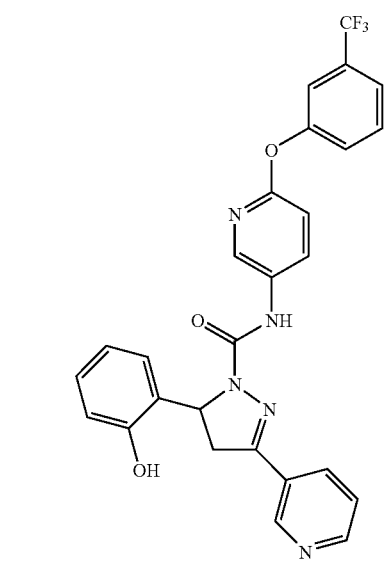
I-231
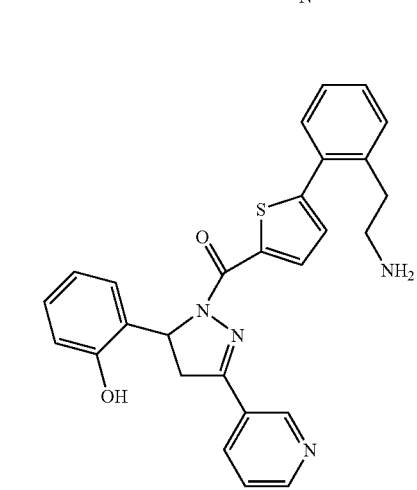

TABLE 1-continued
Raf Kinase Inhibitors
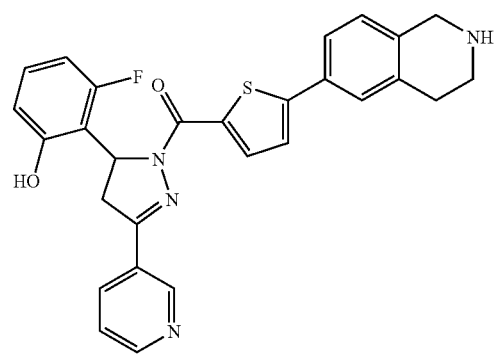
I-232
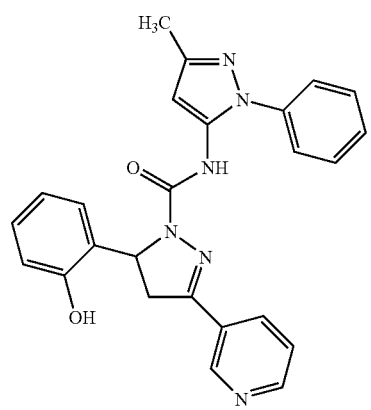
I-233
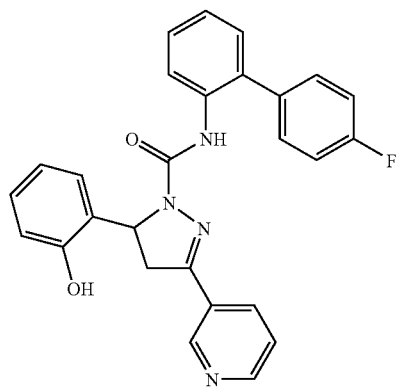
I-234
TABLE 1-continued
Raf Kinase Inhibitors
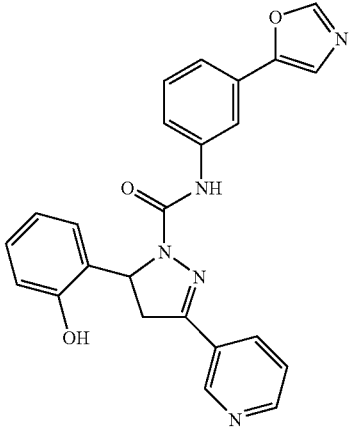
I-235
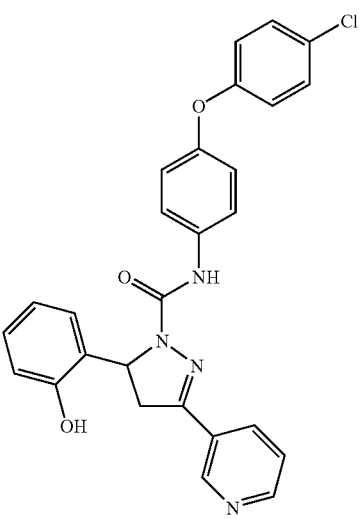
I-236
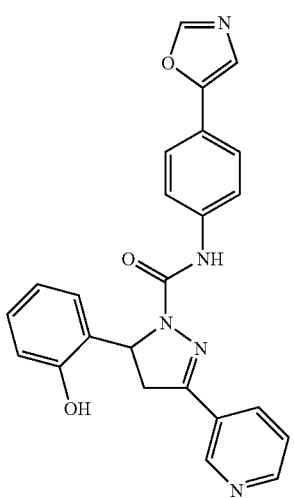
I-237

TABLE 1-continued
Raf Kinase Inhibitors
I-238
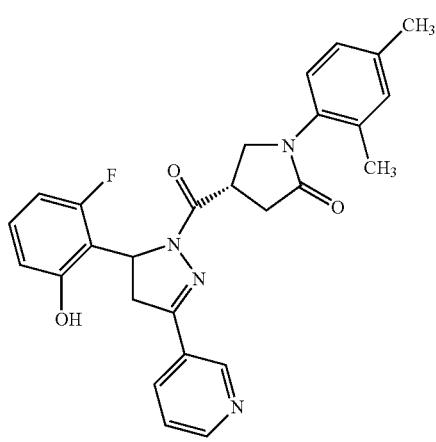
I-240
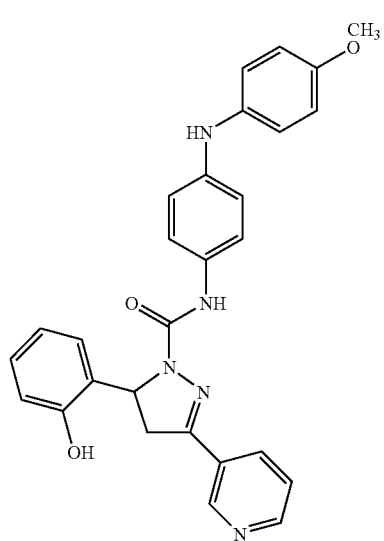
I-241
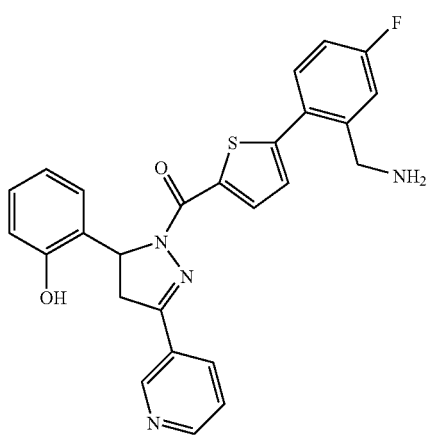
TABLE 1-continued
Raf Kinase Inhibitors
I-242
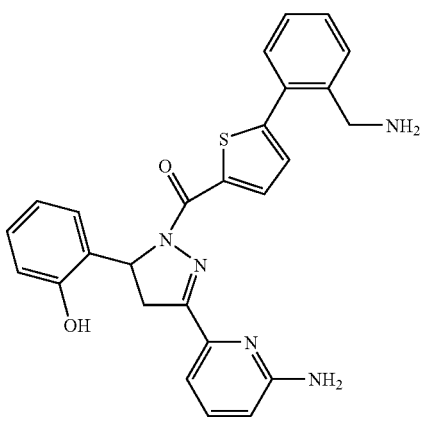
I-243
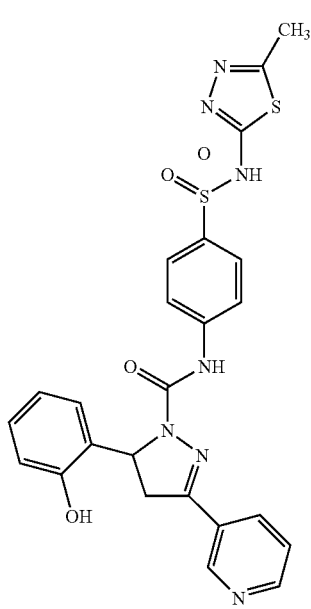
I-244
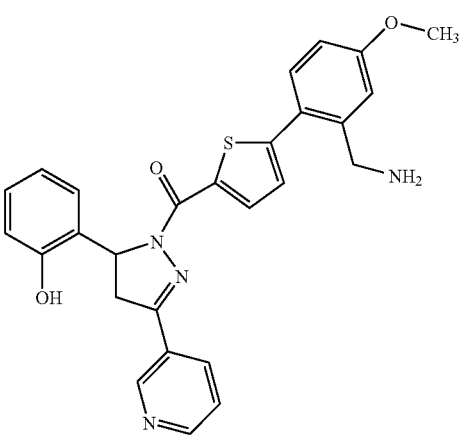

TABLE 1-continued
Raf Kinase Inhibitors
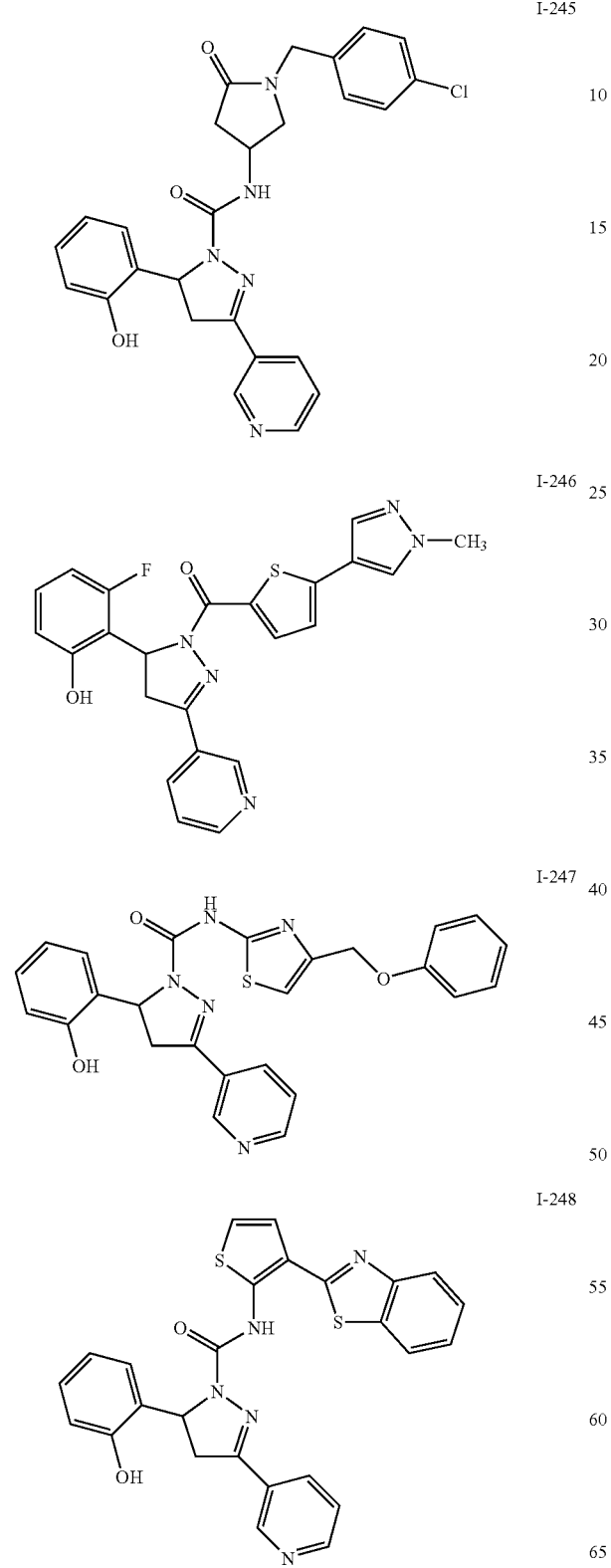
I-245
I-246
I-247
I-248
I-249
I-250
I-251

TABLE 1-continued
Raf Kinase Inhibitors
I-252
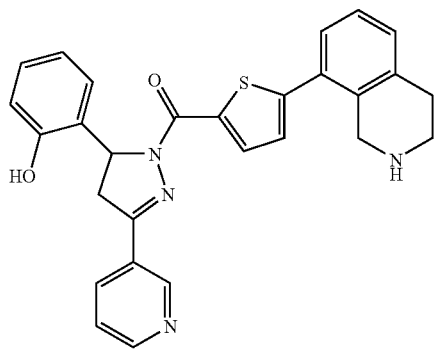
I-253
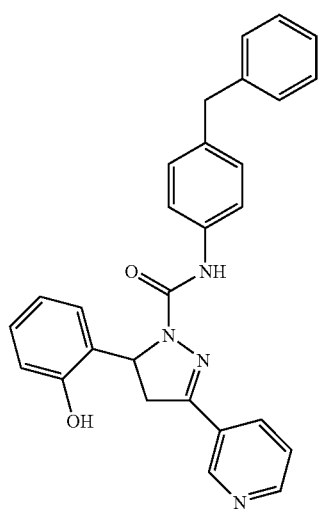
I-254
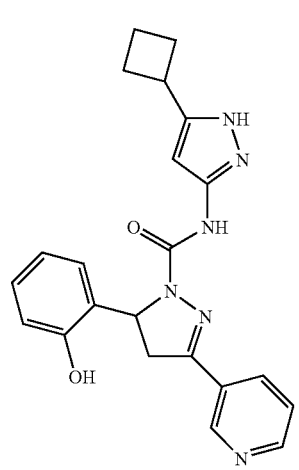
TABLE 1-continued
Raf Kinase Inhibitors
I-255
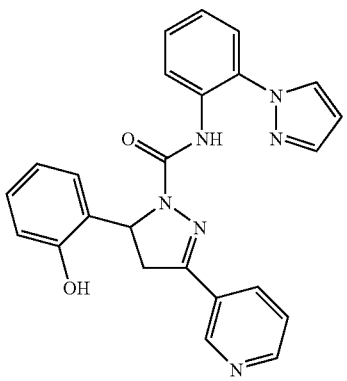
I-256
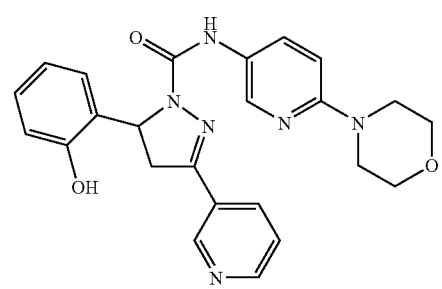
I-257
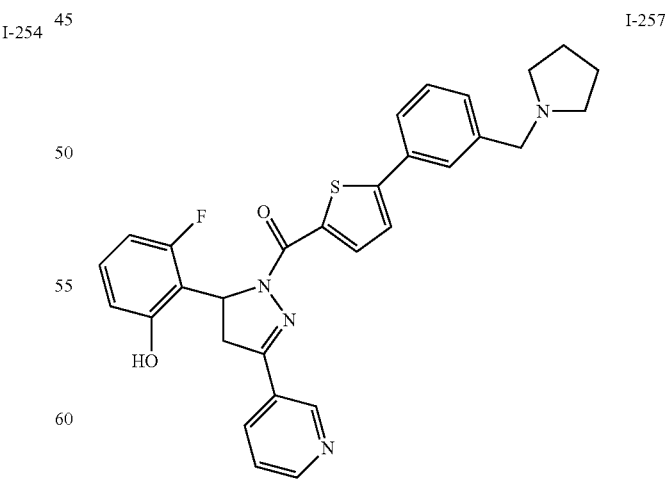

TABLE 1-continued
Raf Kinase Inhibitors
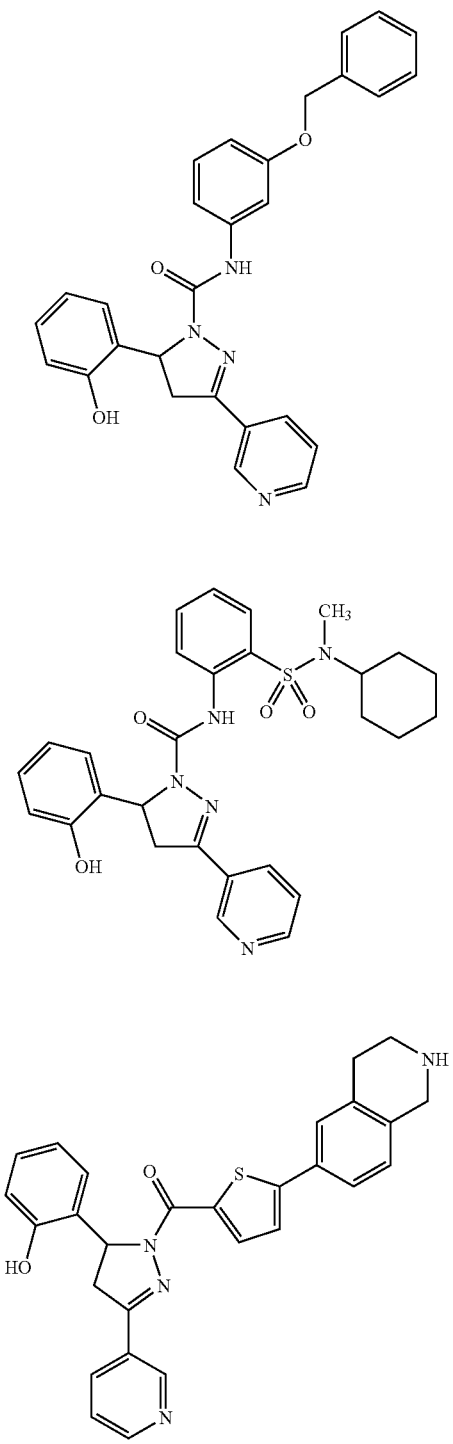
I-258
I-259
I-260
TABLE 1-continued
Raf Kinase Inhibitors
I-261
I-262
I-263

TABLE 1-continued
Raf Kinase Inhibitors
I-264
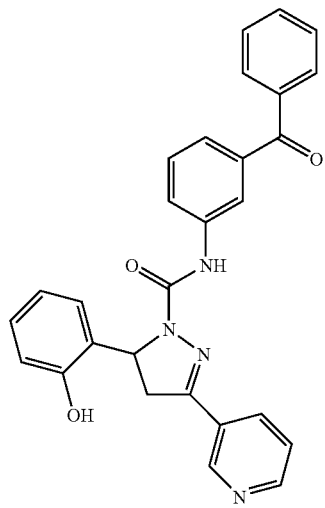
I-265
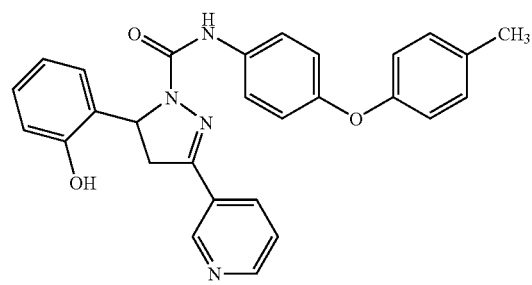
I-266
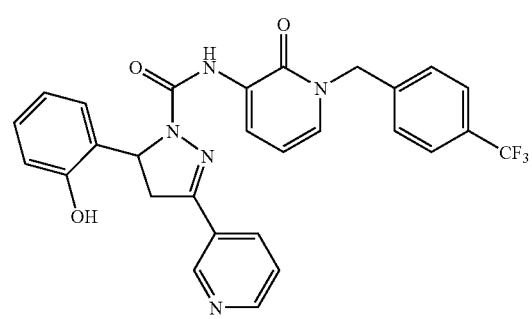
I-267
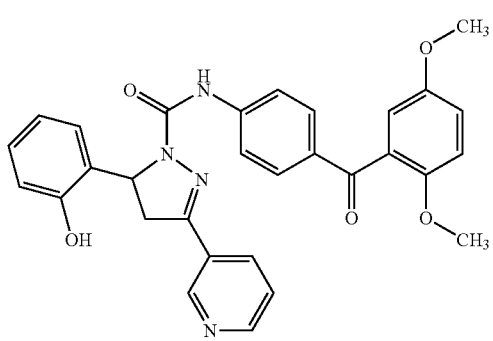
I-268
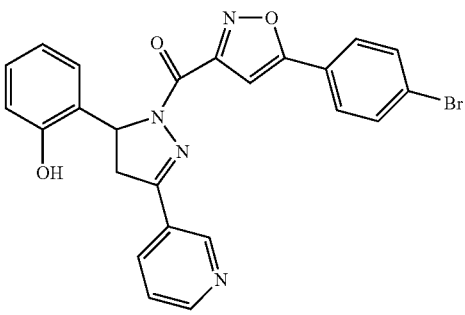
I-269
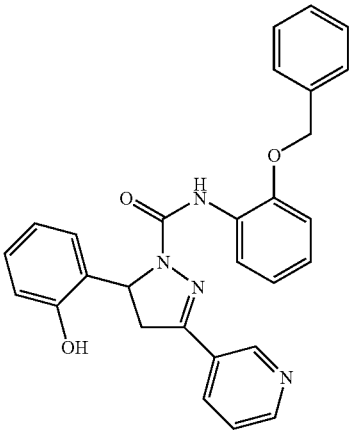
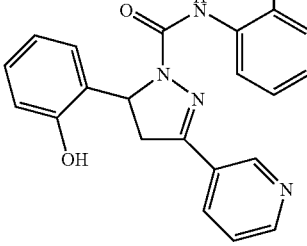
I-270
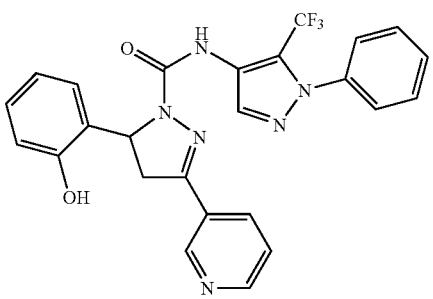
I-271
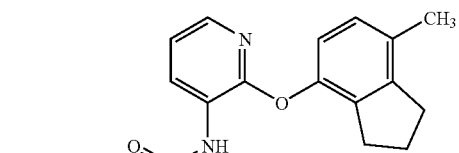
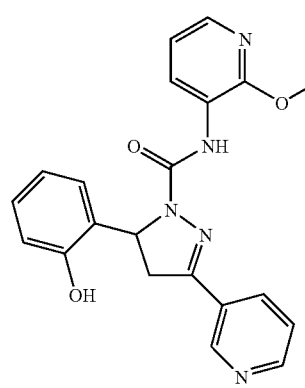

TABLE 1-continued
Raf Kinase Inhibitors
I-272
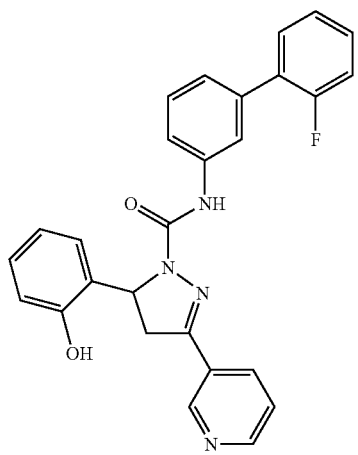
I-273
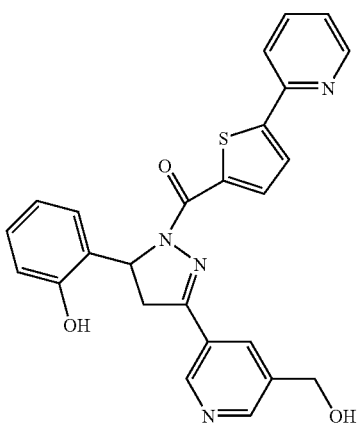
I-274
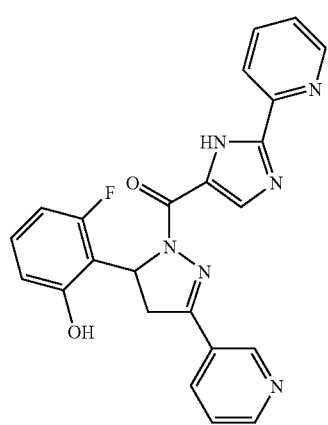
TABLE 1-continued
Raf Kinase Inhibitors
I-276
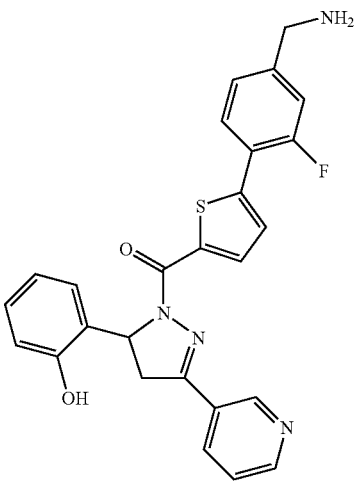
I-277
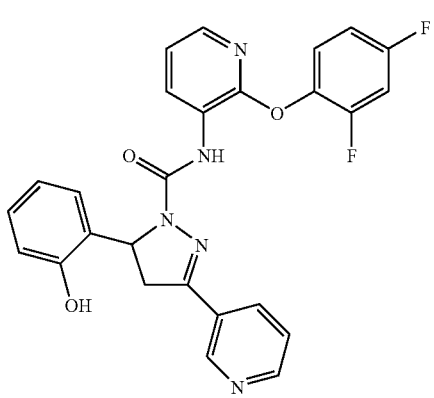
I-278
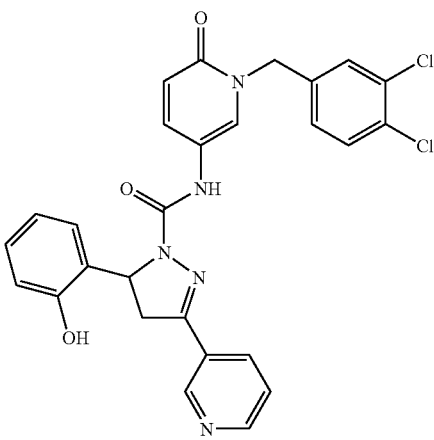

TABLE 1-continued
Raf Kinase Inhibitors
I-279
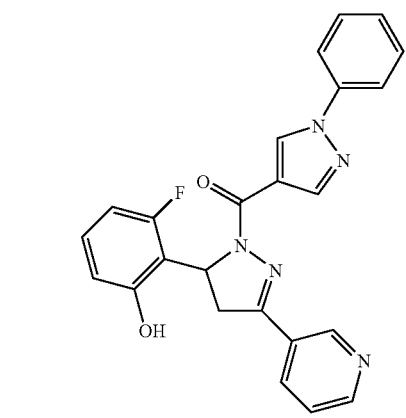
I-280
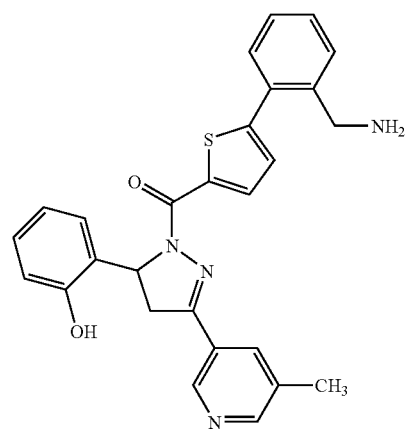
I-281
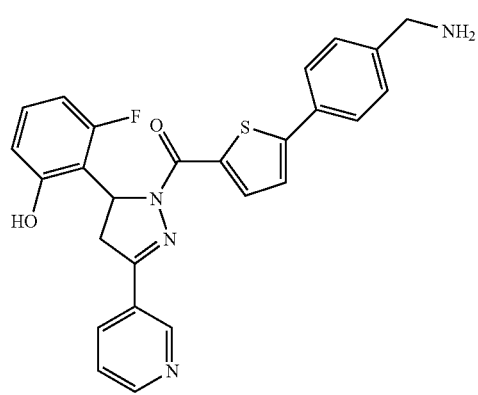
TABLE 1-continued
Raf Kinase Inhibitors
I-282
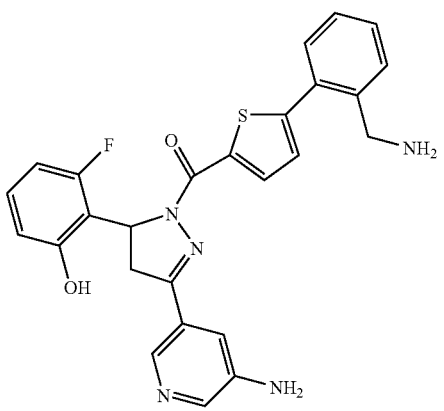
I-283
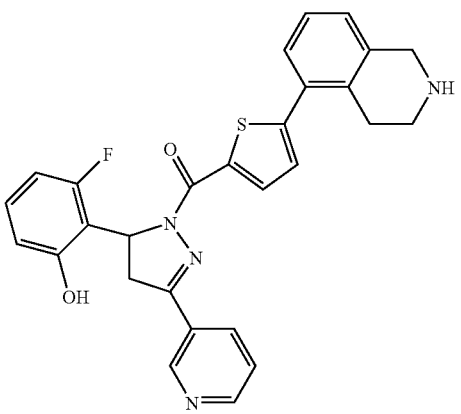
I-284
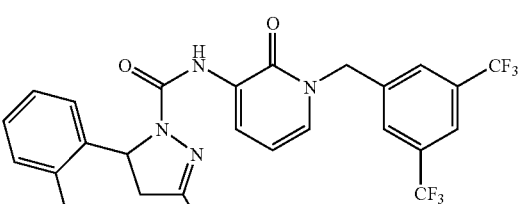
I-285
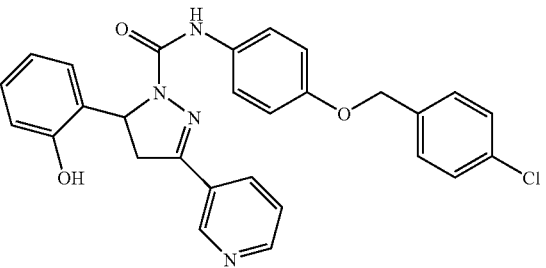

TABLE 1-continued
Raf Kinase Inhibitors
I-286
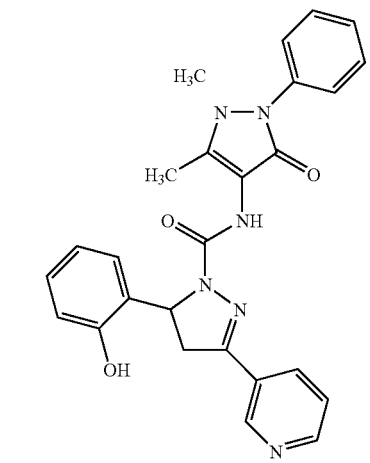
I-287
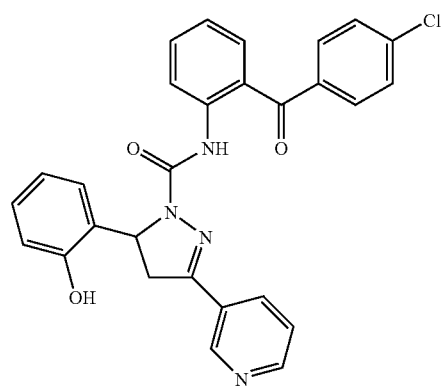
I-288
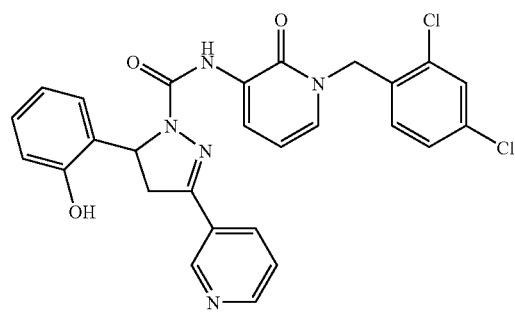
TABLE 1-continued
Raf Kinase Inhibitors
I-289
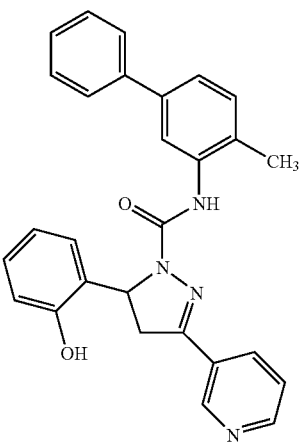
I-290
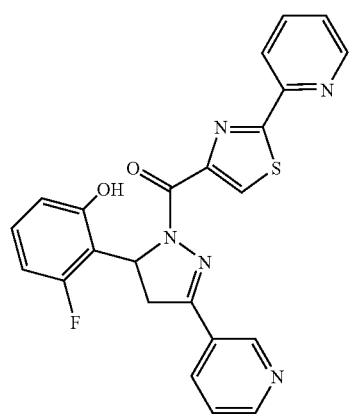
I-291
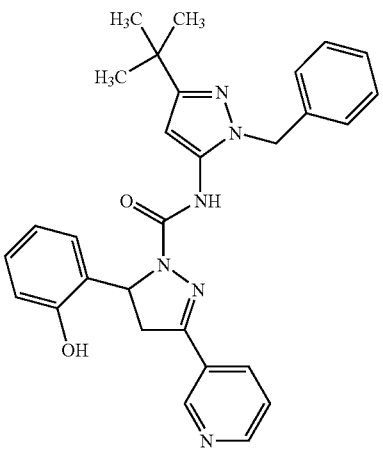

TABLE 1-continued
Raf Kinase Inhibitors
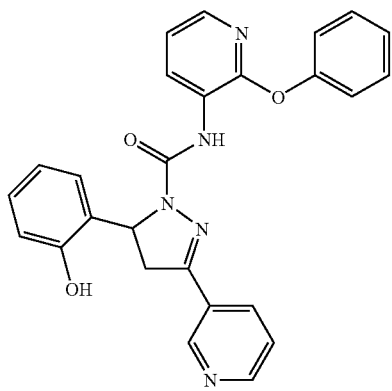
I-292
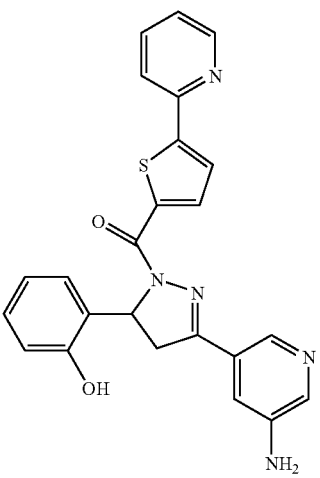
I-296
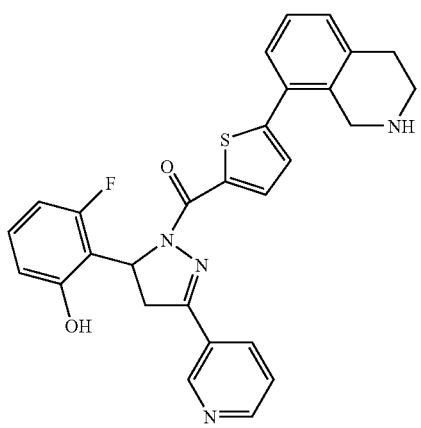
I-294
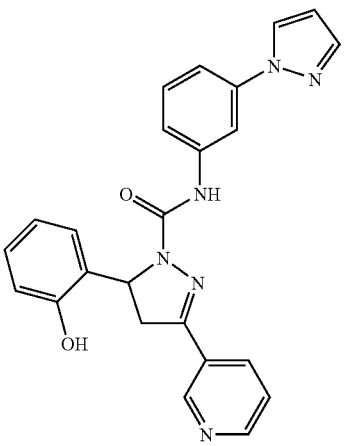
I-297
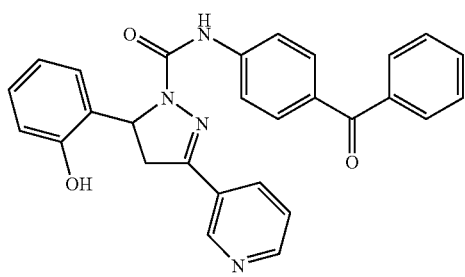
I-295
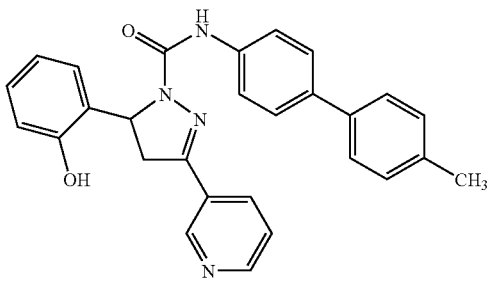
I-298

TABLE 1-continued
Raf Kinase Inhibitors
I-299
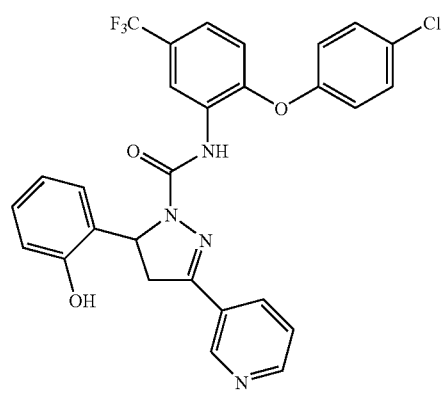
I-300
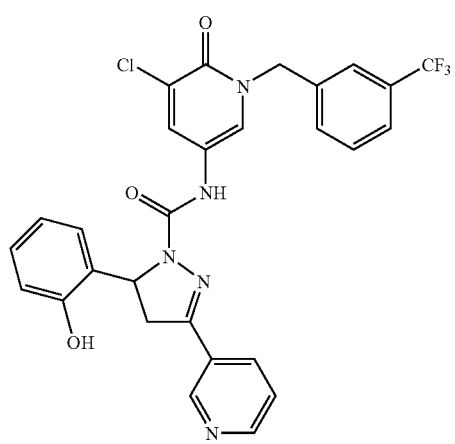
I-301
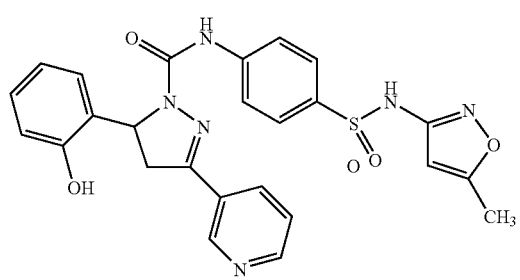
I-303
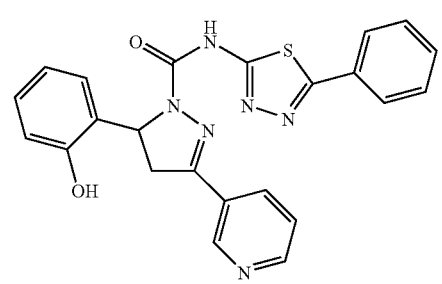
TABLE 1-continued
Raf Kinase Inhibitors
I-304
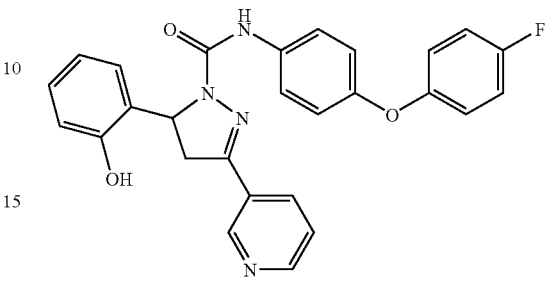
I-305
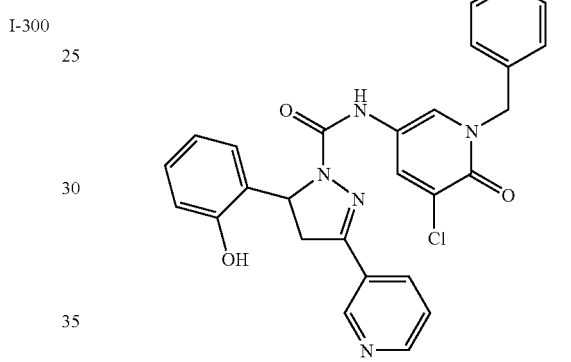
I-306
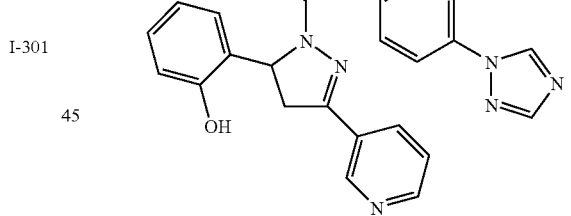
I-307
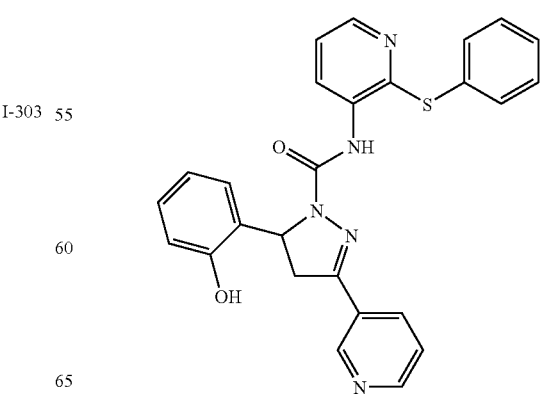

TABLE 1-continued

Raf Kinase Inhibitors

I-308, I-309, I-310, I-311, I-312, I-313, I-314, I-315

TABLE 1-continued
Raf Kinase Inhibitors
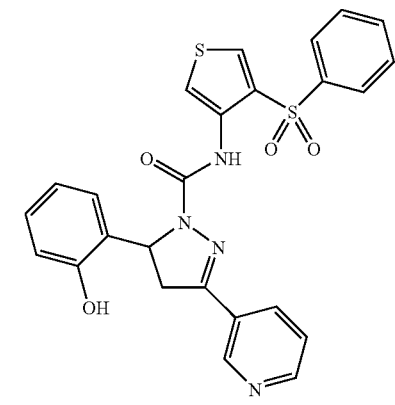
I-316
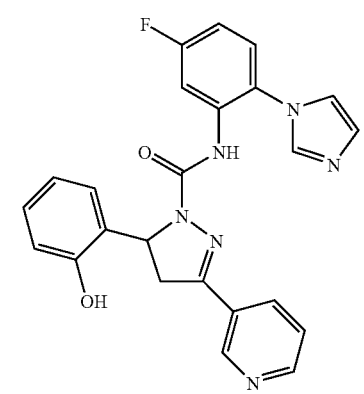
I-317
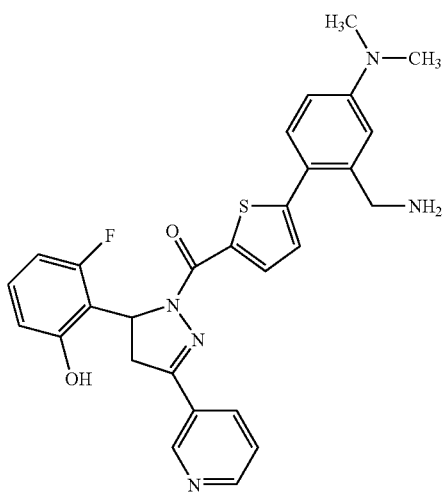
I-318
TABLE 1-continued
Raf Kinase Inhibitors
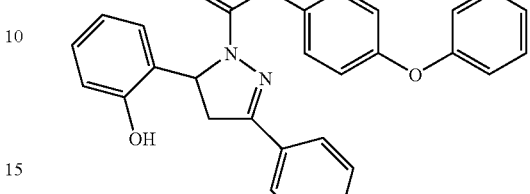
I-319
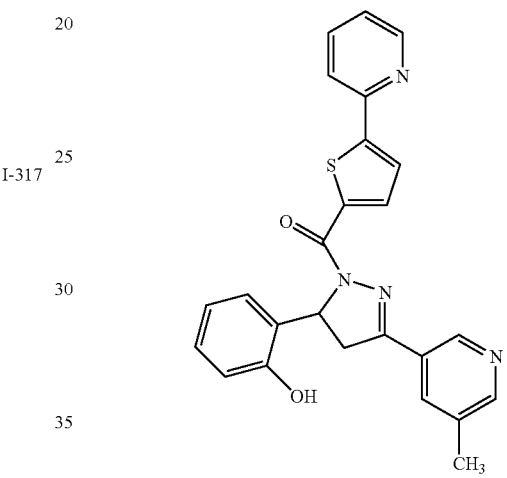
I-320
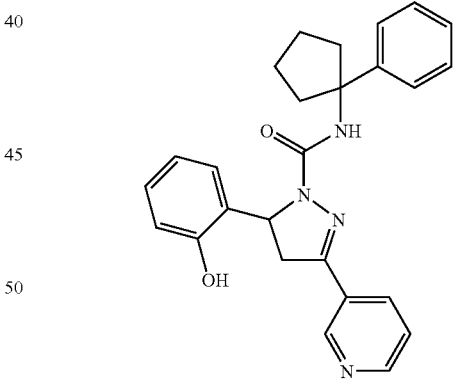
I-321
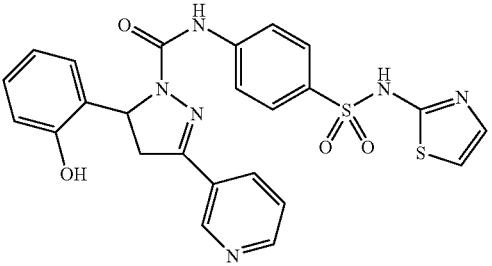
I-322

TABLE 1-continued
Raf Kinase Inhibitors
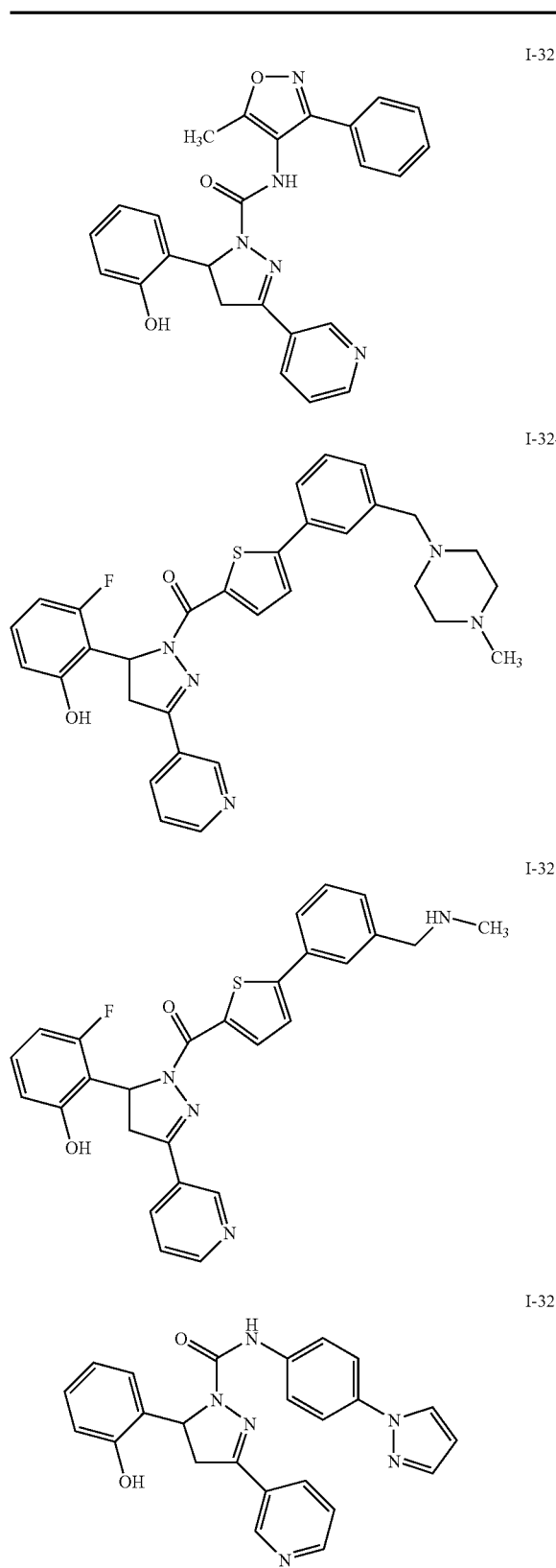
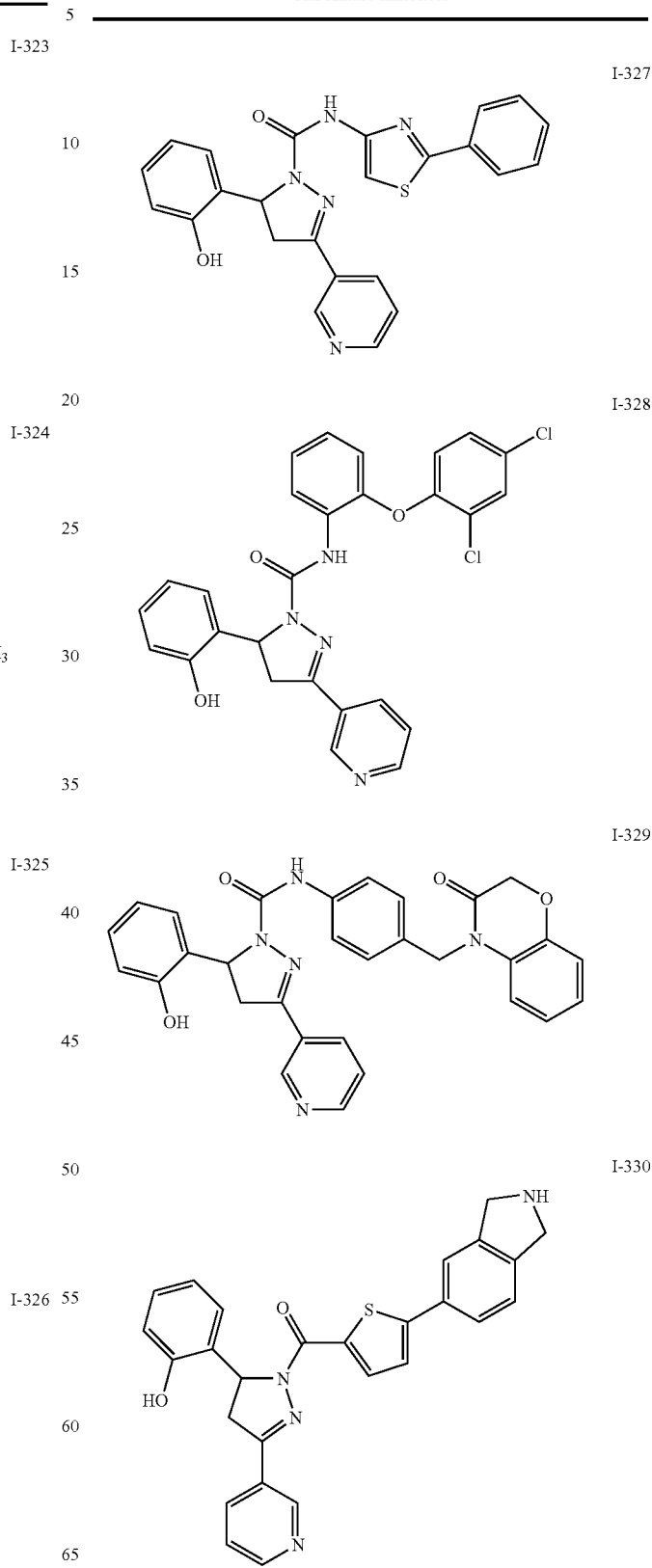

TABLE 1-continued

Raf Kinase Inhibitors

I-331
I-332
I-333
I-334
I-335
I-336
I-337
I-338

TABLE 1-continued
Raf Kinase Inhibitors
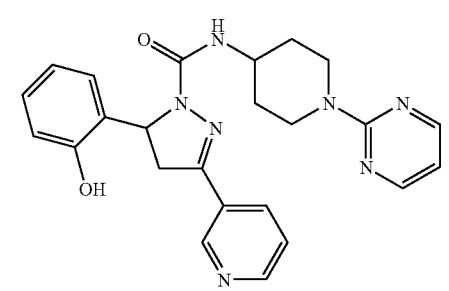
I-339
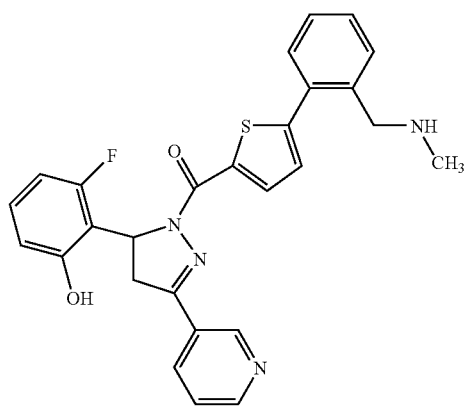
I-340
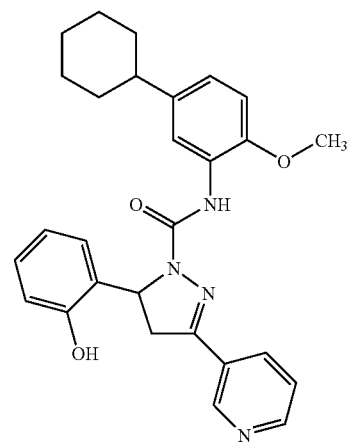
I-341
TABLE 1-continued
Raf Kinase Inhibitors
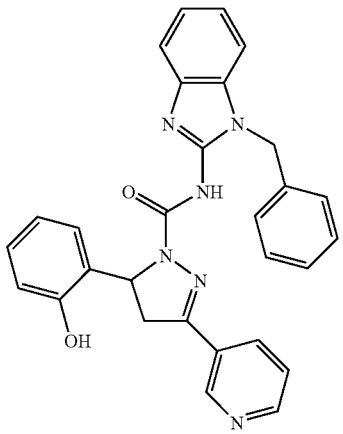
I-342
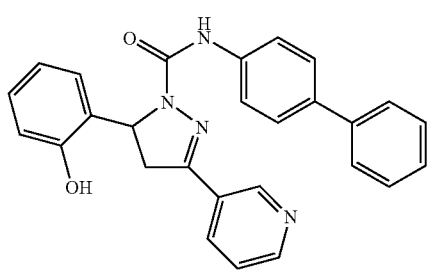
I-343
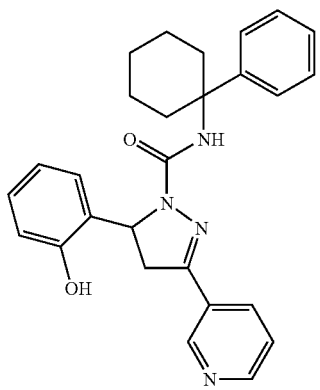
I-344
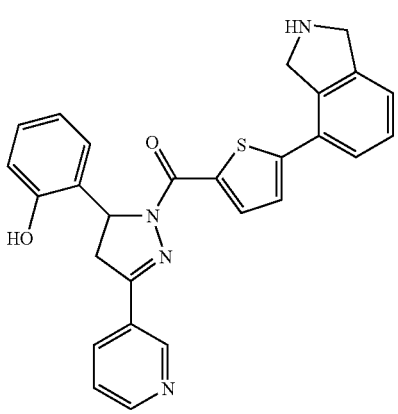
I-347

TABLE 1-continued
Raf Kinase Inhibitors
I-348
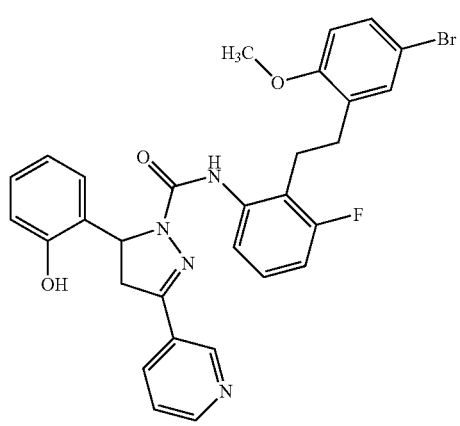
I-349
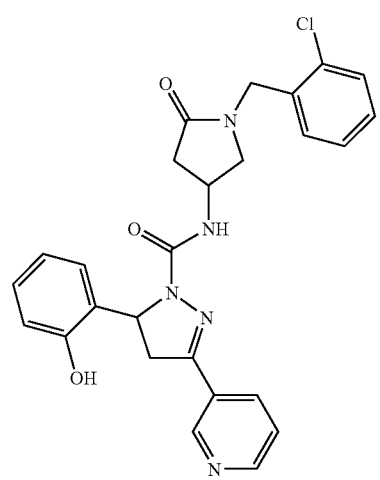
I-350
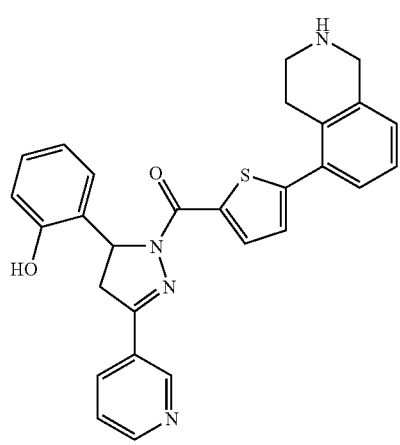
TABLE 1-continued
Raf Kinase Inhibitors
I-351
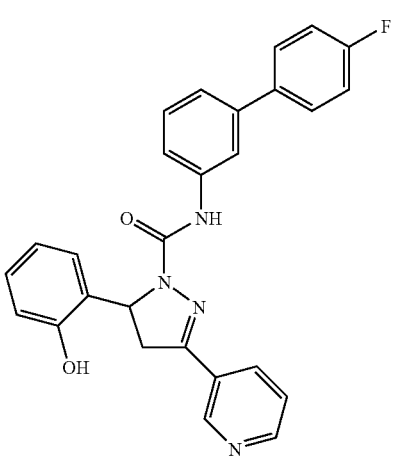
I-352
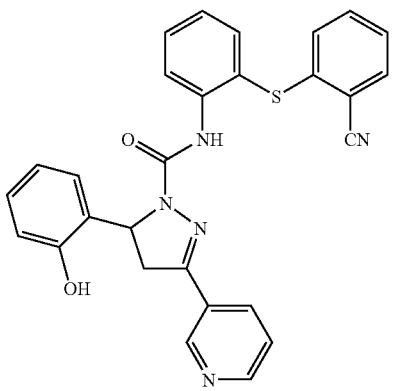
I-353
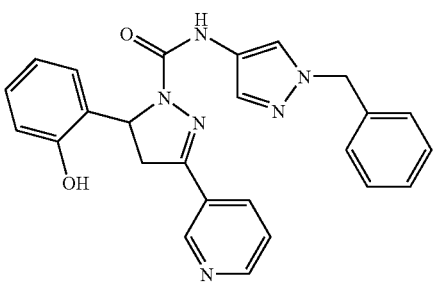

TABLE 1-continued
Raf Kinase Inhibitors
I-354
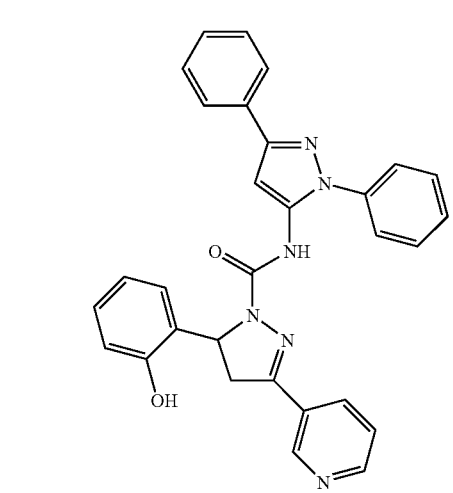
I-355
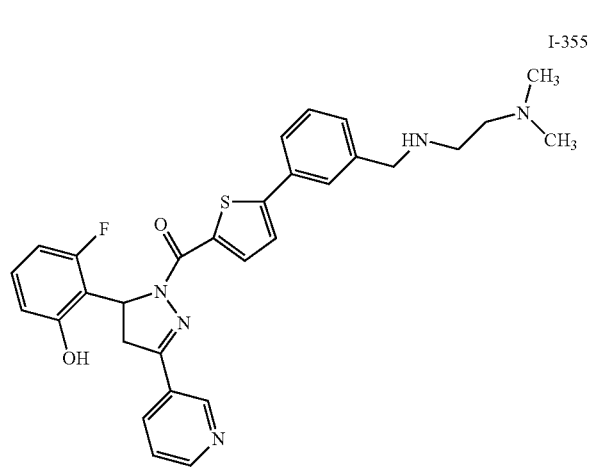
I-356
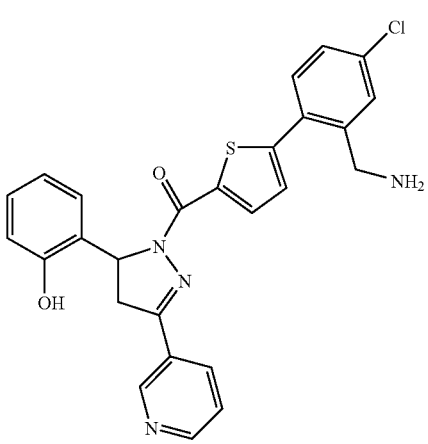
TABLE 1-continued
Raf Kinase Inhibitors
I-357
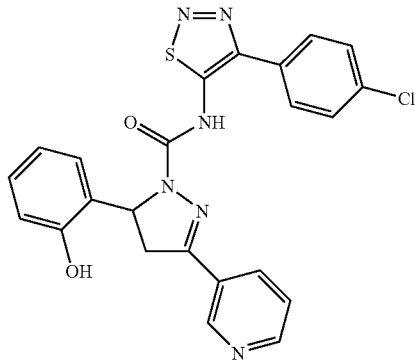
I-358
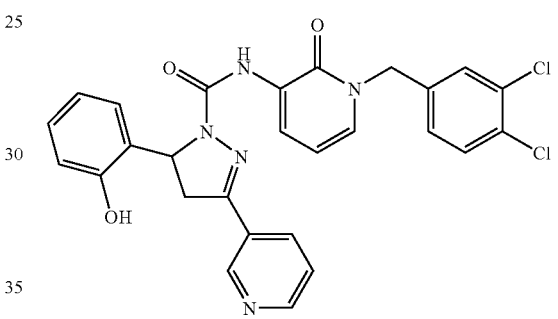
I-359
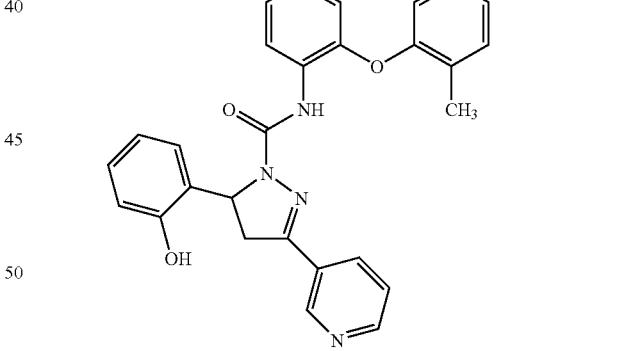
I-360
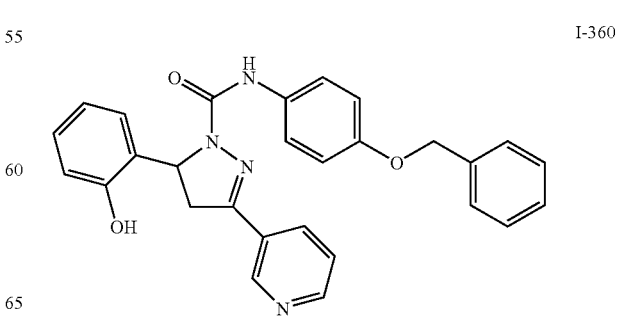

TABLE 1-continued
Raf Kinase Inhibitors
I-361
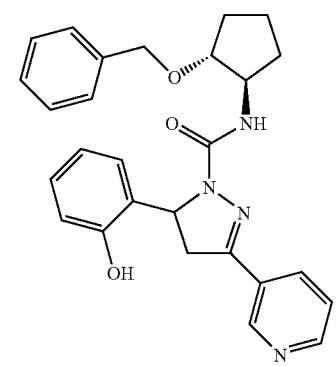
I-362
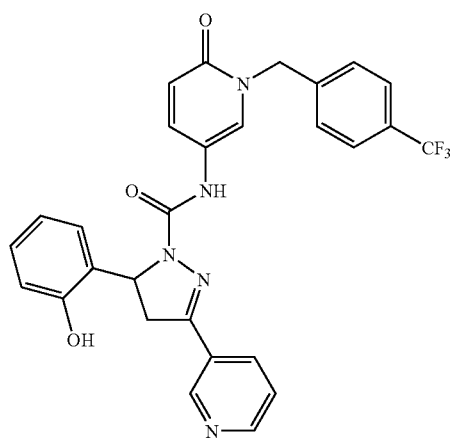
I-364
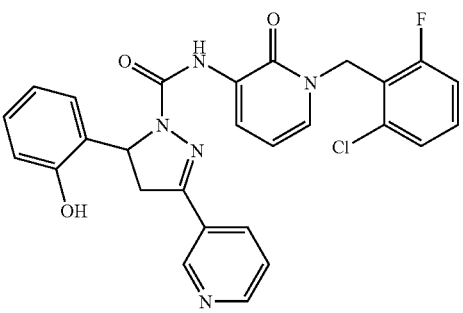
TABLE 1-continued
Raf Kinase Inhibitors
I-365
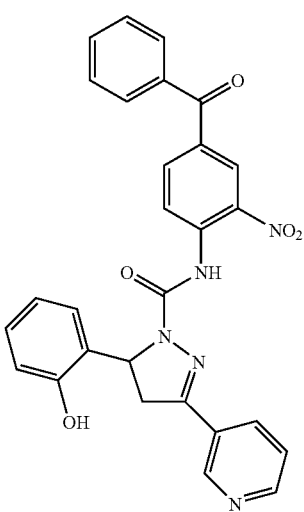
I-366
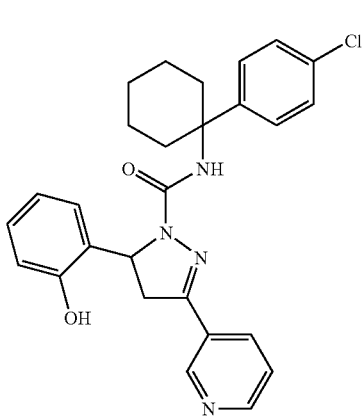
I-367
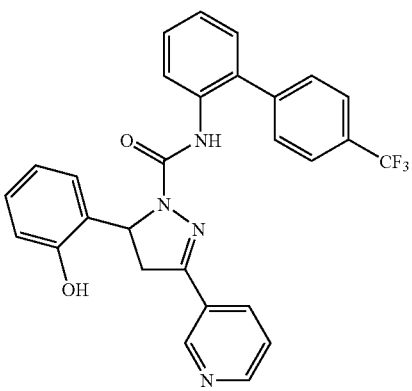

TABLE 1-continued

Raf Kinase Inhibitors

I-368

I-369

I-370

I-371

I-372

I-373

TABLE 1-continued
Raf Kinase Inhibitors
I-374
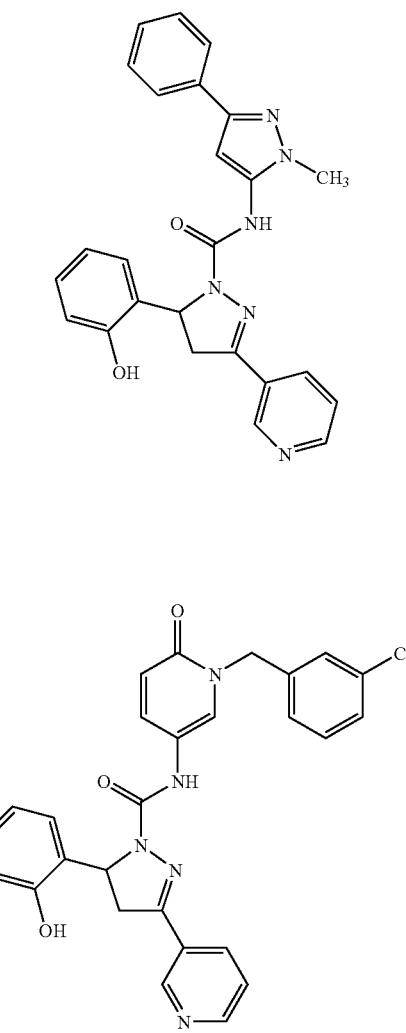
I-376
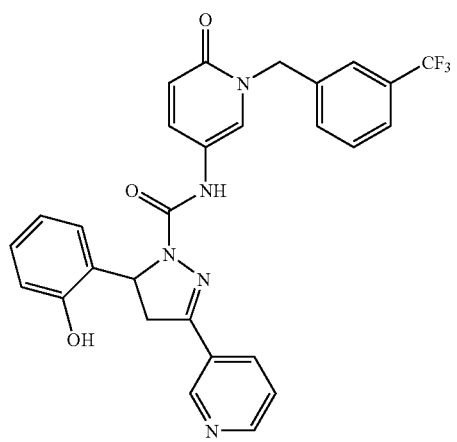
I-377
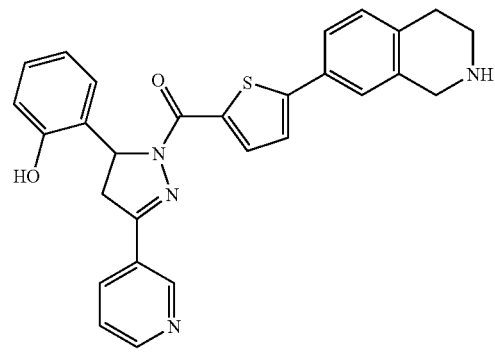
TABLE 1-continued
Raf Kinase Inhibitors
I-378
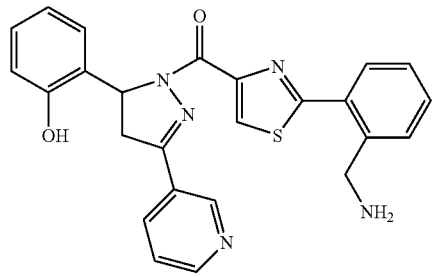
I-379
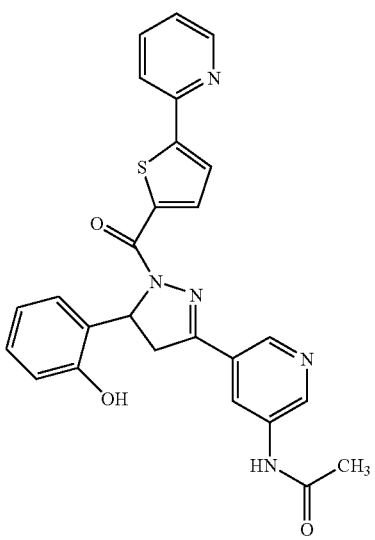
I-380
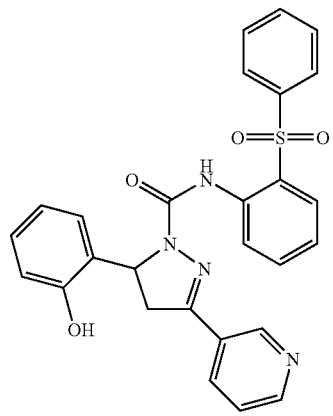

TABLE 1-continued
Raf Kinase Inhibitors
I-381
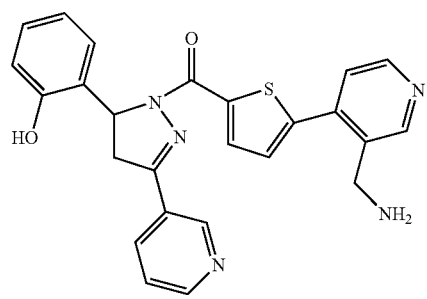
I-382
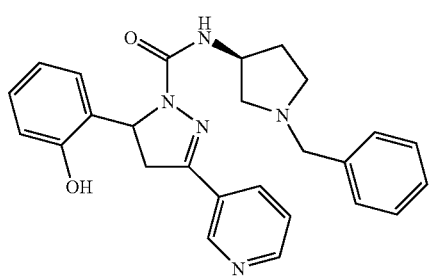
I-383
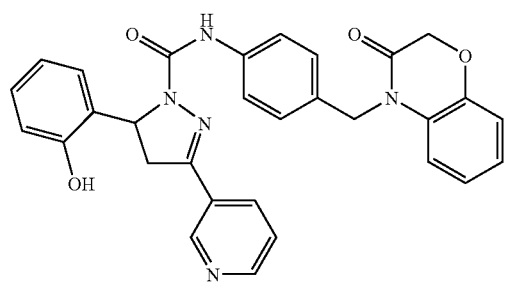
I-384
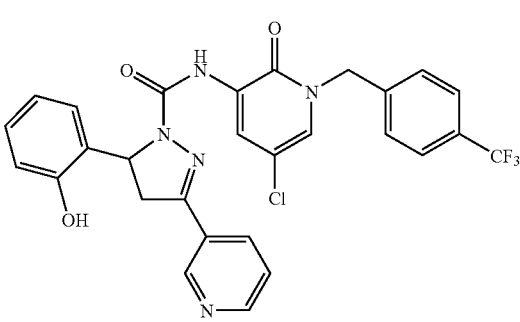
I-385
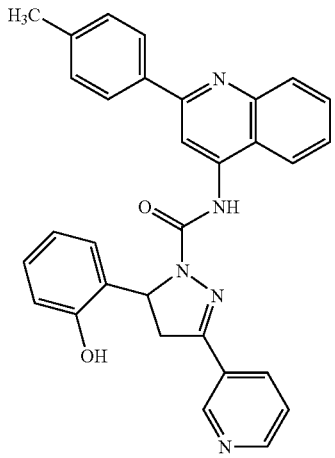
I-386
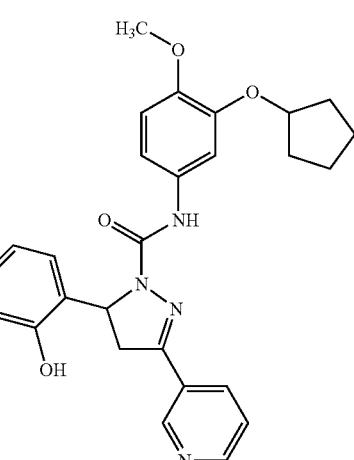
I-387
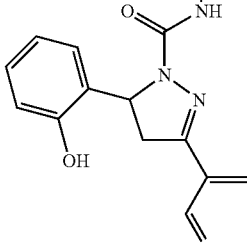
I-388
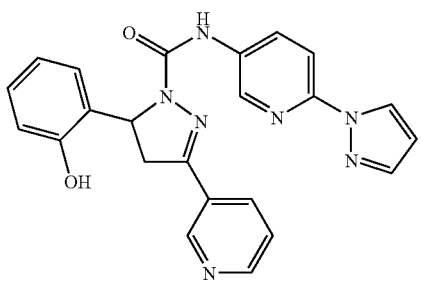

TABLE 1-continued
Raf Kinase Inhibitors
I-389
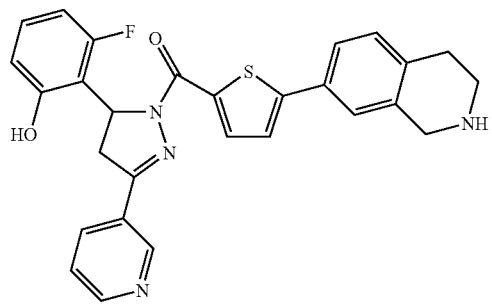
I-390
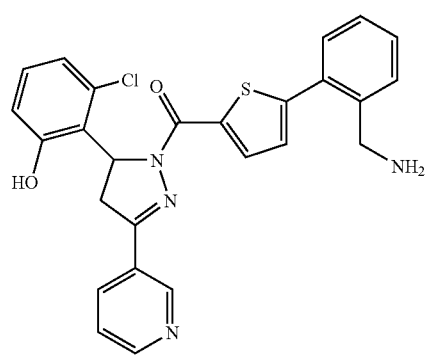
I-391
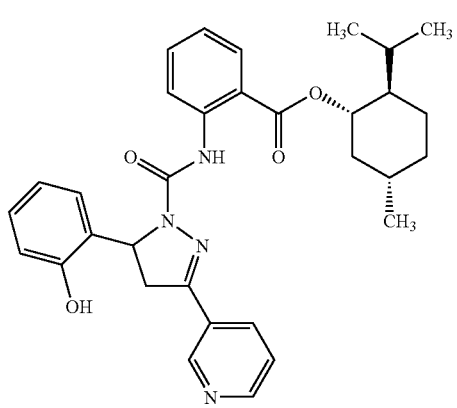
I-392
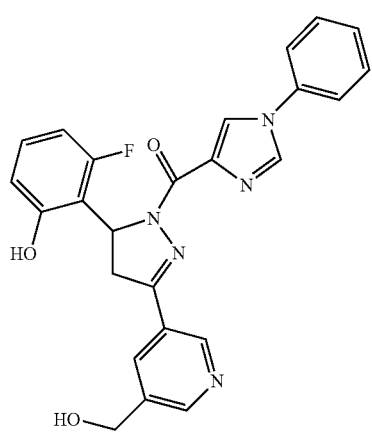
I-393
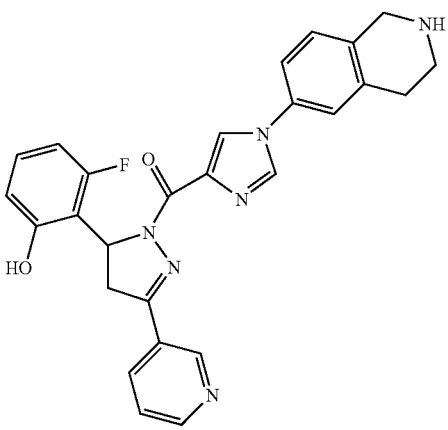
I-394
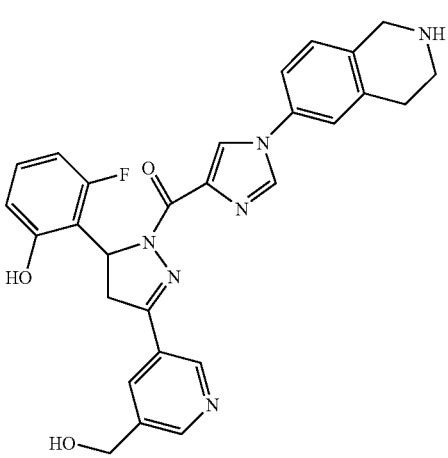
I-395
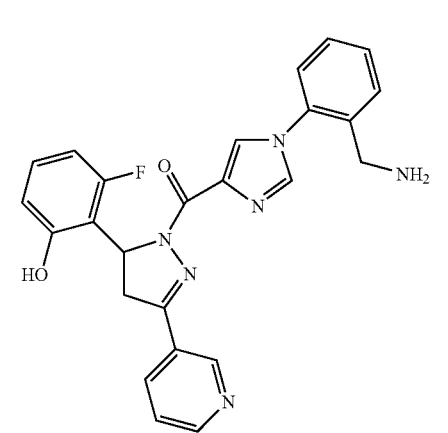

TABLE 1-continued
Raf Kinase Inhibitors
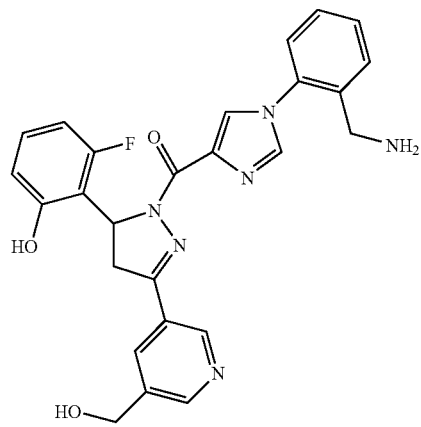
I-396
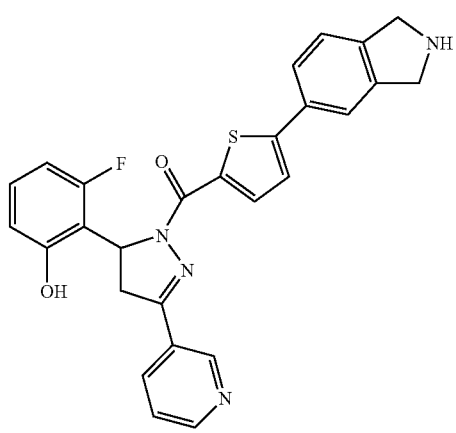
I-397
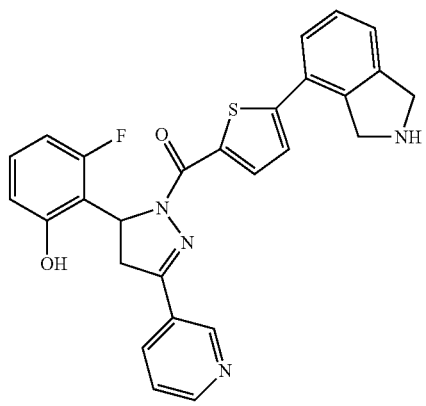
I-398
TABLE 1-continued
Raf Kinase Inhibitors
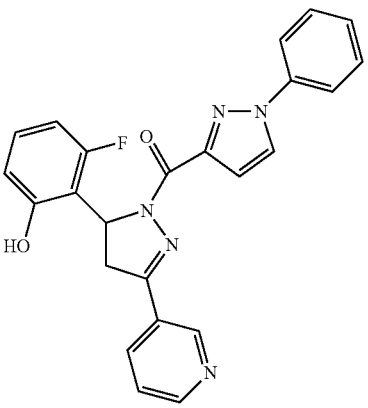
I-399
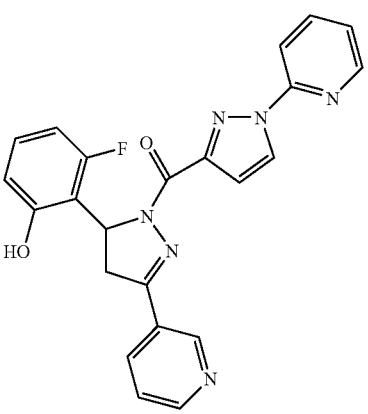
I-400
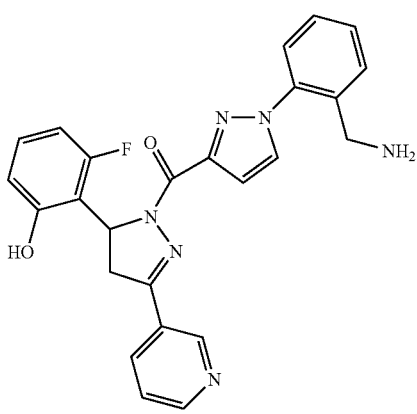
I-401

TABLE 1-continued
Raf Kinase Inhibitors
I-402
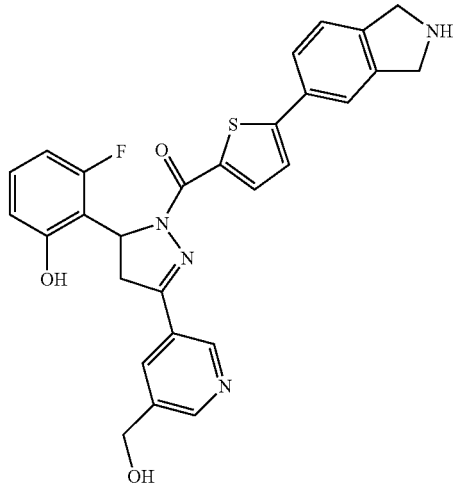
I-403
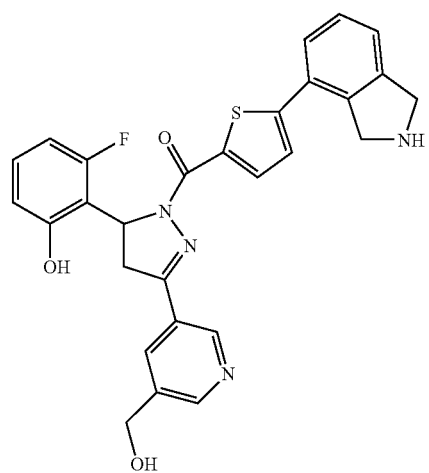
I-404
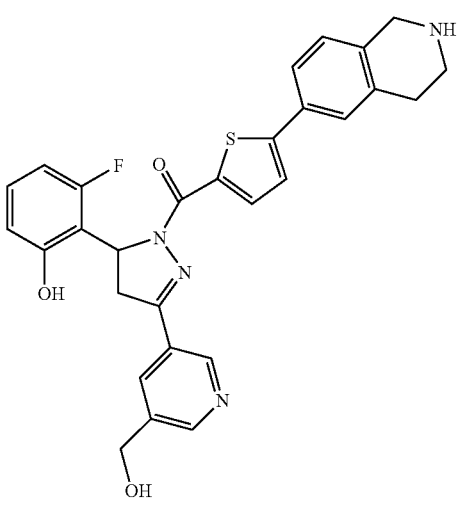
TABLE 1-continued
Raf Kinase Inhibitors
I-405
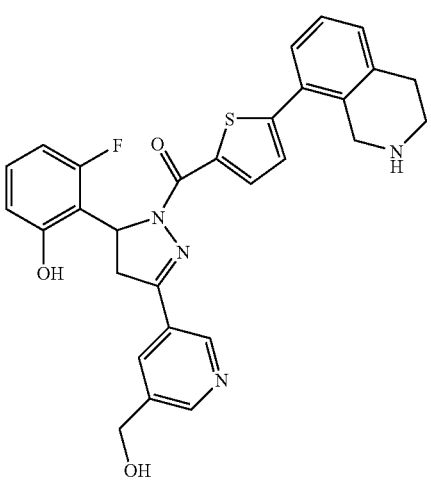
I-406
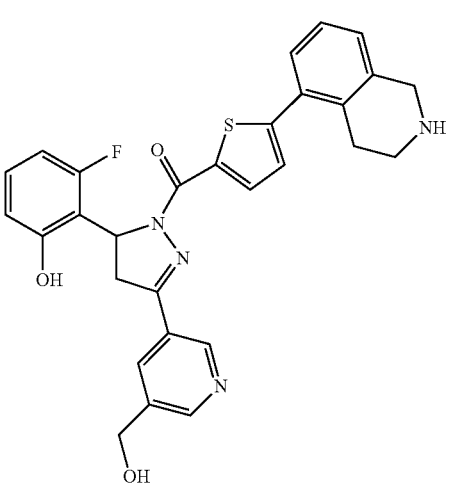
I-407
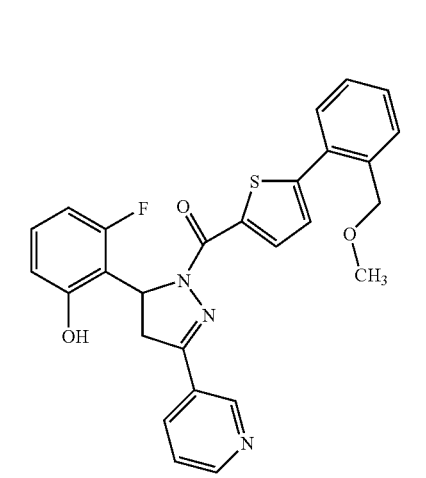

TABLE 1-continued
Raf Kinase Inhibitors
I-408
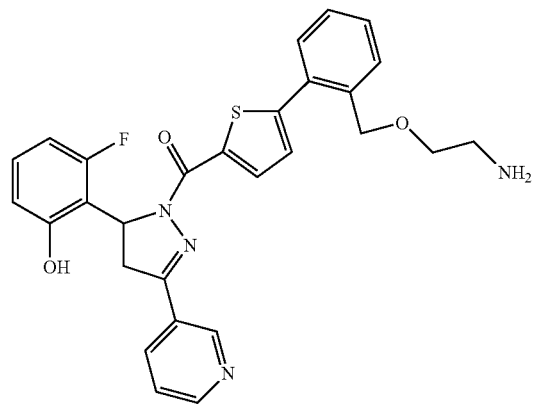
I-409
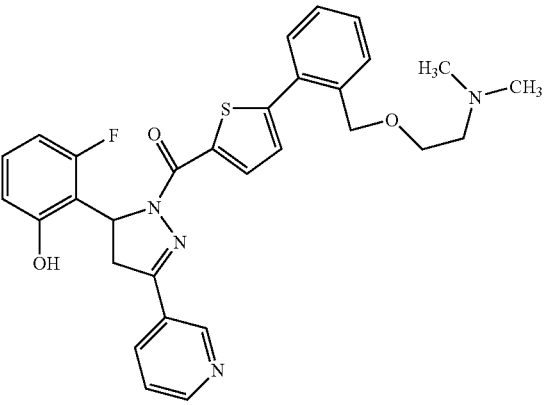
I-410
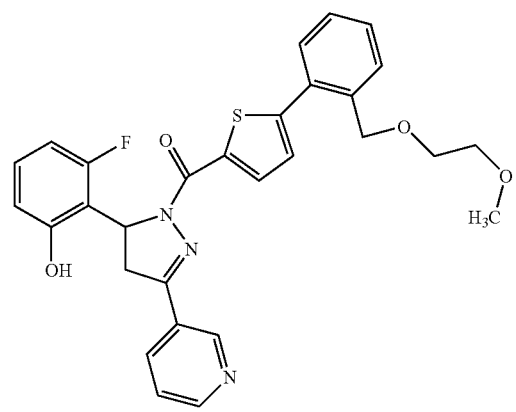
TABLE 1-continued
Raf Kinase Inhibitors
I-411
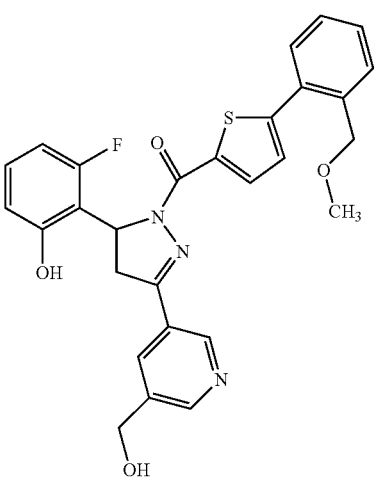
I-412
I-413
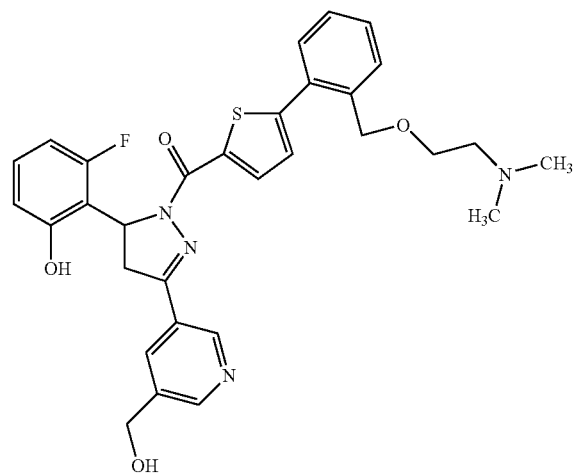

TABLE 1-continued
Raf Kinase Inhibitors
I-414
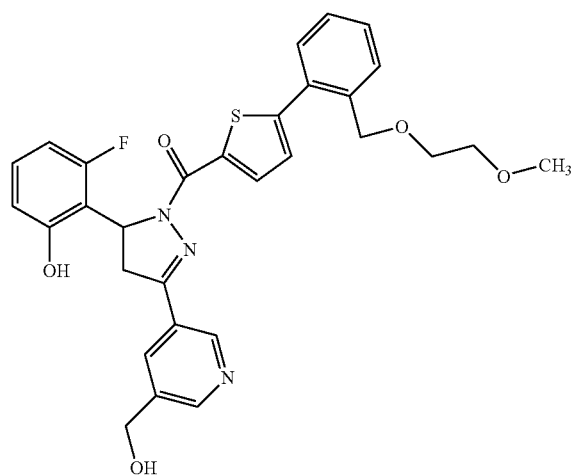
I-415
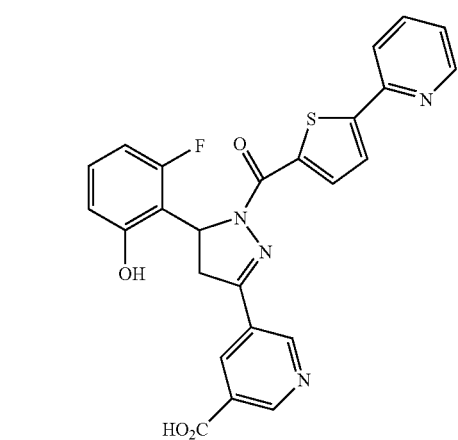
I-416
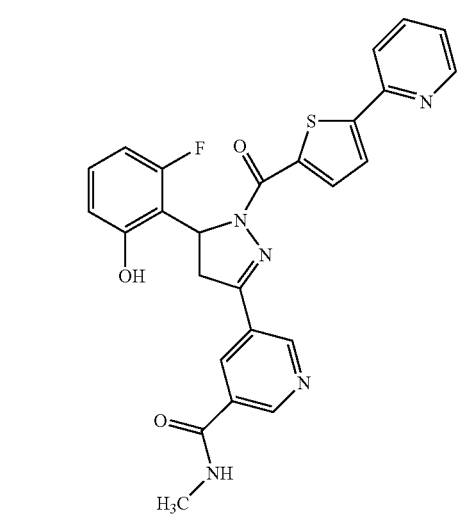
TABLE 1-continued
Raf Kinase Inhibitors
I-417
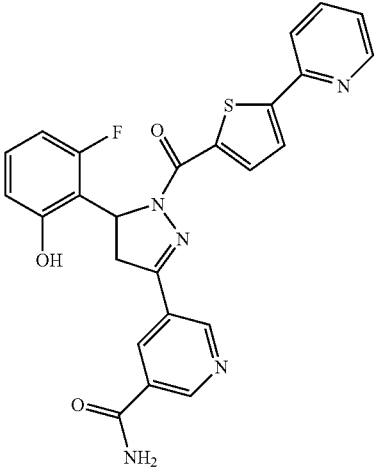
I-418
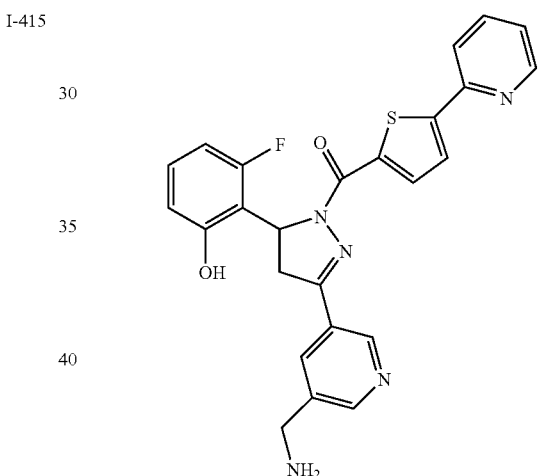
I-419
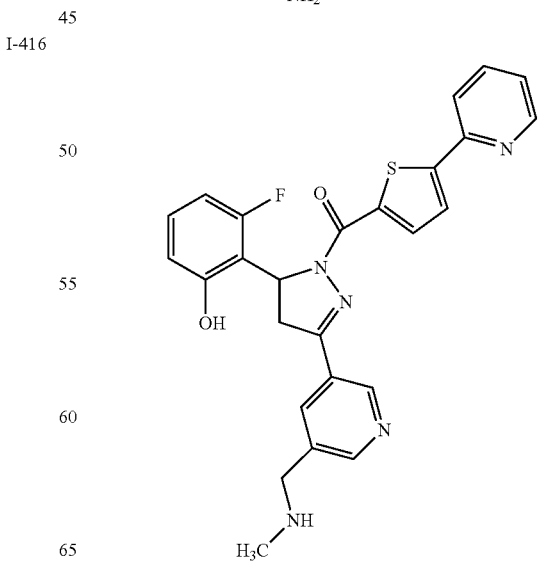

TABLE 1-continued
Raf Kinase Inhibitors
I-420
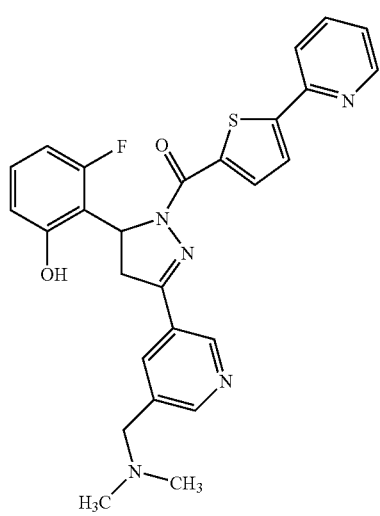
I-421
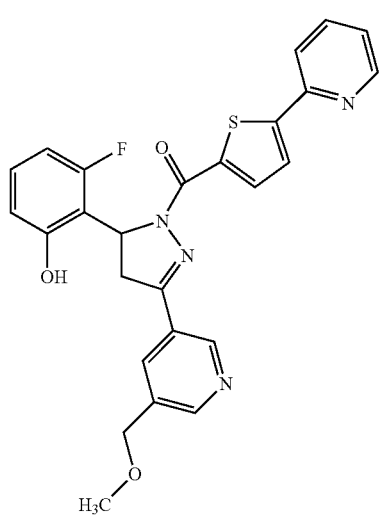
TABLE 1-continued
Raf Kinase Inhibitors
I-422
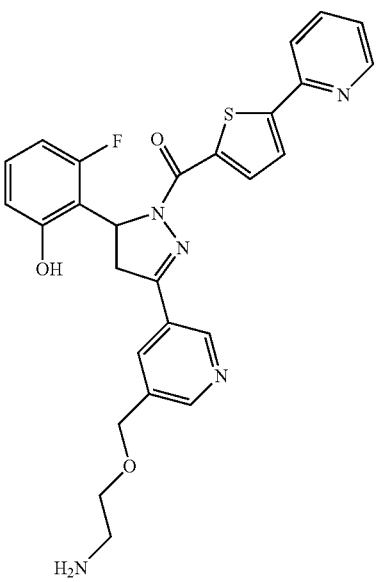
I-423
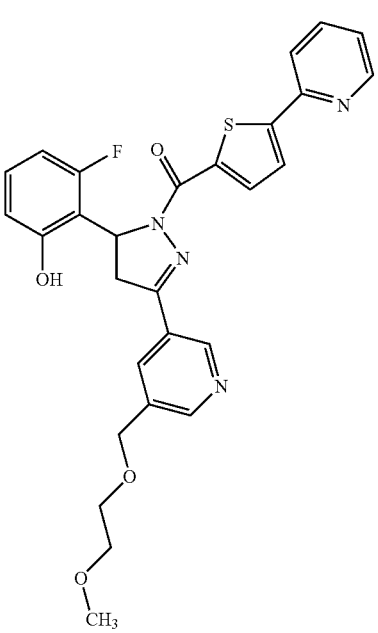

TABLE 1-continued

Raf Kinase Inhibitors

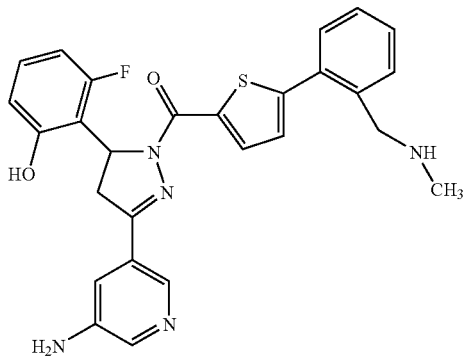

I-422

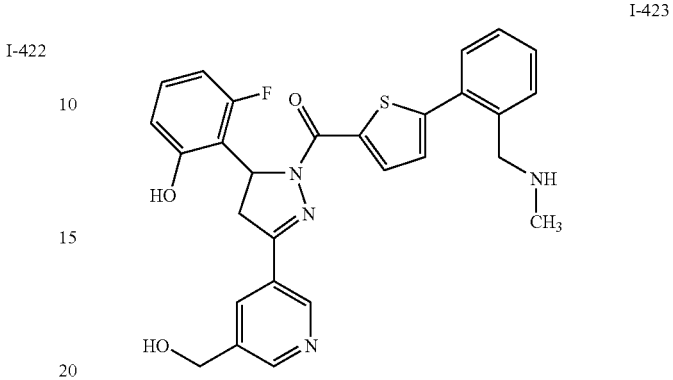

I-423

The compounds in Table 1 above also may be identified by the following chemical names:

TABLE 2

Chemical Names

| | Chemical Name |
|---|---|
| I-1 | 2-{3-pyridin-3-yl-1-[(2-pyridin-4-yl-1,3-thiazol-5-yl)carbonyl]-4,5-dihydro-1H-pyrazol-5-yl}phenol |
| I-2 | 2-[1-({5-[3-(aminomethyl)phenyl]-2-thienyl}carbonyl)-3-pyridin-3-yl-4,5-dihydro-1H-pyrazol-5-yl]phenol |
| I-3 | 2-[1-(3-phenoxybenzoyl)-3-pyridin-3-yl-4,5-dihydxo-1H-pyrazol-5-yl]phenol |
| I-4 | 2-(1-{[1-(6-methylpyridin-2-yl)-1H-imidazol-4-yl]carbonyl}-3-pyridin-3-yl-4,5-dihydro-1H-pyrazol-5-yl)phenol |
| I-5 | 2-{1-[5-(piperidin-1-ylmethyl)-2-furoyl]-3-pyridin-3-yl-4,5-dihydro-1H-pyrazol-5-yl}phenol |
| I-6 | 2-(1-{[5-(1-methyl-1H-pyrazol-4-yl)-2-thienyl]carbonyl}-3-pyridin-3-yl-4,5-dihydro-1H-pyrazol-5-yl)phenol |
| I-7 | 2-(1-{[5-(3-methylphenyl)-2-thienyl]carbonyl}-3-pyridin-3-yl-4,5-dihydro-1H-pyrazol-5-yl)phenol |
| I-8 | 2-{3-pyrazin-2-yl-1-[(5-pyridin-2-yl-2-thienyl)carbonyl]-4,5-dihydro-1H-pyrazol-5-yl}phenol |
| I-9 | 2-(1-{[5-(phenylsulfonyl)-2-thienyl]sulfonyl}-3-pyridin-3-yl-4,5-dihydro-1H-pyrazol-5-yl)phenol |
| I-10 | N-[(3-{[5-(2-hydroxyphenyl)-3-pyridin-3-yl-4,5-dihydro-1H-pyrazol-1-yl]carbonyl})-2-furyl)methyl]-5-methyl-2-furamide |
| I-11 | 5-fluoro-2-{3-pyridin-3-yl-1-[(5-pyridin-2-yl-2-thienyl)carbonyl]-4,5-dihydro-1H-pyrazol-5-yl}phenol |
| I-12 | 4-{[5-(2-hydroxyphenyl)-3-pyridin-3-yl-4,5-dihydro-1H-pyrazol-1-yl]carbonyl}-1-(4-methoxyphenyl)pyrrolidin-2-one |
| I-13 | 2-(1-{[5-(4-hydroxyphenyl)isoxazol-3-yl]carbonyl}-3-pyridin-3-yl-4,5-dihydro-1H-pyrazol-5-yl)phenol |
| I-14 | 2-(1-{[2-(1-methyl-1H-pyrazol-4-yl)-1,3-thiazol-5-yl]carbonyl}-3-pyridin-3-yl-4,5-dihydro-1H-pyrazol-5-yl)phenol |
| I-15 | 2-{1-[5-(phenylethynyl)-2-furoyl]-3-pyridin-3-yl-4,5-dihydro-1H-pyrazol-5-yl}phenol |
| I-16 | 5-(2-hydroxyphenyl)-N-[(1R,2S)-2-phenylcyclopropyl]-3-pyridin-3-yl-4,5-dihydro-1H-pyrazole-1-carboxamide |
| I-17 | 4-(5-{[5-(2-hydroxyphenyl)-3-pyridin-3-yl-4,5-dihydro-1H-pyrazol-1-yl]carbonyl}-1,3-thiazol-2-yl)benzamide |
| I-18 | 2-{1-[(5-{2-[(ethylamino)methyl]phenyl}-2-thienyl)carbonyl]-3-pyridin-3-yl-4,5-dihydro-1H-pyrazol-5-yl}phenol |
| I-19 | 4-(5-{[5-(2-hydroxyphenyl)-3-pyridin-3-yl-4,5-dihydro-1H-pyrazol-1-yl]carbonyl}-1,3-thiazol-2-yl)benzonitrile |
| I-20 | 2-{1-[5-(4-methoxyphenyl)-2-furoyl]-3-pyridin-3-yl-4,5-dihydro-1H-pyrazol-5-yl}phenol |
| I-21 | 2-(1-{[5-(4-methoxyphenyl)isoxazol-3-yl]carbonyl}-3-pyridin-3-yl-4,5-dihydro-1H-pyrazol-5-yl)phenol |
| I-22 | 2-{1-[3-(cyclopentyloxy)-4-methoxybenzoyl]-3-pyridin-3-yl-4,5-dihydro-1H-pyrazol-5-yl}phenol |
| I-23 | 2-[3-pyridin-3-yl-1-({5-[2-(pyrrolidin-1-ylmethyl)phenyl]-2-thienyl}carbonyl)-4,5-dihydro-1H-pyrazol-5-yl]phenol |

TABLE 2-continued

Chemical Names

| | Chemical Name |
|---|---|
| I-24 | 2-{1-[3-(benzyloxy)-4-methoxybenzoyl]-3-pyridin-3-yl-4,5-dihydro-1H-pyrazol-5-yl}phenol |
| I-25 | 2-{3-pyridin-2-yl-1-[(5-pyridin-2-yl-2-thienyl)carbonyl]-4,5-dihydro-1H-pyrazol-5-yl}phenol |
| I-26 | 2-(1-{[5-(1,3-oxazol-5-yl)-2-thienyl]sulfonyl}-3-pyridin-3-yl-4,5-dihydro-1H-pyrazol-5-yl)phenol |
| I-27 | 1-(4-fluorobenzyl)-4-{[5-(2-hydroxyphenyl)-3-pyridin-3-yl-4,5-dihydro-1H-pyrazol-1-yl]carbonyl}pyrrolidin-2-one |
| I-28 | tert-butyl 4-[(5-{[5-(2-hydroxyphenyl)-3-pyridin-3-yl-4,5-dihydro-1H-pyrazol-1-yl]carbonyl}-2-thienyl)methyl]piperazine-1-carboxylate |
| I-29 | 2-{1-[5-(2-fluorophenyl)-2-furoyl]-3-pyridin-3-yl-4,5-dihydro-1H-pyrazol-5-yl}phenol |
| I-30 | 2-(1-{[5-(3,4-dimethoxyphenyl)isoxazol-3-yl]carbonyl}-3-pyridin-3-yl-4,5-dihydro-1H-pyrazol-5-yl)phenol |
| I-31 | 2-(1-{[3-(2-chlorophenyl)-1H-pyrazol-5-yl]carbonyl}-3-pyridin-3-yl-4,5-dihydro-1H-pyrazol-5-yl)phenol |
| I-32 | 2-(1-{5-[(3-methoxyphenoxy)methyl]-2-furoyl}-3-pyridin-3-yl-415-dihydro-1H-pyrazol-5-yl)phenol |
| I-33 | 2-[1-({5-[1-(2-morpholin-4-ylethyl)-1H-pyrazol-4-yl]-2-thienyl}carbonyl)-3-pyridin-3-yl-4,5-dihydro-1H-pyrazol-5-yl]phenol |
| I-34 | 2-(1-{[5-(1,3-benzodioxol-5-yl)isoxazol-3-yl]carbonyl}-3-pyridin-3-yl-4,5-dihydro-1H-pyrazol-5-yl)phenol |
| I-35 | 2-{1-[(5-methyl-1-phenyl-1H-pyrazol-4-yl)carbonyl]-3-pyridin-3-yl-4,5-dihydro-1H-pyrazol-5-yl}phenol |
| I-36 | 2-(1-{[2,5-dimethyl-1-(pyridin-4-ylmethyl)-1H-pyrrol-3-yl]carbonyl}-3-pyridin-3-yl-4,5-dihydro-1H-pyrazol-5-yl)phenol |
| I-37 | 2-(1-{[1-(phenylsulfonyl)-1H-indol-3-yl]carbonyl}-3-pyridin-3-yl-4,5-dihydro-1H-pyrazol-5-yl)phenol |
| I-39 | 2-{1-[3-(1H-pyrazol-1-yl)benzoyl]-3-pyridin-3-yl-4,5-dihydro-1H-pyrazol-5-yl}phenol |
| I-40 | 2-[1-({1-[2-(aminomethyl)phenyl]-1H-pyrazol-4-yl}carbonyl)-3-pyridin-3-yl-4,5-dihydro-1H-pyrazol-5-yl]phenol |
| I-41 | 3-{1-[4-(1H-benzimidazol-1-ylmethyl)benzoyl]-3-pyridin-3-yl-4,5-dihydro-1H-pyrazol-5-yl}phenol |
| 1-42 | N,N-dibenzyl-5-{[5-(2-hydroxyphenyl)-3-pyridin-3-yl-4,5-dihydro-1H-pyrazol-1-yl]carbonyl}-1-methyl-1H-pyrrole-2-sulfonamide |
| I-43 | 2-{1-[5-(4-chlorophenyl)-2-methyl-3-furoyl]-3-pyridin-3-yl-4,5-dihydro-1H-pyrazol-5-yl}phenol |
| I-44 | 2-{1-[2-methyl-5-(piperidin-1-ylsulfonyl)-3-furoyl]-3-pyridin-3-yl-4,5-dihydro-1H-pyrazol-5-yl}phenol |
| I-45 | 2-(1-{[5-(1H-pyrazol-4-yl)-2-thienyl]carbonyl}-3-pyridin-3-yl-4,5-dihydro-1H-pyrazol-5-yl)phenol |
| I-46 | 2-{1-[5-methyl-4-(pyrrolidin-1-ylmethyl)-2-furoyl]-3-pyridin-3-yl-4,5-dihydro-1H-pyrazol-5-yl}phenol |
| I-47 | 2-{1-[(5-phenyl-1,3-oxazol-4-yl)carbonyl]-3-pyridin-3-yl-4,5-dihydro-1H-pyrazol-5-yl}phenol |
| I-48 | 2-(1-{[4-(4-chlorophenyl)-2-thienyl]carbonyl}-3-pyridin-3-yl-4,5-dihydro-1H-pyrazol-5-yl)phenol |
| I-49 | 2-{1-[5-(morpholin-4-ylmethyl)-2-furoyl]-3-pyridin-3-yl-4,5-dihydro-1H-pyrazol-5-yl}phenol |
| I-50 | 4-(5-{[5-(2-hydroxyphenyl)-3-pyridin-3-yl-4,5-dihydro-1H-pyrazol-1-yl]carbonyl}-2-thienyl)benzoic acid |
| I-51 | 3-(5-{[5-(2-hydroxyphenyl)-3-pyridin-3-yl-4,5-dihydro-1H-pyrazol-1-yl]carbonyl}-2-thienyl)benzonitrile |
| I-52 | 2-{1-[5-methyl-4-(morpholin-4-ylmethyl)-2-furoyl]-3-pyridin-3-yl-4,5-dihydro-1H-pyrazol-5-yl}phenol |
| I-53 | 2-(1-{[5-(2-methylphenyl)-2-thienyl]carbonyl}-3-pyridin-3-yl-4,5-dihydro-1H-pyrazol-5-yl)phenol |
| I-54 | 2-{1-[5-(4-fluorophenyl)-2-methyl-3-furoyl]3-pyridin-3-yl-4,5-dihydro-1H-pyrazol-5-yl}phenol |
| I-56 | 2-[3-pyridin-3-yl-1-({5-[4-(pyrrolidin-1-ylmethyl)phenyl]-2-thienyl}carbonyl)-4,5-dihydro-1H-pyrazol-5-yl]phenol |
| I-57 | 2-[3-pyridin-3-yl-1-(4-pyridin-2-ylbenzoyl)-4,5-dihydro-1H-pyrazol-5-yl]phenol |
| I-58 | 2-(4-{[5-(2-hydroxyphenyl)-3-pyridin-3-yl-4,5-dihydro-1H-pyrazol-1-yl]carbonyl}-1H-pyrazol-1-yl)benzonitrile |
| I-59 | 3-{1-[2-methyl-5-(piperidin-1-ylsulfonyl)-3-furoyl]-3-pyridin-3-yl-4,5-dihydro-1H-pyrazol-5-yl}phenol |
| I-60 | 2-(1-{[5-(3-methoxyphenyl)isoxazol-3-yl]carbonyl}-3-pyridin-3-yl-4,5-dihydro-1H-pyrazol-5-yl)phenol |
| I-61 | 2-{1-[2-methyl-5-(morpholin-4-ylmethyl)-3-furoyl]-3-pyridin-3-yl-4,5-dihydro-1H-pyrazol-5-yl}phenol |
| I-62 | N-[(5-{[5-(2-hydroxyphenyl)-3-pyridin-3-yl-4,5-dihydro-1H-pyrazol-1-yl]carbonyl}-2-furyl)methyl]-2-methyl-3-furamide |
| I-63 | 2-{1-[(5-{4-[(4-ethylpiperazin-1-yl)methyl]phenyl}-2-thienyl)carbonyl]-3-pyridin-3-yl-4,5-dihydro-1H-pyrazol-5-yl}phenol |
| I-64 | 2-[-(5-phenyl-2-furoyl)-3-pyridin-3-yl-4,5-dihydro-1H-pyrazol-5-yl]phenol |

TABLE 2-continued

Chemical Names

| | Chemical Name |
|---|---|
| I-65 | 2-{3-pyridin-3-yl-1-[(2-pyridin-4-yl-1,3-thiazol-4-yl)carbonyl]-4,5-dihydro-1H-pyrazol-5-yl}phenol |
| I-66 | 2-{1-[5-(4-nitrophenyl)-2-furoyl]-3-pyridin-3-yl-4,5-dihydro-1H-pyrazol-5-yl}phenol |
| I-67 | 2-{3-pyridin-3-yl-1-[(2-pyridin-2-yl-1,3-thiazol-5-yl)carbonyl]-4,5-dihydro-1H-pyrazol-5-yl}phenol |
| I-68 | 2-{3-pyridin-3-yl-1-[3-(1H-tetrazol-1-yl)benzoyl]-4,5-dihydro-1H-pyrazol-5-yl}phenol |
| I-69 | 2-{1-[(5-phenyl-2-thienyl)carbonyl]-3-pyridin-3-yl-4,5-dihydro-1H-pyrazol-5-yl}phenol |
| I-70 | 2-(3-pyridin-3-yl-1-{[5-(1H-tetrazol-1-yl)-1H-pyrazol-4-yl]carbonyl}-4,5-dihydro-1H-pyrazol-5-yl)phenol |
| I-71 | 2-(1-{[3-(3,4-dimethoxyphenyl)-1H-pyrazol-5-yl]carbonyl}-3-pyridin-3-yl-4,5-dihydro-1H-pyrazol-5-yl)phenol |
| I-72 | 2-(1-{[5-(4-chlorophenyl)-1H-pyrrol-2-yl]carbonyl}-3-pyridin-3-yl-4,5-dihydro-1H-pyrazol-5-yl)phenol |
| I-73 | 2-{1-[2-methyl-5-(pyrrolidin-1-ylsulfonyl)-3-furoyl]-3-pyridin-3-yl-4,5-dihydro-1H-pyrazol-5-yl}phenol |
| I-74 | 2-[1-(2,2'-bithien-5-ylcarbonyl)-3-pyridin-3-yl-4,5-dihydro-1H-pyrazol-5-yl]phenol |
| I-75 | 2-{1-[(5-methyl-3-phenylisoxazol-4-yl)carbonyl]-3-pyridin-3-yl-4,5-dihydro-1H-pyrazol-5-yl}phenol |
| I-76 | 2-{3-pyridin-3-yl-1-[(5-pyridin-2-yl-2-thienyl)carbonyl]-4,5-dihydro-1H-pyrazol-5-yl}phenol |
| I-77 | 4-{[5-(2-hydroxyphenyl)-3-pyridin-3-yl-4,5-dihydro-1H-pyrazol-1-yl]carbonyl}-1-(3-methoxyphenyl)pyrrolidin-2-one |
| I-78 | 2{1-[(5-methyl-2-phenyl-1,3-oxazol-4-yl)acetyl]-3-pyridin-3-yl-4,5-dihydro-1H-pyrazol-5-yl}phenol |
| I-79 | 2-[1-({5-[4-(piperazin-1-ylmethyl)phenyl]-2-thienyl}carbonyl)-3-pyridin-3-yl-4,5-dihydro-1H-pyrazol-5-yl]phenol |
| I-80 | 2-{1-[(5-{2-[(isopropylamino)methyl]phenyl}-2-thienyl)carbonyl]-3-pyridin-3-yl-4,5-dihydro-1H-pyrazol-5-yl}phenol |
| I-81 | 2-(3-pyridin-3-yl-1-{[5-(2-thienyl)pyridin-3-yl]carbonyl}-4,5-dihydro-1H-pyrazol-5-yl)phenol |
| I-82 | 2-{3-pyridin-3-yl-1-[(1-pyridin-2-yl-1H-pyrazol-4-yl)carbonyl]-4,5-dihydro-1H-pyrazol-5-yl}phenol |
| I-83 | 2-{3-pyridin-3-yl-1-[(5-pyridin-4-yl-2-thienyl)carbonyl]-4,5-dihydro-1H-pyrazol-5-yl}phenol |
| I-84 | 2-{3-pyridin-3-yl-1-[4-(1H-pyrrol-1-yl)benzoyl]-4,5-dihydro-1H-pyrazol-5-yl}phenol |
| I-85 | 5-(2-hydroxyphenyl)-N-(2-phenoxyphenyl)-3-pyridin-3-yl-4,5-dihydro-1H-pyrazole-1-carboxamide |
| I-86 | 3-fluoro-2-{3-pyridin-3-yl-1-[(5-pyridin-2-yl-2-thienyl)carbonyl]-4,5-dihydro-1H-pyrazol-5-yl}phenol |
| I-87 | 2-(1-{5-[(benzylsulfanyl)methyl]-2-furoyl}-3-pyridin-3-yl-4,5-dihydro-1H-pyrazol-5-yl)phenol |
| I-88 | 2-{1-[5-methyl-4-(piperidin-1-ylmethyl)-2-furoyl]-3-pyridin-3-yl-4,5-dihydro-1H-pyrazol-5-yl}phenol |
| I-89 | 2-[3-pyridin-3-yl-1-(3-pyridin-2-ylbenzoyl)-4,5-dihydro-1H-pyrazol-5-yl]phenol |
| I-90 | 2-{1-[(4-methyl-2-pyrazin-2-yl-1,3-thiazol-5-yl)carbonyl]-3-pyridin-3-yl-4,5-dihydro-1H-pyrazol-5-yl}phenol |
| I-91 | 2-(1-{[5-(4-methylphenyl)isoxazol-3-yl]carbonyl}-3-pyridin-3-yl-4,5-dihydro-1H-pyrazol-5-yl)phenol |
| I-92 | 2-[1-({5-[4-(morpholin-4-ylmethyl)phenyl]-2-thienyl}carbonyl)-3-pyridin-3-yl-4,5-dihydro-1H-pyrazol-5-yl]phenol |
| I-93 | 2-{1-[(2'-fluorobiphenyl-3-yl)carbonyl]-3-pyridin-3-yl-4,5-dihydro-1H-pyrazol-5-yl}phenol |
| I-94 | 2-(1-{[5-(4-methylphenyl)-1H-pyrrol-2-yl]carbonyl}-3-pyridin-3-yl-4,5-dihydro-1H-pyrazol-5-yl)phenol |
| I-95 | 2-(1-{[2-(3-chlorophenyl)-1,3-thiazol-4-yl]carbonyl}-3-pyridin-3-yl-4,5-dihydro-1H-pyrazol-5-yl)phenol |
| I-96 | 2-{1-[(2-phenyl-1,3-thiazol-4-yl)carbonyl]-3-pyridin-3-yl-4,5-dihydro-1H-pyrazol-5-yl}phenol |
| I-97 | 2-(1,3-benzoxazol-2-ylamino)-5-{2-[5-(2-hydroxyphenyl)-3-pyridin-3-yl-4,5-dihydro-1H-pyrazol-1-yl]-2-oxoethyl}-1,5-dihydro-4H-imidazol-4-one |
| I-98 | 2-{1-[(2,4-diphenyl-1,3-thiazol-5-yl)acetyl]-3-pyridin-3-yl-4,5-dihydro-1H-pyrazol-5-yl}phenol |
| I-99 | 2-[1-({5-[2-(hydroxymethyl)phenyl]-2-thienyl}carbonyl)-3-pyridin-3-yl-4,5-dihydro-1H-pyrazol-5-yl]phenol |
| I-100 | 2-(3-pyridin-3-yl-1-{[5-(2-pyridin-2-ylethyl)-2-thienyl]carbonyl}-4,5-dihydro-1H-pyrazol-5-yl)phenol |
| I-101 | 2-{1-[(5-amino-1-phenyl-1H-pyrazol-4-yl)carbonyl]-3-pyridin-3-yl-4,5-dihydro-1H-pyrazol-5-yl}phenol |
| I-102 | 2-(1-{[5-(2-methyl-1,3-thiazol-4-yl)isoxazol-3-yl]carbonyl}-3-pyridin-3-yl-4,5-dihydro-1H-pyrazol-5-yl)phenol |
| I-103 | 2-{1-[(5-phenyl-1H-pyrrol-2-yl)carbonyl]-3-pyridin-3-yl-4,5-dihydro-1H-pyrazol-5-yl}phenol |
| I-104 | 2-(1-{[2-(2,3-dihydro-1-benzofuran-5-yl)-1,3-thiazol-4-yl]carbonyl}-3-pyridin-3-yl-4,5-dihydro-1H-pyrazol-5-yl)phenol |

TABLE 2-continued

Chemical Names

Chemical Name

I-105 2-(5-{[5-(2-hydroxyphenyl)-3-pyridin-3-yl-4,5-dihydro-1H-pyrazol-1-yl]carbonyl}-2-thienyl)benzaldehyde
I-106 2-[3-pyridin-3-yl-1-({5-[3-(pyrrolidin-1-ylmethyl)phenyl]-2-thienyl}carbonyl)-4,5-dihydro-1H-pyrazol-5-yl]phenol
I-107 N-(4-{[5-2-hydroxyphenyl)-3-pyridin-3-yl-4,5-dihydro-1H-pyrazol-1-yl]carbonyl}phenyl)-1-phenylmethanesulfonamide
I-108 2-(1-{[5-(6-methoxypyridin-3-yl)-2-thienyl]carbonyl}-3-pyridin-3-yl-4,5-dihydro-1H-pyrazol-5-yl)phenol
I-109 2-{1-[(5-phenylisoxazol-3-yl)carbonyl]-3-pyridin-3-yl-4,5-dihydro-1H-pyrazol-5-yl}phenol
I-110 2-{1-[(4-methyl-2-pyridin-3-yl-1,3-thiazol-5-yl)carbonyl]-3-pyridin-3-yl-4,5-dihydro-1H-pyrazol-5-yl}phenol
I-111 2-{1-[(4-methyl-2-phenyl-1,3-thiazol-5-yl)carbonyl]-3-pyridin-3-yl-4,5-dihydro-1H-pyrazol-5-yl}phenol
I-112 2-[1-(2-methyl-5-phenyl-3-furoyl)-3-pyridin-3-yl-4,5-dihydro-1H-pyrazol-5-yl]phenol
I-113 2-(1-{[3-(2,3-dihydro-1,4-benzodioxin-6-yl)-1H-pyrazol-5-yl]carbonyl}-3-pyridin-3-yl-4,5-dihydro-1H-pyrazol-5-yl)phenol
I-114 2-fluoro-6-{3-pyridin-3-yl-1-[(5-pyridin-2-yl-2-thienyl)carbonyl]-4,5-dihydro-1H-pyrazol-5-yl}phenol
I-115 1-(2,4-dimethylphenyl)-4-{[5-(2-hydroxyphenyl)-3-pyridin-3-yl-4,5-dihydro-1H-pyrazol-1-yl]carbonyl}pyrrolidin-2-one
I-116 2-(3-pyridin-3-yl-1-{[3-(2-thienyl)-1H-pyrazol-5-yl]carbonyl}-4,5-dihydro-1H-pyrazol-5-yl)phenol
I-117 2-(1-{[1-(4-methoxyphenyl)cyclopentyl]carbonyl}-3-pyridin-3-yl-4,5-dihydro-1H-pyrazol-5-yl)phenol
I-118 1-(2-furylmethyl)-4-{[5-(2-hydroxyphenyl)-3-pyridin-3-yl-4,5-dihydro-1H-pyrazol-1-yl]carbonyl}pyrrolidin-2-one
I-119 2-(1-{[1-(4-fluorophenyl)cyclopentyl]carbonyl}-3-pyridin-3-yl-4,5-dihydro-1H-pyrazol-5-yl)phenol
I-120 2-(3-pyridin-3-yl-1-{[(1S,2R)-2-pyridin-2-ylcyclopropyl]carbonyl}-4,5-dihydro-1H-pyrazol-5-yl)phenol
I-121 2-(1-{[2-(4-methylphenyl)-1,3-thiazol-4-yl]carbonyl}-3-pyridin-3-yl-4,5-dihydro-1H-pyrazol-5-yl)phenol
I-123 2-(1-{5-[(4-fluorophenoxy)methyl]-2-furoyl}-3-pyridin-3-yl-4,5-dihydro-1H-pyrazol-5-yl)phenol
I-125 2-(1-{[5-(2-chlorophenyl)-2-thienyl]carbonyl}-3-pyridin-3-yl-4,5-dihydro-1H-pyrazol-5-yl)phenol
I-126 2-{3-pyridin-3-yl-1-[(5-pyridin-2-yl-2-thienyl)sulfonyl]-4,5-dihydro-1H-pyrazol-5-yl}phenol
I-127 2-{1-[5-(1H-pyrazol-1-ylmethyl)-2-furoyl]-3-pyridin-3-yl-4,5-dihydro-1H-pyrazol-5-yl}phenol
I-128 2-(3-pyridin-3-yl-1-{[2-(2-thienyl)-1,3-thiazol-4-yl]carbonyl}-4,5-dihydro-1H-pyrazol-5-yl)phenol
I-129 2-(3-pyridin-3-yl-1-{[(1S,2S)-2-pyridin-4-ylcyclopropyl]carbonyl}-4,5-dihydro-1H-pyrazol-5-yl)phenol
I-130 2-(1-{[5-(3-hydroxyphenyl)isoxazol-3-yl]carbonyl}-3-pyridin-3-yl-4,5-dihydro-1H-pyrazol-5-yl)phenol
I-132 2-(1-{[5-(6-morpholin-4-ylpyridin-3-yl)-2-thienyl]carbonyl)-3-pyridin-3-yl-4,5-dihydro-1H-pyrazol-5-yl)phenol
I-133 2-{1-[3-methyl-5-(morpholin-4-ylmethyl)-2-furoyl]-3-pyridin-3-yl-4,5-dihydro-1H-pyrazol-5-yl}phenol
I-134 2-(1-{[5-(2-methyl-1,3-thiazol-4-yl)-2-thienyl]carbonyl}-3-pyridin-3-yl-4,5-dihydro-1H-pyrazol-5-yl)phenol
I-135 4-(5-{[5-(2-hydroxyphenyl)-3-pyridin-3-yl-4,5-dihydro-1H-pyrazol-1-yl]carbonyl}-2-thienyl)benzonitrile
I-136 N-[(5-{[5-(2-hydroxyphenyl)-3-pyridin-3-yl-4,5-dihydro-1H-pyrazol-1-yl]carbonyl}-2-thienyl)methyl]pyridine-2-carboxamide
I-137 2-(3-pyridin-3-yl-1-{[5-(pyrrolidin-1-ylmethyl)-2-thienyl]carbonyl}-4,5-dihydro-1H-pyrazol-5-yl)phenol
I-138 2-(1-{[5-(4-chlorophenyl)isoxazol-3-yl]carbonyl}-3-pyridin-3-yl-4,5-dihydro-1H-pyrazol-5-yl)phenol
I-139 2-{3-pyridin-3-yl-1-[(5-pyrimidin-5-yl-2-thienyl)carbonyl]-4,5-dihydro-1H-pyrazol-5-yl}phenol
I-140 2-(1-{[5-(2-furyl)isoxazol-3-yl]carbonyl}-3-pyridin-3-yl-4,5-dihydro-1H-pyrazol-5-yl)phenol
I-142 2-{1-[(1-benzyl-5-methyl-1H-1,2,3-triazol-4-yl)carbonyl]-3-pyridin-3-yl-4,5-dihydro-1H-pyrazol-5-yl}phenol
I-143 4-{[5-(3-hydroxyphenyl)-3-pyridin-3-yl-4,5-dihydro-1H-pyrazol-1-yl]carbonyl}-2,5-dimethyl-N-(2-thienylmethyl)furan-3-sulfonamide
I-144 2-(1-{[5-(3-chlorophenyl)-2-thienyl]carbonyl}-3-pyridin-3-yl-4,5-dihydro-1H-pyrazol-5-yl)phenol
I-145 2-(1-{[2-(4-methoxyphenyl)-1,3-thiazol-4-yl]cabonyl}-3-pyridin-3-yl-4,5-dihydro-1H-pyrazol-5-yl)phenol
I-146 3-fluoro-2-{1-[(3-phenyl-1H-pyrazol-5-yl)carbonyl]-3-pyridin-3-yl-4,5-dihydro-1H-pyrazol-5-yl}phenol TABLE 2-continued

| | Chemical Names |
|---|---|
| | Chemical Name |
| I-147 | 2-{1-[5-(4-chlorophenyl)-2-furoyl]-3-pyridin-3-yl-4,5-dihydro-1H-pyrazol-5-yl}phenol |
| I-148 | 2-{1-[2-methyl-5-(morpholin-4-ylsulfonyl)-3-furoyl]-3-pyridin-3-yl-4,5-dihydro-1H-pyrazol-5-yl}phenol |
| I-149 | N-biphenyl-2-yl-5-(2-hydroxyphenyl)-3-pyridin-3-yl-4,5-dihydro-1H-pyrazole-1-carboxamide |
| I-150 | 2-{1-[2-methyl-5-(4-methylphenyl)-3-furoyl]-3-pyridin-3-yl-4,5-dihydro-1H-pyrazol-5-yl}phenol |
| I-151 | 2-{5-[(5-phenyl-3-pyridin-3-yl-4,5-dihydro-1H-pyrazol-1-yl)carbonyl]-2-thienyl}pyridine |
| I-152 | 4-{[5-(2-hydroxyphenyl)-3-pyridin-3-yl-4,5-dihydro-1H-pyrazol-1-yl]carbonyl}-1-(2-methylphenyl)pyrrolidin-2-one |
| I-153 | 2-(3-pyridin-3-yl-1-{[5-(pyridin-2-ylethynyl)-2-thienyl]carbonyl}-4,5-dihydro-1H-pyrazol-5-yl)phenol |
| I-154 | 3-{[5-(2-hydroxyphenyl)-3-pyridin-3-yl-4,5-dihydro-1H-pyrazol-1-yl]carbonyl}-1-phenylpyrrolidin-2-one |
| I-155 | 2-{1-[5-(1-morpholin-4-ylethyl)-2-furoyl]-3-pyridin-3-yl-4,5-dihydro-1H-pyrazol-5-yl}phenol |
| I-156 | 2-{1-[(5-{2-[(methylamino)methyl]phenyl}-2-thienyl)carbonyl]-3-pyridin-3-yl-4,5-dihydro-1H-pyrazol-5-yl}phenol |
| I-158 | 2-{3-pyridin-3-yl-1-[(2-pyridin-3-yl-1,3-thiazol-4-yl)carbonyl]-4,5-dihydro-1H-pyrazol-5-yl}phenol |
| I-160 | N-[(4-{[5-(2-hydroxyphenyl)-3-pyridin-3-yl-4,5-dihydro-1H-pyrazol-1-yl]carbonyl}-2-furyl)methyl]-5-methyl-3-furamide |
| I-161 | 2-{1-[(5-phenylisoxazol-4-yl)carbonyl]-3-pyridin-3-yl-4,5-dihydro-1H-pyrazol-5-yl}phenol |
| I-162 | 2-{1-[5-(3-methoxyphenyl)-2-furoyl]-3-pyridin-3-yl-4,5-dihydro-1H-pyrazol-5-yl}phenol |
| I-163 | 4-fluoro-2-{3-pyridin-3-yl-1-[(5-pyridin-2-yl-2-thienyl)carbonyl]-4,5-dihydro-1H-pyrazol-5-yl}phenol |
| I-164 | 2-(5-{[5-(2-hydroxyphenyl)-3-pyridin-3-yl-4,5-dihydro-1H-pyrazol-1-y1]carbonyl}-2-thienyl)benzonitrile |
| I-165 | 2-[1-({2-[(4-methoxyphenyl)amino]-1,3-thiazol-4-yl}acetyl)-3-pyridin-3-yl-4,5-dihydro-1H-pyrazol-5-yl]phenol |
| I-166 | 3-chloro-2-{3-pyridin-3-yl-1-[(5-pyridin-2-yl-2-thienyl)carbonyl]-4,5-dihydro-1H-pyrazol-5-yl}phenol |
| I-167 | 2-(1-{[5-(1-propyl-1H-pyrazol-4-yl)-2-thienyl]carbonyl}-3-pyridin-3-yl-4,5-dihydro-1H-pyrazol-5-yl)phenol |
| I-168 | 2-{3-pyridin-3-yl-1-[5-(pyrrolidin-1-ylmethyl)-2-furoyl]-4,5-dihydro-1H-pyrazol-5-yl}phenol |
| I-169 | 2-(1-{[1-benzyl-2-(methylsulfanyl)-1H-imidazol-5-yl]carbonyl}-3-pyridin-3-yl-4,5-dihydro-1H-pyrazol-5-yl)phenol |
| I-170 | 2-[3-pyridin-3-yl-1-(5-pyridin-2-yl-2-furoyl)-4,5-dihydro-1H-pyrazol-5-yl]phenol |
| I-171 | 2-{1-[(6-morpholin-4-ylpyridin-3-yl)sulfonyl]-3-pyridin-3-yl-4,5-dihydro-1H-pyrazol-5-yl}phenol |
| I-172 | 2-(1-{[3-(4-fluorophenyl)-5-methylisoxazol-4-yl]carbonyl}-3-pyridin-3-yl-4,5-dihydro-1H-pyrazol-5-yl)phenol |
| I-173 | 2-{3-pyridin-3-yl-1-{(5-pyridin-3-yl-2-thienyl)carbonyl}-4,5-dihydro-1H-pyrazol-5-yl}phenol |
| I-174 | 2-(1-{[5-(2-hydroxyphenyl)isoxazol-3-yl]carbonyl}-3-pyridin-3-yl-4,5-dihydro-1H-pyrazol-5-yl)phenol |
| I-175 | 2-(1-{[5-(4-methylphenyl)-2-thienyl]carbonyl}-3-pyridin-3-yl-4,5-dihydro-1H-pyrazol-5-yl)phenol |
| I-176 | 2-{1-[5-(4-methylphenyl)-2-furoyl]-3-pyridin-3-yl-4,5-dihydro-1H-pyrazol-5-yl}phenol |
| I-177 | 2-{1-[(3-phenyl-1H-pyrazol-5-yl)carbonyl]-3-pyridin-3-yl-4,5-dihydro-1H-pyrazol-5-yl}phenol |
| I-178 | 2-(3-pyridin-3-yl-1-{[5-(1,2,3-thiadiazol-4-yl)-2-thienyl]sulfonyl}-4,5-dihydro-1H-pyrazol-5-yl)phenol |
| I-179 | 2-(1-{[2,5-dimethyl-1-(2-thienylmethyl)-1H-pyrrol-3-yl]carbonyl}-3-pyridin-3-yl-4,5-dihydro-1H-pyrazol-5-yl)phenol |
| I-180 | 2-[1-({5-[2-(aminomethyl)phenyl]-2-thienyl}carbonyl)-3-pyridin-3-yl-4,5-dihydro-1H-pyrazol-5-yl]-3-fluorophenol |
| I-181 | 3-methoxy-2-{3-pyridin-3-yl-1-[(5-pyridin-2-yl-2-thienyl)carbonyl]-4,5-dihydro-1H-pyrazol-5-yl}phenol |
| I-182 | 2-(1-{[2-(benzylamino)-1,3-thiazol-5-yl]carbonyl}-3-pyridin-3-yl-4,5-dihydro-1H-pyrazol-5-yl)phenol |
| I-183 | 4-{[5-(2-hydroxyphenyl)-3-pyridin-3-yl-4,5-dihydro-1H-pyrazol-1-yl]carbonyl}-1-phenylpyrrolidin-2-one |
| I-184 | 2-(1-{[3-(2-furyl)-1H-pyrazol-5-yl]carbonyl}-3-pyridin-3-yl-4,5-dihydro-1H-pyrazol-5-yl)phenol |
| I-185 | 3-{3-pyridin-3-yl-1-[(5-pyridin-2-yl-2-thienyl)carbonyl]-4,5-dihydro-1H-pyrazol-5-yl}phenol |
| I-186 | 2-{1-[(3-phenylisoxazol-5-yl)carbonyl]-3-pyridin-3-yl-4,5-dihydro-1H-pyrazol-5-yl}phenol |
| I-188 | 2-(1-{[3-(3-methylphenyl)-1H-pyrazol-5-yl]carbonyl}-3-pyridin-3-yl-4,5-dihydro-1H-pyrazol-5-yl)phenol |

TABLE 2-continued

Chemical Names

| | Chemical Name |
|---|---|
| I-190 | 2-(1-{[5-(4-chlorophenyl)-2-thienyl]carbonyl}-3-pyridin-3-yl-4,5-dihydro-1H-pyrazol-5-yl)phenol |
| I-191 | 2-(3-pyridin-3-yl-1-{5-[3-(trifluromethyl)phenyl]-2-furoyl}-4,5-dihydro-1H-pyrazol-5-yl)phenol |
| I-192 | 3-(3-pyridin-3-yl-1-{5-[3-(trifluromethyl)phenyl]-2-furoyl}-4,5-dihydro-1H-pyrazol-5-yl)phenol |
| I-193 | 2-[1-({5-[4-(aminomethyl)phenyl]-2-thienyl}carbonyl)-3-pyridin-3-yl-4,5-dihydro-1H-pyrazol-5-yl]phenol |
| I-194 | 2-[1-({5-[4-(hydroxymethyl)phenyl]-2-thienyl}carbonyl)-3-pyridin-3-yl-4,5-dihydro-1H-pyrazol-5-yl]phenol |
| I-195 | 2-[1-({5-[2-(aminomethyl)phenyl]-2-thienyl}carbonyl)-3-pyridin-3-yl-4,5-dihydro-1H-pyrazol-5-yl]phenol |
| I-196 | 2-[1-({5-[4-(aminomethyl)-2-methylphenyl]-2-thienyl}carbonyl)-3-pyridin-3-yl-4,5-dihydro-1H-pyrazol-5-yl]phenol |
| I-197 | 2-(5-{[5-(2-hydroxyphenyl)-3-pyridin-3-yl-4,5-dihydro-1H-pyrazol-1-yl]carbonyl}-2-thienyl)benzoic acid |
| I-198 | 2-[1-({5-[2-(aminomethyl)phenyl]-1H-pyrazol-3-yl}carbonyl)-3-pyridin-3-yl-4,5-dihydro-1H-pyrazol-5-yl]phenol |
| I-200 | 2-[1-({2-[2-(aminomethyl)phenyl]-1,3-thiazol-5-yl}carbonyl)-3-pyridin-3-yl-4,5-dihydro-1H-pyrazol-5-yl]phenol |
| I-201 | 3-fluoro-4-(5-{[5-(2-hydroxyphenyl)-3-pyridin-3-yl-4,5-dihydro-1H-pyrazol-1-yl]carbonyl}-2-thienyl)benzonitrile |
| I-202 | 2-[1-({5-[2-(aminomethyl)phenyl]-2-thienyl}carbonyl)-3-(6-aminopyridin-3-yl)-4,5-dihydro-1H-pyrazol-5-yl]phenol |
| I-203 | 2-(5{[5-(2-hydroxyphenyl)-3-pyridin-3-yl-4,5-dihydro-1H-pyrazol-1-yl]carbonyl}-2-thienyl)benzamide |
| I-204 | 2-[1-({1[2-(aminomethyl)phenyl]-1H-imidazol-4-yl}carbonyl)-3-pyridin-3-yl-4,5-dihydro-1H-pyrazol-5-yl]phenol |
| I-205 | 2-[1-({5-[2-(aminomethyl)phenyl]-2-thienyl)carbonyl)-3-pyrazin-2-yl-4,5-dihydro-1H-pyrazol-5-yl]phenol |
| I-207 | 2-(1-{[5-(6-piperazin-1-ylpyridin-3-yl)-2-thienyl]carbonyl}-3-pyridin-3-yl-4,5-dihydro-1H-pyrazol-5-yl)phenol |
| I-208 | 2-(1-{[5-(2-isopropylphenyl)-2-thienyl]carbonyl}-3-pyridin-3-yl-4,5-dihydro-1H-pyrazol-5-yl)phenol |
| I-209 | 5-(2-hydroxyphenyl)-N-[2-methoxy-5-(1-methyl-1-phenylethyl)pheny]-3-pyridin-3-yl-4,5-dihydro-1H-pyrazole-1-carboxamide |
| I-211 | 5-(2-hydroxyphenyl)-N-[2-(phenoxymethyl)phenyl]-3-pyridin-3-yl-4,5-dihydro-1H-pyrazole-1-carboxamide |
| I-212 | N-(3-{[ethyl(phenyl)amino]sulfonyl}-4-methylphenyl)-5-(2-hydroxyphenyl)-3-pyridin-3-yl-4,5-dihydro-1H-pyrazole-1-carboxamide |
| I-213 | N-[3-(4-bromo-1-methyl-1H-pyrazol-3-yl)phenyl]-5-(2-hydroxyphenyl)-3-pyridin-3-yl-4,5-dihydro-1H-pyrazole-1-carboxamide |
| I-214 | N-(2-benzylphenyl)-5-(2-hydroxyphenyl)-3-pyridin-3-yl-4,5-dihydro-1H-pyrazole-1-carboxamide |
| I-215 | 5-(2-hydroxyphenyl)-N-(6-phenoxypyridin-3-yl)-3-pyridin-3-yl-4,5-dihydro-1H pyrazole-1-carboxamide |
| I-216 | 5-(2-hydroxyphenyl)-N-[4-(1H-imidazol-1-yl)phenyl]-3-pyridin-3-yl-4,5-dihydro-1H-pyrazole-1-carboxamide |
| I-217 | 2-[1-({5-[2-(aminomethyl)phenyl]-2-thienyl}carbonyl)-3-(5-aminopyridin-3-yl)-4,5-dihydro-1H-pyrazol-5-yl]phenol |
| I-218 | 5-(2-hydroxyphenyl)-N-(4-methyl-2-phenylpyrimidin-5-yl)-3-pyridin-3-yl-4,5-dihydro-1H-pyrazole-1-carboxamide |
| I-219 | N-[5-(1,1-dimethylpropyl)-2-phenoxyphenyl]-5-(2-hydroxyphenyl)-3-pyridin-3-yl-4,5-dihydro-1H-pyrazole-1-carboxamide |
| I-220 | 5-(2-hydroxyphenyl)-N-(4-methoxybiphenyl-3-yl)-3-pyridin-3-yl-4,5-dihydro-1H-pyrazole-1-carboxamide |
| I-221 | 2-[1-({5-[4-(2-amino-1,1-dimethylethyl)phenyl]-2-thienyl}carbonyl)-3-pyridin-3-yl-4,5-dihydro-1H-pyrazol-5-yl]phenol |
| I-222 | 2-[1-({2-[2-(aminomethyl)phenyl]-1H-imidazol-5-yl}carbonyl)-3-pyridin-3-yl-4,5-dihydro-1H-pyrazol-5-yl]phenol |
| I-223 | 4-(5-{[5-(2-hydroxyphenyl)-3-pyridin-3-yl-4,5-dihydro-1H-pyrazol-1-yl]carbonyl}-2-thienyl)isoindolin-1-one |
| I-224 | N-[3-(2-chloro-6-fluorophenyl)-5-methylisoxazol-4-yl]-5-(2-hydroxyphenyl)-3-pyridin-3-yl-4,5-dihydro-1H-pyrazole-1-carboximde |
| I-225 | 5-(2-hydroxyphenyl)-N-[3-(2-methyl-1,3-thiazole-4-yl)phenyl]-3-pyridin-3-yl-4,5-dihydro-1H-pyrazole-1-carboxamide |
| I-226 | 3-fluoro-2-(3-pyridin-3-yl-1-{[5-(2H-tetrazol-5-yl)-2-thienyl]carbonyl}-4,5-dihydro-1H-pyrazol-5-yl)phenol |
| I-227 | 3-fluoro-2-{1-[(1-phenyl-1H-imidazol-4-yl)carbonyl]-3-pyridin-3-yl-4,5-dihydro-1H-pyrazol-5-yl}phenol |
| I-228 | N-[4-(1,1-dioxido-1,2-thiazinan-2-yl)phenyl]-5-(2-hydroxyphenyl)-3-pyridin-3-yl-4,5-dihydro-1H-pyrazole-1-carboxamide |
| I-229 | N-[2-(2,3-dimethylphenoxy)pyridin-3-yl]-5-(2-hydroxyphenyl)-3-pyridin-3-yl-4,5-dihydro-1H-pyrazole-1-carboxamide |

TABLE 2-continued

Chemical Names

| | Chemical Name |
|---|---|
| I-230 | 5-(2-hydroxyphenyl)-3-pyridin-3-yl-N-{6-[3-(trifluoromethyl)phenoxy]pyridin-3-yl}-4,5-dihydro-1H-pyrazole-1-carboxamide |
| I-231 | 2-[1-({5-[2-(2-aminoethyl)phenyl]-2-thienyl}carbonyl)-3-pyridin-3-yl-4,5-dihydro-1H-pyrazol-5-yl]phenol |
| I-232 | 3-fluoro-2-(3-pyridin-3-yl-1-{[5-(1,2,3,4-tetrahydroisoquinolin-6-yl)-2-thienyl]carbonyl}-4,5-dihydro-1H-pyrazol-5-yl)phenol |
| I-233 | 5-(2-hydroxyphenyl)-N-(3-methyl-1-phenyl-1H-pyrazol-5-yl)-3-pyridin-3-yl-4,5-dihydro-1H-pyrazole-1-carboxamide |
| I-234 | N-(4'-fluorobiphenyl-2-yl)-5-(2-hydroxyphenyl)-3-pyridin-3-yl-4,5-dihydro-1H-pyrazole-1-carboxamide |
| I-235 | 5-(2-hydroxyphenyl)-N-[3-(1,3-oxazol-5-yl)phenyl]-3-pyridin-3-yl-4,5-dihydro-1H-pyrazole-1-carboxamide |
| I-236 | N-[4-(4-chlorophenoxy)phenyl]-5-(2-hydroxyphenyl)-3-pyridin-3-yl-4,5-dihydro-1H-pyrazole-1-carboxamide |
| I-237 | 5-(2-hydroxyphenyl)-N-[4-(1,3-oxazol-5-yl)phenyl]-3-pyridin-3-yl-4,5-dihydro-1H-pyrazole-1-carboxamide |
| I-238 | (4S)-1-(2,4-dimethylphenyl)-4-{[5-(2-fluoro-6-hydroxyphenyl)-3-pyridin-3-yl-4,5-dihydro-1H-pyrazol-1-yl]carbonyl}pyrrolidin-2-one |
| I-240 | 5-(2-hydroxyphenyl)-N-{4-[4-methoxyphenyl)amino]phenyl}-3-pyridin-3-yl-4,5-dihydro-1H-pyrazole-1-carboxamide |
| I-241 | 2-[1-({5-[2-(aminomethyl)-4-fluorophenyl]-2-thienyl}carbonyl)-3-pyridin-3-yl-4,5-dihydro-1H-pyrazol-5-yl]phenol |
| I-242 | 2-[1-({5-[2-(aminomethyl)phenyl]-2-thienyl}carbonyl)-3-(6-aminopyridin-2-yl)-4,5-dihydro-1H-pyrazole-5-yl]phenol |
| I-243 | 5-(2-hydroxyphenyl)-N-(4-{[(5-methyl-1,3,4-thiadiazol-2-yl)amino]sulfonyl}phenyl)-3-pyridin-3-yl-4,5-dihydro-1H-pyrazole-1-carboxamide |
| I-244 | 2-[1-({5-[2-(aminomethyl)-4-methoxyphenyl]-2-thienyl}carbonyl)-3-pyridin-3-yl-4,5-dihydro-1H-pyrazole-5-yl]phenol |
| I-245 | N-[1-(4-chlorobenzyl)-5-oxopyrrolidin-3-yl]-5-(2-hydroxyphenyl)-3-pyridin-3-yl-4,5-dihydro-1H-pyrazole-1-carboxamide |
| I-246 | 3-fluoro-2-(1-{[5-(1-methyl-1H-pyrazol-4-yl)-2-thienyl]carbonyl}-3-pyridin-3-yl-4,5-dihydro-1H-pyrazol-5-yl)phenol |
| I-247 | 5-(2-hydroxyphenyl)-N-[4-(phenoxymethyl)-1,3-thiazol-2-yl]-3-pyridin-3-yl-4,5-dihydro-1H-pyrazole-1-carboxamide |
| I-248 | N-[3-(1,3-benzothiazol-2-yl)-2-thienyl]-5-(2-hydroxyphenyl)-3-pyridin-3-yl-4,5-dihydro-1H-pyrazole-1-carboxamide |
| I-249 | 5-(2-hydroxyphenyl)-3-pyridin-3-yl-N-[4-(1H-pyrrol-1-yl)phenyl]-4,5-dihydro-1H-pyrazole-1-carboxamide |
| I-250 | N-(4-cyclohexylphenyl)-5-(2-hydroxyphenyl)-3-pyridin-3-yl-4,5-dihydro-1H-pyrazole-1-carboxamide |
| I-251 | N-[(3S)-1-benzylpyrrolidin-3-yl]-5-(2-hydroxyphenyl)-3-pyridin-3-yl-4,5-dihydro-1H-pyrazole-1-carboxamide |
| I-252 | 2-(3-pyridin-3-yl-1-{[5-(1,2,3,4-tetrahydroisoquinolin-8-yl)-2-thienyl]carbonyl}-4,5-dihydro-1H-pyrazol-5-yl)phenol |
| I-253 | N-(4-benzylphenyl)-5-(2-hydroxyphenyl)-3-pyridin-3-yl-4,5-dihydro-1H-pyrazole-1-carboxamide |
| I-254 | N-(5-cyclobutyl-1H-pyrazol-3-yl)-5-(2-hydroxyphenyl)-3-pyridin-3-yl-4,5-dihydro-1H-pyrazole-1-carboxamide |
| I-255 | 5-(2-hydroxyphenyl)-N-[2-(1H-pyrazol-1-yl)phenyl]-3-pyridin-3-yl-4,5-dihydro-1H-pyrazole-1-carboxamide |
| I-256 | 5-(2-hydroxyphenyl)-N-(6-morpholin-4-ylpyridin-3-yl)-3-pyridin-3-yl-4,5-dihydro-1H-pyrazole-1-carboxamide |
| I-257 | 3-fluoro-2-[3-pyridin-3-yl-1-({5-[3-(pyrrolidin-1-ylmethyl)phenyl]-2-thienyl}carbonyl)-4,5-dihydro-1H-pyrazol-5-yl]phenol |
| I-258 | N-[3-(benzyloxy)phenyl]-5-(2-hydroxyhenyl)-3-pyridin-3-yl-4,5-dihydro-1H-pyrazol-1-carboxamide |
| I-259 | N-(2-{[cyclohexyl(methyl)amino]sulfonyl}phenyl)-5-(2-hydroxyphenyl)-3-pyridin-3-yl-4,5-dihydro-1H-pyrazole-1-carboxamide |
| I-260 | 2-(3-pyridin-3-yl-1-{[5-(1,2,3,4-tetrahydroisoquinolin-6-yl)-2-thienyl]carbonyl}-4,5-dihydro-1H-pyrazol-5-yl)phenol |
| I-261 | N-{4-[(2-chlorobenzyl)oxy]phenyl}-5-(2-hydroxyphenyl)-3-pyridin-3-yl-4,5-dihydro-1H-pyrazole-1-carboxamide |
| I-262 | 5-(2-hydroxyphenyl)-N-(4'-methoxybiphenyl-2-yl)-3-pyridin-3-yl-4,5-dihydro-1H-pyrazole-1-carboxamide |
| I-263 | 5-(2-hydroxyphenyl)-N-(2-phenylquinolin-4-yl)-3-pyridin-3-yl-4,5-dihydro-1H-pyrazole-1-carboxamide |
| I-264 | N-(3-benzoylphenyl)-5-(2-hydroxyphenyl)-3-pyridin-3-yl-4,5-dihydro-1H-pyrazole-1-carboxamide |
| I-265 | 5-(2-hydroxyphenyl)-N-[4-(4-methylphenoxy)phenyl]-3-pyridin-3-yl-4,5-dihydro-1H-pyrazole-1-carboxamide |
| I-266 | 5-(2-hydroxyphenyl)-N-{2-oxo-1-[4-(trifluoromethyl)benzyl]-1,2-dihydropyridin-3-yl}-3-pyridin-3-yl-4,5-dihydro-1H-pyrazole-1-carboxamide |
| I-267 | N-[4-(2,5-dimethoxybenzoyl)phenyl]-5-(2-hydroxyphenyl)-3-pyridin-3-yl-4,5-dihydro-1H-pyrazole-1-carboxamide |

TABLE 2-continued

Chemical Names

| | Chemical Name |
|---|---|
| I-268 | 2-(1-{[5-(4-bromophenyl)isoxazol-3-yl]carbonyl}-3-pyridin-3-yl-4,5-dihydro-1H-pyrazol-5-yl)phenol |
| I-269 | N-[2-(benzyloxy)phenyl]-5-(2-hydroxyphenyl)-3-pyridin-3-yl-4,5-dihydro-1H-pyrazole-1-carboxamide |
| I-270 | 5-(2-hydroxyphenyl)-N-[1-phenyl-5-(trifluoromethyl)-1H-pyrazol-4-yl]-3-pyridin-3-yl-4,5-dihydro-1H-pyrazole-1-carboxamide |
| I-271 | 5-(2-hydroxyphenyl)-N-{2-[(7-methyl-2,3-dihydro-1H-inden-4-yl)oxy]pyridin-3-yl}-3-pyridin-3-yl-4,5-dihydro-1H-pyrazole-1-carboxamide |
| I-272 | N-(2'-flurobiphenyl-3-yl)-5-(2-hydroxyphenyl)-3-pyridin-3-yl-4,5-dihydro-1H-pyrazole-1-carboxamide |
| I-273 | 2-{3-[5-(hydroxymethyl)pyridin-3-yl]-1-[(5-pyridin-2-yl-2-thienyl)carbonyl]-4,5-dihydro-1H-pyrazol-5-yl}phenol |
| I-274 | 3-fluoro-2-{3-pyridin-3-yl-1-[(2-pyridin-2-yl-1H-imidazol-5-yl)carbonyl]-4,5-dihydro-1H-pyrazol-5-yl}phenol |
| I-276 | 2-[1-({5-[4-(aminomethyl)-2-flurophenyl]-2-thienyl}carbonyl)-3-pyridin-3-yl-4,5-dihydro-1H-pyrazole-5-yl]phenol |
| I-277 | N-[2-(2,4-difluorophenoxy)pyridin-3-yl]-5-(2-hydroxyphenyl)-3-pyridin-3-yl-4,5-dihydro-1H-pyrazole-1-carboxamide |
| I-278 | N-[1-(3,4-dichlorobenzyl)-6-oxo-1,6-dihydropyridin-3-yl]-5-(2-hydroxyphenyl)-3-pyridin-3-yl-4,5-dihydro-1H-pyrazole-1-carboxamide |
| I-279 | 3-fluoro-2-{1-[(1-phenyl-1H-pyrazol-4-yl)carbonyl]-3-pyridin-3-yl-4,5-dihydro-1H-pyrazol-5-yl}phenol |
| I-280 | 2-[1-({5-[2-(aminomethyl)phenyl]-2-thienyl}carbonyl)-3-(5-methylpyridin-3-yl)-4,5-dihydro-1H-pyrazol-5-yl]phenol |
| I-281 | 2[1-({5-[4-(aminomethyl)phenyl]-2-thienyl}carbonyl)-3-pyridin-3-yl-4,5-dihydro-1H-pyrazol-5-yl]-3-fluorophenol |
| I-282 | 2-[1-({5-[2-(aminomethyl)phenyl]-2-thienyl}carbonyl)-3-(5-aminopyridin-3-yl)-4,5-dihydro-1H-pyrazol-5-yl]-3-flurophenol |
| I-283 | 3-fluoro-2-(3-pyridin-3-yl-1-{[5-(1,2,3,4-tetrahydroisoquinolin-5-yl)-2-thienyl]carbonyl}-4,5-dihydro-1H-pyrazol-5-yl)phenol |
| I-284 | N-{1-[3,5-bis(trifluoromethyl)benzyl]-2-oxo-1,2-dihydropyridin-3-yl}-5-(2-hydroxyphenyl)-3-pyridin-3-yl-4,5-dihydro-1H-pyrazole-1-carboxamide |
| I-285 | N-{4-[(4-chlorobenzyl)oxy]phenyl}-5-(2-hydroxyphenyl)-3-pyridin-3-yl-4,5-dihydro-1H-pyrazole-1-carboxamide |
| I-286 | N-(1,5-dimethyl-3-oxo-2-phenyl-2,3-dihydro-1H-pyrazol-4-yl)-5-(2-hydroxyphenyl)-3-pyridin-3-yl-4,5-dihydro-1H-pyrazole-1-carboxamide |
| I-287 | N-[2-(4-chlorobenzoyl)phenyl]-5-(2-hydroxyphenyl)-3-pyridin-3-yl-4,5-dihydro-1H-pyrazole-1-carboxamide |
| I-288 | N-[1-(2,4-dichlorobenzyl)-2-oxo-1,2-dihydropyridin-3-yl]-5-(2-hydroxyphenyl)-3-pyridin-3-yl-4,5-dihydro-1H-pyrazole-1-carboxamide |
| I-289 | 5-(2-hydroxyphenyl)-N-(4-methylbiphenyl-3-yl)-3-pyridin-3-yl-4,5-dihydro-1H-pyrazole-1-carboxamide |
| I-290 | 3-fluoro-2-{3-pyridin-3-yl-1-[(2-pyridin-2-yl-1,3-thiazol-4-yl)carbonyl]-4,5-dihydro-1H-pyrazol-5-yl}phenol |
| I-291 | N-(1-benzyl-3-tert-butyl-1H-pyrazol-5-yl)-5-(2-hydroxyphenyl)-3-pyridin-3-yl-4,5-dihydro-1H-pyrazole-1-carboxamide |
| I-292 | 5-(2-hydroxyphenyl)-N-(2-phenoxypyridin-3-yl)-3-pyridin-3-yl-4,5-dihydro-1H-pyrazole-1-carboxamide |
| I-294 | 3-fluoro-2-(3-pyridin-3-yl-1-{[5-(1,2,3,4-tetrahydroisoquinolin-8-yl)-2-thienyl]carbonyl}-4,5-dihydro-1H-pyrazol-5-yl)phenol |
| I-295 | N-(4-benzoylphenyl)-5-(2-hydroxyphenyl)-3-pyridin-3-yl-4,5-dihydro-1H-pyrazole-1-carboxamide |
| I-296 | 2-{3-(5-aminopyridin-3-yl)-1-[(5-pyridin-2-yl-2-thienyl)carbonyl]-4,5-dihydro-1H-pyrazol-5-yl}phenol |
| I-297 | 5-(2-hydroxyphenyl)-N-[3-(1H-pyrazol-1-yl)phenyl]-3-pyridin-3-yl-4,5-dihydro-1H-pyrazole-1-carboxamide |
| I-298 | 5-(2-hydroxyphenyl)-N-(4'-methylbiphenyl-4-yl)-3-pyridin-3-yl-4,5-dihydro-1H-pyrazole-1-carboxamide |
| I-299 | N-[2-(4-chlorophenoxy)-5-(trifluoromethyl)phenyl]-5-(2-hydroxyphenyl)-3-pyridin-3-yl-4,5-dihydro-1H-pyrazole-1-carboxamide |
| I-300 | N-{5-cloro-6-oxo-1-[3-(trifluromethyl)benzyl]-1,6-dihydropyridin-3-yl}-5-(2-hydroxyphenyl)-3-pyridin-3-yl-4,5-dihydro-1H-pyrazole-1-carboxamide |
| I-301 | 5-(2-hydroxyphenyl)-N-(4-{[5-methylisoxazole-3-yl)amino]sulfonyl}phenyl)-3-pyridin-3-yl-4,5-dihydro-1H-pyrazole-1-carboxamide |
| I-303 | 5-(2-hydroxyphenyl)-N-(5-phenyl-1,3,4-thiadiazol-2-yl)-3-pyridin-3-yl-4,5-dihydro-1H-pyrazole-1-carboxamide |
| I-304 | N-[4-(4-fluorophenoxy)phenyl]-5-(2-hydroxyphenyl)-3-pyridin-3-yl-4,5-dihydro-1H-pyrazole-1-carboxamide |
| I-305 | N-[5-chloro-1-(4-chlorobenzyl)-6-oxo-1,6-dihydropyridin-3-yl]-5-(2-hydroxyphenyl)-3-pyridin-3-yl-4,5-dihydro-1H-pyrazole-1-carboxamide |
| I-306 | 5-(2-hydroxyphenyl)-3-pyridin-3-yl-N-[4-(1H-1,2,4-triazol-1-yl)phenyl]-4,5-dihydro-1H-pyrazole-1-carboxamide |
| I-307 | 5-(2-hydroxyphenyl)-N-[2-(phenylsulfanyl)pyridin-3-yl]3-pyridin-3-yl-4,5-dihydro-1H-pyrazole-1-carboxamide |

TABLE 2-continued

Chemical Names

| | Chemical Name |
|---|---|
| I-308 | 3-fluoro-2-(1-{[5-(3-{[(2-hydroxyethyl)amino]methyl}phenyl)-2-thienyl]carbonyl}-3-pyridin-3-yl-4,5-dihydro-1H-pyrazol-5-yl)phenol |
| I-309 | 5-(2-hydroxyphenyl)-N-[1-methyl-3-(2-thienyl)-1H-pyrazol-5-yl]-3-pyridin-3-yl-4,5-dihydro-1H-pyrazole-1-carboxamide |
| I-310 | N-{5-[(dibenzylamino)sulfonyl]-1-methyl-1H-pyrrol-2-yl}-5-(2-hydroxyphenyl)-3-pyridin-3-yl-4,5-dihydro-1H-pyrazole-1-carboxamide |
| I-311 | 5-(2-hydroxyphenyl)-3-pyridin-3-yl-N-{4-[(pyrimidin-2-ylamino)sulfonyl]phenyl}-4,5-dihydro-1H-pyrazole-1-carboxamide |
| I-312 | 3-fluro-2-{3-pyridin-3-yl-1-[(1-pyridin-2-yl-1H-pyrazol-4-yl)carbonyl]-4,5-dihydro-1H-pyrazol-5-yl}phenol |
| I-313 | N-(1-benzylpiperidin-4-yl)-5-(2-hydroxyphenyl)-3-pyridin-3-yl-4,5-dihydro-1H-pyrazole-1-carboxamide |
| I-314 | 3-fluoro-2-{1-[(2-phenyl-1H-imidazol-5-yl)carbonyl]-3-pyridin-3-yl-4,5-dihydro-1H-pyrazol-5-yl}phenol |
| I-315 | benzyl 2-({[5-(2-hydroxyphenyl)-3-pyridin-3-yl-4,5-dihydro-1H-pyrazol-1-yl]carbonyl}amino)benzoate |
| I-316 | 5-(2-hydroxyphenyl)-N-[4-(phenylsulfonyl)-3-thienyl]-3-pyridin-3-yl-4,5-dihydro-1H-pyrazole-1-carboxamide |
| I-317 | N-[5-fluoro-2-(1H-imidazol-1-yl)phenyl]-5-(2-hydroxyphenyl)-3-pyridin-3-yl-4,5-dihydro-1H-pyrazole-1-carboxamide |
| I-318 | 2-[1-({5-[2-(aminomethyl)-4-(dimethylamino)phenyl]-2-thienyl}carbonyl)-3-pyridin-3-yl-4,5-dihydro-1H-pyrazol-5-yl]-3-fluorophenol |
| I-319 | 5-(2-hydroxyphenyl)-N-(4-phenoxyphenyl)-3-pyridin-3-yl-4,5-dihydro-1H-pyrazole-1-carboxamide |
| I-320 | 2-{3-(5-methylpyridin-3-yl)-1-[(5-pyridin-2-yl-2-thienyl)carbonyl]-4,5-dihydro-1H-pyrazol-5-yl}phenol |
| I-321 | 5-(2-hydroxyphenyl)-N-(1-phenylcyclopentyl)-3-pyridin-3-yl-4,5-dihydro-1H-pyrazole-1-carboxamide |
| I-322 | 5-(2-hydroxyphenyl)-3-pyridin-3-yl-N-{4-[(1,3-thiazol-2-ylamino)sulfonyl]phenyl}-4,5-dihydro-1H-pyrazole-1-carboxamide |
| I-323 | 5-(2-hydroxyphenyl)-N-(5-methyl-3-phenylisoxazol-4-yl)-3-pyridin-3-yl-4,5-dihydro-1H-pyrazole-1-carboxamide |
| I-325 | 3-fluoro-2-{1-[(5-{3-[(4-methylpiperazin-1-yl)methyl]phenyl}-2-thienyl)carbonyl]-3-pyridin-3-yl-4,5-dihydro-1H-pyrazol-5-yl}phenol |
| I-326 | 3-fluoro-2-{1-[(5-{3-[(methylamino)methyl]phenyl}-2-thienyl)carbonyl]-3-pyridin-3-yl-4,5-dihydro-1H-pyrazol-5-yl}phenol |
| I-327 | 5-(2-hydroxyphenyl)-N-[4-(iH-pyrazol-1-yl)phenyl]-3-pyridin-3-yl-4,5-dihydro-1H-pyrazole-1-carboxamide |
| I-328 | 5-(2-hydroxyphenyl)-N-(2-phenyl-1,3-thiazol-4-yl)-3-pyridin-3-yl-4,5-dihydro-1H-pyrazole-1-carboxamide |
| I-329 | N-[2-(2,4-dichlorophenoxy)phenyl]-5-(2-hydroxyphenyl)-3-pyridin-3-yl-4,5-dihydro-1H-pyrazole-1-carboxamide |
| I-330 | 2-(1-{[5-(2,3-dihydro-1H-isoindol-5-yl)-2-thienyl]carbonyl}-3-pyridin-3-yl-4,5-dihydro-1H-pyrazol-5-yl)phenol |
| I-331 | N-[3-(benzyloxy)-4-methoxyphenyl]-5-(2-hydroxyphenyl)-3-pyridin-3-yl-4,5-dihydro-1H-pyrazole-1-carboxamide |
| I-332 | 5-(2-hydroxyphenyl)-N-[4-(4-methylpiperazin-1-yl)phenyl]-3-pyridin-3-yl-4,5-dihydro-1H-pyrazole-1-carboxamide |
| I-333 | N-[5-chloro-1-(3-chlorobenzyl)-6-oxo-1,6-dihydropyridin-3-yl]-5-(2-hydroxyphenyl)-3-pyridin-3-yl-4,5-dihydro-1H-pyrazole-1-carboxamide |
| I-334 | N-[1-(3,4-difluorobenzyl)-6-oxo-1,6-dihydropyridin-3-yl]5-2(hydroxyphenyl)-3-pyridin-3-yl-4,5-dihydro-1H-pyrazole-1-carboxamide |
| I-335 | 5-(2-hydroxyphenyl)-N-[4-(4-methoxyphenyl)-3-methylisoxazol-5-yl]-3-pyridin-3-yl-4,5-dihydro-1H-pyrazole-1-carboxamide |
| I-336 | N-{4-[3,5-bis(trifluoromethyl)phenoxy]phenyl}-5-(2-hydroxyphenyl)-3-pyridin-3-yl-4,5-dihydro-1H-pyrazole-1-carboxamide |
| I-337 | 5-(2-hydroxyphenyl)-N-[3-(4-methylpiperazin-1-yl)phenyl]-3-pyridin-3-yl-4,5-dihydro-1H-pyrazole-1-carboxamide |
| I-338 | 5-(2-hydroxyphenyl)-N-{4-[(4-nitrophenyl)sulfanyl]phenyl}-3-pyridin-3-yl-4,5-dihydro-1H-pyrazole-1-carboxamide |
| I-339 | 5-(2-hydroxyphenyl)-3-pyridin-3-yl-N-(1-pyrimidin-2-ylpiperidin-4-yl)-4,5-dihydro-1H-pyrazole-1-carboxamide |
| I-340 | 3-fluoro-2-{1-[(5-{2-[(methylamino)methyl]phenyl}-2-thienyl)carbonyl]-3-pyridin-3-yl-4,5-dihydro-1H-pyrazol-5-yl}phenol |
| I-341 | N-(5-cyclohexyl-2-methoxyphenyl)-5-(2-hydroxyphenyl)-3-pyridin-3-yl-4,5-dihydro-1H-pyrazole-1-carboxamide |
| I-342 | N-(1-benzyl-1H-benzimidazol-2-yl)-5-(2-hydroxyphenyl)-3-pyridin-3-yl-4,5-dihydro-1H-pyrazole-1-carboxamide |
| I-343 | N-biphenyl-4-yl-5-(2-hydroxyphenyl)-3-pyridin-3-yl-4,5-dihydro-1H-pyrazole-1-carboxamide |
| I-344 | 5-(2-hydroxyphenyl)-N-(1-phenylcyclohexyl)-3-pyridin-3-yl-4,5-dihydro-1H-pyrazole-1-carboxamide |
| I-347 | 2-(1-{[5-(2,3-dihydro-1H-isoindol-4-yl)-2-thienyl]carbonyl}-3-pyridin-3-yl-4,5-dihydro-1H-pyrazol-5-yl)phenol |

TABLE 2-continued

Chemical Names

| | Chemical Name |
|---|---|
| I-348 | N-{2-[2-(5-bromo-2-methoxyphenyl)ethyl]-3-fluorophenyl}-5-(2-hydroxyphenyl)-3-pyridin-3-yl-4,5-dihydro-1H-pyrazole-1-carboxamide |
| I-349 | N-[1-(2-chlorobenzyl)-5-oxopyrrolidin-3-yl]-5-(2-hydroxyphenyl)-3-pyridin-3-yl-4,5-dihydro-1H-pyrazole-1-carboxamide |
| I-350 | 2-(3-pyridin-3-yl-1-{[5-(1,2,3,4-tetrahydroisoquinolin-5-yl)-2-thienyl]carbonyl}-4,5-dihydro-1H-pyrazol-5-yl)phenol |
| I-351 | N-(4'-flurobiphenyl-3-yl)-5-(2-hydroxyphenl)-3-pyridin-3-yl-4,5-dihydro-1H-pyrazole-1-carboxamide |
| I-352 | N-{2-[(2-cyanophenyl)sulfanyl]phenyl}-5-(2-hydroxyphenyl)-3-pyridin-3-yl-4,5-dihydro-1H-pyrazole-1-carboxamide |
| I-353 | N-(1-benzyl-1H-pyrazol-4-yl)-5-(2-hydroxyphenyl)-3-pyridin-3-yl-4,5-dihydro-1H-pyrazole-1-carboxamide |
| I-354 | N-(1,3-diphenyl-1H-pyrazol-5-yl)-5-(2-hydroxyphenyl)-3-pyridin-3-yl-4,5-dihydro-1H-pyrazole-1-carboxamide |
| I-355 | 2-[1-({5-[3-({[2-(dimethylamino)ethyl]amino}methyl)phenyl]-2-thienyl}carbonyl)-3-pyridin-3-yl-4,5-dihydro-1H-pyrazol-5-yl]-3-fluorophenol |
| I-356 | 2-[1-({5-[2-(aminomethyl)-4-chlorophenyl]-2-thienyl}carbonyl)-3-pyridin-3-yl-4,5-dihydro-1H-pyrazol-5-yl]phenol |
| I-357 | N-[4-(4-chlorophenyl)-1,2,3-thiadiazol-5-yl]-5-(2-hydroxyphenyl)-3-pyridin-3-yl-4,5-dihydro-1H-pyrazole-1-carboxamide |
| I-358 | N-[1-(3,4-dichlorobenzyl)-2-oxo-1,2-dihydropyridin-3-yl]-5-(2-hydroxyphenyl)-3-pyridin-3-yl-4,5-dihydro-1H-pyrazole-1-carboxamide |
| I-359 | 5-(2-hydroxyphenyl)-N-[2-(2-methylphenoxy)phenyl]-3-pyridin-3-yl-4,5-dihydro-1H-pyrazole-1-carboxamide |
| I-360 | N-[4-(benzyloxy)phenyl]-5-(2-hydroxyphenyl)-3-pyridin-3-yl-4,5-dihydro-1H-pyrazole-1-carboxamide |
| I-361 | N-[(1R,2R)-2-(benzyloxy)cyclopentyl]-5-(2-hydroxyphenyl)-3-pyridin-3-yl-4,5-dihydro-1H-pyrazole-1-carboxamide |
| I-362 | 5-(2-hydroxyphenyl)-N-{6-oxo-1-[4-(trifluoromethyl)benzyl]-1,6-dihydropyridin-3-yl}-3-pyridin-3-yl-4,5-dihydro-1H-pyrazole-1-carboxamide |
| I-364 | N-[1-(2-chloro-6-flurobenzyl)-2-oxo-1,2-dihydropyridin-3-yl]-5-(2-hydroxyphenyl)3-pyridin-3-yl-4,5-dihydro-1H-pyrazole-1-carboxamide |
| I-365 | N-(4-benzoyl-2-nitrophenyl)-5-(2-hydroxyphenyl)-3-pyridin-3-yl-4,5-dihydro-1H-pyrazole-1-carboxamide |
| I-366 | N-[1-(4-chlorophenyl)cyclohexyl]-5-(2-hydroxyphenyl)-3-pyridin-3-yl-4,5-dihydro-1H-pyrazole-1-carboxamide |
| I-367 | 5-(2-hydroxyphenyl)-3-pyridin-3-yl-N-[4'-(trifluoromethyl)biphenyl-2-yl]-4,5-dihydro-1H-pyrazole-1-carboxamide |
| I-368 | 5-(2-hydroxyphenyl)-N-[4-(4-methoxyphenyl)-1,2,3-thiadiazol-5-yl]-3-pyridin-3-yl-4,5-dihydro-1H-pyrazole-1-carboxamide |
| I-369 | 2-{3-(5-aminopyridin-3-yl)-1-[(5-pyridin-2-yl-2-thienyl)carbonyl]-4,5-dihydro-1H-pyrazol-5-yl}-3-fluorophenol |
| I-370 | 2-[1-({5-[4-(aminomethyl)-2-chlorophenyl]-2-thienyl}carbonyl)-3-pyridin-3-yl-4,5-dihydro-1H-pyrazol-5-yl]phenol |
| I-371 | 2-[1-({5-[2-(aminomethyl)phenyl]-2-thienyl}carbonyl)-3-(5-fluoropyridin-3-yl)-4,5-dihydro-1H-pyrazol-5-yl]phenol |
| I-372 | 5-(2-hydroxyphenyl)-N-(5-methyl-1-phenyl-1H-pyrazol-4-yl)-3-pyridin-3-yl-4,5-dihydro-1H-pyrazole-1-carboxamide |
| I-373 | N-[2-(1,3-dioxo-1,3-dihydro-2H-isoindol-2-yl)phenyl]-5-(2-hydroxyphenyl)-3-pyridin-3-yl-4,5-dihydro-1H-pyrazole-1-carboxamide |
| I-374 | 5-(2-hydroxyphenyl-N-(1-methyl-3-phenyl-1H-pyrazol-5-yl)-3-pyridin-3-yl-4,5-dihydro-1H-pyrazole-1-carboxamide |
| I-376 | 5-(2-hydroxyphenyl)-N-{6-oxo-1-[3-(trifluoromethyl)benzyl]-1,6-dihydropyridin-3-yl}-3-pyridin-3-yl-4,5-dihydro-1H-pyrazole-1-carboxamide |
| I-377 | 2-(3-pyridin-3-yl-1-{[5-(1,2,3,4-tetrahydroisoquinolin-7-yl)-2-thienyl)carbonyl}-4,5-dihydro-1H-pyrazol-5-yl)phenol |
| I-378 | 2-[1-({2-[2-(aminomethyl)phenyl]-1,3-thiazol-4-yl}carbonyl)-3-pyridin-3-yl-4,5-dihydro-1H-pyrazol-5-yl]phenol |
| I-379 | N-(5-{5-(2-hydroxyphenyl)-1-[(5-pyridin-2-yl-2-thienyl)carbonyl]-4,5-dihydro-1H-pyrazol-3-yl}pyridin-3-yl)acetamide |
| I-380 | 5-(2-hydroxyphenyl)-N-[2-(phenylsulfonyl)phenyl]-3-pyridin-3-yl-4,5-dihydro-1H-pyrazole-1-carboxamide |
| I-381 | 2-[1-({5-[3-(aminomethyl)pyridin-4-yl]-2-thienyl}carbonyl)-3-pyridin-3-yl-4,5-dihydro-1H-pyrazol-5-yl]phenol |
| I-382 | N-[(3R)-1-benzylpyrrolidin-3-yl]-5-(2-hydroxyphenyl)-3-pyridin-3-yl-4,5-dihydro-1H-pyrazole-1-carboxamide |
| I-383 | 5-(2-hydroxyphenyl)-N-{4-[(3-oxo-2,3-dihydro-4H-1,4-benzoxazin-4-yl)methyl]phenyl}-3-pyridin-3-yl-4,5-dihydro-1H-pyrazole-1-carboxamide |
| I-384 | N-{5-chloro-2-oxo-1-[4-(trifluoromethyl)benzyl]-1,2-dihydropyridin-3-yl}-5-(2-hydroxyphenyl)-3-pyridin-3-yl-4,5-dihydro-1H-pyrazole-1-carboxamide |
| I-385 | 5-(2-hydroxyphenyl)-N-[2-(4-methylphenyl)quinolin-4-yl]-3-pyridin-3-yl-4,5-dihydro-1H-pyrazole-1-carboxamide |
| I-386 | N-[3-(cyclopentyloxy)-4-methoxyphenyl]-5-(2-hydroxyphenyl)-3-pyridin-3-yl-4,5-dihydro-1H-pyrazole-1-carboxamide |

TABLE 2-continued

Chemical Names

Chemical Name

I-387 5-(2-hydroxyphenyl)-N-[6-(IH-pyrazol-1-yl)pyridin-3-yl]-3-pyridin-3-yl-4,5-dihydro-1H-pyrazole-1-carboxamide I-388 5-(2-hydroxyphenyl)-N-(4-morpholin-4-ylphenyl)-3-pyridin-3-yl-4,5-dihydro-1H-pyrazole-1-carboxamide I-389 3-fluoro-2-(3-pyridin-3-yl-1-{[5-(1,2,3,4-tetrahydroisoquinolin-7-yl)-2-thienyl]carbonyl}-4,5-dihydro-1H-pyrazol-5-yl)phenol I-390 2-[1-({5-[2-(aminomethyl)phenyl]-2-thienyl}carbonyl)-3-pyridin-3-yl-4,5-dihydro-1H-pyrazol-5-yl]-3-chlorophenol I-391 (1S,2R,5S)-2-isopropyl-5-methylcyclohexyl 2-({[5-(2-hydroxyphenyl)-3-pyridin-3-yl-4,5-dihydro-1H-pyrazol-1-yl]carbonyl}amino)benzoate I-392 3-fluoro-2-{3-[5-(hydroxymethyl)pyridin-3-yl]-1-[(1-phenyl-1H-imidazol-4-yl)carbonyl]-4,5-dihydro-1H-pyrazol-5-yl}phenol I-393 3-fluoro-2-(3-pyridin-3-yl-1-{[1-(1,2,3,4-tetrahydroisoquinolin-6-yl)-1H-imidazol-4-yl]carbonyl}-4,5-dihydro-1H-pyrazol-5-yl)phenol I-394 3-fluoro-2-(3-[5-(hydroxymethyl)pyridin-3-yl]-1-{[1-(1,2,3,4-tetrahydroisoquinolin-6-yl)-1H-imidazol-4-yl]carbonyl}-4,5-dihydro-1H-pyrazol-5-yl)phenol I-395 2-[1-({1-[2-(aminomethyl)phenyl]-1H-imidazol-4-yl}carbonyl)-3-pyridin-3-yl-4,5-dihydro-1H-pyrazol-5-yl]-3-fluorophenol I-396 2-{1-({1-[2-(aminomethyl)phenyl]-1H-imidazol-4-yl}carbonyl)-3-[5-(hydroxymethyl)pyridin-3-yl]-4,5-dihydro-1H-pyrazol-5-yl}-3-fluorophenol I-397 2-(1-{[5-(2,3-dihydro-1H-isoindol-5-yl)-2-thienyl]carbonyl}-3-pyridin-3-yl-4,5-dihydro-1H-pyrazol-5-yl)-3-fluorophenol I-398 2-(1-{[5-(2,3-dihydro-1H-isoindol-4-yl)-2-thienyl]carbonyl}-3-pyridin-3-yl-4,5-dihydro-1H-pyrazol-5-yl)-3-fluorophenol I-399 3-fluoro-2-{1-[(1-phenyl-1H-pyrazol-3-yl)carbonyl]-3-pyridin-3-yl-4,5-dihydro-1H-pyrazol-5-yl}phenol I-400 3-fluoro-2-{3-pyridin-3-yl-1-[(1-pyridin-2-yl-1H-pyrazol-3-yl)carbonyl]-4,5-dihydro-1H-pyrazol-5-yl}phenol I-401 2-[1-({1-[2-(aminomethyl)phenyl]-1H-pyrazol-3-yl}carbonyl)-3-pyridin-3-yl-4,5-dihydro-1H-pyrazol-5-yl]-3-fluorophenol I-402 2-{1-{[5-(2,3-dihydro-1H-isoindol-5-yl)-2-thienyl]carbonyl}-3-[5-(hydroxymethyl)pyridin-3-yl]-4,5-dihydro-1H-pyrazol-5-yl}-3-fluorophenol I-403 2-{1-{[5-(2,3-dihydro-1H-isoindol-4-yl)-2-thienyl]carbonyl}-3-[5-(hydroxymethyl)pyridin-3-yl]-4,5-dihydro-1H-pyrazol-5-yl}-3-flurophenol I-404 3-fluro-2-(3-[5-(hydroxymethyl)pyridin-3-yl]-1-{[5-(1,2,3,4-tetrahydroisoquinolin-6-yl)-2-thienyl]carbonyl}-4,5-dihydro-1H-pyrazol-5-yl)phenol I-405 3-fluro-2-(3-[5-(hydroxymethyl)pyridin-3-yl]-1-{[5-(1,2,3,4-tetrahydroisoquinolin-8-yl)-2-thienyl]carbonyl}-4,5-dihydro-1H-pyrazol-5-yl)phenol I-406 3-fluro-2-(3-[5-(hydroxymethyl)pyridin-3-yl]-1-{[5-(1,2,3,4-tetrahydroisoquinolin-5-yl)-2-thienyl]carbonyl}4,5-dihydro-1H-pyrazol-5-yl)phenol I-407 3-fluoro-2-[1-({5-[2-(methoxymethyl)phenyl]-2-thienyl}carbonyl)-3-pyridin-3-yl-4,5-dihydro-1H-pyrazol-5-yl]phenol I-408 2-{1-[(5-{2-[(2-aminoethoxy)methyl]phenyl}-2-thienyl)carbonyl]-3-pyridin-3-yl-4,5-dihydro-1H-pyrazol-5-yl}-3-flurophenol I-409 2-(1-{[5-(2-{[2-(dimethylamino)ethoxy]methyl}phenyl)-2-thienyl]carbonyl}-3-pyridin-3-yl-4,5-dihydro-1H-pyrazol-5-yl)-3-fluorophenol I-410 3-fluoro-2-{1-[(5-{2-[(2-methoxyethoxy)methyl]phenyl}-2-thienyl)carbonyl]-3-pyridin-3-yl-4,5-dihydro-1H-pyrazol-5-yl}phenol I-411 3-fluoro-2-[3-[5-(hydroxymethyl)pyridin-3-yl]-1-(1{-[2-(methoxymethyl)phenyl]-2-thienyl}carbonyl)-4,5-dihydro-1H-pyrazol-5-yl]phenol
{2-f 1-1(5-f 2-II(2-aminoethoxy)methyl]phenyl}-2-thienyl)carbonyl]-3-[5-

I-412 2-{1-[(5-{2-[(2-aminoethoxy)methyl]phenyl}-2-thienyl)carbonyl]-3-[5-(hydroxymethyl)pyridin-3-yl]-4,5-dihydro-1H-pyrazol-5-yl}-3-fluorophenol I-413 2-{1-{[5-(2-{[2-(dimethylamino)ethoxy]methyl}phenyl)-2-thienyl]carbonyl}-3-[5-(hydroxymethyl)pyridin-3-yl]-4,5-dihydro-1H-pyrazol-5-yl}-3-fluorophenol I-414 3-fluoro-2-{3-[5-(hydroxymethyl)pyridin-3-yl]-1-[(5-{2-[(2-methoxyethoxy)methyl]phenyl}-2-thienyl)carbonyl]-4,5-dihydro-1H-pyrazol-5-yl}phenol I-415 5-{5-(2-fluoro-6-hydroxyphenyl)-1-[(5-pyridin-2-yl-2-thienyl)carbonyl]-4,5-dihydro-1H-pyrazol-3-yl}nicotinic acid I-416 5-{5-(2-fluoro-6-hydroxyphenyl)-1-[(5-pyridin-2-yl-2-thienyl)carbonyl]-4,5-dihydro-1H-pyrazol-3-yl}-N-methylnicotinamide I-417 5-{5-(2-fluoro-6-hydroxyphenyl)-1-[(5-pyridin-2-yl-2-thienyl)carbonyl]-4,5-dihydro-1H-pyrazol-3-yl}nicotinamide I-418 2-{3-[5-(aminomethyl)pyridin-3-yl]-1-[(5-pyridin-2-yl-2-thienyl)carbonyl]-4,5-dihydro-1H-pyrazol-5-yl}-3-fluorophenol I-419 3-fluoro-2-{3-{5-[(methylamino)methyl]pyridin-3-yl}-1-[(5-pyridin-2-yl-2-thienyl)carbonyl]4,5-dihydro-1H-pyrazol-5-yl}phenol I-420 2-{3-{5-[(dimethylamino)methyl]pyridin-3-yl}-1-[(5-pyridin-2-yl-2-thienyl)carbonyl]-4,5-dihydro-1H-pyrazol-5-yl}-3-fluorophenol I-421 3-fluoro-2-{3-[5-(methoxymethyl)pyridin-3-yl]-1-[(5-pyridin-2-yl-2-thienyl)carbonyl]-4,5-dihydro-1H-pyrazol-5-yl}phenol I-422 2-{3-{5-[(2-aminoethoxy)methyl]pyridin-3-yl}-1-[(5-pyridin-2-yl-2-thienyl)carbonyl]4,5-dihydro-1H-pyrazol-5-yl}-3-flurophenol TABLE 2-continued Chemical Names

| | Chemical Name |
|---|---|
| I-423 | 3-fluro-2-{3-{5-[(2-methoxyethoxy)methyl]pyridin-3-yl}-1-[(5-pyridin-2-yl-2-thienyl)carbonyl]-4,5-dihydro-1H-pyrazol-5-yl}phenol |
| I-424 | 2-{3-(5-aminopyridin-3-yl)-1-[(5-{2-[(methylamino)methyl]phenyl}-2-thienyl)carbonyl]-4,5-dihydro-1H-pyrazol-5-yl}-3-flurophenol |
| I-425 | 3-fluoro-2-{3-[5-(hydroxymethyl)pyridin-3-yl]-1-[(5-{2-[(methylamino)-methyl]phenyl}-2-thienyl)carbonyl]-4,5-dihydro-1H-pyrazol-5-yl}phenol |

The compounds of the present invention can be prepared by methods known to one of ordinary skill in the art and/or by reference to the schemes shown below and the synthetic examples that follow. Exemplary synthetic routes are set forth in Schemes 1 and 2 below, and in the Examples.

Scheme 1

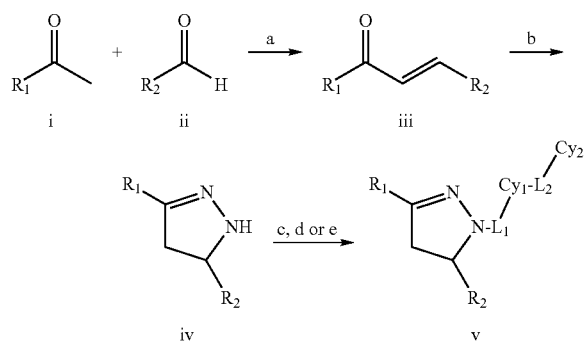

Reaction conditions:
(a) 2.5M NaOH, 0° C., 2 hr; or piperidine, 100° C., 1 hr;
(b) $H_2N-NH_2 \cdot H_2O$, EtOH, 80° C., overnight;
(c) EDCI, $HO_2C$-$Cy_1L_2Cy_2$, DCM, overnight;
(d) $ClO_2S$-$Cy_1L_2Cy_2$, pyridine, rt, 18 hr;
(e) OCN-$Cy_1L_2Cy_2$, DMF, DCE, rt, 20 hr.

Scheme 1 above shows a general route for preparing compounds of formula (I). Reaction of i and ii where $R_1$ and $R_2$ are appropriately substituted cycles, gives chalcone iii (a). Treatment with hydrazine monohydrate in EtOH gives pyrazoline iv (b). Compounds v are prepared by reacting iv with carboxylic acids to give amides (c), sulfonyl chlorides to give sulfonamides (d) and isocyanates to give substituted ureas (e).

Scheme 2

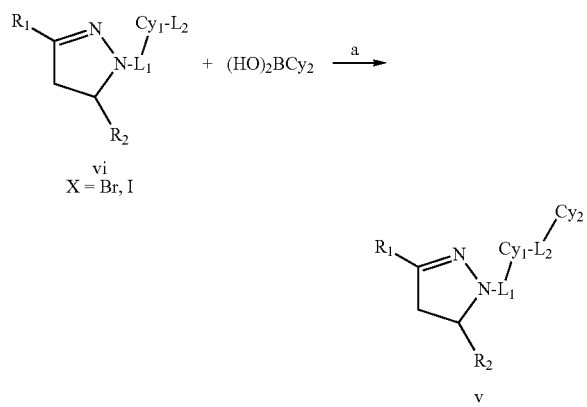

Reaction conditions:
(a) $Pd(PPh_3)_4$, DMF, MeOH, $H_2O$, MWI, 100° C., 15 mins.

Alternatively, compound v can be prepared by transition metal-mediated cross-coupling of compound vi with $Cy_2$-M, where M is a boronic acid, zinc, or tin moiety. For example, as depicted in Scheme 2, compound v can be prepared by Suzuki coupling of compound vi with a boronic acid derivative of $Cy_2$ in the presence of a palladium catalyst.

One of ordinary skill in the art will recognize that additional compounds of formula (I) may be prepared by methods analogous to those depicted above by changing the starting materials or reagents.

As discussed above, the present invention provides compounds that are inhibitors of Raf kinases. The compounds can be assayed in vitro or in vivo for their ability to bind to and/or inhibit a Raf kinase. In vitro assays include assays to determine inhibition of the ability of the kinase to phosphorylate a substrate protein or peptide. Alternate in vitro assays quantitate the ability of the compound to bind to the kinase. Inhibitor binding may be measured by radiolabelling the inhibitor prior to binding, isolating the inhibitor/kinase complex and determining the amount of radiolabel bound. Alternatively, inhibitor binding may be determined by running a competition experiment in which new inhibitors are incubated with the kinase bound to a known radioligand. The compounds also can be assayed for their ability to affect cellular or physiological functions mediated by protein kinase activity. Assays for each of these activities are described in the Examples and/or are known in the art.

In another aspect, therefore, the invention provides a method for inhibiting Raf kinase activity in a cell, comprising contacting a cell in which inhibition of a Raf kinase is desired with a compound of formula (I). In some embodiments, the compound of formula (I) interacts with and reduces the activity of more than one Raf kinase enzyme in the cell. By way of example, when assayed against B-Raf and C-Raf, some compounds of formula (I) show inhibition of both enzymes. In some embodiments, the compound of formula (I) is selective, i.e., the concentration of the compound that is required for inhibition of one Raf kinase enzymes is lower, preferably at least 2-fold, 5-fold, 10-fold, or 50-fold lower, than the concentration of the compound required for inhibition of another Raf kinase enzyme.

In some embodiments, the compound of formula (I) inhibits one or more Raf kinase enzymes at a concentration that is lower than the concentration of the compound required for inhibition of other, unrelated, kinase enzymes. In some other embodiments, in addition to inhibiting Raf kinase, the compound formula (I) also inhibits one or more other kinase enzymes, preferably other kinase enzymes involved in tumor cell proliferation.

The invention thus provides a method for inhibiting cell proliferation, comprising contacting a cell in which such inhibition is desired with a compound of formula (I). The phrase "inhibiting cell proliferation" is used to denote the ability of a compound of formula (I) to inhibit cell number or cell growth in contacted cells as compared to cells not contacted with the inhibitor. An assessment of cell proliferation can be made by counting cells using a cell counter or by an assay of cell viability, e.g., an MTT or WST assay. Where the cells are in a solid growth (e.g., a solid tumor or organ), such an assessment of cell proliferation can be made by measuring the growth, e.g., with calipers, and comparing the size of the growth of contacted cells with non-contacted cells.

Preferably, the growth of cells contacted with the inhibitor is retarded by at least about 50% as compared to growth of non-contacted cells. In various embodiments, cell proliferation of contacted cells is inhibited by at least about 75%, at least about 90%, or at least about 95% as compared to non-contacted cells. In some embodiments, the phrase "inhibiting cell proliferation" includes a reduction in the number of contacted cells, as compare to non-contacted cells. Thus, a kinase inhibitor that inhibits cell proliferation in a contacted cell may induce the contacted cell to undergo growth retardation, to undergo growth arrest, to undergo programmed cell death (i.e., apoptosis), or to undergo necrotic cell death.

In another aspect, the invention provides a pharmaceutical composition comprising a compound of formula (I) as defined above, or a pharmaceutically acceptable salt thereof, and a pharmaceutically acceptable carrier.

If pharmaceutically acceptable salts of the compounds of the invention are utilized in these compositions, the salts preferably are derived from inorganic or organic acids and bases. For reviews of suitable salts, see, e.g., Berge et al, J. Pharm. Sci. 66:1-19 (1977) and Remington: The Science and Practice of Pharmacy, 20th Ed., ed. A. Gennaro, Lippincott Williams & Wilkins, 2000.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, formate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include, without limitation, ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bioavailability modifiers and combinations of these.

Pharmaceutical formulations may be prepared as liquid suspensions or solutions using a liquid, such as, but not limited to, an oil, water, an alcohol, and combinations of these. Pharmaceutically suitable surfactants, suspending agents, or emulsifying agents, may be added for oral or parenteral administration. Suspensions may include oils, such as but not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The pharmaceutical compositions of the invention preferably are formulated for administration to a patient having, or at risk of developing or experiencing a recurrence of, a Raf kinase-mediated disorder. The term "patient", as used herein, means an animal, preferably a mammal, more preferably a human. Preferred pharmaceutical compositions of the invention are those formulated for oral, intravenous, or subcutaneous administration. However, any of the above dosage forms containing a therapeutically effective amount of a compound of the invention are well within the bounds of routine experimentation and therefore, well within the scope of the instant invention. In some embodiments, the pharmaceutical composition of the invention may further comprise another therapeutic agent. In some embodiments, such other therapeutic agent is one that is normally administered to patients with the disease or condition being treated.

By "therapeutically effective amount" is meant an amount sufficient to cause a detectable decrease in protein kinase activity or the severity of a Raf kinase-mediated disorder. The amount of Raf kinase inhibitor needed will depend on the effectiveness of the inhibitor for the given cell type and the length of time required to treat the disorder. It should also be understood that a specific dosage and treatment regimen for any particular patient will depend upon a variety of factors, including the activity of the specific compound employed, the age, body weight, general health, sex, and diet of the patient, time of administration, rate of excretion, drug combinations, the judgment of the treating physician, and the severity of the particular disease being treated. The amount of additional therapeutic agent present in a composition of this invention typically will be no more than the amount that would normally be administered in a composition comprising that therapeutic agent as the only active agent. Preferably, the amount of additional therapeutic agent will range from about 50% to about 100% of the amount normally present in a composition comprising that agent as the only therapeutically active agent.

In another aspect, the invention provides a method for treating a patient having, or at risk of developing or experiencing a recurrence of, a Raf kinase-mediated disorder. As used herein, the term "Raf kinase-mediated disorder" includes any disorder, disease or condition which is caused or characterized by an increase in Raf kinase expression or activity, or which requires Raf kinase activity. The term "Raf kinase-mediated disorder" also includes any disorder, disease or condition in which inhibition of Raf kinase activity is beneficial.

The Raf kinase inhibitors of the invention can be used to achieve a beneficial therapeutic or prophylactic effect, for example, in subjects with a proliferative disorder. Non-limiting examples of proliferative disorders include chronic inflammatory proliferative disorders, e.g., psoriasis and rheumatoid arthritis; proliferative ocular disorders, e.g., diabetic retinopathy; benign proliferative disorders, e.g., hemangiomas; and cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

Non-limiting examples of solid tumors that can be treated with the disclosed Raf kinase inhibitors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; skin cancer, including e.g., malignant melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; soft tissue sarcoma; and thyroid carcinoma.

Non-limiting examples of hematologic malignancies that can be treated with the disclosed Raf kinase inhibitors include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

The compounds of formula (I) are particularly useful in the treatment of cancers or cell types characterized by aberrant activation of the Ras-Raf-MEK-ERK pathway, including, without limitation, those characterized by an activating Ras and/or Raf mutation. In some embodiments, the compound or composition of the invention is used to treat a patient having or at risk of developing or experiencing a recurrence in a cancer selected from the group consisting of melanoma, colon, lung, breast, ovarian, sarcoma and thyroid cancer. In certain embodiments, the cancer is a melanoma.

In some embodiments, the Raf kinase inhibitor of the invention is administered in conjunction with another therapeutic agent. In some embodiments, the other therapeutic agent is one that is normally administered to patients with the disease or condition being treated. The Raf kinase inhibitor of the invention may be administered with the other therapeutic agent in a single dosage form or as a separate dosage form. When administered as a separate dosage form, the other therapeutic agent may be administered prior to, at the same time as, or following administration of the protein kinase inhibitor of the invention.

In some embodiments, a Raf kinase inhibitor of formula (I) is administered in conjunction with an anticancer agent. As used herein, the term "anticancer agent" refers to any agent that is administered to a subject with cancer for purposes of treating the cancer. Nonlimiting examples anticancer agents include: radiotherapy; immunotherapy; DNA damaging chemotherapeutic agents; and chemotherapeutic agents that disrupt cell replication.

Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide and related analogs (e.g., CC-5013 and CC-4047); protein tyrosine kinase inhibitors (e.g., imatinib mesylate and gefitinib); proteasome inhibitors (e.g., bortezomib); NF-.kappa.B inhibitors, including inhibitors of I.kappa.B kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

In order that this invention be more fully understood, the following preparative and testing examples are set forth. These examples illustrate how to make or test specific compounds, and are not to be construed as limiting the scope of the invention in any way.

EXAMPLES

| | Definitions |
|---|---|
| AcOH | acetic acid |
| ACN | acetonitrile |
| ATP | adenosine triphosphate |
| BCA | bicinchoninic acid |
| BSA | bovine serum albumin |
| BOC | tert-butoxycarbonyl |
| DCE | dichloroethane |
| DCM | dichloromethane |
| DIPEA | diisopropyl ethyl amine |
| DMEM | Dulbecco's Modified Eagle's Medium |
| DMF | N,N-dimethylformamide |
| DMSO | dimethylsulfoxide |
| DTT | dithiothreitol |
| dppf | diphenylphosphinoferrocene |
| EDCI | N-(3-dimethylaminopropyl)-N'-ethylcarbodiimide hydrochloride |
| EDTA | ethylenediaminetetraacetic acid |
| EtOAc | ethyl acetate |
| EtOH | ethanol |
| FA | formic acid |
| FBS | fetal bovine serum |
| h | hours |
| HEPES | N-(2-Hydroxyethyl)piperazine-N'-(2-ethanesulfonic acid) |
| HPLC | high performance liquid chromatography |
| HRMS | high resolution mass spectrum |
| LAH | lithium aluminum hydride |
| LCMS | liquid chromatography mass spectrum |
| m/z | mass to charge |
| Me | methyl |
| MeOH | methanol |

-continued

Definitions

| | |
|---|---|
| min | minutes |
| MS | mass spectrum |
| MTT | methylthiazoletetrazolium |
| MWI | microwave irradiation |
| PBS | phosphate buffered saline |
| PKA | cAMP-dependent protein kinase |
| RP-HPLC | reverse phase high performance liquid chromatography |
| rt | room temperature |
| TEA | triethylamine |
| TFFA | trifluoroacetic anhydride |
| THF | tetrahydrofuran |
| TMB | 3,3•,5,5•-Tetramethylbenzidine |
| WST | (4-[3-(4-iodophenyl)-2-(4-nitrophenyl)-2H-5-tetrazolio]-1,3-benzene disulfonate sodium salt) |

Analytical LC-MS Methods

LCMS Conditions

Spectra were run on a Phenominex Luna 5 μm C18 50×4.6 mm column on a Hewlett-Packard HP1100 using the following gradients:

Method Formic Acid (FA): Acetonitrile containing zero to 100 percent 0.1% formic acid in water (2.5 mL/min for a 3 minute run).

Method Formic Acid Long (FAL): Acetonitrile containing zero to 100 percent 0.1% formic acid in water (1.0 mL/min for a 16 minute run).

Method Nonpolar Formic Acid (NFA) Acetonitrile containing 70 to 100 percent 0.1% formic acid in water (2.5 mL/min for a 3 minute run).

Method Polar Ammonium Acetate (PAA): Acetonitrile containing zero to 50 percent 10 mM ammonium acetate in water (2.5 mL/min for a 3 minute run).

Method Ammonium Acetate (AA): Acetonitrile containing zero to 100 percent 10 mM ammonium acetate in water (2.5 mL/min for a 3 minute run).

Method Nonpolar Ammonium Acetate (NAA). Acetonitrile containing 70 to 100 percent 10 mM ammonium acetate in water (2.5 mL/min for a 3 minute run).

Example 1

Preparation of Intermediates and Reagents 2-chloro-6-hydroxybenzaldehyde

To a solution of 2-chloro-6-fluorobenzaldehyde (2.44 g, 15.4 mmol) in DMSO (20 mL) at 0° C. was added potassium hydroxide (2.23 g, 33.8 mmol) slowly. The reaction mixture was allowed to stir and warm to rt overnight and then diluted with water (65 mL). The mixture was acidified to pH<1 with conc. HCl. A white solid formed and was filtered, washed with water, and dried to give 2-chloro-6-hydroxybenzaldehyde (1.48 g, 61%). LCMS: (FA) ES-155.0.

1-(5-{[(4-methoxybenzyl)oxy]methyl}pyridin-3-yl)ethanone

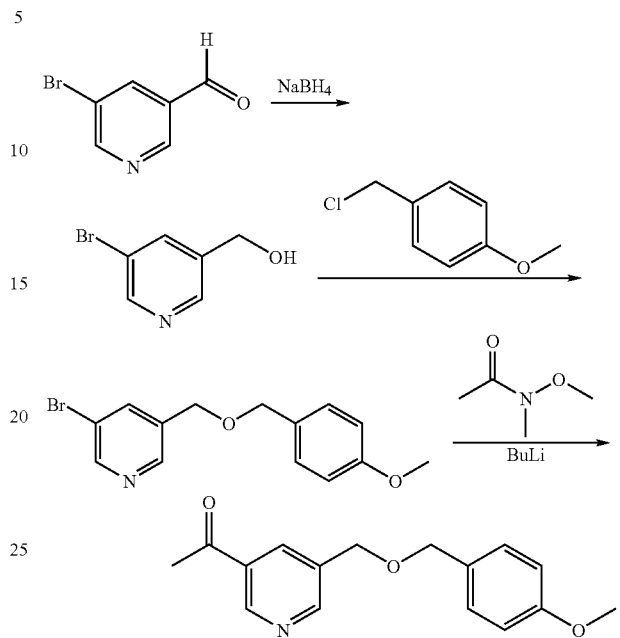

Step 1: (5-bromopyridin-3-yl)methanol

To a solution of 5-bromonicotinaldehyde (4.36 g, 23.4 mmol) in EtOH (90 mL) at 0° C. was added sodium borohydride (4.4 g, 120 mmol). The reaction mixture was allowed to stir and warm to rt overnight and then quenched by the addition of saturated aq. NH₄Cl. The mixture was concentrated to small volume and the residue was extracted with EtOAc. The organic solutions were combined, dried over Na₂SO₄, filtered and concentrated to give (4.21 g, 86%) as a light yellow oil which was used without purification. LCMS: (FA) ES+ 186.0.

Step 2: 3-bromo-5-{[(4-methoxybenzyl)oxy]methyl}pyridine

To a suspension of NaH (1.12 g, 28.0 mmol) in DMF (75 mL) was added a solution of (5-bromopyridin-3-yl)methanol (4.21 g, 22.4 mmol) in DMF (8 mL) at 0° C. The mixture was allowed to stir at 0° C. for 15 min and then 1-(chloromethyl)-4-methoxybenzene (5.41 g, 34.6 mmol) was added followed by tetra-N-butylammonium iodide (0.91 g, 2.4 mmol). The reaction mixture was allowed to vigorously stir and warm to rt overnight. The reaction mixture was partitioned between EtOAc and water. The aqueous solution was extracted with EtOAc. The organic solutions were combined, washed with brine, dried over Na₂SO₄, filtered and concentrated. The residue was purified by column chromatography to give 3-bromo-5-{[(4-methoxybenzyl)oxy]methyl}pyridine (4.40 g, 64%) as a yellow oil. LCMS: (FA) ES+ 308.1.

Step 3: 1-(5-{[(4-methoxybenzyl)oxy]methyl}pyridin-3-yl)ethanone

To a solution of 3-bromo-5-{[(4-methoxybenzyl)oxy]methyl}pyridine (4.4 mmol) in methyl t-butyl ether (20 mL)

was added n-BuLi (2.5M in hexane, 1.96 mL) dropwise at −78° C. The reaction mixture was allowed to stir for 15 min and then N-methoxy-N-methylacetamide (6.7 mmol) in methyl t-butyl ether (3 mL) was added dropwise. The reaction mixture was allowed to stir for 30 min at −78° C. and then diluted with water and allowed to warm to rt. After stirring for 30 min, the phases were separated and the aqueous solution was extracted with EtOAc. The organic solutions were combined, dried over Na₂SO₄, filtered and concentrated. The residue was purified by column chromatography to give 1-(5-{[(4-methoxybenzyl)oxy]methyl}pyridin-3-yl)ethanone (3.1 mmol, 70%) as a white solid. LCMS: (FA) ES+ 272.1.

N-(5-acetylpyridin-3-yl)acetamide

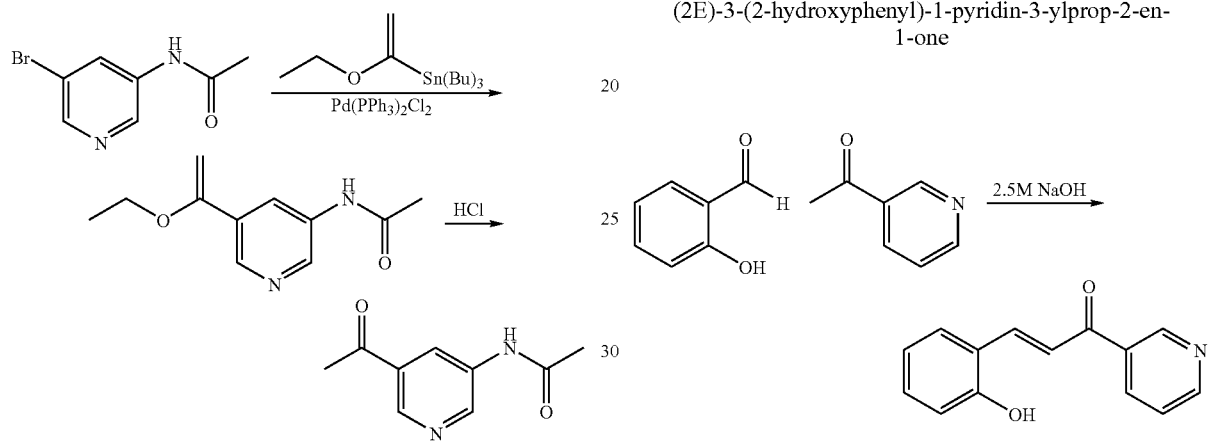

Step 1: N-[5-(1-ethoxyvinyl)pyridin-3-yl]acetamide

To a solution of N-(5-bromopyridin-3-yl)acetamide (2.7 mmol) and Pd(PPh₃)₂Cl₂ (0.13 mmol) in DMF (5 mL) under an atmosphere of nitrogen was added tributyl(1-ethoxyvinyl) stannane (2.97 mmol). The reaction was allowed to stir at 80° C. until for approximately 24 hrs. The reaction mixture was allowed to cool to rt and then diluted with aq KF solution (10 mL) and allowed to stir for 30 min. A thick white precipitate formed and was filtered. The filter cake was washed with water and Et₂O. The filtrate was diluted with water and extracted with Et₂O. The organic solutions were combined, dried over Na₂SO₄, filtered, and concentrated. The residue was purified by column chromatography to give N-[5-(1-ethoxyvinyl)pyridin-3-yl]acetamide in quantitative yield. LCMS: (FA) ES+ 205.2.

Step 2: N-(5-acetylpyridin-3-yl)acetamide

To a solution of N-[5-(1-ethoxyvinyl)pyridin-3-yl]acetamide (2.4 mmol) in acetone (9 mL) was added 1N HCl (1 mL). The reaction mixture was allowed to stir at rt overnight and then basified with sat NaHCO₃ and extracted with EtOAc. The organic solutions were combined, dried over Na₂SO₄, filtered, and concentrated. The residue was purified by column chromatography to give N-(5-acetylpyridin-3-yl)acetamide (0.180 g, 42%) as a white solid. LCMS: (FA) ES+ 179.1.

(2E)-3-(2-hydroxyphenyl)-1-pyridin-3-ylprop-2-en-1-one

To a vigorously stirred solution of salicylaldehyde (45 mL, 0.42 mol) in 2.5 M NaOH (330 mL) at 0° C. was added 1-(pyridin-3-yl)ethanone (46.2 mL, 0.422 mol) dropwise over 50 min. After stirring at 0° C. for 2 h, the reaction mixture was diluted with water (150 mL) and EtOH (150 mL). The mixture was acidified with conc. HCl to pH=3. The resulting yellow solid was filtered and dried to give (2E)-3-(2-hydroxyphenyl)-1-pyridin-3-ylprop-2-en-1-one (69.8 g, 73%) which was used without further purification. LCMS: (FA) ES+ 226.2, ES− 224.2.

Compounds in the following table were prepared from the appropriate starting materials in a method analogous to that described for (2E)-3-(2-hydroxyphenyl)-1-pyridin-3-ylprop-2-en-1-one:

| Structure | Name | LCMS |
|---|---|---|
| 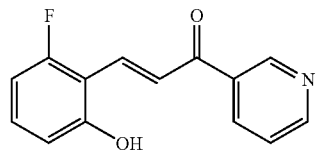 | (2E)-3-(2-fluoro-6-hydroxyphenyl)-1-pyridin-3-ylprop-2-en-1-one | LCMS: (FA) ES+ 244.2, ES− 242.3. |
| 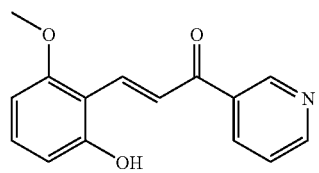 | (2E)-3-(2-hydroxy-6-methoxyphenyl)-1-pyridin-3-ylprop-2-en-1-one | LCMS: (FA) ES+ 256.2, ES− 254.3. |

| | | |
|---|---|---|
| 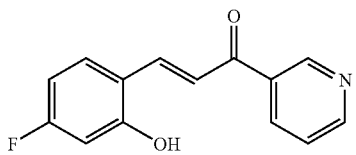 | (2E)-3-(4-fluoro-2-hydroxyphenyl)-1-pyridin-3-ylprop-2-en-1-one | LCMS: (FA) ES+ 244.2, ES− 242.3. |
| 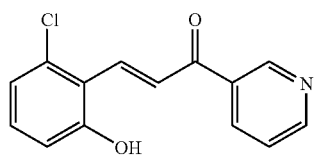 | (2E)-3-(2-chloro-6-hydroxyphenyl)-1-pyridin-3-ylprop-2-en-1-one | LCMS: (FA) ES+ 260.2, ES− 258.2. |
| 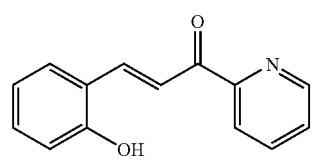 | (2E)-3-(2-hydroxyphenyl)-1-pyridin-2-ylprop-2-en-1-one | LCMS: (FA) ES+ 226.2, ES− 224.3. |
| 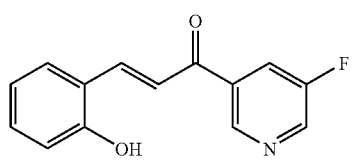 | (2E)-1-(5-fluoropyridin-3-yl)-3-(2-hydroxyphenyl)prop-2-en-1-one | LCMS: (FA) ES+ 244.2, ES− 242.3. |
| 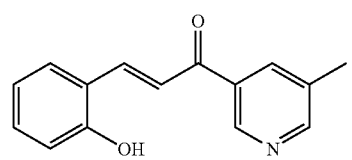 | (2E)-3-(2-hydroxyphenyl)-1-(5-methylpyridin-3-yl)prop-2-en-1-one | LCMS: (FA) ES+ 240.3. |
| 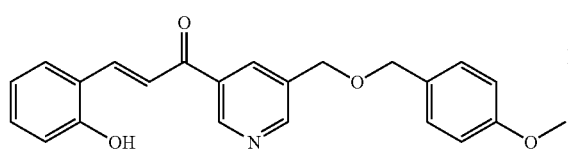 | (2E)-3-(2-hydroxyphenyl)-1-(5-{[(4-methoxybenzyl)oxy]methyl}pyridin-3-yl)prop-2-en-1-one | LCMS: (FA) ES+ 376.1. |
| 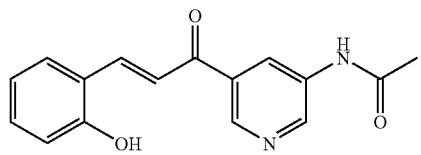 | N-{5-[(2E)-3-(2-hydroxyphenyl)prop-2-enoyl]pyridin-3-yl}acetamide | LCMS: (FA) ES+ 283.2. |

(2E)-3-(2-chloro-6-fluorophenyl)-1-pyridin-3-yl-prop-2-en-1-one

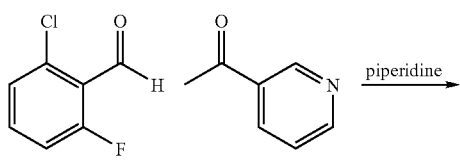

A mixture of 2-chloro-6-fluorobenzaldehyde (0.599 g, 3.8 mmol) and 1-phenylethanone (0.414 mL, 0.38 mmol) in piperidine (1 mL) was heated at 100° C. for 1 h. The reaction mixture was allowed to cool to rt and was concentrated. The residue was purified by column chromatography to give (2E)-3-(2-chloro-6-fluorophenyl)-1-pyridin-3-ylprop-2-en-1-one (0.28 g, 28%).

Compounds in the following table were prepared from the appropriate starting materials in a method analogous to that described for (2E)-3-(2-chloro-6-fluorophenyl)-1-pyridin-3-ylprop-2-en-1-one:

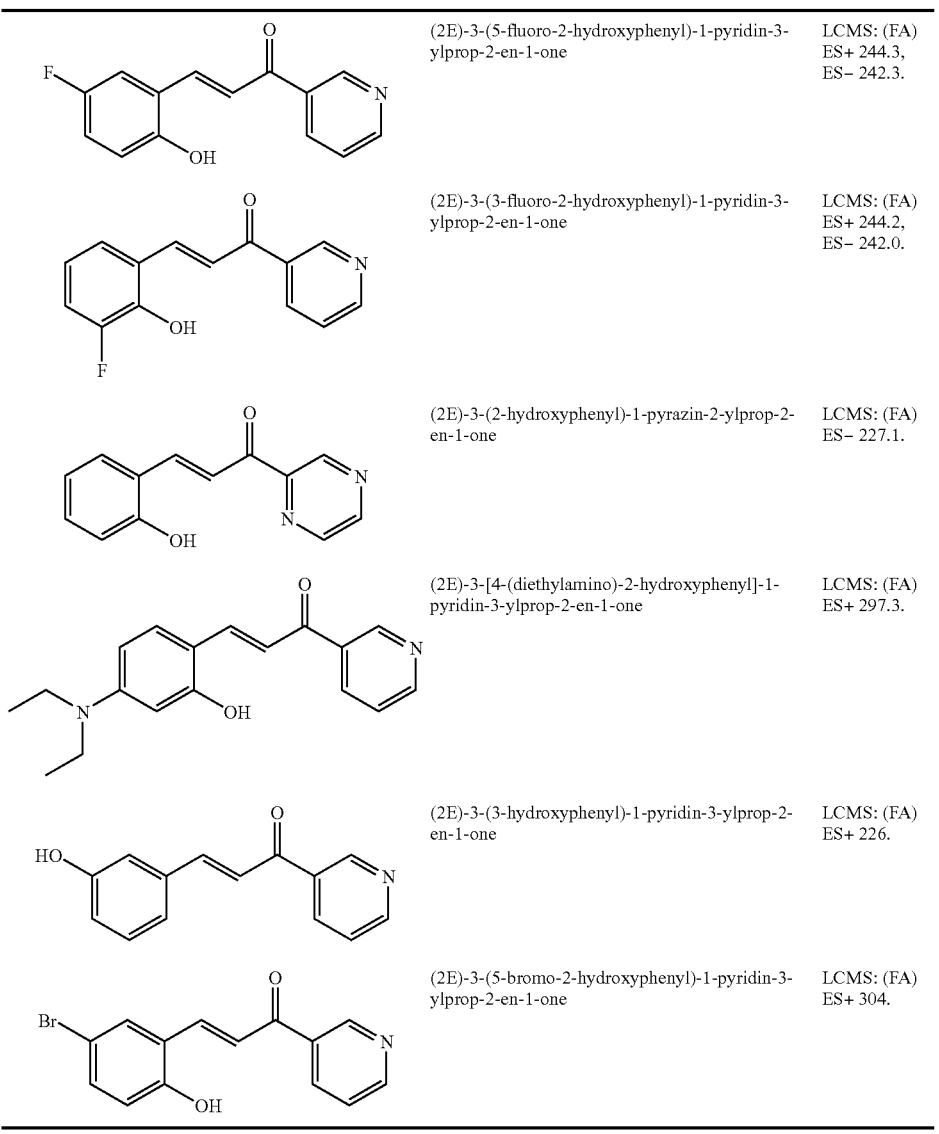

2-phenyl-1H-imidazole-5-carboxylic acid

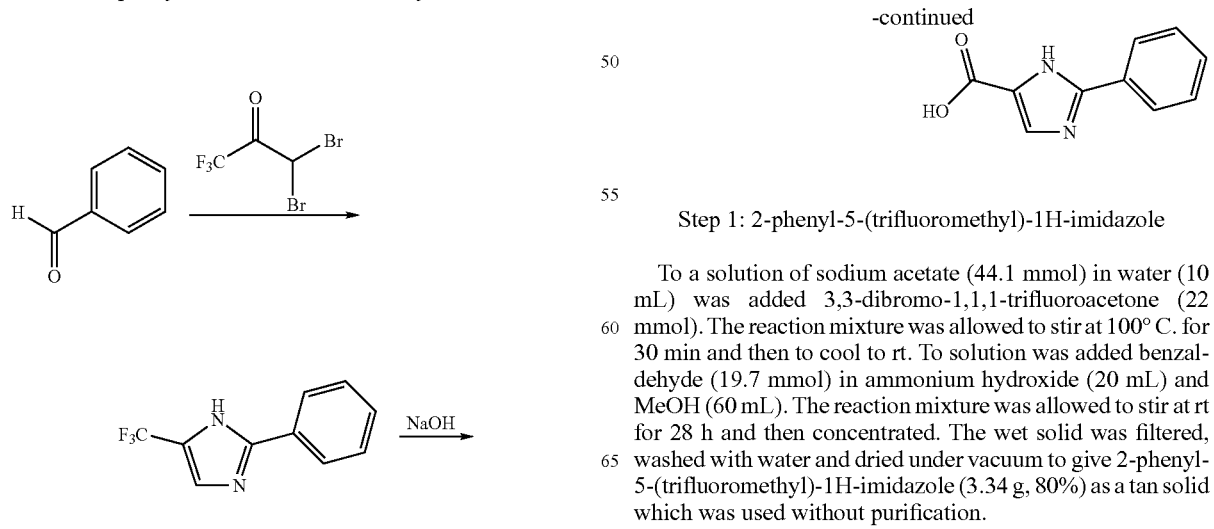

Step 1: 2-phenyl-5-(trifluoromethyl)-1H-imidazole

To a solution of sodium acetate (44.1 mmol) in water (10 mL) was added 3,3-dibromo-1,1,1-trifluoroacetone (22 mmol). The reaction mixture was allowed to stir at 100° C. for 30 min and then to cool to rt. To solution was added benzaldehyde (19.7 mmol) in ammonium hydroxide (20 mL) and MeOH (60 mL). The reaction mixture was allowed to stir at rt for 28 h and then concentrated. The wet solid was filtered, washed with water and dried under vacuum to give 2-phenyl-5-(trifluoromethyl)-1H-imidazole (3.34 g, 80%) as a tan solid which was used without purification.

Step 2: 2-phenyl-1H-imidazole-5-carboxylic acid

A mixture of 2-phenyl-5-(trifluoromethyl)-1H-imidazole (47.1 mmol) and NaOH (63.8 mmol) in water (20 mL) was allowed to stir at 95° C. overnight. The reaction mixture was allowed to cool to rt and was diluted with water and extracted with DCM. The pH of the aqueous solution was adjusted to pH=7 with 1N HCl and the solution was extracted again with DCM. The aqueous solution was concentrated to give 2-phenyl-1H-imidazole-5-carboxylic acid as a white solid which was used without further purification.

Compounds in the following table were prepared from the appropriate starting materials in a method analogous to that described for 2-phenyl-1H-imidazole-5-carboxylic acid:

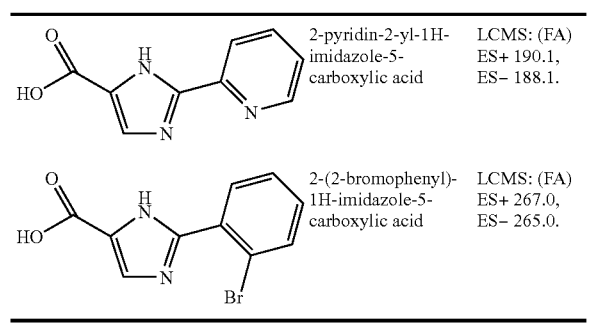

| | | |
|---|---|---|
| | 2-pyridin-2-yl-1H-imidazole-5-carboxylic acid | LCMS: (FA) ES+ 190.1, ES− 188.1. |
| | 2-(2-bromophenyl)-1H-imidazole-5-carboxylic acid | LCMS: (FA) ES+ 267.0, ES− 265.0. |

Trans-2-pyridin-4-ylcyclopropanecarboxylic acid

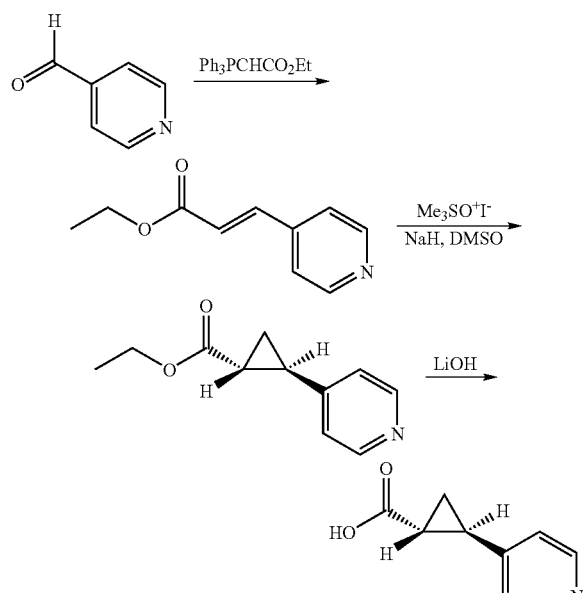

Step 1: ethyl (2E)-3-pyridin-4-ylacrylate

To a solution of isonicotinaldehyde (0.811 mL, 8.61 mmol) in DCM (30 mL) was added ethyl (triphenylphosphoranylidene)acetate (3.00 g, 8.61 mmol) in DCM (5 mL) dropwise. The reaction mixture was allowed to stir at rt for 5 h and then concentrated. The residue was purified by column chromatography to give ethyl (2E)-3-pyridin-4-ylacrylate (1.47 g, 96%). LCMS: (FA) ES+ 178.3.

Step 2: ethyl trans-2-pyridin-4-ylcyclopropanecarboxylate

Trimethylsulfoxonium iodide (2.37 g, 10.8 mmol) and sodium hydride (60% in mineral oil, 0.431 g, 10.8 mmol) were combined and stirred under an atmosphere of argon. To these solids was added DMSO (40 mL) dropwise via addition funnel over 10 min. Hydrogen gas evolved and the solution turned cloudy. To this cloudy solution was added ethyl (2E)-3-pyridin-4-ylacrylate (1.42 g, 8.01 mmol) in DMSO (60 mL) dropwise over 20 min. The reaction mixture was allowed to stir at rt for 18 h. The reaction was quenched by the addition of water. The solution was diluted with Et 20 and the aqueous and organic solutions were separated. The aqueous solution was extracted with $Et_2O$. The combined organic solutions were washed with brine, dried over $Na_2SO_4$, filtered and concentrated. The residue was purified by column chromatography to give ethyl trans-2-pyridin-4-ylcyclopropanecarboxylate (1.58 g, 52%). LCMS: (FA) ES+ 192.3.

Step 3: trans-2-pyridin-4-ylcyclopropanecarboxylic acid

To a solution of ethyl trans-2-pyridin-4-ylcyclopropanecarboxylate (0.918 g, 4.80 mmol) in THF (10 mL) and water (10 mL) was added lithium hydroxide (0.345 g, 14.4 mmol). The reaction mixture was allowed to stir at rt for 24 h and then diluted with 2N HCl (10 mL). The mixture was concentrated to give trans-2-pyridin-4-ylcyclopropanecarboxylic acid which was used without purification in the next step. LCMS: (FA) ES+ 164.0, ES-162.1.

Compounds in the following table were prepared from the appropriate starting materials in a method analogous to that described for trans-2-pyridin-4-ylcyclopropane-carboxylic acid:

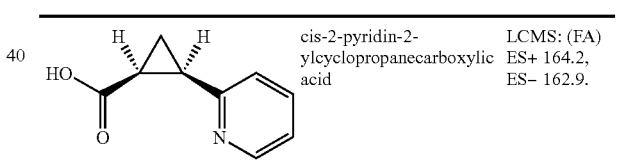

| | | |
|---|---|---|
| | cis-2-pyridin-2-ylcyclopropanecarboxylic acid | LCMS: (FA) ES+ 164.2, ES− 162.9. |

4-pyridin-2-ylbenzoic acid

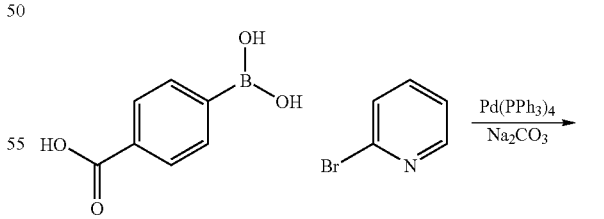

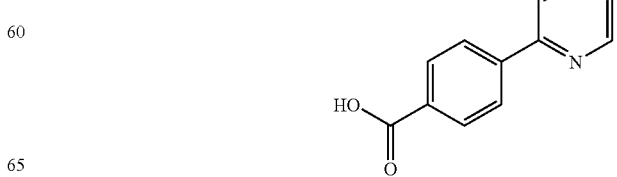

To a solution of 4-(dihydroxyboryl)benzoic acid (1.03 g, 6.21 mmol) and 2-bromopyridine (0.59 mL, 6.21 mmol) in ACN (20 mL) was added sodium carbonate (0.396 g, 3.74 mmol) in water (20 mL). The reaction mixture was degassed with argon and then tetrakis(triphenylphosphine)palladium (0.108 g, 0.09 mmol) was added. The reaction mixture was allowed to stir at 90° C. overnight and then filtered. The solution was concentrated to remove ACN and the aqueous solution was washed with DCM. The aqueous solution was acidified with 1N HCl and the resulting white precipitate was filtered and dried to give 4-pyridin-2-ylbenzoic acid (1.06 g, 85%). LCMS: (FA) ES+ 200.1.

Compounds in the following table were prepared from the appropriate starting materials in a method analogous to that described for 4-pyridin-2-ylbenzoic acid:

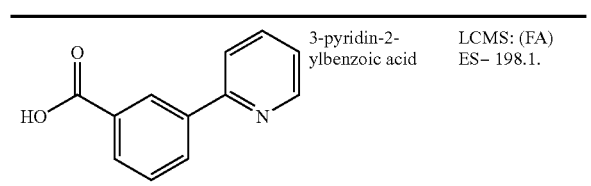

| | | |
|---|---|---|
| | 3-pyridin-2-ylbenzoic acid | LCMS: (FA) ES– 198.1. |

5-(pyridine-2-ylethynyl)thiophene-2-carboxylic acid

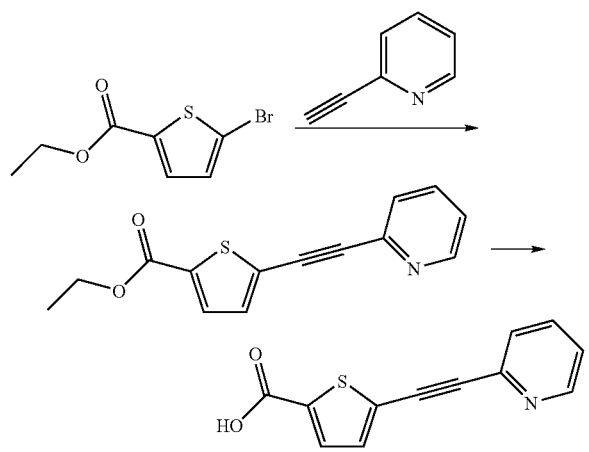

Step 1: ethyl 5-(pyridine-2-ylethynyl)thiophene-2-carboxylate

A solution of ethyl 5-bromothiophene-2-carboxylate (2.00 g, 8.51 mmol) and 2-ethynylpyridine (0.99 mL, 9.80 mmol) in diethylamine (30 mL) and THF (60 mL) was degassed with argon. To the reaction mixture was added bis(triphenylphosphine)palladium(II) chloride (0.422 g, 0.601 mmol) and copper iodide (0.154 g, 0.809 mmol). The reaction mixture was allowed to stir at rt for 12 h. The reaction mixture was diluted with water and EtOAc, and then extracted with more EtOAc. The organic solutions were combined, washed with brine, dried over MgSO₄, filtered, and concentrated. The residue was purified by column chromatography to give ethyl 5-(.yridine-2-ylethynyl)thiophene-2-carboxylate (1.43 grams, 5.54 mmol) as an oil. LCMS: (FA) ES+ 258.2.

Step 2: 5-(pyridine-2-ylethynyl)thiophene-2-carboxylic acid

To a solution of 5-(pyridine-2-ylethynyl)thiophene-2-carboxylate (1.43 g, 5.54 mmol) in ethanol (40 mL) was added sodium hydroxide (0.585 g, 14.6 mmol). The reaction mixture was allowed to stir at rt for 20 h. The solution was concentrated and diluted with 1N aqueous HCl. A precipitate formed and was filtered to give 5-(pyridine-2-ylethynyl)thiophene-2-carboxylic acid (1.02 g, 4.46 mmol) as a yellow solid. LCMS: (FA) ES+ 230.2, ES-229.4.

2-pyridin-4-yl-1,3-thiazole-5-carboxylic acid

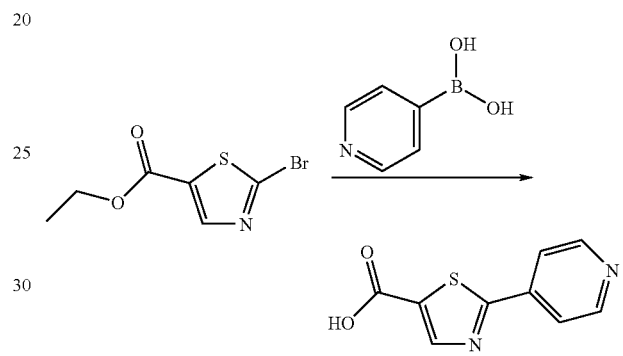

A mixture of ethyl 2-bromo-1,3-thiazole-5-carboxylate (0.095 mL, 0.64 mmol), pyridine-4-ylboronic acid (0.094 g, 0.76 mmol), tetrakis(triphenylphosphine)palladium(0) (0.007 g, 0.006 mmol), and potassium carbonate (0.263 g, 1.91 mmol) in 1,4-dioxane (10 mL) and water (0.5 mL) was subjected to MWI at 160° C. for 20 min. The reaction mixture was diluted with water and extracted with EtOAc. The organic solutions were combined, acidified and concentrated. The residue was dissolved in EtOAc and brine was added. The organic solution was separated, dried over Na₂SO₄, filtered and concentrated to give 2-pyridin-4-yl-1,3-thiazole-5-carboxylic acid which was used without further purification. LCMS: (FA) ES+ 207.

Compounds in the following table were prepared from the appropriate starting materials in a method analogous to that described for 2-pyridin-4-yl-1,3-thiazole-5-carboxylic acid:

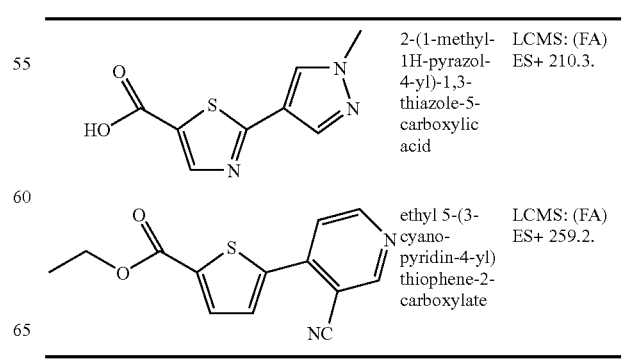

| | | |
|---|---|---|
| | 2-(1-methyl-1H-pyrazol-4-yl)-1,3-thiazole-5-carboxylic acid | LCMS: (FA) ES+ 210.3. |
| | ethyl 5-(3-cyano-pyridin-4-yl)thiophene-2-carboxylate | LCMS: (FA) ES+ 259.2. |

183

2-pyridin-2-yl-1,3-thiazole-5-carboxylic acid

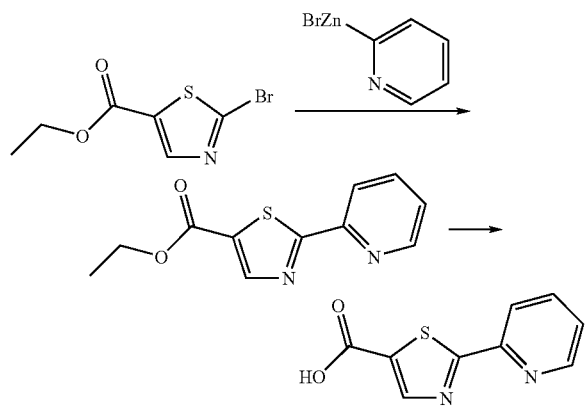

Step 1: ethyl 2-pyridin-2-yl-1,3-thiazole-5-carboxylate

A mixture of bromo(pyridine-2-yl)zinc (0.5 M in THF, 1.27 mL), ethyl 2-bromo-1,3-thiazole-5-carboxylate (0.063 mL, 0.42 mmol) and tetrakis(triphenylphosphine)palladium (0) (0.02 g, 0.02 mmol) in 1,4-dioxane (3 mL) and water (0.03 mL) was subjected to MWI at 120° C. for 10 min. The reaction mixture was diluted with water and extracted with EtOAc. The organic solutions were combined, dried over $Na_2SO_4$, filtered, and concentrated to give ethyl 2-pyridin-2-yl-1,3-thiazole-5-carboxylate (0.12 g) which was used without further purification. LCMS: (FA) ES+ 235.

Step 2: 2-pyridin-4-yl-1,3-thiazole-5-carboxylic acid

A mixture of ethyl 2-pyridin-2-yl-1,3-thiazole-5-carboxylate (0.12 g, 0.51 mmol) in 1M HCl (10 mL) and MeOH (10 mL) was heated at 100° C. for 4 h. Concentrated HCl was added and the mixture was heated until no starting material remained. The mixture was concentrated to give 2-pyridin-4-yl-1,3-thiazole-5-carboxylic acid which was used directly in the next reaction. LCMS: (FA) ES+ 207.3.

Compounds in the following table were prepared from the appropriate starting materials in a method analogous to that described for 2-pyridin-2-yl-1,3-thiazole-5-carboxylic acid and its intermediates:

| Structure | Name | LCMS |
|---|---|---|
| 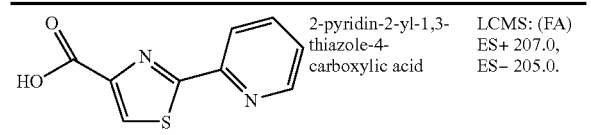 | 2-pyridin-2-yl-1,3-thiazole-4-carboxylic acid | (FA) ES+ 207.0, ES− 205.0. |

184

5-pyridin-2-yl-2-furoic acid

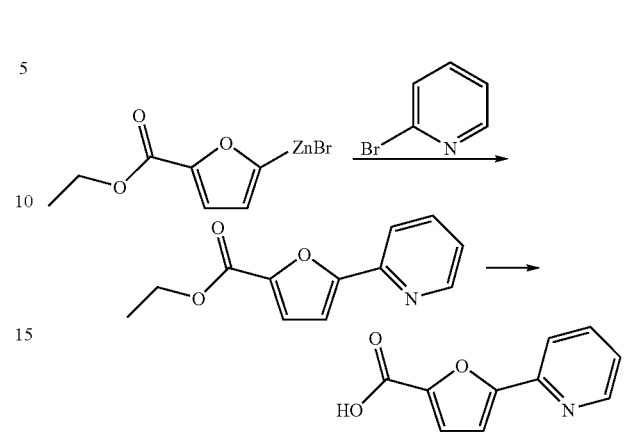

Step 1: ethyl 5-pyridin-2-yl-2-furoate

A mixture of 2-bromopyridine (1.4 mL, 15 mmol) and bromo[5-(ethoxycarbonyl)-2-furyl]zinc (0.5 M in THF, 30 mL) was degassed. To this mixture was added tetrakis(triphenylphosphine)palladium(0) (0.9 g, 0.8 mmol). The reaction mixture was allowed to stir at 70° C. overnight and then to cool to rt. The mixture was diluted with EtOAc and washed with aq. Sat. $NaHCO_3$. A precipitate formed and was filtered. The filtrate was washed with brine, dried over $MgSO_4$, filtered and concentrated. The residue was purified by column chromatography to give ethyl 5-pyridin-2-yl-2-furoate (2.02 g, 62%). LCMS: (FA) ES+ 218.

Step 2: 5-pyridin-2-yl-2-furoic acid

To a solution of ethyl 5-pyridin-2-yl-2-furoate (2.00 g, 9.21 mmol) in EtOH (10 mL) was added NaOH (0.74 g) in water. The reaction mixture was allowed to stir at rt for 1 h and then concentrated. The residue was diluted with 1M HCl to pH 3-4. A precipitate formed and was collected by filtration and identified as 5-pyridin-2-yl-2-furoic acid (0.41 g). The aqueous solution was extracted with EtOAc. The organic solutions were combined, washed with brine, dried over $MgSO_4$, filtered and concentrated to give additional 5-pyridin-2-yl-2-furoic acid (0.57 g). LCMS: (FA) ES+ 190.

Compounds in the following table were prepared from the appropriate starting materials in a method analogous to that described for 5-pyridin-2-yl-2-furoic acid and its intermediates:

| Structure | Name | LCMS |
|---|---|---|
| 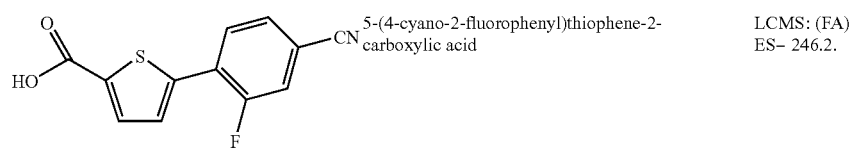 | 5-(4-cyano-2-fluorophenyl)thiophene-2-carboxylic acid | (FA) ES− 246.2. |

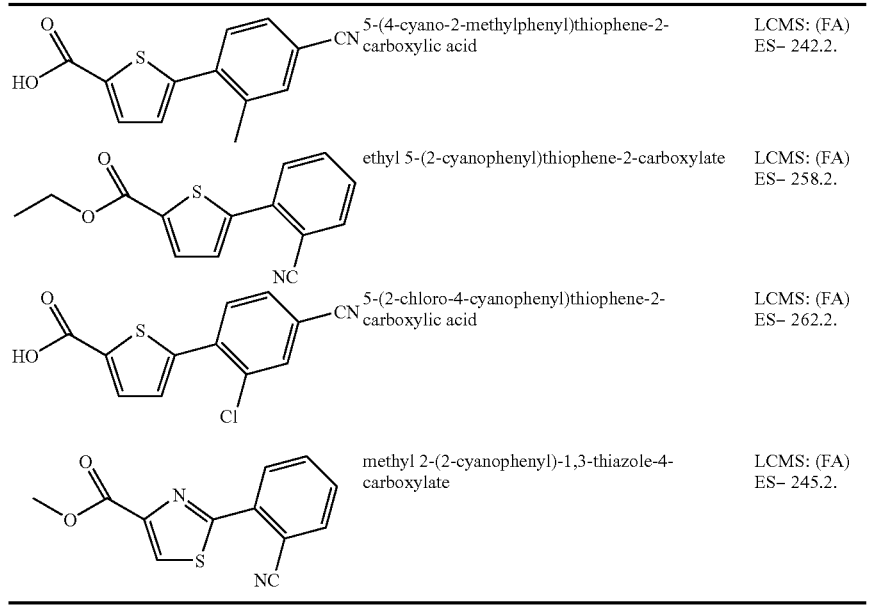

| | | |
|---|---|---|
| | 5-(4-cyano-2-methylphenyl)thiophene-2-carboxylic acid | LCMS: (FA) ES− 242.2. |
| | ethyl 5-(2-cyanophenyl)thiophene-2-carboxylate | LCMS: (FA) ES− 258.2. |
| | 5-(2-chloro-4-cyanophenyl)thiophene-2-carboxylic acid | LCMS: (FA) ES− 262.2. |
| | methyl 2-(2-cyanophenyl)-1,3-thiazole-4-carboxylate | LCMS: (FA) ES− 245.2. | methyl 1-(2-cyanophenyl)-1H-imidazole-4-carboxylate

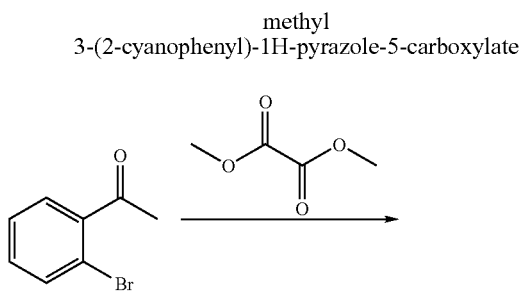

A mixture of methyl 1H-imidazole-4-carboxylate (400 mg, 0.003 mol), 2-iodobenzonitrile (800 mg, 0.0035 mol), L-proline (0.073 g, 0.00063 mol), potassium carbonate (0.88 g, 0.0063 mol) and copper(I) iodide (0.060 g, 0.00032 mol) in DMSO (8 mL) was allowed to stir and heated at 90° C. in a sealed tube overnight. The mixture was diluted with EtOAc, washed with water and brine, dried over Na$_2$SO$_4$, filtered and concentrated. The residue was purified by column chromatography to afford methyl 1-(2-cyanophenyl)-1H-imidazole-4-carboxylate. LCMS: (FA) ES+ 228.1 methyl 3-(2-cyanophenyl)-1H-pyrazole-5-carboxylate

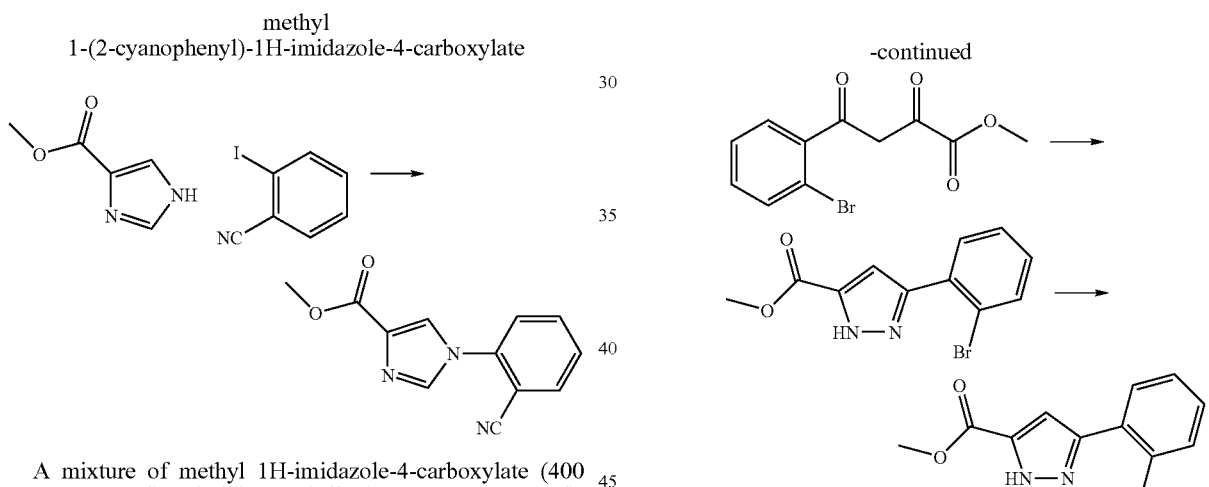

Step 1: methyl 4-(2-bromophenyl)-2,4-dioxobutanoate

Sodium (120 mg, 0.0051 mol) was added slowly to MeOH (2.5 mL, 0.062 mol) at −5° C. To this solution were added dimethyl oxalate (500 mg, 0.0042 mol) and 1-(2-bromophenyl)ethanone (840 mg, 0.0042 mol) in Et$_2$O (5 mL). The reaction mixture was allowed to stir for 12 h and then concentrated and partitioned between Et$_2$O and water. The aqueous solution was separated and cooled in an ice bath. AcOH was added followed by 1N HCl until the solution was acidic. The mixture was extracted with Et$_2$O, and organic solution was dried over Na$_2$SO$_4$, filtered and concentrated to afford methyl 4-(2-bromophenyl)-2,4-dioxobutanoate (1.08 g, 89%) which was used without purification in the next step. LCMS: (FA) ES+ 287.0

Step 2: methyl 3-(2-bromophenyl)-1H-pyrazole-5-carboxylate

To a solution of methyl 4-(2-bromophenyl)-2,4-dioxobutanoate (540 mg, 0.0019 mol) in AcOH (4 mL) was added hydrazine monohydrate (67 mg, 0.00208 mol). The reaction mixture was allowed to stir at 130° C. overnight and then concentrated. The residue was dissolved in EtOAc, washed with aq. NaHCO$_3$ and brine, dried over Na$_2$SO$_4$, filtered and concentrated to give methyl 3-(2-bromophenyl)-1H-pyrazole-5-carboxylate (0.516 g, 97%) as a white solid. LCMS: (FA) ES+ 283.2, ES-281.2.

Step 3: methyl 3-(2-cyanophenyl)-1H-pyrazole-5-carboxylate

A mixture of methyl 5-(2-bromophenyl)-1H-pyrazole-5-carboxylate (0.225 g, 0.000800 mol) and copper cyanide (0.093 g, 0.0010 mol) in NMP (10 mL) was subjected to MWI at 170° C. for 20 min. The reaction mixture was diluted with EtOAc and filtered. The filtrate was evaporated to give methyl 3-(2-cyanophenyl)-1H-pyrazole-5-carboxylate (0.178 g, 98%) which was used without purification. LCMS: (AA) ES+ 228.1, ES-226.2.

1-pyridin-2-yl-1H-pyrazole-4-carboxylic acid

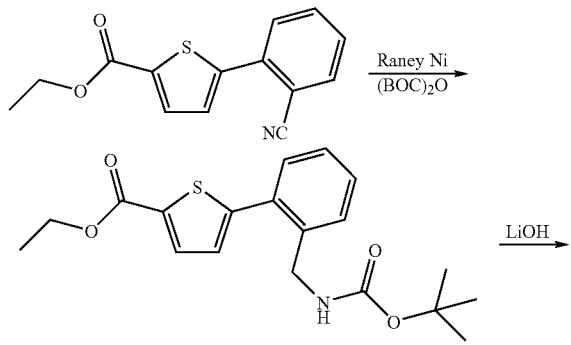

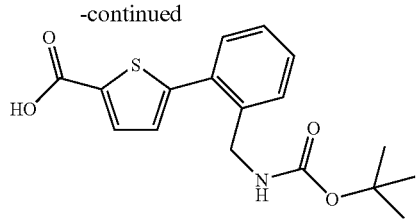

Step 1: ethyl 5-(2-{[(tert-butoxycarbonyl)amino]methyl}phenyl)thiophene-2-carboxylate To a slurry of ethyl 5-(2-cyanophenyl)thiophene-2-carboxylate (1.09 gm 4.24 mmol) in MeOH (8 mL) was added (BOC)$_2$O (1.11 g, 5.08 mmol) and Raney Nickel (3.6 mL). The reaction mixture was allowed to stir at rt under an atmosphere of hydrogen overnight and then filtered through celite. The filtrate was concentrated and the residue was purified by column chromatography to give ethyl 5-(2-{[(tert-butoxycarbonyl)-amino]methyl}phenyl)thiophene-2-carboxylate (1.32 g, 86%).

Step 2: 5-(2-{[(tert-butoxycarbonyl)amino]methyl}phenyl)thiophene-2-carboxylic acid A mixture of ethyl 5-(2-{[(tert-butoxycarbonyl)-amino]methyl}phenyl)thiophene-2-carboxylate (2.05 g, 5.67 mmol) and lithium hydroxide (0.679 g, 28.4 mmol) in water (20 mL) and ACN (20 mL) was allowed to stir at rt for 24 h. The reaction mixture was diluted with EtOAc and 1N KHSO$_4$. The organic solution was removed and the aqueous mixture was extracted with EtOAc. The organic solutions were combined, dried over Na$_2$SO$_4$, filtered, and concentrated. The residue was dried under vacuum to give 5-(2-{[(tert-butoxycarbonyl)amino]methyl}phenyl)thiophene-2-carboxylic acid (1.71 g, 90%) as a white solid which was used without purification. LCMS: (FA) ES-332.3.

Compounds in the following table were prepared from the appropriate starting materials in a method analogous to that described for 5-(2-{[(tert-butoxycarbonyl)amino]-methyl}phenyl)thiophene-2-carboxylic acid:

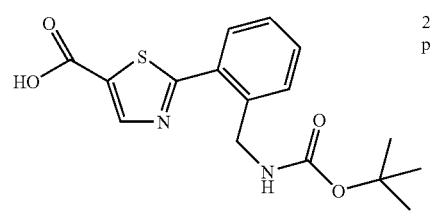

| | |
|---|---|
| 2-(2-{[(tert-butoxycarbonyl)amino]methyl}-phenyl)-1,3-thiazole-5-carboxylic acid | LCMS: (FA) ES+ 335.2, ES- 333.1. |

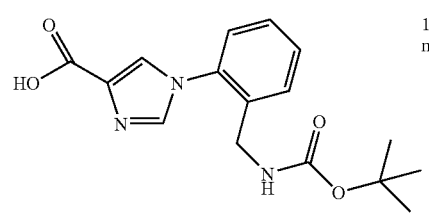

| | |
|---|---|
| 1-(2-{[(tert-butoxycarbonyl)amino]-methyl}phenyl)-1H-imidazole-4-carboxylic acid | LCMS: (FA) ES+ 318.3, ES- 316.3. |

-continued

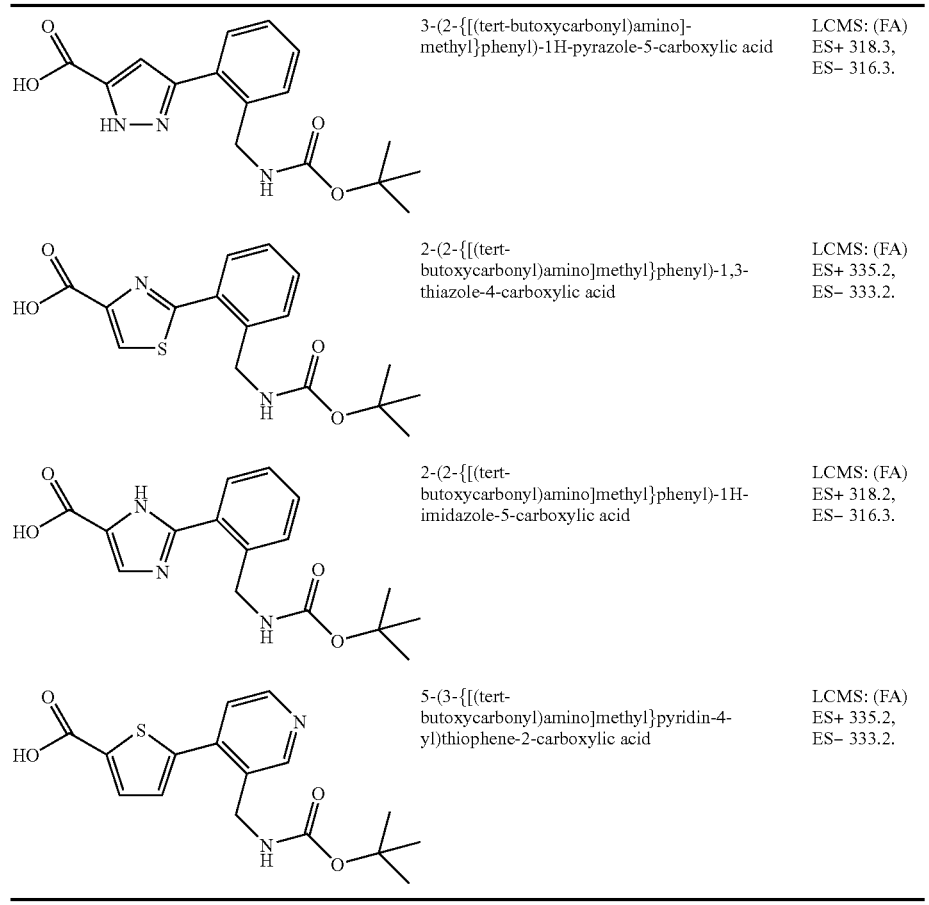

| | 3-(2-{[(tert-butoxycarbonyl)amino]-methyl}phenyl)-1H-pyrazole-5-carboxylic acid | LCMS: (FA) ES+ 318.3, ES− 316.3. |
| | 2-(2-{[(tert-butoxycarbonyl)amino]methyl}phenyl)-1,3-thiazole-4-carboxylic acid | LCMS: (FA) ES+ 335.2, ES− 333.2. |
| | 2-(2-{[(tert-butoxycarbonyl)amino]methyl}phenyl)-1H-imidazole-5-carboxylic acid | LCMS: (FA) ES+ 318.2, ES− 316.3. |
| | 5-(3-{[(tert-butoxycarbonyl)amino]methyl}pyridin-4-yl)thiophene-2-carboxylic acid | LCMS: (FA) ES+ 335.2, ES− 333.2. |

5-[2-{[(tert-butoxycarbonyl)amino]methyl}-4-(dimethylamino)phenyl]thiophene-2-carboxylic acid

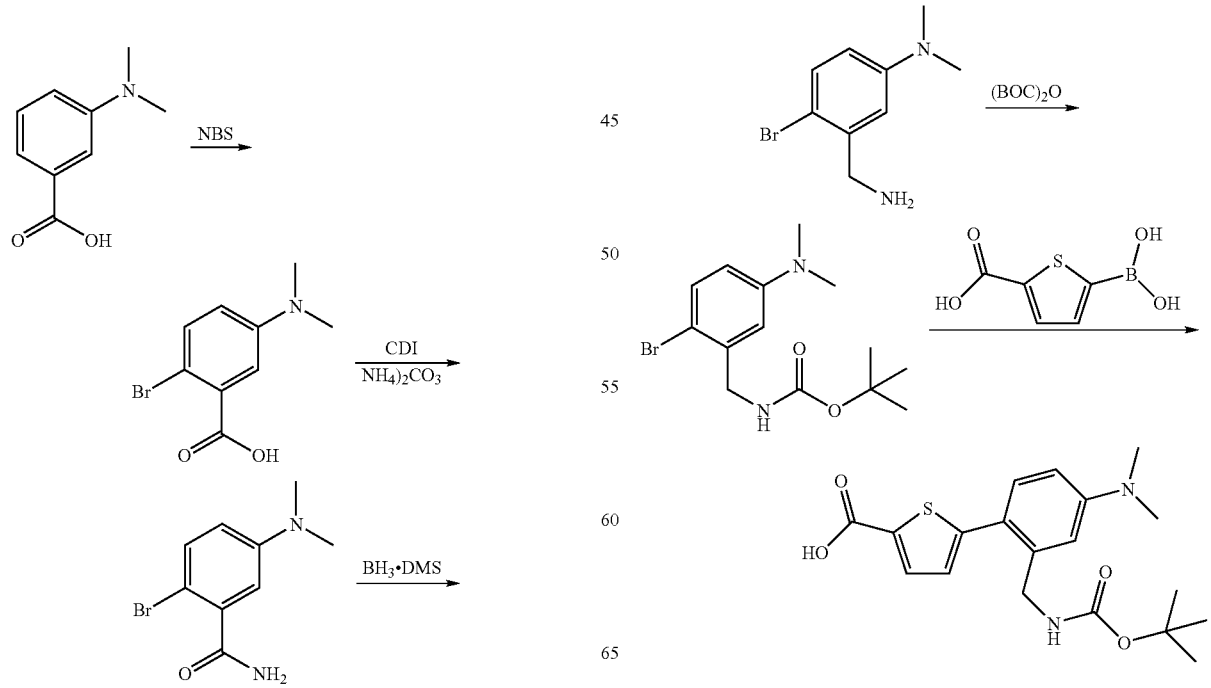

Step 1: 2-bromo-5-(dimethylamino)benzoic acid

A solution of 3-(dimethylamino)benzoic acid (5.13 g, 31.0 mmol) in DMF (20 mL) was cooled to 5° C. To this cold solution was added NBS (6.23 g, 35.0 mmol) in several portions in order to keep the internal reaction temperature at 5° C. The reaction mixture was allowed to stir at this temperature for 15 min and then to warm to rt. The mixture was poured into water and extracted with EtOAc. The organic solutions were combined, washed with water and brine, dried over $Na_2SO_4$, filtered, and concentrated to give 2-bromo-5-(dimethylamino)benzoic acid (7.89 g, 93%) which was used without purification in the next step.

Step 2: 2-bromo-5-(dimethylamino)benzamide

To a solution of give 2-bromo-5-(dimethylamino)benzoic acid (7.89 g, 32.3 mmol) in DMF (25 mL) was added N,N-carbonyldiimidazole (13.1 g, 80.8 mmol). The reaction mixture was allowed to stir at rt for 30 min and then ammonium carbonate (14.0 g, 145 mmol) was added. The reaction mixture was allowed to stir at rt overnight and then poured into water. The mixture was extracted with EtOAc. The organic solutions were combined, washed with water and brine, dried over $Na_2SO_4$, filtered and concentrated to give 2-bromo-5-(dimethylamino)benzamide (2.14 g, 27%). The product could be further purified by recrystallization from MeOH.

Step 3: 3-(aminomethyl)-4-bromo-N,N-dimethylaniline

To a suspension of 3-(aminomethyl)-4-bromo-N,N-dimethylaniline (0.544 g, 2.24 mmol) in THF (5 mL) at 0° C. was added 2M borane-dimethylsulfide complex in THF (2.8 mL) dropwise via syringe. The reaction mixture was heated at 70° C. and allowed to stir overnight. The mixture was cooled to 0° C. and treated with conc. HCl (0.5 mL). Vigorous gas evolution was observed, and the reaction mixture was allowed to stir at 0° C. for 15 min and then concentrated. The residue was diluted with water (10 mL) and heated at reflux for 20 min. The mixture was allowed to cool to rt and was basified with sat $NaHCO_3$. The mixture was extracted with EtOAc. The organic solutions were combined, washed with brine, dried over $Na_2SO_4$, filtered and concentrated. The residue was purified by column chromatography to give 3-(aminomethyl)-4-bromo-N,N-dimethylaniline (0.174 g, 32%).

Step 4: tert-butyl [2-bromo-5-(dimethylamino)benzyl]carbamate

To a solution of 3-(aminomethyl)-4-bromo-N,N-dimethylaniline (0.174 g, 0.76 mmol) in DCM (4 mL) was added $BOC_2O$ (0.166 g, 0.76 mmol). The reaction mixture was allowed to stir at rt overnight and then concentrated. The residue was purified by column chromatography to give tert-butyl (2-bromo-5-methoxybenzyl)carbamate (0.238 g, 90%).

Step 5: 5-[2-{[(tert-butoxycarbonyl)amino]methyl}-4-(dimethylamino)phenyl]thiophene-2-carboxylic acid A solution of tert tert-butyl (2-bromo-5-methoxybenzyl) carbamate (0.226 g, 0.69 mmol), 5-(dihydroxyboryl) thiophene-2-carboxylic acid (0.118 g, 0.69 mmol) and cesium carbonate (0.492 g, 1.51 mmol) in DMF (2 mL) and water (1 mL) was degassed. To this solution was added $PdCl_2dppf$ (1:1 complex with DCM, 0.020 g, 0.03 mmol).

The reaction mixture was heated at 100° C. for 36 hr and then allowed to cool to rt and concentrated. The residue was suspended in acetonitrile (15 mL) and MeOH (2 mL) containing 0.1% TFA and adsorbed onto celite and purified by reverse phase chromatography to give a mixture of the desired product and remaining starting material. This mixture was suspended in half-saturated sodium bicarbonate solution (10 mL) and washed with EtOAc (20 mL). The organic solution was extracted with half-saturated sodium bicarbonate solution until no product was apparent in the organic solution. The pH of the aqueous solution was adjusted to 5 with 1N HCl and then was extracted with EtOAc. The organic solutions were combined, washed with brine, dried over $Na_2SO_4$, filtered and concentrated to give 5-[2-{[(tert-butoxycarbonyl)amino] methyl}-4-(dimethylamino)phenyl]thiophene-2-carboxylic acid (0.036 g, 13%) as a yellow oil. LCMS: (AA) ES+ 377.2, ES-375.3.

1-pyridin-2-yl-1H-pyrazole-4-carboxylic acid

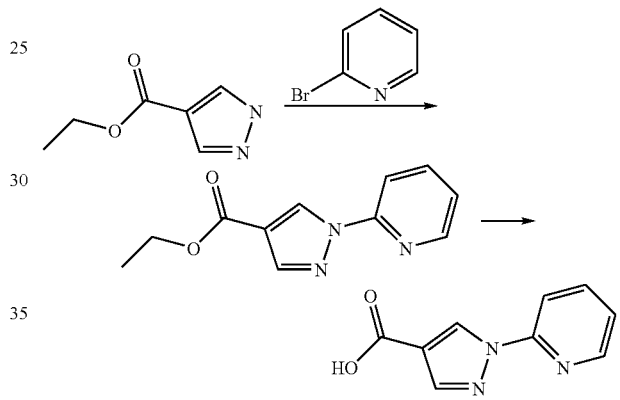

Step 1: ethyl 1-pyridin-2-yl-1H-pyrazole-4-carboxylate

A mixture of ethyl 1H-pyrazole-4-carboxylate (1.57 g, 11.2 mmol), 2-bromopyridine (5.5 mL, 57.7 mmol), copper iodide (0.463 g, 2.43 mmol), N,N'-dimethylethane-1,2-diamine (1.00 mL, 9.17 mmol) and potassium carbonate (3.32 g, 24.0 mmol) in toluene (50 mL) was allowed to stir at 110° C. overnight. The reaction mixture was allowed to cool to rt and then diluted with EtOAc. The organic mixture was filtered (filter paper) and the residue was purified by column chromatography to give ethyl 1-pyridin-2-yl-1H-pyrazole-4-carboxylate (1.66 g) as a white solid. LCMS: (FA) ES+ 218.4.

Step 2: 2-pyridin-4-yl-1,3-thiazole-5-carboxylic acid

A solution of ethyl 1-pyridin-2-yl-1H-pyrazole-4-carboxylate (0.078 g, 0.36 mmol) in water (1 mL) and 4M HCl in dioxane (3 mL) was heated at 100° C. for 10 h. The mixture was concentrated to give 2-pyridin-4-yl-1,3-thiazole-5-carboxylic acid, which was used without further purification. LCMS: (FA) ES+ 190.3.

Compounds in the following table were prepared from the appropriate starting materials in a method analogous to that described for 2-pyridin-4-yl-1,3-thiazole-5-carboxylic acid:

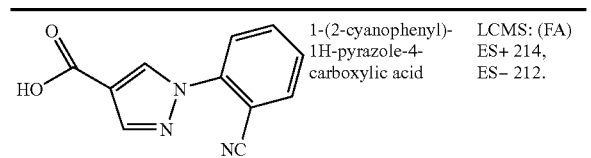

| | 1-(2-cyanophenyl)-1H-pyrazole-4-carboxylic acid | LCMS: (FA) ES+ 214, ES− 212. |
|---|---|---|

5-{[4-(tert-butoxycarbonyl)piperazin-1-yl]methyl}thiophene-2-carboxylic acid

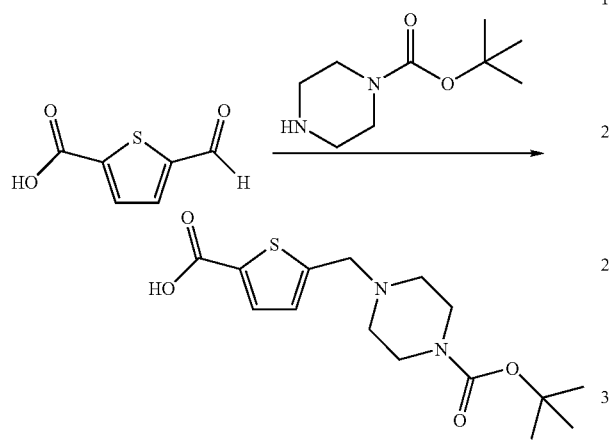

To a solution of 5-formylthiophene-2-carboxylic acid (0.505 g, 3.23 mmol) in MeOH (35 mL) and acetic acid (0.30 mL) was added tert-butyl piperazine-1-carboxylate (1.20 g, 6.47 mmol) and sodium cyanoborohydride (0.406 g, 6.47 mmol). The reaction mixture was allowed to stir at rt for 15 h and was then concentrated to give 5-{[4-(tert-butoxycarbonyl)piperazin-1-yl]methyl}thiophene-2-carboxylic acid (2.05 g, 6.27 mmol) as a white solid. LCMS: (FA) ES+ 327.3, ES-325.4.

Compounds in the following table were prepared from the appropriate starting materials in a method analogous to that described for 5-{[4-(tert-butoxycarbonyl)piperazin-1-yl]methyl}thiophene-2-carboxylic acid:

| | 5-(pyrrolidin-1-ylmethyl)-thiophene-2-carboxylic acid | LCMS: (FA) ES+ 212.2. |
|---|---|---|

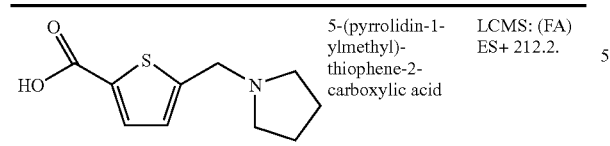

tert-butyl 6-(4,4,5,5-tetramethyl-1,3,2-dioxaborolan-2-yl)-3,4-dihydroisoquinoline-2(1H)-carboxylate and tert-butyl 8-(4,4,5,5-tetramethyl-1,3,2-dioxaborolan-2-yl)-3,4-dihydroisoquinoline-2(1H)-carboxylate

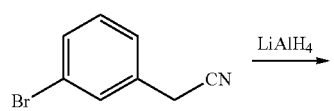

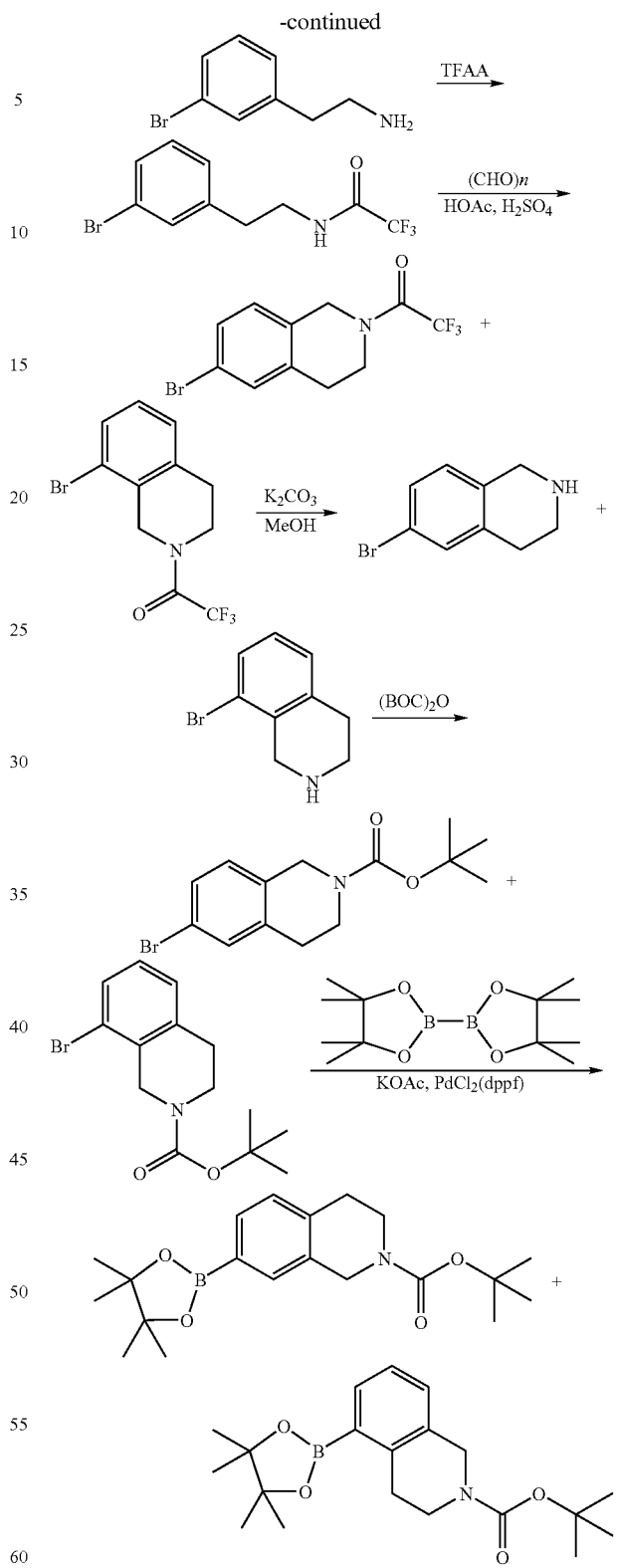

Step 1: 2-(3-bromophenyl)ethanamine

To a solution of 2M LAH (31 mL) in THF (37 mL) at 0° C. was added sulfuric acid (1.6 mL) dropwise. This mixture was allowed to stir for 30 min and then (3-bromophenyl)-acetonitrile (30.6 mmol) in THF (7.5 mL) was slowly added. The reaction mixture was allowed to warm to rt and stir for 1 hr. The reaction was cooled to 0° C. and then a 1:1 v:v mixture of THF:water (20 mL) was added, followed by diethyl ether (40 mL). A precipitate formed. 4N NaOH was added until the solution reached pH=9. The mixture was filtered and the solid was washed with ether. The solution was dried over $Na_2SO_4$ and concentrated to give 2-(3-bromophenyl)ethanamine (28.1 mmol, 92%) as an oil, which was used without further purification.

Step 2: N-[2-(3-bromophenyl)ethyl]-2,2,2-trifluoroacetamide

To a solution of 2-(3-bromophenyl)ethanamine (28.1 mmol) in DMC (100 mL) was added 2,6-lutidine (29 mmol). The reaction mixture was cooled to 0° C. and then TFAA (28.1 mmol) was slowly added. The reaction mixture was allowed to stir and warm to rt overnight. Water (90 mL) was added and the organic solution was separated. The aqueous solution was extracted with DCM. The organic solutions were combined, washed with 1N HCl and aq. Sat. $NaHCO_3$, dried over $Na_2SO_4$, filtered and concentrated to give N-[2-(3-bromophenyl)ethyl]-2,2,2-trifluoroacetamide (25.1 mmol, 89%) as a white solid which was used without further purification.

Step 3: 6-bromo-2-(trifluoroacetyl)-1,2,3,4-tetrahydroisoquinoline and 8-bromo-2-(trifluoroacetyl)-1,2,3,4-tetrahydroisoquinoline To a mixture of N-[2-(3-bromophenyl)ethyl]-2,2,2-trifluoroacetamide (25.1 mmol) and paraformaldehyde (40.2 mmol) was added a mixture of glacial acetic acid (42 mL) and $H_2SO_4$ (28 mL). The reaction mixture was allowed to stir at rt overnight and then poured into cold water (500 mL). The aqueous solution was extracted with EtOAc (250 mL, 150 mL). The organic solutions were combined, washed with sat. $NaHCO_3$ and brine, dried over $Na_2SO_4$, filtered, and concentrated. The residue was purified by column chromatography to give a mixture of 6-bromo-2-(trifluoroacetyl)-1,2,3,4-tetrahydroisoquinoline and 8-bromo-2-(trifluoroacetyl)-1,2,3,4-tetrahydroisoquinoline (5.1 g, 66%). This mixture was carried on to the next step without attempting to separate the isomers.

Step 4: 6-bromo-1,2,3,4-tetrahydroisoquinoline and 8-bromo-1,2,3,4-tetrahydroisoquinoline Potassium carbonate (66.2 mmol) was added in one portion to a solution of 6-bromo-2-(trifluoroacetyl)-1,2,3,4-tetrahydroisoquinoline and 8-bromo-2-(trifluoroacetyl)-1,2,3,4-tetrahydroisoquinoline (17.6 mmol) in MeOH (130 mL) and water (45 mL). The reaction mixture was allowed to stir at rt overnight and then diluted with EtOAc (150 mL). The mixture was washed with brined, dried over $Na_2SO_4$, filtered, and concentrated to give 6-bromo-1,2,3,4-tetrahydroisoquinoline and 8-bromo-1,2,3,4-tetrahydroisoquinoline (5.0 g, 100%) as a white solid.

Step 5: tert-butyl 6-bromo-3,4-dihydroisoquinoline-2 (1H)-carboxylate and tert-butyl 8-bromo-3,4-dihydroisoquinoline-2(1H)-carboxylate To a mixture of 6-bromo-1,2,3,4-tetrahydroisoquinoline and 8-bromo-1,2,3,4-tetrahydroisoquinoline (22.1 mmol) in THF (100 mL) was added DIPEA (22.1 mmol) and $BOC_2O$ (24 mmol). The reaction mixture was allowed to stir at rt over the weekend and then concentrated. Water (5 mL) was added to the residue and the pH was adjusted to 2 by the addition of 1N $H_3PO_4$. The mixture was extracted with EtOAc. The organic solutions were combined, dried over $Na_2SO_4$, filtered and concentrated. The residue was purified by column chromatography to give tert-butyl 6-bromo-3,4-dihydroisoquinoline-2(1H)-carboxylate and tert-butyl 8-bromo-3,4-dihydroisoquinoline-2(1H)-carboxylate (6.04 g, 88%) as a yellow oil.

Step 6: tert-butyl 6-(4,4,5,5-tetramethyl-1,3,2-dioxaborolan-2-yl)-3,4-dihydroisoquinoline-2(1H)-carboxylate and tert-butyl 8-(4,4,5,5-tetramethyl-1,3,2-dioxaborolan-2-yl)-3,4-dihydroisoquinoline-2(1H)-carboxylate A solution of tert-butyl 6-bromo-3,4-dihydroisoquinoline-2(1H)-carboxylate and tert-butyl 8-bromo-3,4-dihydroisoquinoline-2(1H)-carboxylate (19.5 mmol), bis(pinacolato) diboron (21.4 mmol) and potassium acetate (61 mmol) in DMF (100 mL) was degassed. To this solution was added $PdCl_2$dppf (1:1 complex with DCM, 0.8 mmol). The reaction mixture was heated at 85° C. for 4 hr and then allowed to cool to room temperature and diluted with EtOAc. The solution was washed with water and brine, dried over $Na_2SO_4$, filtered and concentrated. The residue was purified by column chromatography to give tert-butyl 6-(4,4,5,5-tetramethyl-1,3,2-dioxaborolan-2-yl)-3,4-dihydroisoquinoline-2(1H)-carboxylate and tert-butyl 8-(4,4,5,5-tetramethyl-1,3,2-dioxaborolan-2-yl)-3,4-dihydroisoquinoline-2(1H)-carboxylate. LCMS: (FA) ES+ 360 (for each).

Compounds in the following table were prepared from the appropriate starting materials in a method analogous to that described for tert-butyl 6-(4,4,5,5-tetramethyl-1,3,2-dioxaborolan-2-yl)-3,4-dihydroisoquinoline-2(1H)-carboxylate and tert-butyl 8-(4,4,5,5-tetramethyl-1,3,2-dioxaborolan-2-yl)-3,4-dihydroisoquinoline-2(1H)-carboxylate

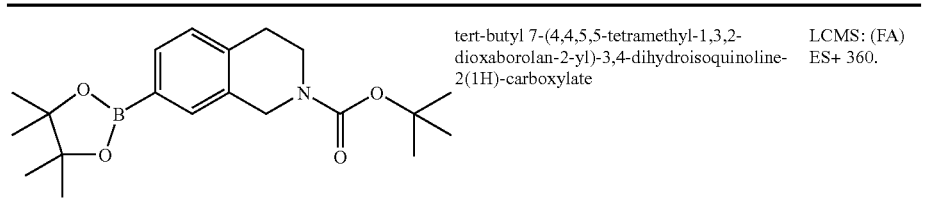

| | | |
|---|---|---|
| | tert-butyl 7-(4,4,5,5-tetramethyl-1,3,2-dioxaborolan-2-yl)-3,4-dihydroisoquinoline-2(1H)-carboxylate | LCMS: (FA) ES+ 360. |

| | tert-butyl 5-(4,4,5,5-tetramethyl-1,3,2-dioxaborolan-2-yl)-3,4-dihydroisoquinoline-2(1H)-carboxylate | LCMS: (FA) ES+ 360. |
|---|---|---|
| 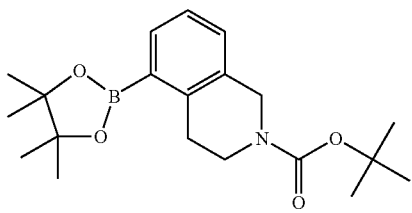 | | |

Tert-butyl 5-(4,4,5,5-tetramethyl-1,3,2-dioxaborolan-2-yl)-1,3-dihydro-2-H-isoindole-2-carboxylate

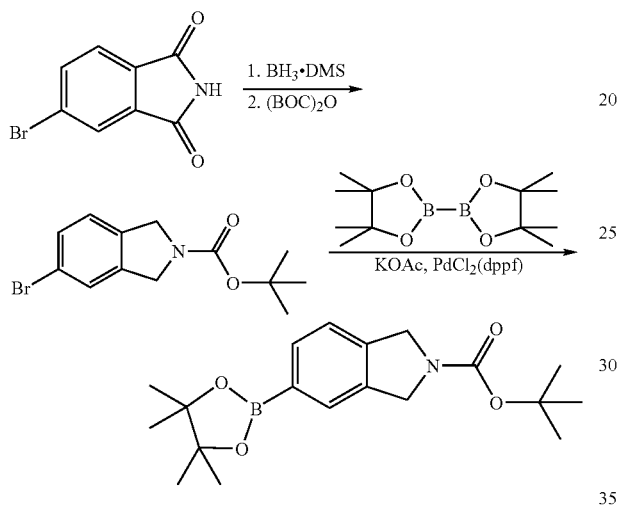

Step 1: tert-butyl 5-bromo-1,3-dihydro-2H-isoindole-2-carboxylate

To a solution of 5-bromo-1H-isoindole-1,3(2H)-dione (4 mmol) in THF (10 mL) was added borane-dimethyl sulfide complex (2M in THF, 14 mL) at 0° C. The reaction mixture was allowed to stir at reflux overnight and was then cooled to 0° C. The reaction mixture was quenched by the slow addition of MeOH (10 mL) and then 2N HCl (10 mL). The reaction mixture was allowed to stir at reflux for 3 hr and then concentrated. Water (10 mL) was added to the residue. Remaining starting material was removed by extraction with DCM. To the aqueous solution was added 4N NaOH until pH>9. The solution was extracted with DCM. The organic solutions from this basic extraction were combined, dried over $Na_2SO_4$, filtered and concentrated to give 5-bromoisoindoline, which was dissolved in THF (20 mL). To this solution was added potassium carbonate (8 mmol) in water (1 mL), and $BOC_2O$. The reaction mixture was allowed to stir at rt over the weekend. The reaction mixture was diluted with EtOAc, washed with brine, dried over $Na_2SO_4$, filtered and concentrated. The residue was purified by column chromatography to give tert-butyl 5-bromo-1,3-dihydro-2H-isoindole-2-carboxylate (2.5 mmol, 60%).

Step 2: tert-butyl 5-(4,4,5,5-tetramethyl-1,3,2-dioxaborolan-2-yl)-1,3-dihydro-2H-isoindole-2-carboxylate A solution of tert-butyl 5-bromo-1,3-dihydro-2H-isoindole-2-carboxylate (0.80 mmol), bis(pinacolato)diboron (0.96 mmol) and potassium acetate (2.5 mmol) in DMF (4 mL) was degassed. To this solution was added $PdCl_2dppf$ (1:1 complex with DCM, 0.04 mmol). The reaction mixture was heated at 85° C. for 4 hr and then allowed to cool to rt and diluted with EtOAc. The solution was washed with water and brine, dried over $Na_2SO_4$, filtered and concentrated. The residue was purified by column chromatography (10-30% EtOAc in hexane) to give tert-butyl 5-(4,4,5,5-tetramethyl-1,3,2-dioxaborolan-2-yl)-1,3-dihydro-2H-isoindole-2-carboxylate (0.57 mmol, 72%) as a white solid. LCMS: (FA) ES+ 346.

Tert-butyl 5-(4,4,5,5-tetramethyl-1,3,2-dioxaborolan-2-yl)-1,3-dihydro-2H-isoindole-2-carboxylate

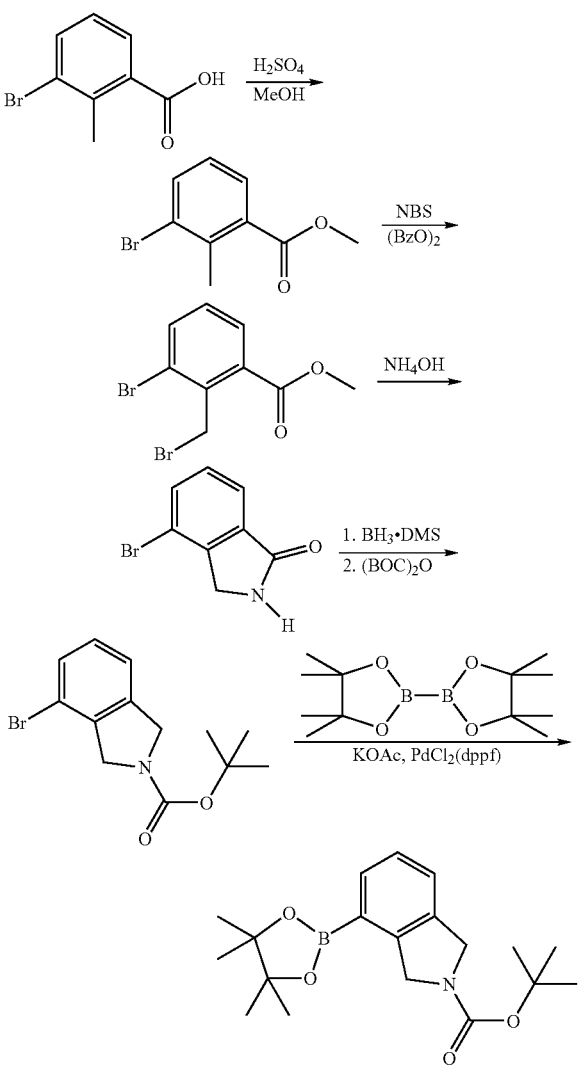

Step 1: methyl 3-bromo-2-methylbenzoate

Concentrated sulfuric acid (1 mL) was added to a solution of 3-bromo-2-methylbenzoic acid (27.9 mmol) in MeOH (60 mL) at rt. The reaction mixture was allowed to stir at reflux overnight and then concentrated to ~half volume. The solution was diluted with diethyl ether and washed with saturated NaHCO$_3$ and brine. The organic solution was dried over Na$_2$SO$_4$, filtered and concentrated to give methyl 3-bromo-2-methylbenzoate (27 mmol, 95%) as an oil which was used without further purification.

Step 2: methyl 3-bromo-2-(bromomethyl)benzoate

A suspension of methyl 3-bromo-2-methylbenzoate (26.6 mmol), benzoyl peroxide (2.7 mmol) and NBS (32 mmol) in benzene (80 mL) was allowed to stir at reflux for 5 hr. The reaction mixture was filtered and the solid was washed with diethyl ether. The organic solutions were combined and washed with 10% Na$_2$S$_2$O$_3$ and brine, dried over Na$_2$SO$_4$, filtered and concentrated. The residue was purified by column chromatography to give methyl 3-bromo-2-(bromomethyl)benzoate (26.6 mmol, 100%) as an oil.

Step 3: 4-bromoisoindolin-1-one

To a solution of methyl 3-bromo-2-(bromomethyl)benzoate (27 mmol) in THF (100 mmol) was added ammonium hydroxide (9 mL) dropwise at rt. The reaction mixture was allowed to stir overnight and then diluted with 30 mL of water. The solution was extracted with DCM, dried over Na$_2$SO$_4$, filtered and concentrated to give 4-bromoisoindolin-1-one (5.20 g, 91%).

Step 4: tert-butyl 4-bromo-1,3-dihydro-2H-isoindole-2-carboxylate

To a solution of 4-bromoisoindolin-1-one (4 mmol) in THF (8 mL) was added borane-dimethyl sulfide complex (2M in THF, 14 mL) at 0° C. The reaction mixture was allowed to stir at reflux overnight and was then cooled to 0° C. The reaction mixture was quenched by the slow addition of MeOH (2 mL) and then 3N HCl. The reaction mixture was allowed to stir at reflux for 3 hr and then concentrated. Water was added to the residue and the pH of the solution was adjusted to >9 with 4N NaOH. The solution was extracted with diethyl ether. The organic solutions from this basic extraction were combined, dried over Na$_2$SO$_4$, filtered and concentrated to give 4-bromoisoindoline, which was dissolved in THF (5 mL). To this solution was added potassium carbonate (4 mmol) in water (0.5 mL), and BOC$_2$O (2 mmol). The reaction mixture was allowed to stir at rt overnight. The reaction mixture was diluted with EtOAc, washed with brine, dried over Na$_2$SO$_4$, filtered and concentrated. The residue was purified by column chromatography to give tert-butyl 4-bromo-1,3-dihydro-2H-isoindole-2-carboxylate (0.8 mmol, 20%).

Step 5: tert-butyl 4-(4,4,5,5-tetramethyl-1,3,2-dioxaborolan-2-yl)-1,3-dihydro-2H-isoindole-2-carboxylate A solution of tert-butyl 4-bromo-1,3-dihydro-2H-isoindole-2-carboxylate (0.80 mmol), bis(pinacolato)diboron (0.96 mmol) and potassium acetate (2.5 mmol) in DMF (4 mL) was degassed. To this solution was added PdCl$_2$dppf (1:1 complex with DCM, 0.04 mmol). The reaction mixture was heated at 85° C. for 4 hr and then allowed to cool to rt and diluted with EtOAc. The solution was washed with water and brine, dried over Na$_2$SO$_4$, filtered and concentrated. The residue was purified by column chromatography to give tert-butyl 4-(4,4,5,5-tetramethyl-1,3,2-dioxaborolan-2-yl)-1,3-dihydro-2H-isoindole-2-carboxylate (0.64 mmol, 80%) as a white solid. LCMS: (FA) ES+ 346.

3-fluoro-4-(4,4,5,5-tetramethyl-1,3,2-dioxaborolan-2-yl)benzonitrile

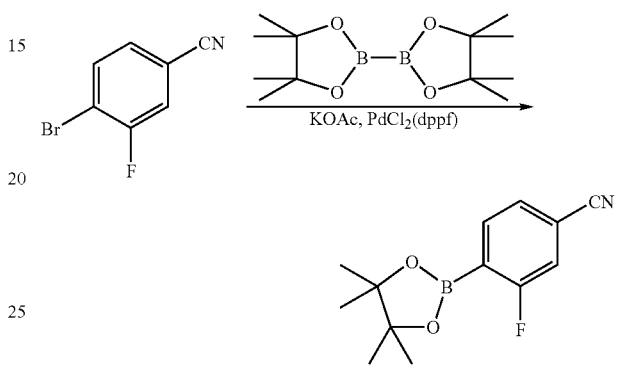

A solution of 4-bromo-3-fluorobenzonitrile (6.34 mmol), bis(pinacolato)diboron (8.16 mmol) and potassium acetate (19.9 mmol) in DMF (30 mL) was degassed. To this solution was added PdCl$_2$dppf (1:1 complex with DCM, 0.3 mmol). The reaction mixture was heated at 85° C. for 4 hr and then allowed to cool to rt and diluted with EtOAc. The solution was washed with water and brine, dried over Na$_2$SO$_4$, filtered and concentrated. The residue was purified by column chromatography to give 3-fluoro-4-(4,4,5,5-tetramethyl-1,3,2-dioxaborolan-2-yl)benzonitrile (0.29 g, 37%) as a white solid.

(2-{[(tert-butoxycarbonyl)amino]methyl}-4-methoxyphenyl)boronic acid

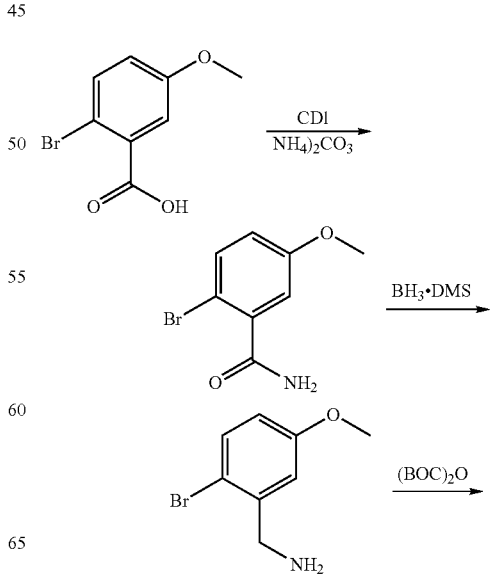

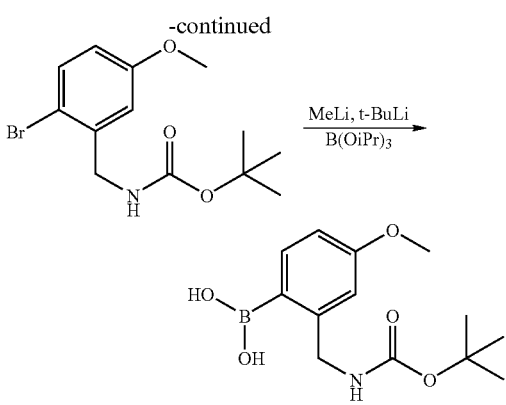

Step 1: 2-bromo-5-methoxybenzamide

To a solution of 2-bromo-5-methoxybenzoic acid (21.6 mmol) in DMF (20 mL) was added N,N-carbonyldiimidazole (54.1 mmol). The reaction mixture was allowed to stir at rt for 30 min and then ammonium carbonate (97.4 mmol) was added in portions over several minutes. The reaction mixture was allowed to stir until for 5 days and then poured into water. A white precipitate formed. The mixture was extracted with EtOAc. The organic solutions were combined, washed sequentially with water, 1N HCl, sat. aq. $NaHCO_3$ and brine, dried over $Na_2SO_4$ filtered and concentrated to give 2-bromo-5-methoxybenzamide (18.5 mmol, 85%), which was used without further purification.

Step 2: 1-(2-bromo-5-methoxyphenyl)methanamine

Immediately prior to reaction, 2-bromo-5-methoxybenzamide (6.4 mmol) was azeotropically dried with toluene and then further dried under vacuum. This dry material was suspended in THF (15 mL) and the suspension was cooled to 0° C. To the reaction mixture was added 2M borane-dimethylsulfide complex in THF (8 mL) via syringe. The reaction mixture was heated at 70° C. and allowed to stir overnight. The mixture was cooled to 0° C. and treated with conc. HCl (0.5 mL). Vigorous gas evolution is observed, and the reaction mixture was allowed to stir at 0° C. for 15 min and then concentrated. The residue was diluted with water (10 mL) and heated at reflux for 20 min. The mixture was allowed to cool to rt and was basified with sat $NaHCO_3$. The mixture was extracted with EtOAc. The organic solutions were combined, washed with brine, dried over $Na_2SO_4$, filtered and concentrated. The residue was purified by column chromatography to give 1-(2-bromo-5-methoxyphenyl)methanamine (3.1 mmol, 47%). LCMS: (FA) ES+ 216.

Step 3: tert-butyl (2-bromo-5-methoxybenzyl)carbamate

To a solution of 1-(2-bromo-5-methoxyphenyl)methanamine (3.2 mmol) in DCM (15 mL) was added $BOC_2O$ (3.2 mmol). The reaction mixture was allowed to stir at rt overnight and then concentrated. The residue was purified by column chromatography to give tert-butyl (2-bromo-5-methoxybenzyl)carbamate (3.1 mmol, 95%).

Step 4: (2-{[(tert-butoxycarbonyl)amino]methyl}-4-methoxyphenyl)boronic acid Immediately prior to reaction, tert-butyl (2-bromo-5-methoxybenzyl)carbamate (1.5 mmol) was azeotropically dried in toluene and further dried under vacuum. This dry material was dissolved in THF (7.25 mL) and the solution was cooled to −78° C. under an atmosphere of nitrogen. To this cold solution was added MeLi (1.6M in Ether, 1.05 mL) dropwise via syringe. The reaction mixture was allowed to stir at −78° C. for 1 hour and then tert-BuLi (1.7M in pentane, 1.90 mL) was added via syringe. The reaction mixture turned dark red/brown upon addition of t-BuLi. The reaction mixture was allowed to stir at −78° C. for 1 hour (reaction color fades to lighter orange/brown) and was then allowed to warm to rt and stir for 2 h. The mixture was cooled to 0° C. and then reaction was quenched by the addition of sat. aq. $NH_4Cl$ and diluted with EtOAc. The mixture was stirred vigorously for 10 minutes and then the aqueous and organic solutions were separated. The aqueous solution was further extracted with EtOAc. The organic solutions were combined, washed with brine, dried over $Na_2SO_4$, filtered and concentrated. The residue was purified by column chromatography to give (2-{[(tert-butoxycarbonyl)amino]methyl}-4-methoxyphenyl)boronic acid (0.32 mmol, 21%). LCMS: (AA) ES+ 282.2, ES- 280.3.

Compounds in the following table were prepared from the appropriate starting materials in a method analogous to that described (2-{[(tert-butoxycarbonyl)amino]methyl}-4-methoxyphenyl)boronic acid:

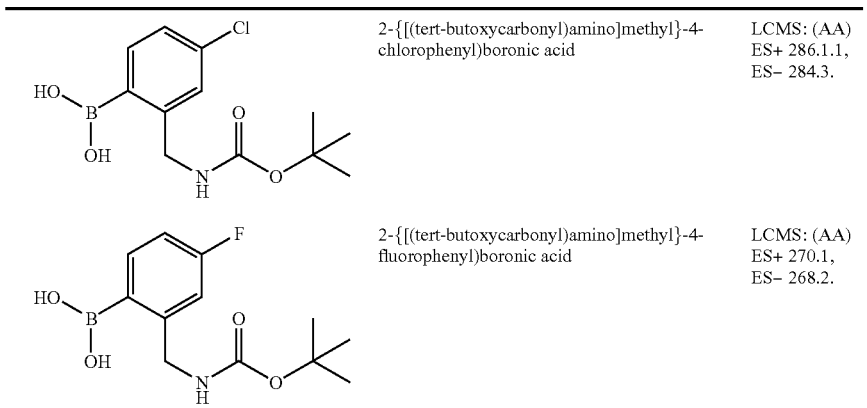

| Structure | Name | LCMS |
|---|---|---|
| (Cl-substituted) | 2-{[(tert-butoxycarbonyl)amino]methyl}-4-chlorophenyl)boronic acid | LCMS: (AA) ES+ 286.1.1, ES− 284.3. |
| (F-substituted) | 2-{[(tert-butoxycarbonyl)amino]methyl}-4-fluorophenyl)boronic acid | LCMS: (AA) ES+ 270.1, ES− 268.2. |

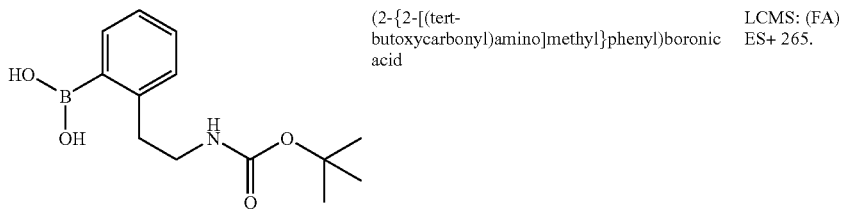

| | (2-{2-[(tert-butoxycarbonyl)amino]methyl}phenyl)boronic acid | LCMS: (FA) ES+ 265. |

Example 2

Synthesis of 2-{3-pyridin-3-yl-1-[(5-pyridin-2-yl-2-thienyl)carbonyl]-4,5-dihydro-1H-pyrazol-5-yl}phenol (I-76)

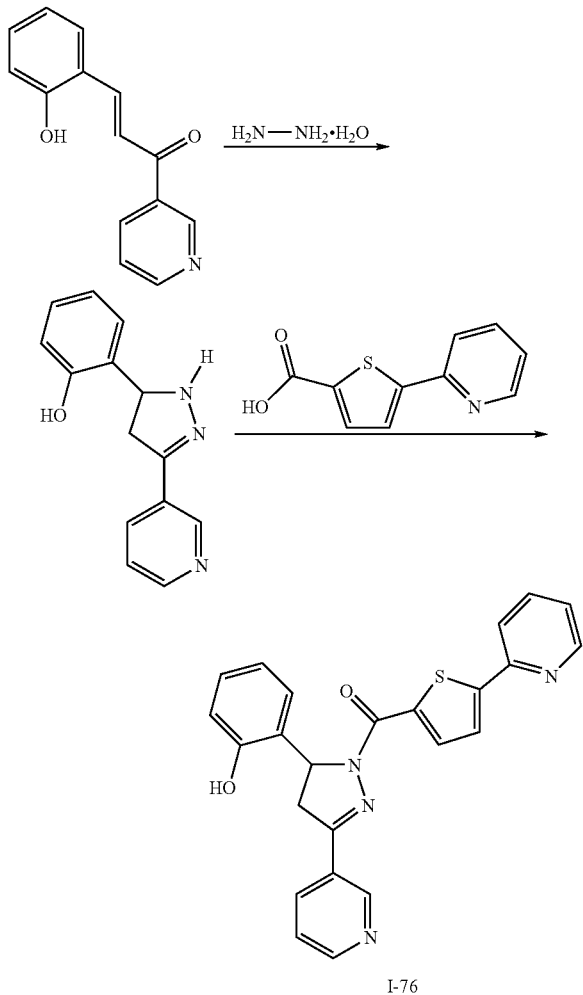

I-76

Step 1: 2-(3-pyridin-3-yl-4,5-dihydro-1H-pyrazol-5-yl)phenol

A solution of (2E)-3-(2-hydroxyphenyl)-1-pyridin-3-yl-prop-2-en-1-one (12.5 g, 55.6 mmol), hydrazine monohydrate (6.00 mL, 123 mmol), and ethanol (160 mL) was allowed to stir at 80° C. overnight. The reaction mixture was filtered over a pad of celite and washed with MeOH and DCM. The resulting filtrate was concentrated to give 2-(3-pyridin-3-yl-4,5-dihydro-1H-pyrazol-5-yl)phenol (12.5 g, 94%) as a light grey solid. $^1$H NMR (400 MHz, $d_6$-DMSO, HCl salt) δ: 9.52-9.67 (bs, 1H), 8.78 (s, 1H), 8.45-8.51 (m, 1H), 7.97 (d, 1H), 7.61 (s, 1H), 7.38 (t, 1H), 7.26 (d, 1H), 7.07 (t, 1H), 6.81 (d, 1H), 6.76 (t, 1H), 5.04 (t, 1H), 3.44 (dd, 1H), and 2.76 (dd, 1H). LCMS: (FA) ES+ 240.2, ES-238.5.

Step 2: 2-{3-pyridin-3-yl-1-[(5-pyridin-2-yl-2-thienyl)carbonyl]-4,5-dihydro-1H-pyrazol-5-yl}phenol (I-76)

To a solution of 2-(3-pyridin-3-yl-4,5-dihydro-1H-pyrazol-5-yl)phenol (1.01 g, 4.22 mmol) and 5-pyridin-2-ylthiophene-2-carboxylic acid (0.886 g, 4.32 mmol) in DCM (50 mL) was added EDCI (0.970 g, 5.10 mmol). The reaction mixture was allowed to stir at rt overnight. The solution was filtered and the resulting precipitate was washed with DCM to give a light tan solid. The filtrate was concentrated and the resulting residue was purified by column chromatography to give a yellow solid. The two batches of product were combined to give 2-{3-pyridin-3-yl-1-[(5-pyridin-2-yl-2-thienyl)carbonyl]4,5-dihydro-1H-pyrazol-5-yl}phenol (I-76) (1.293 g, 72%) as a tan solid. $^1$H NMR (400 MHz, $d_6$-DMSO, HCl salt) δ: 9.71-9.84 (bs, 1H), 9.11-9.16 (m, 1H), 8.72-8.77 (m, 1H), 8.60-8.65 (m, 1H), 8.35-8.42 (m, 1H), 8.06 (d, 1H), 8.01-8.04 (m, 1H), 7.84-7.94 (m, 2H), 7.66-7.73 (m, 1H), 7.34-7.41 (m, 1H), 7.04-7.12 (m, 1H), 6.93-6.99 (m, 1H), 6.82-6.87 (m, 1H), 6.73 (t, 1H), 5.87 (dd, 1H), 3.92 (dd, 1H), and 3.22 (dd, 1H). LCMS: (FA) ES+ 427.5, ES-425.4.

Compounds in the following table were prepared from the appropriate starting materials in a method analogous to that of Example 2:

| | |
|---|---|
| I-8 | LCMS: (FA) ES+ 428.6, ES− 426.7. |
| I-114 | LCMS: (FA) ES+ 445.6. |
| I-25 | LCMS: (FA) ES+ 427.3. |
| I-86 | LCMS: (FA) ES+ 445.2, ES− 443.3. |
| I-163 | LCMS: (FA) ES+ 445.2, ES− 443.3. |
| I-129 | LCMS: (FA) ES+ 385.3, ES− 383.4. |
| I-120 | LCMS: (FA) ES+ 385.3, ES− 383.3. |
| I-4 | LCMS: (FA) ES+ 426, ES− 424. |
| I-67 | LCMS: (FA) ES+ 429. |
| I-14 | LCMS: (FA) ES+ 431.5. |
| I-1 | LCMS: (FA) ES+ 428.4. |
| I-82 | LCMS: (FA) ES+ 411.1, ES− 409.1. |
| I-146 | LCMS: (FA) ES+ 428. |
| I-170 | LCMS: (FA) ES+ 411. |
| I-28 | LCMS: (FA) ES+ 548.2, ES− 546.3. |
| I-137 | LCMS: (FA) ES+ 433.2, ES− 431.2. |
| I-89 | LCMS: (FA) ES+ 421.3, ES− 419.6. |
| I-57 | LCMS: (FA) ES+ 421.1, ES− 419.1. |
| I-153 | LCMS: (FA) ES+ 451.3, ES− 449.4. |

-continued

| | |
|---|---|
| I-33 | LCMS: (FA) ES+ 529.4, ES− 527.5. |
| I-11 | LCMS: (FA) ES+ 445, ES− 443. |
| I-181 | LCMS: (FA) ES+ 457, ES− 455. |
| I-166 | LCMS: (FA) ES+ 461, ES− 459. |
| I-58 | LCMS: (FA) ES+ 435.3, ES− 433.3. |
| I-201 | LCMS: (FA) ES+ 469.1, ES− 467.2. |
| I-312 | LCMS: (FA) ES+ 429.2, ES− 427.3. |
| I-279 | LCMS: (FA) ES+ 428.3, ES− 426.3. |
| I-314 | LCMS: (FA) ES+ 428.1, ES− 426.2. |
| I-320 | LCMS: (FA) ES+ 441.4, ES− 439.6. |
| I-290 | LCMS: (FA) ES+ 446.1, ES− 444.1. |
| I-274 | LCMS: (FA) ES+ 429.1, ES− 427.1. |
| I-379 | LCMS: (FA) ES+ 484.4, ES− 482.6. |
| I-246 | LCMS: (FA) ES+ 448.1, ES− 446.0 |
| I-227 | LCMS: (FA) ES+ 428.1, ES− 426.1 |
| I-268 | LCMS: (FA) ES+ 489, ES− 487. |

Example 3

Synthesis of 2-{3-pyridin-3-yl-1-[(5-pyridin-2-yl-2-thienyl)carbonyl]-4,5-dihydro-1H-pyrazol-5-yl}phenol (I-76)

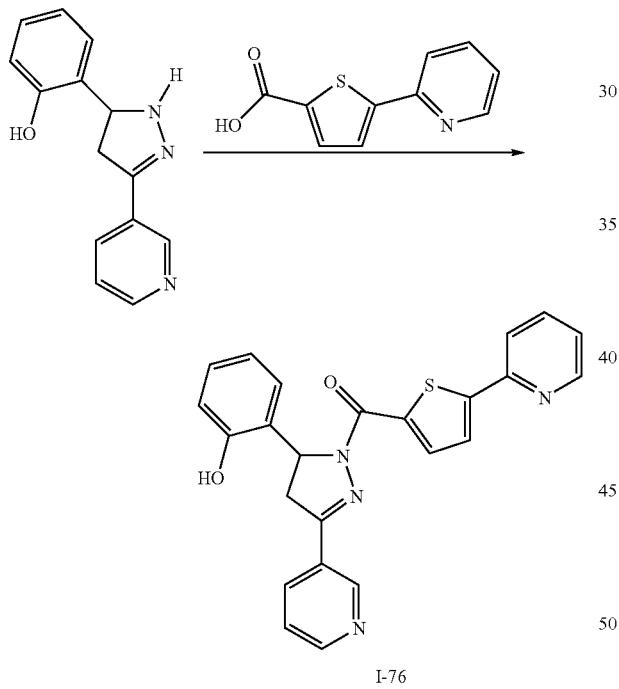

To a solution of 2-(3-pyridin-3-yl-4,5-dihydro-1H-pyrazol-5-yl)phenol (600 mg, 2.51 mmol) and pyridine-2-ylthiophene-2-carboxylic acid (515 mg, 2.51 mmol) in DCM (10 mL) was added EDCI (580 mg, 3.00 mmol) and DMF (3 mL). After stirring for 12 h, water and EtOAc were added. The resulting solid was filtered and washed with EtOAc and cold MeOH and dried under vacuum to give 2-[3-pyridin-3-yl-1-[(5-pyridin-2-yl-2-thienyl)carbonyl]-4,5-dihydro-1H-pyrazol-5-yl]phenol (I-76) (520 mg, 49%). LCMS: (AA) ES+ 427.4.

Compounds in the following table were prepared from the appropriate starting materials in a method analogous to that of Example 3:

| | |
|---|---|
| I-84 | LCMS: (FA) ES+ 409.5. |
| I-191 | LCMS: (FA) ES+ 478.4. |
| I-117 | LCMS: (FA) ES+ 442.5. |
| I-81 | LCMS: (FA) ES+ 427.4. |
| I-119 | LCMS: (FA) ES+ 430.5. |
| I-148 | LCMS: (FA) ES+ 497.9. |
| I-179 | LCMS: (FA) ES+ 457.1. |
| I-93 | LCMS: (FA) ES+ 438.0. |
| I-74 | LCMS: (FA) ES+ 432.0. |
| I-44 | LCMS: (FA) ES+ 495.0. |
| I-3 | LCMS: (FA) ES+ 436.0. |
| I-37 | LCMS: (FA) ES+ 523.1. |
| I-107 | LCMS: (FA) ES+ 513.1. |
| I-24 | LCMS: (FA) ES+ 480.0. |
| I-22 | LCMS: (FA) ES+ 458.1. |
| I-68 | LCMS: (FA) ES+ 412.3. |
| I-73 | LCMS: (FA) ES+ 481.1. |
| I-39 | LCMS: (FA) ES+ 410.1. |
| I-42 | LCMS: (FA) ES+ 606.2. |
| I-124 | LCMS: (FA) ES+ 427.4. |
| I-189 | LCMS: (FA) ES+ 427.4. |
| I-185 | LCMS: (FA) ES+ 427.3. |
| I-69 | LCMS: (FA) ES+ 424.3. |
| I-151 | LCMS: (FA) ES+ 411.4. |
| I-143 | LCMS: (FA) ES+ 537.3. |
| I-59 | LCMS: (FA) ES+ 495.4. |
| I-192 | LCMS: (FA) ES+ 478.4. |
| I-41 | LCMS: (FA) ES+ 474.4. |
| I-184 | LCMS: (FA) ES+ 398.3. |
| I-52 | LCMS: (FA) ES+ 445.3. |
| I-71 | LCMS: (FA) ES+ 468.3. |
| I-123 | LCMS: (FA) ES+ 456.3. |
| I-30 | LCMS: (FA) ES+ 469.1. |
| I-98 | LCMS: (FA) ES+ 517.3. |
| I-169 | LCMS: (FA) ES+ 468.1. |
| I-142 | LCMS: (FA) ES+ 437.3. |
| I-130 | LCMS: (FA) ES+ 425.3. |
| I-13 | LCMS: (FA) ES+ 425.3. |
| I-32 | LCMS: (FA) ES+ 468.3. |
| I-10 | LCMS: (FA) ES+ 469.3. |
| I-160 | LCMS: (FA) ES+ 469.2. |
| I-111 | LCMS: (FA) ES+ 439.3. |
| I-46 | LCMS: (FA) ES+ 429.4. |
| I-62 | LCMS: (FA) ES+ 469.2. |
| I-88 | LCMS: (FA) ES+ 443.4. |
| I-155 | LCMS: (FA) ES+ 445.3. |
| I-133 | LCMS: (FA) ES+ 445.3. |
| I-145 | LCMS: (FA) ES+ 455.2. |
| I-157 | LCMS: (FA) ES+ 447.3. |
| I-103 | LCMS: (FA) ES+ 407.3. |
| I-48 | LCMS: (FA) ES+ 458.2. |
| I-118 | LCMS: (FA) ES+ 429.2. |
| I-60 | LCMS: (FA) ES+ 439.3. |
| I-150 | LCMS: (FA) ES+ 436.3. |
| I-116 | LCMS: (FA) ES+ 414.3. |
| I-128 | LCMS: (FA) ES+ 431.2. |
| I-77 | LCMS: (FA) ES+ 455.3. |
| I-34 | LCMS: (FA) ES+ 453.3. |
| I-35 | LCMS: (FA) ES+ 422.3. |
| I-154 | LCMS: (FA) ES+ 425.3. |
| I-96 | LCMS: (FA) ES+ 425.3. |
| I-27 | LCMS: (FA) ES+ 457.3. |
| I-15 | LCMS: (FA) ES+ 432.3. |
| I-49 | LCMS: (FA) ES+ 431.3. |
| I-158 | LCMS: (FA) ES+ 426.3. |
| I-183 | LCMS: (FA) ES+ 425.3. |
| I-186 | LCMS: (FA) ES+ 409.3. |
| I-115 | LCMS: (FA) ES+ 453.4. |
| I-47 | LCMS: (FA) ES+ 409.3. |
| I-102 | LCMS: (FA) ES+ 430.2. |
| I-176 | LCMS: (FA) ES+ 422.3. |
| I-104 | LCMS: (FA) ES+ 467.3. |
| I-94 | LCMS: (FA) ES+ 421.4. |
| I-31 | LCMS: (FA) ES+ 442.3. |
| I-168 | LCMS: (FA) ES+ 415.4. |
| I-61 | LCMS: (FA) ES+ 445.4. |
| I-109 | LCMS: (FA) ES+ 409.3. |
| I-177 | LCMS: (FA) ES+ 408.3. |
| I-20 | LCMS: (FA) ES+ 438.3. |

| | |
|---|---|
| I-65 | LCMS: (FA) ES+ 426.3. |
| I-134 | LCMS: (FA) ES+ 445.3. |
| I-66 | LCMS: (FA) ES+ 453.3. |
| I-127 | LCMS: (FA) ES+ 412.3. |
| I-140 | LCMS: (FA) ES+ 399.3. |
| I-121 | LCMS: (FA) ES+ 439.3. |
| I-112 | LCMS: (FA) ES+ 422.3. |
| I-78 | LCMS: (FA) ES+ 437.3. |
| I-110 | LCMS: (FA) ES+ 440.3. |
| I-162 | LCMS: (FA) ES+ 438.3. |
| I-152 | LCMS: (FA) ES+ 439.3. |
| I-43 | LCMS: (FA) ES+ 456.3. |
| I-12 | LCMS: (FA) ES+ 455.3. |
| I-72 | LCMS: (FA) ES+ 441.3. |
| I-70 | LCMS: (FA) ES+ 400.3. |
| I-90 | LCMS: (FA) ES+ 441.3. |
| I-138 | LCMS: (FA) ES+ 443.3. |
| I-91 | LCMS: (FA) ES+ 423.3. |
| I-21 | LCMS: (FA) ES+ 439.3. |
| I-147 | LCMS: (FA) ES+ 442.3. |
| I-174 | LCMS: (FA) ES+ 425.3. |
| I-161 | LCMS: (FA) ES+ 409.2. |
| I-172 | LCMS: (FA) ES+ 441.3. |
| I-5 | LCMS: (FA) ES+ 429.3. |
| I-95 | LCMS: (FA) ES+ 459.2. |
| I-54 | LCMS: (FA) ES+ 440.3. |
| I-64 | LCMS: (FA) ES+ 408.2. |
| I-75 | LCMS: (FA) ES+ 423.3. |
| I-182 | LCMS: (FA) ES+ 454.3. |
| I-101 | LCMS: (FA) ES+ 423.3. |
| I-87 | LCMS: (FA) ES+ 468.3. |
| I-113 | LCMS: (FA) ES+ 466.3. |
| I-165 | LCMS: (FA) ES+ 484.3. |
| I-131 | LCMS: (FA) ES+ 447.3. |
| I-29 | LCMS: (FA) ES+ 426.3. |
| I-36 | LCMS: (FA) ES+ 450.2. |
| I-97 | LCMS: (FA) ES+ 494.3. |
| I-188 | LCMS: (FA) ES+ 424.3. |

Example 4

Synthesis of 2-[3-pyridin-3-yl-1-[(5-pyridin-2-yl-2-thienyl)sulfonyl]-4,5-dihydro-1H-pyrazol-5-yl]phenol (I-126)

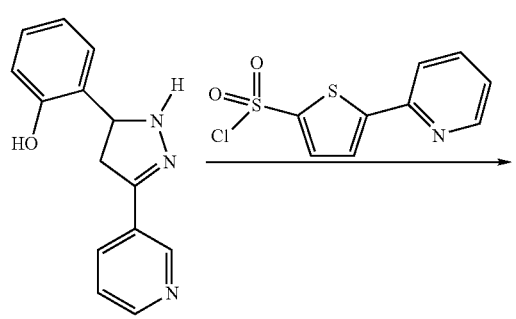

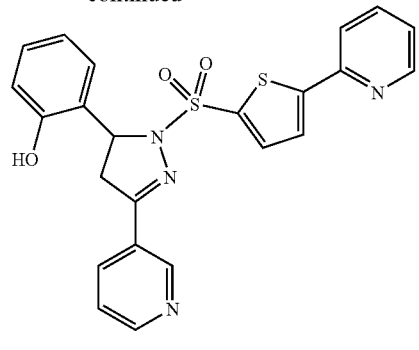

I-126

To 2-(3-pyridin-3-yl-4,5-dihydro-1H-pyrazol-5-yl)phenol (29.85 mg, 0.1149 mmol) placed in a sealed tube was added a solution of 5-pyridin-2-ylthiophene-2-sulfonyl chloride (29.85 mg, 0.1045 mmol) in pyridine (0.5 mL). The reaction mixture was shaken at rt for 18 h. The reaction mixture was diluted with a saturated solution of sodium bicarbonate (2.0 mL) and extracted with DCM. The organic solutions were combined, dried over $MgSO_4$, filtered, and concentrated. The residue was purified by RP-HPLC to give 2-{3-pyridin-3-yl-1-[(5-pyridin-2-yl-2-thienyl)sulfonyl]-4,5-dihydro-1H-pyrazol-5-yl}phenol (I-126) (14.50 mg, 30.0%). $^1$H NMR (300 MHz, $d_6$-DMSO) δ: 9.77 (s, 1H), 8.87 (bd, 1H), 8.64 (dd, 1H), 8.56 (bd, 1H), 8.12 (dt, 1H), 8.03 (d, 1H), 7.87-7.92 (m, 2H), 7.72 (d, 1H), 7.48 (dd, 1H), 7.35-7.40 (m, 2H), 7.11-7.17 (m, 1H), 6.81-6.85 (m, 2H), 5.24 (dd, 1H), 3.74 (dd, 1H), and 3.20 (dd, 1H). LCMS: (FA) ES+ 463.0, ES-460.9.

Compounds in the following table were prepared from the appropriate starting materials in a method analogous to that of Example 4:

| | |
|---|---|
| I-26 | LCMS: (FA) ES+ 453.1. |
| I-171 | LCMS: (FA) ES+ 466.2. |
| I-9 | LCMS: (FA) ES+ 526.1. |
| I-178 | LCMS: (FA) ES+ 470.1. |

Example 5

Synthesis of 5-(2-hydroxyphenyl)-N-(2-phenoxyphenyl)-3-pyridin-3-yl-4,5-dihydro-1H-pyrazole-1-carboxamide (I-85)

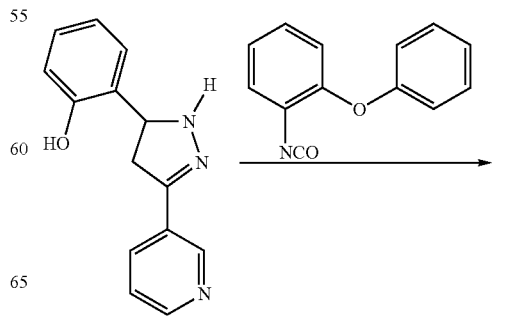

-continued

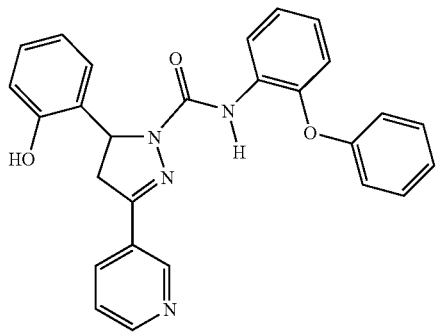

I-85

To a solution of 1-isocyanato-2-phenoxybenzene (29.14 mg, 0.138 mmol) in DMF (0.5 mL) was added a solution of 2-(3-pyridin-3-yl-4,5-dihydro-1H-pyrazol-5-yl)phenol (29.9 mg, 0.125 mmol) in DMF (0.5 mL) and DCE (0.5 mL) at rt. The reaction mixture was shaken at rt for 20 h. The reaction mixture was diluted with a saturated solution of sodium bicarbonate (2 mL) and extracted with DCM. The organic solutions were combined, dried over MgSO$_4$, filtered, and concentrated. The residue was purified by RP-HPLC to give 5-(2-hydroxyphenyl)-N-(2-phenoxyphenyl)-3-pyridin-3-yl-4,5-dihydro-1H-pyrazole-1-carboxamide (I-85) (7.24 mg, 12.8%). LCMS: (FA) ES+ 451.3.

Compounds in the following table were prepared from the appropriate starting materials in a method analogous to that of Example 5:

| I-122 | LCMS: (FA) ES+ 449.3, ES− 447.4. |
| I-149 | LCMS: (FA) ES+ 435.3, ES− 433.4. |
| I-16  | LCMS: (FA) ES+ 399.2, ES− 397.2. |

Example 6

Synthesis of N-[2-(benzyloxy)phenyl]-5-(2-hydroxyphenyl)-3-pyridin-3-yl-4,5-dihydro-1H-pyrazole-1-carboxamide (I-269)

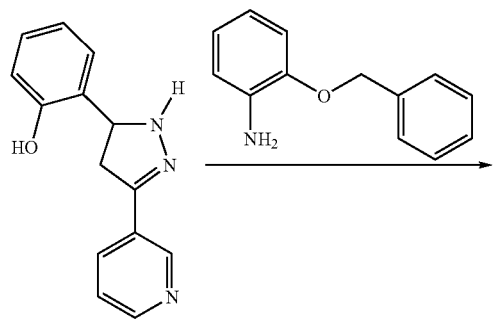

-continued

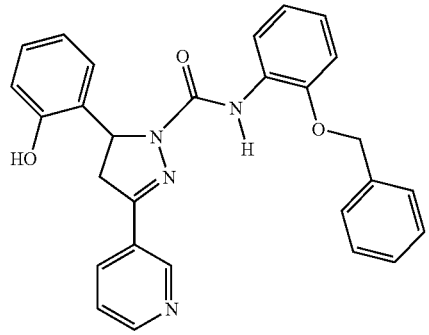

To a solution of 4-benzyloxyaniline hydrochloride (34.5 mg, 0.146 mmol) in DCE (1 mL) was added a solution of DIPEA (0.0525 mL, 0.302 mmol) in DCE (0.5 mL) at rt. Upon cooling to −78° C., triphosgene (14.4 mg, 0.0487 mmol) in DCE (1.0 mL) was added and the reaction mixture was allowed to warm to rt and stir for 1 h. The reaction mixture was then heated at 60° C. for and 2 h. The solution was allowed to cool to rt and then cooled to −78° C. whereupon a solution of 2-(3-pyridin-3-yl-4,5-dihydro-1H-pyrazol-5-yl)phenol (35.0 mg, 0.146 mmol) in DMF (0.5 mL) was added. The reaction mixture was shaken at rt for 15 hours. The reaction was quenched with the addition of water (2 mL) and extracted with DCM. The organic solutions were combined, dried over anhydrous MgSO4, filtered, and concentrated. The residue was purified by RP-HPLC to give N-[2-(benzyloxy) phenyl]-5-(2-hydroxyphenyl)-3-pyridin-3-yl-4,5-dihydro-1H-pyrazole-1-carboxamide (19.20 mg, 28.2%). LCMS: (FA) ES+ 465.6, ES-463.2.

Compounds in the following table were prepared from the appropriate starting materials in a method analogous to that of Example 6:

| I-286 | LCMS: (FA) ES+ 469.1, ES− 467.0. |
| I-319 | LCMS: (FA) ES+ 451.1, ES− 449.1. |
| I-259 | LCMS: (FA) ES+ 534.1, ES− 532.1. |
| I-229 | LCMS: (FA) ES+ 480.1, ES− 478.2. |
| I-361 | LCMS: (FA) ES+ 457.1, ES− 455.1. |
| I-215 | LCMS: (FA) ES+ 452.1, ES− 450.0. |
| I-368 | LCMS: (FA) ES+ 473.0, ES− 471.0. |
| I-328 | LCMS: (AAC) ES+ 519.3, ES− 517.4. |
| I-253 | LCMS: (FA) ES+ 449.1, ES− 447.1. |
| I-354 | LCMS: (FA) ES+ 501.1, ES− 499.0. |
| I-365 | LCMS: (FA) ES+ 508.0, ES− 506.0. |
| I-213 | LCMS: (FA) ES+ 517.0, ES− 515.0. |
| I-336 | LCMS: (FA) ES+ 587.0, ES− 585.1. |
| I-261 | LCMS: (FA) ES+ 499.1, ES− 497.1. |
| I-301 | LCMS: (FA) ES+ 519.0, ES− 517.0. |
| I-225 | LCMS: (FA) ES+ 425.1, ES− 423.1. |
| I-332 | LCMS: (FA) ES+ 457.1. |
| I-382 | LCMS: (FA) ES+ 442.1. |
| I-243 | LCMS: (FA) ES+ 535.9, ES− 534.0. |
| I-360 | LCMS: (AAC) ES+ 465.4, ES− 463.4. |
| I-214 | LCMS: (FA) ES+ 449.1. |
| I-309 | LCMS: (FA) ES+ 445.1, ES− 443.1. |
| I-374 | LCMS: (FA) ES+ 439.1, ES− 437.1. |
| I-254 | LCMS: (FA) ES+ 403.1, ES− 401.1. |
| I-271 | LCMS: (FA) ES+ 506.2, ES− 504.2. |
| I-317 | LCMS: (FA) ES+ 443.1, ES− 441.0. |
| I-233 | LCMS: (FA) ES+ 439.1. |
| I-295 | LCMS: (FA) ES+ 463.2, ES− 461.2. |
| I-359 | LCMS: (FA) ES+ 465.1, ES− 463.1. |
| I-335 | LCMS: (FA) ES+ 470.1, ES− 468.1. |
| I-219 | LCMS: (FA) ES+ 521.1, ES− 519.1. |
| I-235 | LCMS: (FA) ES+ 426.1, ES− 424.1. |

-continued

| | |
|---|---|
| I-216 | LCMS: (FA) ES+ 425.1. |
| I-351 | LCMS: (FA) ES+ 453.1, ES− 451.2. |
| I-306 | LCMS: (FA) ES+ 426.1, ES− 424.1. |
| I-248 | LCMS: (FA) ES+ 498.0, ES− 496.0. |
| I-264 | LCMS: (FA) ES+ 463.6. |
| I-285 | LCMS: (FA) ES+ 499.1, ES− 497.1. |
| I-326 | LCMS: (FA) ES+ 425.2, ES− 423.2. |
| I-338 | LCMS: (FA) ES− 510.0. |
| I-240 | LCMS: (FA) ES+ 480.1, ES− 478.2. |
| I-258 | LCMS: (FA) ES+ 465.1, ES− 463.1. |
| I-303 | LCMS: (FA) ES+ 443.0, ES− 441.0. |
| I-289 | LCMS: (FA) ES+ 449.1. |
| I-351 | LCMS: (FA) ES+ 453.1, ES− 451.2. |
| I-209 | LCMS: (FA) ES+ 507.2, ES− 505.2. |
| I-357 | LCMS: (FA) ES+ 477.0, ES− 475.0. |
| I-212 | LCMS: (FA) ES+ 556.0, ES− 554.0. |
| I-247 | LCMS: (FA) ES+ 472.1, ES− 470.1. |
| I-316 | LCMS: (FA) ES+ 505.0, ES− 503.0. |
| I-341 | LCMS: (FA) ES+ 471.2, ES− 469.2. |
| I-299 | LCMS: (AAC) ES+ 553.2, ES− 551.2. |
| I-250 | LCMS: (AAC) ES+ 441.4, ES− 439.4. |
| I-313 | LCMS: (AAC) ES+ 456.4, ES− 454.4. |
| I-262 | LCMS: (AAC) ES+ 465.4. |
| I-342 | LCMS: (AAC) ES+ 489.4. |
| I-311 | LCMS: (AAC) ES+ 516.2. |
| I-322 | LCMS: (AAC) ES+ 521.1, ES− 519.2. |
| I-277 | LCMS: (AAC) ES+ 488.3, ES− 486.3. |
| I-236 | LCMS: (AAC) ES+ 485.3, ES− 483.3. |
| I-237 | LCMS: (AAC) ES+ 426.4, ES− 424.4. |
| I-388 | LCMS: (AAC) ES+ 444.3, ES− 442.3. |
| I-230 | LCMS: (AAC) ES+ 520.2, ES− 518.3. |
| I-220 | LCMS: (AAC) ES+ 465.4. |
| I-251 | LCMS: (AAC) ES+ 442.4, ES− 440.4. |

Example 7

Synthesis of 5-(2-hydroxyphenyl)-N-(5-methyl-3-phenylisoxazol-4-yl)-3-pyridin-3-yl-4,5-dihydro-1H-pyrazole-1-carboxamide (I-323)

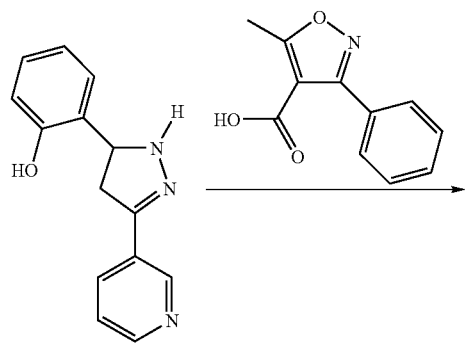

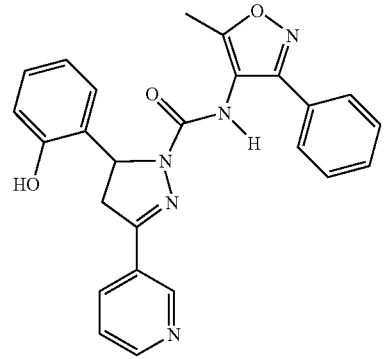

To a solution of 5-methyl-3-phenylisoxazole-4-carboxylic acid (29.7 mg, 0.146 mmol) in DCE (1 mL) was added a solution of TEA (14.8 mg, 0.146 mmol) in DCE (0.5 mL) at rt followed by the addition of a solution of diphenylphosphonic azide (40.2 mg, 0.146 mmol) in DCE (0.5 mL). The reaction mixture was heated at 90° C. for 2 h and then the solution was allowed to cool to rt and further to below −30° C., whereupon a solution of 2-(3-pyridin-3-yl-4,5-dihydro-1H-pyrazol-5-yl)phenol (35.0 mg, 0.146 mmol) in DMF (0.5 mL) was added. The mixture was shaken at rt for 16 h. The residue was partitioned between water (4 mL) and DCM (3 mL). The aqueous solution was extracted with DCM. The organic solutions were combined, dried over anhydrous MgSO$_4$, filtered, and concentrated. The residue was purified by RP-HPLC to give 5-(2-hydroxyphenyl)-N-(5-methyl-3-phenylisoxazol-4-yl)-3-pyridin-3-yl-4,5-dihydro-1H-pyrazole-1-carboxamide (5.53 mg, 8.6%). LCMS: (AAC) ES+ 440.3.

Compounds in the following table were prepared from the appropriate starting materials in a method analogous to that of Example 7:

| | |
|---|---|
| I-380 | LCMS: (AAC) ES+ 440.3. |
| I-337 | LCMS: (AAC) ES+ 441.4. |
| I-343 | LCMS: (AAC) ES+ 481.3. |
| I-228 | LCMS: (AAC) ES+ 492.2. |
| I-348 | LCMS: (AAC) ES+ 589.1. |
| I-349 | LCMS: (AAC) ES+ 490.4, ES− 488.5. |
| I-373 | LCMS: (AAC) ES+ 504.4. |
| I-376 | LCMS: (AAC) ES+ 534.4. |
| I-310 | LCMS: (AAC) ES+ 621.5. |
| I-249 | LCMS: (AAC) ES+ 424.4. |
| I-298 | LCMS: (AAC) ES+ 449.4. |
| I-366 | LCMS: (AAC) ES+ 475.4, ES− 473.5. |
| I-300 | LCMS: (AAC) ES+ 568.4, ES− 566.5. |
| I-291 | LCMS: (AAC) ES+ 495.5, ES− 493.5. |
| I-234 | LCMS: (AAC) ES+ 453.3. |
| I-358 | LCMS: (AAC) ES+ 534.3. |
| I-263 | LCMS: (AAC) ES+ 486.4. |
| I-304 | LCMS: (AAC) ES+ 469.3. |
| I-367 | LCMS: (AAC) ES+ 503.4. |
| I-224 | LCMS: (AAC) ES+ 492.4, ES− 490.4. |
| I-266 | LCMS: (AAC) ES+ 534.4. |
| I-327 | LCMS: (AAC) ES+ 442.4. |
| I-267 | LCMS: (AAC) ES+ 523.4, ES− 521.5. |
| I-321 | LCMS: (AAC) ES+ 427.5, ES− 425.5. |
| I-333 | LCMS: (AAC) ES+ 534.3, ES− 532.4. |
| I-315 | LCMS: (AAC) ES+ 493.4. |
| I-307 | LCMS: (AAC) ES+ 468.4. |
| I-278 | LCMS: (AAC) ES+ 534.3. |
| I-305 | LCMS: (AAC) ES+ 534.3. |
| I-353 | LCMS: (AAC) ES+ 439.4, ES− 437.4. |
| I-344 | LCMS: (AAC) ES+ 441.5, ES− 439.5. |

-continued

| | |
|---|---|
| I-245 | LCMS: (AAC) ES+ 490.4, ES− 488.5. |
| I-218 | LCMS: (AAC) ES+ 451.4. |
| I-272 | LCMS: (AAC) ES+ 453.4. |
| I-270 | LCMS: (AAC) ES+ 493.4, ES− 492.4. |
| I-287 | LCMS: (AAC) ES+ 497.3. |
| I-331 | LCMS: (AAC) ES+ 495.4. |
| I-288 | LCMS: (AAC) ES+ 534.3. |
| I-225 | LCMS: (AAC) ES+ 456.4. |
| I-339 | LCMS: (AAC) ES+ 444.5, ES− 442.5. |
| I-364 | LCMS: (AAC) ES+ 518.3. |
| I-352 | LCMS: (AAC) ES+ 492.4. |
| I-362 | LCMS: (AAC) ES+ 534.4, ES− 532.5. |
| I-211 | LCMS: (AAC) ES+ 465.4. |
| I-292 | LCMS: (AAC) ES+ 452.4. |
| I-256 | LCMS: (AAC) ES+ 445.4, ES− 443.5. |
| I-265 | LCMS: (AAC) ES+ 465.4, ES− 464.4. |
| I-391 | LCMS: (AAC) ES+ 541.4 |
| I-387 | LCMS: (AAC) ES+ 426.4 |
| I-384 | LCMS: (AAC) ES+ 568.4 |
| I-372 | LCMS: (AAC) ES+ 439.5 |
| I-386 | LCMS: (AAC) ES+ 473.5 |
| I-297 | LCMS: (AAC) ES+ 425.5 |
| I-385 | LCMS: (AAC) ES+ 500.4 |
| I-284 | LCMS: (AAC) ES+ 602.4 |
| I-329 | LCMS: (FA) ES+ 520.4, ES− 518.4 |
| I-334 | LCMS: (FA) ES+ 502.4, ES− 500.4 |

Example 8

Synthesis of 2-(1-{[5-(1H-pyrazol-4-yl)-2-thienyl]carbonyl}-3-pyridin-3-yl-4,5-dihydro-1H-pyrazol-5-yl)phenol (I-45)

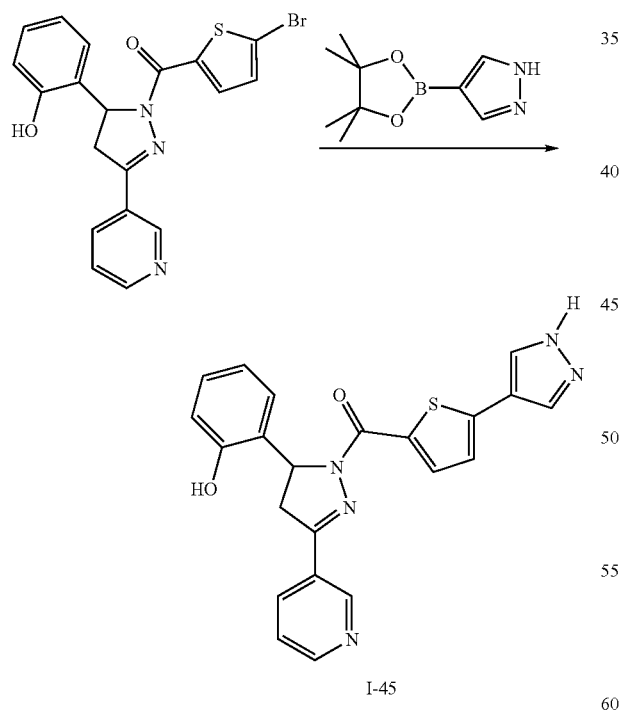

I-45

To a solution of 2-{1-[(5-bromo-2-thienyl)carbonyl]-3-pyridin-3-yl-4,5-dihydro-1H-pyrazol-5-yl}phenol (0.209 g, 0.488 mmol) in MeOH (1 mL), DMF (1 mL), and water (1 mL) was added 4-(4,4,5,5-tetramethyl-1,3,2-dioxaborolan-2-yl)-1H-pyrazole (0.110 g, 0.567 mmol), tetrakis(triphenylphosphine)palladium(0) (0.032 g, 0.028 mmol) and cesium carbonate (0.318 g, 0.976 mmol). The reaction mixture was subjected to MWI at 100° C. for 15 minutes. A precipitate formed and was filtered and washed with water to give 0.197 grams of crude product as a tan solid. The crude material was purified by column chromatography to give 2-(1-{[5-(1H-pyrazol-4-yl)-2-thienyl]carbonyl}-3-pyridin-3-yl-4,5-dihydro-1H-pyrazol-5-yl)phenol (I-45) (0.048 g, 0.116 mmol) as a white solid. LCMS: (FA) ES+ 416.3, ES 414.3. $^1$H NMR (400 MHz, $d_6$-DMSO) δ: 9.73-9.82 (bs, 1H), 9.11 (s, 1H), 8.78 (d, 1H), 8.54 (d, 1H), 8.12 (s, 2H), 7.96 (d, 1H), 7.74-7.80 (m, 1H), 7.29 (d, 1H), 7.08 (t, 1H), 6.92 (d, 1H), 6.85 (d, 1H), 6.72 (t, 1H), 5.85 (dd, 1H), 3.90 (dd, 1H), and 3.21 (dd, 1H).

Compounds in the following table were prepared from the appropriate starting materials in a method analogous to that of Example 8:

| | |
|---|---|
| I-17 | LCMS: (FA) ES− 468.1. |
| I-19 | LCMS: (FA) ES+ 452.2, ES− 450.3. |
| I-173 | LCMS: (FA) ES+ 427.3, ES− 425.6. |
| I-83 | LCMS: (FA) ES+ 427.0, ES− 425.0. |
| I-190 | LCMS: (FA) ES+ 460.3, ES− 457.9. |
| I-144 | LCMS: (FA) ES+ 460.3, ES− 458.7. |
| I-125 | LCMS: (FA) ES+ 460.0, ES− 458.0. |
| I-135 | LCMS: (FA) ES+ 451.6, ES− 449.0. |
| I-51 | LCMS: (FA) ES+ 451.4. |
| I-164 | LCMS: (FA) ES+ 451.4. |
| I-175 | LCMS: (FA) ES+ 440.8, ES− 438.0. |
| I-7 | LCMS: (FA) ES+ 440.1, ES− 438.0. |
| I-105 | LCMS: (FA) ES+ 454.2, ES− 452.7. |
| I-53 | LCMS: (FA) ES+ 440.3, ES− 437.9. |
| I-139 | LCMS: (FA) ES+ 428.2, ES− 426.1. |
| I-108 | LCMS: (FA) ES+ 457.3, ES− 455.3. |
| I-167 | LCMS: (FA) ES+ 458.3, ES− 456.4. |
| I-6 | LCMS: (FA) ES+ 430.3, ES− 428.4. |
| I-132 | LCMS: (FA) ES+ 512.4, ES− 510.5. |
| I-99 | LCMS: (FA) ES+ 456, ES− 454. |
| I-194 | LCMS: (FA) ES+ 456, ES− 454. |
| I-50 | LCMS: (FA) ES+ 470, ES− 468. |
| I-203 | LCMS: (FA) ES+ 469. |
| I-207 | LCMS: (FA) ES+ 511, ES− 509. |
| I-208 | LCMS: (FA) ES+ 468, ES− 466. |
| I-197 | LCMS: (FA) ES+ 470. |
| I-350 | LCMS: (FA) ES+ 481.1. |
| I-377 | LCMS: (FA) ES+ 481.2. |
| I-260 | LCMS: (FA) ES+ 481.2, ES− 479.2. |
| I-252 | LCMS: (FA) ES+ 481.2, ES− 479.2. |
| I-330 | LCMS: (FA) ES+ 467.2, ES− 465.3. |
| I-223 | LCMS: (FA) ES+ 481.4, ES− 479.4. |
| I-347 | LCMS: (FA) ES+ 467.2, ES− 465.4. |
| I-221 | LCMS: (FA) ES+ 497.2, ES− 495.2. |
| I-244 | LCMS: (FA) ES+ 485.1, ES− 483.2. |
| I-241 | LCMS: (AA) ES+ 473.2, ES− 471.3. |
| I-356 | LCMS: (FA) ES+ 489.0, ES− 487.0. |
| I-389 | LCMS: (FA) ES+ 499. |
| I-389 isomer 1 | LCMS: (FA) ES+ 499.2, ES− 497.3. |
| I-389 isomer 2 | LCMS: (FA) ES+ 499.2, ES− 497.3. |
| I-231 | LCMS: (AA) ES+ 469, ES− 467. |

The compound I-389 was separated into isomer 1 and isomer 2 by chiral HPLC, using a Chirobiotic T 20×250 mm column, with a flow rate of 10 mL/min and an isocratic gradient:

Solvent: 40% (0.2 FA in MeOH pH=4 by NH$_4$OH)

60% (0.2 FA in Water pH=4 by NH$_4$OH)

Compounds in the following table were prepared from the appropriate starting materials in a method analogous to that of Example 8, followed by deprotection by an analogous procedure to Example 13 step 2.

| | |
|---|---|
| I-232 | LCMS: (FA) ES+ 499, ES2+ 250. |
| I-294 | LCMS: (FA) ES+ 499, ES2+ 250. |
| I-283 | LCMS: (FA) ES+ 499, ES2+ 250. |
| I-395 | LCMS: (FA) ES+ 457.0 |
| I-397 | LCMS: (FA) ES+ 485.0, ES2+ 243.3 |
| I-398 | LCMS: (FA) ES+ 485.0, ES2+ 243.3 |
| I-406 | LCMS: (FA) ES+ 528.9 |

| | |
|---|---|
| I-195 | LCMS: (FA) ES+ 455.4, ES− 453.5. |
| I-193 | LCMS: (FA) ES+ 455.4, ES− 453.5. |
| I-180 | LCMS: (FA) ES+ 473. |
| I-40 | LCMS: (FA) ES+ 439.2, ES− 437.1. |
| I-196 | LCMS: (FA) ES+ 469.1, ES− 467.3. |
| I-370 | LCMS: (FA) ES+ 489.1, ES− 487.3. |
| I-276 | LCMS: (FA) ES+ 473.2, ES− 471.2. |
| I-281 | LCMS: (FA) ES+ 473, ES− 471. |

Example 9

Synthesis of 2-[1-({5-[3-(aminomethyl)phenyl]-2-thienyl}carbonyl)-3-pyridin-3-yl-4,5-dihydro-1H-pyrazol-5-yl]phenol (I-2)

Example 10

Synthesis of 2-[3-pyridin-3-yl-1-({5-[4-(pyrrolidin-1-ylmethyl)phenyl]-2-thienyl}carbonyl)-4,5-dihydro-1H-pyrazol-5-yl]phenol (I-56)

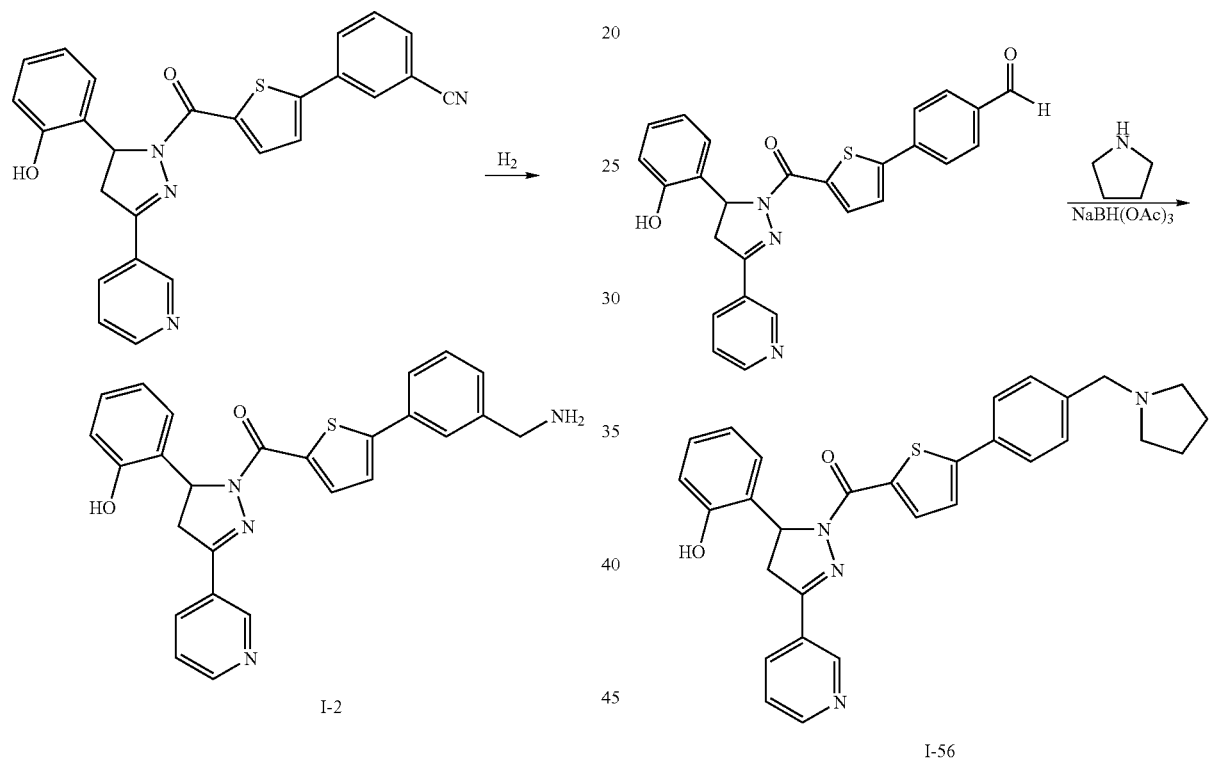

To a solution of 3-(5-{[5-(2-hydroxyphenyl)-3-pyridin-3-yl-4,5-dihydro-1H-pyrazol-1-yl]carbonyl}-2-thienyl)benzonitrile in 7M mixture of ammonia in MeOH was added Raney nickel (3 mL). The reaction mixture was allowed to stir at rt under an atmosphere of hydrogen for 2 days. The resulting solution was filtered over a pad of celite and the filtrate was concentrated. The crude product was purified via HPLC to give 2-[1-({5-[3-(aminomethyl)phenyl]-2-thienyl}carbonyl)-3-pyridin-3-yl-4,5-dihydro-1H-pyrazol-5-yl]phenol (I-2) (0.073 g, 0.138 mmol) as a white solid. LCMS: (FA) ES+ 455.4, ES-453.4. $^1$H NMR (400 MHz, $d_6$-DMSO) δ: 9.05-9.08 (m, 1H), 8.66-8.70 (m, 1H), 8.35 (s, 1H), 8.26-8.31 (m, 1H), 8.05 (d, 1H), 7.78-7.82 (m, 1H), 7.64-7.68 (m, 1H), 7.53-7.59 (m, 2H), 7.36-7.47 (m, 2H), 7.08 (t, 1H), 6.92-6.97 (m, 1H), 6.81-6.86 (m, 1H), 6.72 (t, 1H), 5.85 (dd, 1H), 3.89-3.95 (m, 1H), 3.88 (s, 2H), and 3.16-3.24 (m, 1H).

Compounds in the following table were prepared from the appropriate starting materials in a method analogous to that of Example 9:

To a solution of 4-(5-{[5-(2-hydroxyphenyl)-3-pyridin-3-yl-4,5-dihydro-1H-pyrazol-1-yl]carbonyl}-2-thienyl)benzaldehyde (0.205 g, 0.452 mmol) in THF (72 mL) was added pyrrolidine (0.042 mL, 0.50 mmol) and sodium triacetoxyborohydride (0.105 g, 0.497 mmol). The reaction mixture was allowed to stir at rt for 3 days. The solution was diluted with water and 1N aqueous HCl and extracted with EtOAc. The organic solutions were combined, washed with brine, dried over MgSO$_4$, filtered and concentrated. The residue was purified by column chromatography to give 2-[3-pyridin-3-yl-1-({5-[4-(pyrrolidin-1-ylmethyl)phenyl]-2-thienyl}carbonyl)-4,5-dihydro-1H-pyrazol-5-yl]phenol (I-56) (0.060 g, 0.118 mmol) as a white solid. LCMS: (FA) ES+ 509.4. $^1$H NMR (400 MHz, $d_6$-DMSO) δ: 10.76-10.86 (bs, 1H), 9.74-9.82 (bs, 1H), 9.11 (s, 1H), 8.71-8.77 (m, 1H), 8.36-8.42 (m, 1H), 8.03-8.08 (m, 1H), 7.84-7.90 (m, 2H), 7.62-7.73 (m, 2H), 7.08 (t, 1H), 6.92-6.97 (m, 1H), 6.82-6.88 (m, 1H), 6.72 (t, 1H), 5.82-5.89 (m, 1H), 4.34-4.39 (m, 2H), 3.86-3.98 (m, 1H), 3.31-3.41 (m, 2H), 3.18-3.25 (m, 1H), 3.00-3.12 (m, 2H), 1.96-2.07 (m, 2H), and 1.82-1.94 (m, 2H).

Compounds in the following table were prepared from the appropriate starting materials in a method analogous to that of Example 10:

| | |
|---|---|
| I-156 | LCMS: (FA) ES+ 469.1, ES− 467.2. |
| I-92  | LCMS: (FA) ES+ 525.5. |
| I-63  | LCMS: (FA) ES+ 552.4, ES− 550.5. |
| I-106 | LCMS: (FA) ES+ 509.4. |
| I-23  | LCMS: (FA) ES+ 509.4, ES− 507.5. |
| I-79  | LCMS: (FA) ES+ 524.4, ES− 522.5. |
| I-18  | LCMS: (FA) ES+ 483.2, ES− 481.2. |
| I-80  | LCMS: (FA) ES+ 497.2, ES− 495.2. |
| I-340 | LCMS: (AA) ES+ 487, ES− 485. |
| I-257 | LCMS: (FA) ES+ 527.2 |
| I-325 | LCMS: (FA) ES+ 487.1 |
| I-308 | LCMS: (FA) ES+ 517.1 |
| I-355 | LCMS: (FA) ES+ 544.2 |
| I-324 | LCMS: (FA) ES+ 556.1 |
| I-424 | LCMS: (FA) ES+ 502.0 |
| I-425 | LCMS: (FA) ES+ 517.0 |

Example 11

Synthesis of 2-(3-pyridin-3-yl-1-{[5-(2-pyridin-2-ylethyl)-2-thienyl]carbonyl}-4,5-dihydro-1H-pyrazol-5-yl)phenol (I-100)

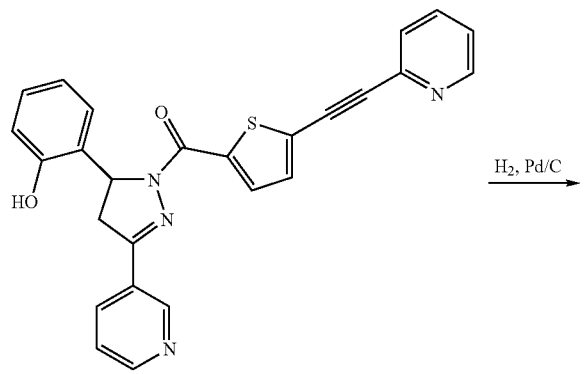

To a solution of 2-(3-pyridin-3-yl-1-{[5-(.yridine-2-yl-ethynyl)-2-thienyl]carbonyl}-4,5-dihydro-1H-pyrazol-5-yl)phenol (I-153) (0.406 g, 0.90 mmol) in EtOH (10 mL) was added 10% Pd on carbon (0.041 g). The reaction mixture was allowed to stir at rt under an atmosphere of hydrogen overnight and then filtered through celite. The residue was purified by column chromatography to give 2-(3-pyridin-3-yl-1-{[5-(2-pyridin-2-ylethyl)-2-thienyl]carbonyl}-4,5-dihydro-1H-pyrazol-5-yl)phenol (I-100) (73 mg). LCMS: (FA) ES+ 455.3. $^1$H NMR (400 MHz, d$_6$-DMSO) δ: 9.74-9.82 (m, 1H), 9.05-9.09 (m, 1H), 8.83 (d, 1H), 8.73-8.78 (m, 1H), 8.48 (t, 1H), 8.39 (d, 1H), 8.00 (d, 1H), 7.84-7.92 (m, 2H), 7.67-7.73 (m, 1H), 7.07 (t, 1H), 6.97-7.00 (m, 1H), 6.89 (d, 1H), 6.84 (d, 1H), 6.70 (t, 1H), 5.78-5.84 (m, 1H), 3.88 (dd, 1H), 3.37-3.49 (m, 4H), and 3.18 (dd, 1H).

Example 12

Synthesis of N-[(5-{[5-(2-hydroxyphenyl)-3-pyridin-3-yl-4,5-dihydro-1H-pyrazol-1-yl]carbonyl}-2-thienyl)methyl]pyridine-2-carboxamide (I-136)

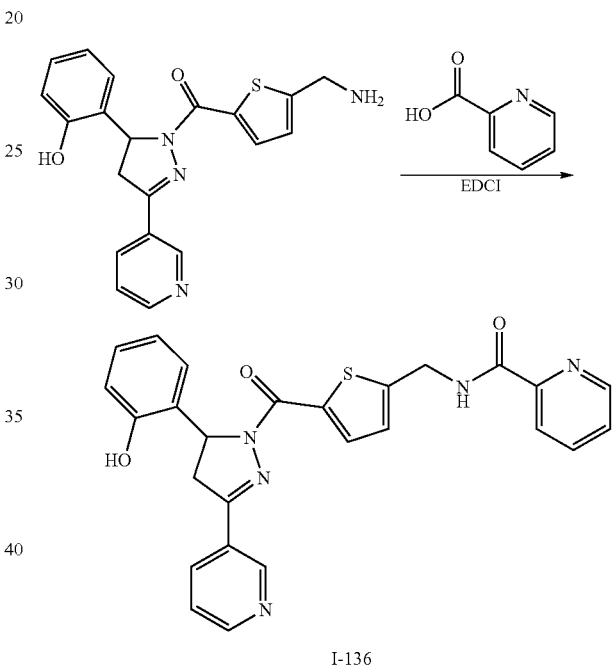

A mixture of 2-(1-{[5-(aminomethyl)-2-thienyl]carbonyl}-3-pyridin-3-yl-4,5-dihydro-1H-pyrazol-5-yl)phenol (0.080 g, 0.21 mmol), EDCI (0.070 g, 0.36 mmol), DIPEA (0.150 mL, 0.86 mmol), and picolinic acid (0.31 g. 0.25 mmol) in DCM (4 mL) was allowed to stir at rt overnight. The reaction mixture was diluted with water and extracted with DCM. The organic solutions were combined, washed with brine, dried over MgSO$_4$, filtered, and concentrated. The residue was purified by column chromatography to give N-[(5-{[5-(2-hydroxyphenyl)-3-pyridin-3-yl-4,5-dihydro-1H-pyrazol-1-yl]carbonyl}-2-thienyl)methyl]pyridine-2-carboxamide (I-136) (0.033 g) as a clear oil. LCMS: (FA) ES+ 484.2. $^1$H NMR (400 MHz, d$_6$-DMSO) δ: 9.53-9.59 (m, 1H), 9.05-9.09 (m, 1H), 8.72-8.76 (m, 1H), 8.65-8.69 (m, 1H), 8.36-8.41 (m, 1H), 8.06-8.11 (m, 1H), 7.98-8.05 (m, 1H), 7.88 (d, 1H), 7.60-7.67 (m, 2H), 7.02-7.12 (m, 2H), 6.86-6.91 (m, 1H), 6.82 (d, 1H), 6.69 (t, 1H), 5.82 (dd, 1H), 4.70 (d, 2H), 3.82-3.92 (m, 1H), and 3.17 (dd, 1H).

Example 13

Synthesis of 2-[1-({5-[2-(aminomethyl)phenyl]-2-thienyl}carbonyl)-3-pyrazin-2-yl-4,5-dihydro-1H-pyrazol-5-yl]phenol (I-205)

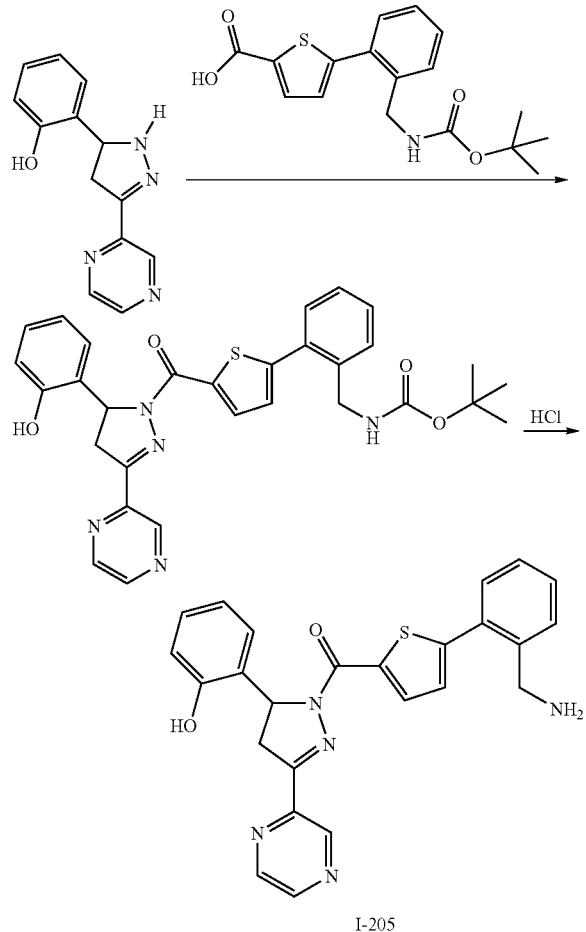

I-205

Step 1: tert-butyl [2-(5-{[5-(2-hydroxyphenyl)-3-pyrazin-2-yl-4,5-dihydro-1H-pyrazol-1-yl]carbonyl}-2-thienyl)benzyl]carbamate A solution of 2-(3-pyrazin-2-yl-4,5-dihydro-1H-pyrazol-5-yl)phenol (0.10 g, 4.2 mmol), 5-(2-{[(tert-butoxycarbonyl) amino]methyl}phenyl)thiophene-2-carboxylic acid (0.134 g, 4.02 mmol), and EDCI (0.116 g, 6.06 mmol) in DCM (4 mL) was allowed to stir at rt for 6 h. The reaction was quenched by the addition of water and the organic and aqueous solutions were separated. The aqueous solution was extracted with EtOAc. The organic solutions were combined, dried over $Na_2SO_4$, filtered and concentrated. The residue was purified by column chromatography to give tert-butyl [2-(5-{[5-(2-hydroxyphenyl)-3-pyrazin-2-yl-4,5-dihydro-1H-pyrazol-1-yl]carbonyl}-2-thienyl)benzyl]carbamate (0.50 g, 23%). LCMS: (FA) ES+ 556.2.

Step 2: 2-[1-({5-[2-(aminomethyl)phenyl]-2-thienyl}carbonyl)-3-pyrazin-2-yl-4,5-dihydro-1H-pyrazol-5-yl]phenol (I-205)

HCl (0.16 mL, 5.4 mmol) was added to a solution of tert-butyl [2-(5-{[5-(2-hydroxyphenyl)-3-pyrazin-2-yl-4,5-dihydro-1H-pyrazol-1-yl]carbonyl}-2-thienyl)benzyl]carbamate (0.030 g, 0.054 mmol) in MeOH (1 mL) over the course of 3 h at rt. A white precipitate formed and was filtered and dried under vacuum to give 2-[1-({5-[2-(aminomethyl)phenyl]-2-thienyl}carbonyl)-3-pyrazin-2-yl-4,5-dihydro-1H-pyrazol-5-yl]phenol (I-205), (25 mg). LCMS: (FA) ES+ 456.1.

Compounds in the following table were prepared from the appropriate starting materials in a method analogous to that of Example 13:

| | |
|---|---|
| I-198 | LCMS: (FA) ES+ 439.3, ES− 437.4. |
| I-204 | LCMS: (FA) ES+ 439.1, ES− 437.1. |
| I-200 | LCMS: (FA) ES+ 456.3, ES− 454.3. |
| I-390 | LCMS: (FA) ES+ 489.0. |
| I-371 | LCMS: (FA) ES+ 473.3, ES− 471.1 |
| I-280 | LCMS: (FA) ES+ 469.1, ES− 467.2 |
| I-318 | LCMS: (FA) ES+ 516.2, ES− 514.1. |
| I-378 | LCMS: (FA) ES+ 456.2, ES− 454.3 |
| I-222 | LCMS: (FA) ES+ 439.3, ES− 437.4 |
| I-381 | LCMS: (FA) ES+ 456.0, ES− 454.1 |

Example 14

2-[1-({5-[2-(aminomethyl)phenyl]-2-thienyl}carbonyl)-3-(6-aminopyridin-3-yl)-4,5-dihydro-1H-pyrazol-5-yl]phenol (I-202)

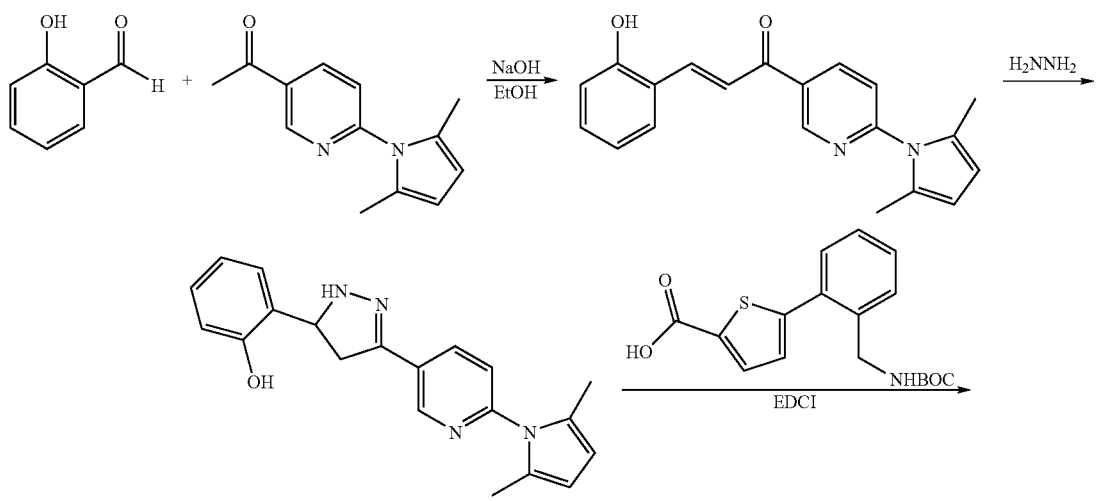

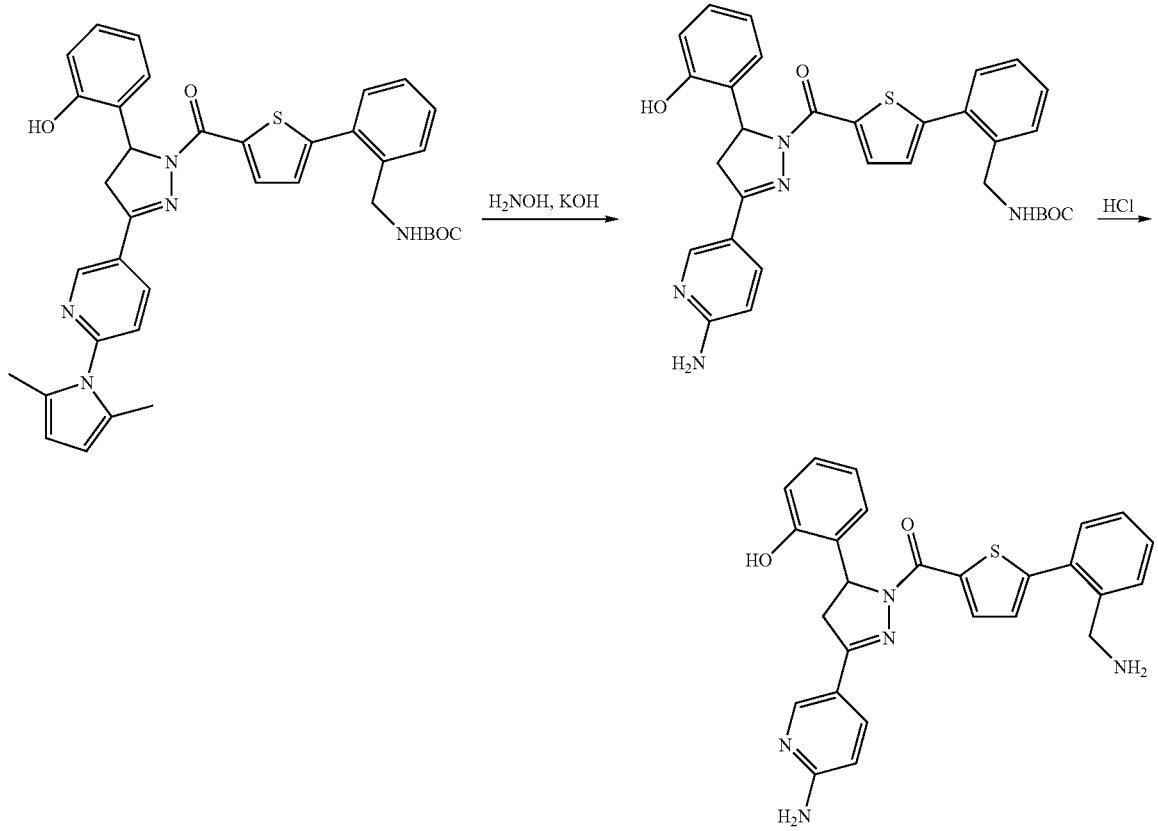

Step 1: Synthesis of (2E)-1-[6-(2,5-dimethyl-1H-pyrrol-1-yl)pyridin-3-yl]-3-(2-hydroxyphenyl)prop-2-en-1-one To a vigorously stirred solution of 2-hydroxybenzaldehyde in 2.5N NaOH (2.2 mL) at 0° C. was added 1-[6-(2,5-dimethyl-1H-pyrrol-1-yl)pyridin-3-yl]ethanone (prepared by a method analogous to that described by Scott et al., *Org. Proc. Res. And Dev.*, 8:587 (2004)) (0.58 g, 2.7 mmol) in EtOH (2 mL). The reaction mixture was allowed to stir and warm to rt whereupon an additional 1 mL of EtOH was added. The mixture turned a dark red color and was allowed to stir for 25 h. The reaction was neutralized by the addition of 1M HCl and the mixture was extracted with EtOAc. The organic solutions were combined, dried over MgSO$_4$, filtered, and concentrated. The residue was purified by column chromatography to give (2E)-1-[6-(2,5-dimethyl-1H-pyrrol-1-yl)pyridin-3-yl]-3-(2-hydroxyphenyl)prop-2-en-1-one as a yellow solid (0.31 g, 36%). LCMS: (FA) ES+ 319.2 (M+1).

Step 2: Synthesis of 2-{3-[6-(2,5-dimethyl-1H-pyrrol-1-yl)pyridin-3-yl]-4,5-dihydro-1H-pyrazol-5-yl}phenol To a suspension of (2E)-1-[6-(2,5-dimethyl-1H-pyrrol-1-yl)pyridin-3-yl]-3-(2-hydroxyphenyl)prop-2-en-1-one (0.31 g, 0.97 mmol) in EtOH (8.5 mL) was added hydrazine hydrate (65% solution, 0.146 mL, 1.95 mmol). After stirring for 15 min, the reaction mixture was concentrated to give 2-{3-[6-(2,5-dimethyl-1H-pyrrol-1-yl)pyridin-3-yl]-4,5-dihydro-1H-pyrazol-5-yl}phenol as a yellow solid (0.32 g, 99%). LCMS: (FA) ES+ 333.2 (M+1).

Step 3: Synthesis of tert-butyl [2-(5-{[3-[6-(2,5-dimethyl-1H-pyrrol-1-yl)pyridin-3-yl]-5-(2-hydroxyphenyl)-4,5-dihydro-1H-pyrazol-1-yl]carbonyl}-2-thienyl)benzyl]carbamate A solution of 2-{3-[6-(2,5-dimethyl-1H-pyrrol-1-yl)pyridin-3-yl]-4,5-dihydro-1H-pyrazol-5-yl}phenol (0.14 g, 0.41 mmol), 5-(2-{[(tert-butoxycarbonyl)amino]methyl}thiophene-2-carboxylic acid (0.13 g, 0.39 mmol), and EDCI (0.11 g, 0.59 mmol) in DCM (4 mL) was allowed to stir under an atmosphere of nitrogen for 3 h. The reaction was quenched by the addition of water. The organic and aqueous solutions were separated and the aqueous solution was subsequently extracted with EtOAc. The organic solutions were combined, dried over MgSO$_4$, filtered, and concentrated. The residue was purified by column chromatography to afford tert-butyl [2-(5-{[3-[6-(2,5-dimethyl-1H-pyrrol-1-yl)pyridin-3-yl]-5-(2-hydroxyphenyl)-4,5-dihydro-1H-pyrazol-1-yl]carbonyl}-2-thienyl)benzyl]carbamate as a white solid (0.14 g, 55%). LCMS: (FA) ES+ 648.3 (M+1).

Step 4: Synthesis of tert-butyl [2-(5-{[3-(6-aminopyridin-3-yl)-5-(2-hydroxyphenyl)-4,5-dihydro-1H-pyrazol-1-yl]carbonyl}-2-thienyl)benzyl]carbamate To a solution of tert-butyl [2-(5-{[3-[6-(2,5-dimethyl-1H-pyrrol-1-yl)pyridin-3-yl]-5-(2-hydroxyphenyl)-4,5-dihydro- 1H-pyrazol-1-yl]carbonyl}-2-thienyl)benzyl]carbamate (0.09 g, 0.14 mmol) in EtOH (1.7 mL) and water (0.75 mL) in a round-bottomed flask equipped with a reflux condenser was added hydroxylamine hydrochloride (0.58 g, 8.3 mmol) and potassium hydroxide (0.31 g, 5.6 mmol). The mixture was heated to 110° C. and allowed to stir vigorously for 5 h. The reaction was then cooled to rt and diluted with water. The aqueous solution was extracted with EtOAc. The organic solutions were combined, dried over MgSO$_4$, filtered, and concentrated. The residue was purified by column chromatography to give tert-butyl [2-(5-{[3-(6-aminopyridin-3-yl)-5-(2-hydroxyphenyl)-4,5-dihydro-1H-pyrazol-1-yl]carbonyl}-2-thienyl)benzyl]carbamate as a white solid (0.04 g, 48%). LCMS: (FA) ES+ 570.6 (M+1).

Step 5: Synthesis of 2-[1-({5-[2-(aminomethyl)phenyl]-2-thienyl}carbonyl)-3-(6-aminopyridin-3-yl)-4,5-dihydro-1H-pyrazol-5-yl]phenol (I-202)

Concentrated HCl (0.1 mL) was added to a solution of tert-butyl [2-(5-{[3-(6-aminopyridin-3-yl)-5-(2-hydroxyphenyl)-4,5-dihydro-1H-pyrazol-1-yl]carbonyl}-2-thienyl)benzyl]carbamate (0.03 g, 0.058 mmol) in MeOH (1 mL) at rt. The resulting solution was allowed to stir at rt for 4 h. The reaction mixture was then concentrated to provide the HCl salt of 2-[1-({5-[2-(aminomethyl)phenyl]-2-thienyl}carbonyl)-3-(6-aminopyridin-3-yl)-4,5-dihydro-1H-pyrazol-5-yl]phenol (I-202) (0.03 g, 100%) as a white solid. $^1$H NMR (300 MHz, d$_6$-DMSO) δ: 9.80 (S, 1H), 8.57 (m, 3H), 8.35 (d, 1H), 8.25 (s, 1H), 8.03 (d, 1H), 7.75 (d, 1H), 7.50-7.60 (m, 3H), 7.30 (d, 1H), 7.05-7.10 (m, 2H), 6.87-6.90 (m, 2H), 6.72 (t, 1H), 5.83 (dd, 1H), 4.12 (d, 2H), 3.80 (dd, 1H), and 3.10 (dd, 1H). LCMS: (FA) ES+ 470.3 (M+1).

Compounds in the following table were prepared from the appropriate starting materials in a method analogous to that of Example 14:

| | |
|---|---|
| I-296 | LCMS: (FA) ES+ 442.2, ES– 440.3 |
| I-217 | LCMS: (FA) ES+ 470.1, ES– 468.1 |
| I-242 | LCMS: (FA) ES+ 470.2 |
| I-369 | LCMS: (FA) ES+ 520.1 |
| I-282 | LCMS: (FA) ES+ 488.2, ES– 486.2 |

Example 15

2-{3-[5-(hydroxymethyl)pyridin-3-yl]-1-[(5-pyridin-2-yl-2-thienyl)carbonyl]-4,5-dihydro-1H-pyrazol-5-yl}phenol (I-273)

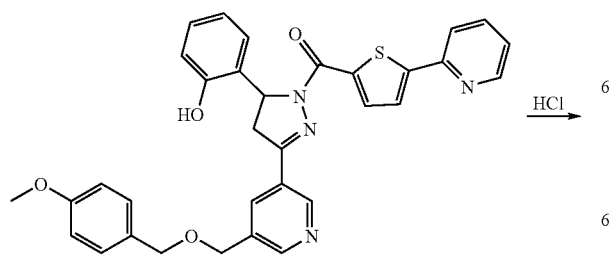

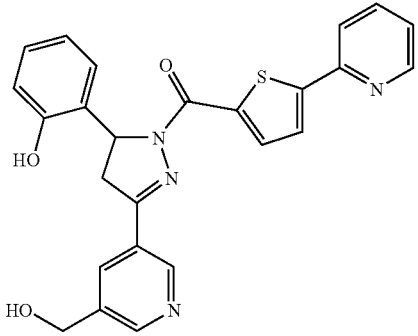

To a suspension of 2-{3-(5-{[(4-methoxybenzyl)oxy]methyl}pyridin-3-yl)-1-[(5-pyridin-2-yl-2-thienyl)carbonyl]-4,5-dihydro-1H-pyrazol-5-yl}phenol (0.070 g, 0.12 mmol) in MeOH (6 mL) was added HCl. The reaction mixture was allowed to stir at 65° C. for 6 h and then at rt overnight. Reaction was incomplete, so the mixture was allowed to stir at 65° C. for an additional 10 h and then cooled to rt and concentrated. The residue was purified by column chromatography to give 2-{3-[5-(hydroxymethyl)pyridin-3-yl]-1-[(5-pyridin-2-yl-2-thienyl)carbonyl]-4,5-dihydro-1H-pyrazol-5-yl}phenol (I-273). LCMS: (FA) ES+ 457.4, ES-455.5.

Example 16

2-(3-pyridin-3-yl-1-{[5-(2H-tetrazol-5-yl)-2-thienyl]carbonyl}-4,5-dihydro-1H-pyrazol-5-yl)phenol (I-226)

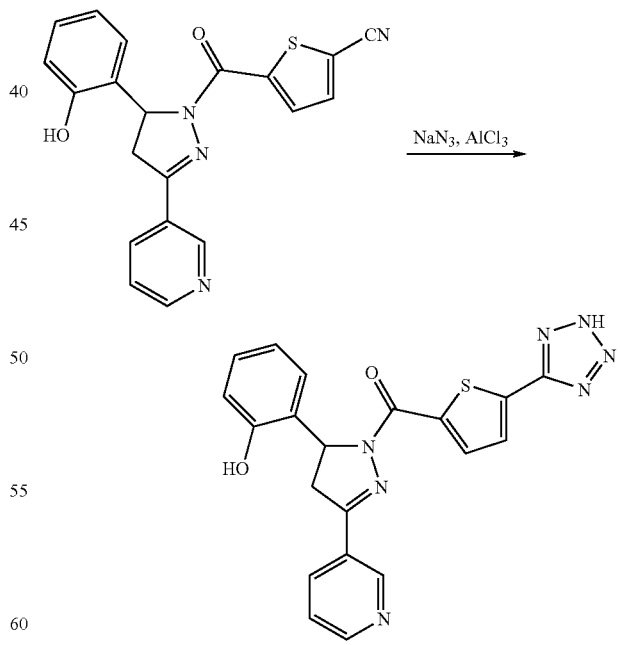

To a solution of 5-{[5-(2-hydroxyphenyl)-3-pyridin-3-yl-4,5-dihydro-1H-pyrazol-1-yl]carbonyl}thiophene-2-carbonitrile (0.300 g, 0.60 mmol) in DMF (5 mL) was added sodium azide (0.120 g, 1.80 mmol) and aluminum trichloride (0.240 g, 1.80 mmol). The reaction mixture was allowed to stir at 100° C. overnight and then concentrated. The residue was purified by column chromatography to give 2-(3-pyridin-3-yl-1-{[5-(2H-tetrazol-5-yl)-2-thienyl]carbonyl}-4,5-dihydro-1H-pyrazol-5-yl)phenol (I-226). LCMS: (FA) ES+ 436, ES-434.

Example 17

Expression and Purification of Raf Kinase Enzymes

Enzymatically active wild-type B-Raf was purchased from Upstate (cat#14-530).
Enzymatically active mutant B-Raf(V599E) was purified in house.
Enzymatically active C-Raf was purchased from Upstate (cat#14-352).

Example 18

Raf Kinase Enzyme Assays

B-Raf Flash Plate® Assay
Enzyme mix (15 µL), containing 50 mM HEPES pH 7.5, 0.025% Brij 35, 10 mM DTT, 20 nM B-Raf (V599E or Wild Type), was added to the wells of an assay plate and incubated for 20 minutes. Substrate mix (15 µL), containing 50 mM HEPES pH 7.5, 0.025% Brij 35, 10 mM $MnCl_2$, 2 µM Peptide 118 (Biotin-DRGFPRARYRARTTNYNSS-RSRFYSGFN-SRPRGRVYRGRARATSWYSPY-NH$_2$, New England Peptide), 1 µM ATP, 0.2 mg/mL BSA, $^{33}$P ATP 0.5 µCi/reaction was then added. Final reagent concentrations in the reaction mixture were 50 mM HEPES pH 7.5, 0.025% Brij 35, 5 mM DTT, 5 mM $MnCl_2$, 1 µM Peptide 118, 0.5 µM ATP, 0.1 mg/mL BSA, 10 nM B-Raf Wild Type, and $^{33}$P ATP 0.5 µCi/reaction. The reaction mixture, with or without Raf kinase inhibitor, was incubated for 180 minutes, and then stopped by the addition of 200 mM EDTA. The stopped reaction mixture (25 µL) was transferred to a Flash Plate™ (Perkin Elmer) and incubated for 2 hours. The wells were washed three times with 0.02% Tween-20. Plates were read on a Leadseeker.

Compounds I-1 to I-246, I-248 to I-253, I-255 to I-302, I-304 to I-334, I-336 to I-341, I-343 to I-391, I-424, and I-425 were tested in this assay. Compounds I-2, I-4, I-6, I-7, I-8, I-11, I-13, I-14, I-17, I-18, I-19, I-20, I-21, I-24, I-28, I-29, 1-30, I-31, I-32, I-33, I-34, I-35, I-36, I-39, I-42, I-43, I-44, I-45, I-49, I-50, I-51, I-53, I-56, I-58, I-60, I-61, I-62, I-63, I-64, I-65, I-67, I-68, I-69, I-73, I-74, I-76, I-79, I-80, I-82, I-83, I-85, I-86, I-89, I-90, I-91, I-92, I-99, I-100, I-101, I-102, 1-103, I-104, I-105, I-106, I-107, I-108, I-109, I-110, I-111, I-112, I-113, I-114, I-116, I-120, I-125, I-127, I-128, I-129, I-130, I-132, I-134, I-135, I-136, I-138, I-139, I-140, I-146, I-148, I-149, I-153, I-156, I-160, I-161, I-162, I-163, I-164, I-166, I-167, I-169, I-170, I-173, I-174, I-175, I-176, I-177, I-180, I-181, I-182, I-184, I-186, I-189, 1-193, I-194, I-195, I-196, I-197, I-198, I-201, I-202, I-203, I-207, I-208, I-214, I-216, I-217, I-221, I-222, I-223, I-226, I-227, I-229, I-231, I-232, I-237, I-241, I-243, I-244, I-246, I-250, I-251, I-252, I-255, I-257, I-260, I-262, I-268, I-271, I-273, I-274, I-276, I-277, I-279, I-280, I-281, I-282, I-283, I-290, I-292, I-294, I-296, I-306, I-307, I-308, I-312, I-313, I-314, I-316, I-317, 1-318, I-320, I-321, I-322, I-325, I-326, I-327, I-329, I-330, I-340, I-344, I-347, I-350, I-352, I-355, I-356, I-357, I-359, I-361, I-365, I-366, I-368, I-369, I-370, I-371, I-372, I-377, I-378, I-379, I-380, I-381, I-389, I-390, I-424, and I-425, exhibited IC$_{50}$ values less than or equal to 100 nM in this assay.

Compounds I-3, I-5, I-10, I-12, I-16, I-22, I-23, I-27, I-37, I-40, I-47, I-48, I-52, I-54, I-57, I-66, I-70, I-72, I-78, I-81, I-84, I-87, I-93, I-94, I-95, I-96, I-97, I-115, I-118, I-121, I-123, I-133, I-137, I-144, I-145, I-147, I-150, I-151, I-154, I-155, I-158, I-165, I-168, I-172, I-179, I-183, I-185, I-190, I-191, I-200, I-205, I-209, I-211, I-213, I-215, I-220, 1-228, I-230, I-233, I-234, I-235, I-242, I-245, I-259, I-266, I-269, I-278, I-286, I-291, I-301, I-309, I-311, I-328, I-332, I-334, I-339, I-349, I-353, I-354, I-358, I-367, I-373, I-382, and I-388, exhibited IC$_{50}$ values greater than 100 nM and less than 1 µM in this assay.

Compounds I-15, I-25, I-46, I-75, I-77, I-88, I-98, I-117, I-119, I-124, I-126, I-142, I-152, I-212, I-218, I-219, I-224, I-225, I-236, I-238, I-240, I-248, I-249, I-253, I-256, I-258, I-261, I-263, I-264, I-265, I-267, I-270, I-272, I-284, I-285, I-287, I-288, I-289, I-295, I-297, I-298, I-299, I-300, I-304, I-305, I-310, I-315, I-319, I-323, I-331, I-333, I-336, I-337, I-338, I-341, I-343, I-348, I-351, I-360, I-362, I-364, I-374, I-376, I-383, I-384, I-385, I-386, I-387, and I-391 exhibited IC$_{50}$ values greater than 1 µM and less than or equal to 10 µM in this assay.

C-Raf Flash Plate® Assay
Enzyme mix (15 µL), containing 50 mM HEPES pH 7.5, 0.025% Brij 35, 10 mM DTT, 20 nM C-Raf (Wild Type), is added to the wells of an assay plate and incubated for 20 minutes. Substrate mix (15 µL), containing 50 mM HEPES pH 7.5, 0.025% Brij 35, 10 mM $MnCl_2$, 4 µM Peptide 118, 1 µM ATP, 0.1 mg/mL BSA, $^{33}$P ATP 0.5 µCi/reaction is then added. Final reagent concentrations in the reaction mixture are 50 mM HEPES pH 7.5, 0.025% Brij 35, 5 mM DTT, 5 mM $MnCl_2$, 2 µM Peptide 118, 1.0 µM ATT, 0.1 mg/mL BSA, 10 nM C-Raf Wild Type, and $^{33}$P ATP 0.5 µCi/reaction. The reaction mixture is incubated for 40 minutes, and then stopped by the addition of 50 µL of 100 mM EDTA. The stopped reaction mixture (25 µL) is transferred to a Flash Plate™ (Perkin Elmer) and incubated for 2 hours. The wells are washed three times with 0.02% Tween-20. Plates are read on a Leadseeker.

Example 19

Raf Kinase Cellular Assays

Phospho-ERK ELISA Assay
Inhibition of Raf kinase activity in whole cell systems can be assessed by determining the decrease in phosphorylation of Raf kinase substrates. Any known Raf kinase substrate can be used to measure inhibition of Raf kinase activity in a whole cell system.

In a specific example, A375 cells were seeded in a 96-well cell culture plate (12×10$^3$ cells/100 µL/well) and incubated overnight at 37° C. Medium was removed, and cells were incubated with Raf kinase inhibitors for 3 hours at 37° C. Medium was not removed, and cells were fixed with 4% paraformaldehyde for 15 minutes at room temperature.

Methanol was added for 20 min. Cells were removed and blocked with 10% sheep serum and 1% BSA in PBS overnight at 4° C. Cells were incubated with anti-p44/42MAPK antibody (1:100, Cell Signaling Technologies, #9101L) (20 µL/well) overnight at 4° C. After washing with PBS three times, cells were stained with anti-rabbit horseradish peroxidase-linked antibody from donkey (1:100, Amersham Bioscience #NA934V) for 1 hour at room temperature. Cells were washed three times with 0.5% Tween-20 in PBS and twice with PBS. 3,3',5,5'-Tetramethylbenzidine (TMB) liquid substrate system (Sigma, #T8665) (50 µL/well) was added, and cells were incubated for 30-45 minutes at room temperature. Optical density was read at 650 nm. Cells were then washed 3-5 times with PBS to remove color solution. Results were normalized for the protein content in each well using a BCA protein assay kit (Pierce). Selected compounds in Table 1 were tested in this assay.

Example 20

Anti-Proliferation Assays

WST Assay

A375 cells (4000) in 100 μL of 1% FBS-DMEM were seeded into wells of a 96-well cell culture plate and incubated overnight at 37° C. Test compounds were added to the wells and the plates were incubated for 48 hours at 37° C. Test compound solution was added (100 μL/well in 1% FBS DMEM), and the plates were incubated at 37° C. for 48 hours. WST-1 reagent (Roche #1644807, 10 μL) was added to each well and incubated for four hours at 37° C. as described by the manufacturer. The optical density for each well was read at 450 nm and 600 nm. A well containing medium only was used as a control. Selected compounds in Table 1 were tested in this assay.

Example 21

In Vivo Assays

In Vivo Tumor Efficacy Model

Raf kinase inhibitors are tested for their ability to inhibit tumor growth in standard xenograft tumor models.

For example, HCT-116 cells (1×10$^6$) in 100 μL of phosphate buffered saline are aseptically injected into the subcutaneous space in the right dorsal flank of female CD-1 nude mice (age 5-8 weeks, Charles River) using a 23-ga needle. Beginning at day 7 after inoculation, tumors are measured twice weekly using a vernier caliper. Tumor volumes are calculated using standard procedures (0.5×length×width$^2$). When the tumors reach a volume of approximately 200 mm$^3$, mice are injected i.v. in the tail vein with test compound (100 μL) at various doses and schedules. All control groups receive vehicle alone. Tumor size and body weight are measured twice a week, and the study is terminated when the control tumors reach approximately 2000 mm. Analogous procedures are followed for melanoma (A375 or A2058 cells), colon (HT-29 or HCT-116 cells), and lung (H460 cells) tumor models.

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

What is claimed is:

1. At least one chemical entity selected from compounds of formula (I):

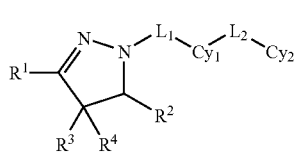

and pharmaceutically acceptable salts thereof, wherein $R^1$ is a substituted or unsubstituted 5- or 6-membered nitrogen-containing heteroaryl ring, which ring optionally is fused to an aryl, heteroaryl, heterocyclyl, or cycloaliphatic ring, each of which is optionally substituted;

$R^2$ is a substituted or unsubstituted 5- or 6-membered aryl or heteroaryl ring, which ring optionally is fused to an aryl, heteroaryl, heterocyclyl, or cycloaliphatic ring, each of which is optionally substituted;

$R^3$ is selected from hydrogen, fluoro, $C_{1-4}$ aliphatic, and $C_{1-4}$ fluoroaliphatic;

$R^4$ is hydrogen, fluoro, or a $C_{1-4}$ aliphatic or $C_{1-4}$ fluoroaliphatic optionally substituted with one or two substituents independently selected from —OH, —O($C_{1-4}$ aliphatic), —N($R^a$)($R^{a'}$), —N($R^a$)C(O)($C_{1-4}$ aliphatic), —N($R^a$)C(O)N($R^a$)$_2$, —C(O)($C_{1-4}$ aliphatic), —CO$_2$H, —CO$_2$($C_{1-4}$ aliphatic), and —C(O)N($R^a$)$_2$; or $R^3$ and $R^4$, taken together with the carbon to which they are bound, form an optionally substituted 3- to 6-membered cycloaliphatic or 4- to 7-membered heterocyclic ring;

$L_1$ is selected from —C(O)NR$^a$—(CR$^b$R$^c$)$_m$—, —C(O)C(R$^b$)=C(R$^b$)—(CR$^b$R$^c$)$_m$—, —C(O)—(CR$^b$R$^c$)$_m$—, and —SO$_2$—(CR$^b$R$^c$)$_m$—, wherein the C(O) or SO$_2$ functionality, respectively, is bound to the nitrogen of the pyrazoline ring;

Cy$_1$ is a bivalent radical derived from a ring system selected from
  optionally substituted 5- or 6-membered aromatic rings having zero to four ring nitrogen atoms and optionally one or two additional ring heteroatoms selected from oxygen and sulfur, which 5- or 6-membered aromatic ring optionally is fused to an aryl, heteroaryl, heterocyclyl, or cycloaliphatic ring, each of which is optionally substituted;
  optionally substituted 4- to 7-membered heterocyclic rings, which 4- to 7-membered heterocyclic ring optionally is fused to an aryl, heteroaryl, heterocyclyl, or cycloaliphatic ring, each of which is optionally substituted; and
  optionally substituted 3- to 7-membered cycloaliphatic rings, which 3- to 7-membered cycloaliphatic ring optionally is fused to an aryl, heteroaryl, heterocyclyl, or cycloaliphatic ring, each of which is optionally substituted;

$L_2$ is —(CR$^b$R$^c$)$_n$— or —(CR$^b$R$^c$)$_n$—X—(CR$^b$R$^c$)$_n$—,

X is chosen from —O—, —C(O)—, —S—, —SO—, —SO$_2$—, —C(R$^f$)=C(R$^f$)—, —NR$^a$C(O)—, —C(O)NR$^a$—, —SO$_2$—NR$^a$, —NR$^a$SO$_2$—, and —NR$^a$C(O)NR$^a$—;

Cy$_2$ is a radical derived from a ring system selected from
  optionally substituted 5- or 6-membered aromatic rings having zero to four ring nitrogen atoms and optionally one or two additional ring heteroatoms selected from oxygen and sulfur, which 5- or 6-membered aromatic ring optionally is fused to an aryl, heteroaryl, heterocyclyl, or cycloaliphatic ring, each of which is optionally substituted; and optionally substituted 4- to 7-membered heterocyclic rings, which 4- to 7-membered heterocyclic ring optionally is fused to an aryl, heteroaryl, heterocyclyl, or cycloaliphatic ring, each of which is optionally substituted; and optionally substituted 3- to 7-membered cycloaliphatic rings, which 3- to 7-membered cycloaliphatic ring optionally is fused to an aryl, heteroaryl, heterocyclyl, or cycloaliphatic ring, each of which is optionally substituted;

m is selected from 0, 1 and 2;

each n is independently selected from 0, 1, and 2;

each $R^a$ independently is hydrogen or optionally substituted aliphatic; or $R^a$ and $R^{a'}$, taken together with the nitrogen atom to which they are attached, form an optionally substituted 4 to 8-membered heterocyclyl ring having, in addition to the nitrogen atom, 0-2 ring heteroatoms independently selected from N, O, and S;

$R^{a'}$ is selected from hydrogen, optionally substituted aliphatic, optionally substituted aryl, optionally substituted heteroaryl, and optionally substituted heterocyclyl; or $R^{a'}$ and $R^a$, taken together with the nitrogen atom to which they are attached, form an optionally substituted 4 to 8-membered heterocyclyl ring having, in addition to the nitrogen atom, 0-2 ring heteroatoms independently selected from N, O, and S;

each $R^b$ independently is selected from hydrogen, fluoro, $C_{1-4}$ aliphatic, and $C_{1-4}$ fluoroaliphatic, and each $R^c$ independently is selected from hydrogen, fluoro, $C_{1-4}$ aliphatic, $C_{1-4}$ fluoroaliphatic, —OH, —O($C_{1-4}$ aliphatic), —N($R^a$)$_2$, —N($R^a$)C(O)($C_{1-4}$ aliphatic), —C(O)($C_{1-4}$ aliphatic), —CO$_2$H, —CO$_2$($C_{1-4}$ aliphatic), and —C(O)N($R^a$)$_2$; or $R^b$ and $R^c$, taken together with the carbon atom to which they are attached, form a 3- to 6-membered cycloaliphatic ring;

each $R^f$ independently is hydrogen, fluoro, or a $C_{1-3}$ aliphatic or $C_{1-3}$ fluoroaliphatic group optionally substituted with a substituent selected from the group consisting of —OH, —O($C_{1-3}$ aliphatic), —O($C_{1-3}$ fluoroaliphatic), —NH$_2$, —NH($C_{1-3}$ aliphatic), and —N($C_{1-3}$ aliphatic)$_2$;

provided that
  $R^1$ is not 6-bromo-1,2-dihydro-2-oxo-4-phenyl-3-quinolinyl.

2. At least one chemical entity of claim 1 wherein $R^1$ is an optionally substituted 6-membered heteroaryl ring with 1 or 2 ring nitrogen atoms, which ring optionally is fused to an aryl, heteroaryl, heterocyclyl, or cycloaliphatic ring, any of which is optionally substituted.

3. At least one chemical entity of claim 2, wherein:
  each of the substitutable ring carbon atoms in $R^1$ independently is unsubstituted or is substituted with halo, —NO$_2$, —CN, —R*, —C(R*)=C(R*)$_2$, —C≡C—R*, —OR*, —SR*, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —OC(O)N(R$^+$)$_2$, —CO$_2$R*, —C(O)R*, —C(O)N(R$^+$)$_2$, —N(R$^+$)C(=NR$^+$)—N(R$^+$)—C(O)R*, —C(=NR$^+$)—N(R$^+$)$_2$, —N(R$^+$)C(=NR$^+$)—N(R$^+$)$_2$, —NR$^+$SO$_2$R$^o$, and —NR$^+$SO$_2$N(R$^+$)$_2$;

$R^o$ is an optionally substituted aliphatic, aryl, or heteroaryl group;

each R* independently is hydrogen or an optionally substituted aliphatic, aryl, heteroaryl, or heterocyclyl group;

each R$^+$ independently is hydrogen or an optionally substituted aliphatic, aryl, heteroaryl, or heterocyclyl group, or two R$^+$ on the same nitrogen atom, taken together with the nitrogen atom, form a 4-8 membered aromatic or non-aromatic ring having, in addition to the nitrogen atom, 0-2 ring heteroatoms selected from N, O, and S; and one ring nitrogen atom in $R^1$ optionally is oxidized.

4. At least one chemical entity of claim 3 wherein $R^1$ is an optionally substituted monocyclic 6-membered heteroaryl ring with 1 or 2 ring nitrogen atoms.

5. At least one chemical entity of claim 4, wherein $R^1$ is pyridinyl, wherein the pyridinyl ring optionally is substituted on any substitutable ring carbon atom and the ring nitrogen atom optionally is oxidized.

6. At least one chemical entity of claim 5 wherein $R^1$ is pyrid-3-yl optionally substituted on any substitutable ring carbon atom.

7. At least one chemical entity of claim 5 wherein $R^1$ is pyrid-3-yl optionally substituted with one or more substituents independently selected from —F, —CN, —OR$^{1*}$, —SR$^{1*}$, —SO$_2$R$^{1o}$, —N(R$^{1+}$)$_2$, —N(R$^{1+}$)C(O)R$^{1*}$, —CO$_2$R$^{1*}$, —C(O)N(R$^{1+}$)$_2$, $C_{6-10}$ ar($C_{1-4}$ alkyl), the aryl portion of which is optionally substituted, an optionally substituted 5- or 6-membered aryl, heteroaryl, or heterocyclyl ring, an optionally substituted 3- to 6-membered cycloaliphatic ring, and a $C_{1-4}$ aliphatic or $C_{1-4}$ fluoroaliphatic group optionally substituted with one or two substituents independently selected from the group consisting of —OR$^{1*}$, —SR$^{1*}$, —SO$_2$R$^{1o}$, —N(R$^{1+}$)$_2$, —N(R$^{1+}$)C(O)R$^{1*}$, —CO$_2$R$^{1*}$, and —C(O)N(R$^{1+}$)$_2$; wherein $R^{1*}$ is hydrogen, $C_{1-4}$ aliphatic, $C_{1-4}$ fluoroaliphatic, or $C_{6-10}$ ar($C_{1-4}$ alkyl), the aryl portion of which is optionally substituted;

$R^{1o}$ is $C_{1-4}$ aliphatic, $C_{1-4}$ fluoroaliphatic, $C_{6-10}$ ar($C_{1-4}$ alkyl), the aryl portion of which is optionally substituted, or an optionally substituted 5- or 6-membered aryl or heteroaryl ring; and each $R^{1+}$ independently is hydrogen, $C_{1-4}$ aliphatic, $C_{1-4}$ fluoroaliphatic, or $C_{6-10}$ ar($C_{1-4}$ alkyl), the aryl portion of which is optionally substituted; or two $R^{1+}$ on the same nitrogen atom, taken together with the nitrogen atom form an optionally substituted pyrrolidinyl, piperidinyl, piperazinyl, or morpholinyl ring.

8. At least one chemical entity of claim 7 wherein $R^1$ is pyrid-3-yl.

9. At least one chemical entity of claim 1 wherein $R^2$ is a 6-membered aryl ring, optionally fused to an aryl, heteroaryl, heterocyclyl, or cycloaliphatic ring, wherein the ring system optionally is substituted on any substitutable ring carbon atom.

10. At least one chemical entity of claim 9 wherein $R^2$ is optionally substituted phenyl, which ring optionally is fused to an aryl, heteroaryl, heterocyclyl, or cycloaliphatic ring, any of which is optionally substituted.

11. At least one chemical entity of claim 10, wherein:
  each of the substitutable ring carbon atoms in $R^2$ independently is unsubstituted or is substituted with halo, —NO$_2$, —CN, —R*, —C(R*)=C(R*)$_2$, —C≡C—R*, —OR*, —SR*, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —OC(O)N(R$^+$)$_2$, —CO$_2$R*, —C(O)R*, —C(O)N(R$^+$)$_2$, —N(R$^+$)C(=NR$^+$)—N(R$^+$)—C(O)R*, —C(=NR⁺)—N(R⁺)₂, —N(R⁺)C(=NR⁺)—N(R⁺)₂, —NR⁺SO₂R°, and —NR⁺SO₂N(R⁺)₂;

R° is an optionally substituted aliphatic, aryl, or heteroaryl group;

each R* independently is hydrogen or an optionally substituted aliphatic, aryl, heteroaryl, or heterocyclyl group; and each R⁺ independently is hydrogen or an optionally substituted aliphatic, aryl, heteroaryl, or heterocyclyl group, or two R⁺ on the same nitrogen atom, taken together with the nitrogen atom, form a 4-8 membered aromatic or non-aromatic ring having, in addition to the nitrogen atom, 0-2 ring heteroatoms selected from N, O, and S.

12. At least one chemical entity of claim 11 wherein $R^2$ is phenyl substituted with one hydroxy group and optionally substituted with one or two additional groups independently selected from —F, —Cl, —CN, —OR²*, —SR²*, —SO₂R²°, —N(R²⁺)₂, —N(R²⁺)C(O)R²*, —CO₂R²*, —C(O)N(R²⁺)₂, $C_{6-10}$ ar($C_{1-4}$ alkyl), the aryl portion of which is optionally substituted, an optionally substituted 5- or 6-membered aryl, heteroaryl, or heterocyclyl ring, an optionally substituted 3- to 6-membered cycloaliphatic ring, and a $C_{1-4}$ aliphatic or $C_{1-4}$ fluoroaliphatic group optionally substituted with one or two substituents independently selected from the group consisting of —OR²*, —SR²*, —SO₂R²°, —N(R²⁺)₂, —N(R²⁺)C(O)R²*, —CO₂R²*, and —C(O)N(R²⁺)₂; wherein R²* is hydrogen, $C_{1-4}$ aliphatic, $C_{1-4}$ fluoroaliphatic, or $C_{6-10}$ ar($C_{1-4}$ alkyl), the aryl portion of which is optionally substituted;

R²° is $C_{1-4}$ aliphatic, $C_{1-4}$ fluoroaliphatic, $C_{6-10}$ ar($C_{1-4}$ alkyl), the aryl portion of which is optionally substituted, or an optionally substituted 5- or 6-membered aryl or heteroaryl ring; and each R²⁺ independently is hydrogen, $C_{1-4}$ aliphatic, $C_{1-4}$ fluoroaliphatic, or $C_{6-10}$ ar($C_{1-4}$ alkyl), the aryl portion of which is optionally substituted; or two R²⁺ on the same nitrogen atom, taken together with the nitrogen atom form an optionally substituted pyrrolidinyl, piperidinyl, piperazinyl, or morpholinyl ring.

13. At least one chemical entity of claim 12 wherein $R^2$ is 2-hydroxyphenyl or 3-hydroxyphenyl, either of which groups optionally is additionally substituted with one or two substituents selected from —F, —Cl, $C_{1-4}$ aliphatic, $C_{1-4}$ fluoroaliphatic, —O($C_{1-4}$ aliphatic), and —O($C_{1-4}$ fluoroaliphatic).

14. At least one chemical entity of claim 13 wherein $R^1$ is pyrid-3-yl optionally substituted on any substitutable ring carbon atom.

15. At least one chemical entity of claim 1 wherein $L_1$ is —C(O)—.

16. At least one chemical entity of claim 1 wherein $L_1$ is —SO₂—.

17. At least one chemical entity of claim 1, wherein $L_1$ is —C(O)NH—.

18. At least one chemical entity of claim 1 wherein $L_2$ is —(CR^bR^c)_n— and n is 0.

19. At least one chemical entity of claim 1 wherein $Cy_1$ is a bivalent radical derived from a ring system selected from benzene, benzimidazole, benzoxazole, benzthiazole, cinnoline, cyclopropane, cyclopentane, cyclohexane, furan, imidazole, imidazolidine, imidazoline, imidazopyridine, indole, indolizine, isoindole, isoquinoline, isothiazole, isoxazole, morpholine, naphthyridine, oxadiazole, oxazolidine, oxazole, oxazolopyridine, 1,3-oxathiolane, phthalazine, piperazine, piperidine, pteridine, purine, pyrazine, pyrazole, pyrazolidine, pyrazoline, pyridazine, pyridine, pyrimidine, pyrrole, pyrrolidine, pyrrolopyridine, pyrrolopyrimidine, quinazoline, quinoline, quinoxaline, tetrahydrofuran, tetrahydro-2H-pyran, tetrahydrothiophene, thiadiazole, thiazole, thiazolopyridine, thiophene, triazine, triazole, triazolopyridine, and triazolopyrimidine, wherein the ring system optionally is substituted on any substitutable ring carbon atom and any substitutable ring nitrogen atom; and one ring nitrogen atom in the ring system optionally is oxidized.

20. At least one chemical entity of claim 19, wherein $Cy_1$ is a bivalent radical derived from a monocyclic 5-membered aryl, heteroaryl, cycloaliphatic, or heterocyclyl ring, wherein the ring optionally is substituted on any substitutable ring carbon atom and on any substitutable ring nitrogen atom, and one ring nitrogen atom optionally is oxidized.

21. At least one chemical entity of claim 20, wherein $Cy_1$ is a bivalent radical derived from a ring system selected from thiophene, thiazole, pyrazole, imidazole, oxazole, isoxazole, furan, cyclopropane, pyrrole, indole, pyridine, benzene, and pyrrolidine, wherein the ring system optionally is substituted on any substitutable ring carbon atom and any ring nitrogen atom, and one ring nitrogen atom in the ring system optionally is oxidized.

22. At least one chemical entity of claim 19 wherein:

each substitutable ring nitrogen atom in $Cy_1$ is unsubstituted or is substituted with —C(O)R⁵*, —C(O)N(R⁵⁺)₂, —CO₂R⁵°, —SO₂R⁵°, —SO₂N(R⁵⁺)₂, $C_{1-4}$ aliphatic, or a $C_{6-10}$ ar($C_{1-4}$)alkyl, the aryl portion of which is optionally substituted;

each substitutable saturated ring carbon atom in $Cy_1$ is unsubstituted or is substituted with =O, =S, =C(R⁵*)₂, or —R⁵;

each substitutable unsaturated ring carbon atom in $Cy_1$ is unsubstituted or is substituted with $R^5$;

$R^5$ is —F, —Cl, —CN, —OR⁵*, —SR⁵*, —SO₂R⁵°, —N(R⁵⁺)₂, —N(R⁵⁺)C(O)—, —CO₂R⁵*, —C(O)N(R⁵⁺)₂, $C_{6-10}$ ar($C_{1-4}$ alkyl), the aryl portion of which is optionally substituted, an optionally substituted 5- or 6-membered aryl, heteroaryl, or heterocyclyl ring, an optionally substituted 3- to 6-membered cycloaliphatic ring, or a $C_{1-4}$ aliphatic or $C_{1-4}$ fluoroaliphatic group optionally substituted with one or two substituents independently selected from the group consisting of —OR⁵*, —N(R⁵⁺)₂, —N(R⁵⁺)C(O)—, —SO₂N(R⁵⁺)₂, —CO₂R⁵*, and —C(O)N(R⁵⁺)₂; wherein R⁵* is hydrogen, $C_{1-4}$ aliphatic, $C_{1-4}$ fluoroaliphatic, or $C_{6-10}$ ar($C_{1-4}$ alkyl), the aryl portion of which is optionally substituted;

R⁵° is $C_{1-4}$ aliphatic, $C_{1-4}$ fluoroaliphatic, $C_{6-10}$ ar($C_{1-4}$ alkyl), the aryl portion of which is optionally substituted, or an optionally substituted 5- or 6-membered aryl or heteroaryl ring;

each R⁵⁺ independently is hydrogen, $C_{1-4}$ aliphatic, $C_{1-4}$ fluoroaliphatic, or $C_{6-10}$ ar($C_{1-4}$ alkyl), the aryl portion of which is optionally substituted; or two R⁵⁺ on the same nitrogen atom, taken together with the nitrogen atom form an optionally substituted pyrrolidinyl, piperidinyl, piperazinyl, or morpholinyl ring.

23. At least one chemical entity of claim 1 wherein $Cy_2$ is a radical derived from a ring system selected from benzene, benzimidazole, benzodioxine, benzodioxole, benzoxazole, benzthiazole, cinnoline, cyclohexane, cyclopentane, dihydrobenzofuran, furan, imidazole, imidazolidine, imidazopyridine, indole, indolizine, isoindole, isoquinoline, isothiazole, isoxazole, morpholine, naphthyridine, oxadiazole, oxazole, oxazolopyridine, phthalazine, piperazine, piperidine, pteridine, purine, pyrazine, pyrazole, pyridazine, pyridine, pyrimidine, pyrrole, pyrrolidine, pyrrolopyridine, pyrrolopyrimidine, quinazoline, quinoline, quinoxaline, tetrazole, thiadiazole, thiazole, thiazolopyridine, thiophene, triazine, triazole, triazolopyridine, and triazolopyrimidine, wherein the ring system optionally is substituted on any substitutable ring carbon atom and any substitutable ring nitrogen atom; and one ring nitrogen atom in the ring system optionally is oxidized.

24. At least one chemical entity of claim 23 wherein $Cy_2$ is a radical derived from a ring system selected from benzene, benzodioxine, benzodioxole, benzoxazole, dihydrobenzofuran, furan, morpholine, piperazine, piperidine, pyrazine, pyrazole, pyridine, pyrimidine, pyrrole, pyrrolidine, tetrazole, thiazole, and thiophene, wherein the ring system optionally is substituted on any substitutable ring carbon atom and any substitutable ring nitrogen atom; and one ring nitrogen atom in the ring system optionally is oxidized.

25. At least one chemical entity of claim 24, wherein:
   each substitutable ring nitrogen atom in $Cy_2$ is unsubstituted or is substituted with —C(O)R*, —C(O)N(R$^+$)$_2$, —CO$_2$R$^o$, —SO$_2$R$^o$, —SO$_2$N(R$^+$)$_2$, C$_{1-4}$ aliphatic, —R$^r$, -T-R$^r$, or -T-R$^s$;
   each substitutable saturated ring carbon atom in $Cy_2$ is unsubstituted or is substituted with =O, =S, =C(R*)$_2$, or —R$^6$;
   each substitutable unsaturated ring carbon atom in $Cy_2$ is unsubstituted or is substituted with R$^6$;
   R$^6$ is selected from C$_{1-4}$ aliphatic, C$_{1-4}$ fluoroaliphatic, halo, —R$^r$, —R$^s$, -T-R$^s$, -T-R$^r$, —V-T-R$^s$, —V-T-R$^r$, and —V—R$^r$;
   each T independently is a C$_{1-4}$ alkylene chain optionally substituted with one or two substituents independently selected from C$_{1-3}$ aliphatic, C$_{1-3}$ fluoroaliphatic, —F, —OH, —O(C$_{1-4}$ alkyl), —CO$_2$H, —CO$_2$(C$_{1-4}$ alkyl), —C(O)NH$_2$, and —C(O)NH(C$_{1-4}$ alkyl), wherein the alkylene chain optionally is interrupted with —N(R$^a$)—, —C(=NR$^a$)—N(R$^a$)—, —C(NR$^a$)=N(R$^a$)—, N(R$^a$)—C(=NR$^a$)—, —N(R$^a$)—C(O)—, or —C(O)N(R$^a$)—;
   V is selected from —C(R$^f$)=C(R$^f$)—, —C≡C—, —O—, —N(R$^a$)—, —N(R$^a$)C(O)—, —C(O)N(R$^a$)—, —C(=NR$^a$)—N(R$^a$)—, —C(NR$^a$)=N(R$^a$)—, and —N(R$^a$)—C(=NR$^a$)—;
   each R$^r$ independently is selected from an optionally substituted aryl, optionally substituted heteroaryl, optionally substituted heterocyclyl, and optionally substituted cycloaliphatic ring;
   each R$^s$ independently is selected from —NO$_2$, —CN, —R*, —C(R*)=C(R*)$_2$, —C≡C—R*, —OR*, —SR*, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —OC(O)N(R$^+$)$_2$, —CO$_2$R*, —C(O)R*, —C(O)N(R$^+$)$_2$, —N(R$^+$)C(=NR$^+$)—N(R$^+$)—C(O)R*, —C(=NR$^+$)—N(R$^+$)$_2$, —N(R$^+$)C(=NR$^+$)—N(R$^+$)$_2$, —NR$^+$SO$_2$R$^o$, and —NR$^+$SO$_2$N(R$^+$)$_2$; wherein
   R$^o$ is an optionally substituted aliphatic, aryl, or heteroaryl group;
   each R* independently is hydrogen or an optionally substituted aliphatic, aryl, heteroaryl, or heterocyclyl group; and
   each R$^+$ independently is hydrogen or an optionally substituted aliphatic, aryl, heteroaryl, or heterocyclyl group, or two R$^+$ on the same nitrogen atom, taken together with the nitrogen atom, form a 4-8 membered aromatic or non-aromatic ring having, in addition to the nitrogen atom, 0-2 ring heteroatoms selected from N, O, and S.

26. At least one chemical entity of claim 25 wherein the substitutable ring carbon atoms of $Cy_2$ are substituted with 0-2 R$^6$ wherein R$^6$ is selected from halo, C$_{1-4}$ aliphatic, C$_{1-4}$ fluoroaliphatic, —R$^s$, -T-R$^s$, —R$^r$, and -T-R$^r$.

27. At least one chemical entity of claim 26, wherein R$^6$ is halo, C$_{1-4}$ aliphatic, C$_{1-4}$ fluoroaliphatic, R$^s$ wherein R$^s$ is —NO$_2$, —CN, morpholin-4-yl, —OH, —O(C$_{1-4}$ aliphatic), —O(C$_{1-4}$ fluoroaliphatic), —CO$_2$H, —CO$_2$(C$_{1-4}$ aliphatic), —C(O)NH$_2$, —C(O)NH(C$_{1-4}$ aliphatic), or —C(O)N(C$_{1-4}$ aliphatic), or -T-R$^s$ wherein R$^s$ is —OH, —O(C$_{1-4}$ aliphatic), —O(C$_{1-4}$ fluoroaliphatic), —NH$_2$, —NH(C$_{1-4}$ aliphatic), or —N(C$_{1-4}$ aliphatic)$_2$.

28. At least one chemical entity of claim 1 wherein R$^3$ is hydrogen.

29. At least one chemical entity of claim 1 wherein R$^4$ is hydrogen.

30. At least one chemical entity of claim 1 wherein the compound of formula (I) is selected from:
   2-{3-pyridin-3-yl-1-[(2-pyridin-4-yl-1,3-thiazol-5-yl)carbonyl]-4,5-dihydro-1H-pyrazol-5-yl}phenol;
   2-[1-({5-[3-(aminomethyl)phenyl]-2-thienyl}carbonyl)-3-pyridin-3-yl-4,5-dihydro-1H-pyrazol-5-yl]phenol;
   2-[1-(3-phenoxybenzoyl)-3-pyridin-3-yl-4,5-dihydro-1H-pyrazol-5-yl]phenol;
   2-(1-{[1-(6-methylpyridin-2-yl)-1H-imidazol-4-yl]carbonyl}-3-pyridin-3-yl-4,5-dihydro-1H-pyrazol-5-yl)phenol;
   2-{1-[5-(piperidin-1-ylmethyl)-2-furoyl]-3-pyridin-3-yl-4,5-dihydro-1H-pyrazol-5-yl}phenol;
   2-(1-{[5-(1-methyl-1H-pyrazol-4-yl)-2-thienyl]carbonyl}-3-pyridin-3-yl-4,5-dihydro-1H-pyrazol-5-yl)phenol;
   2-(1-{[5-(3-methylphenyl)-2-thienyl]carbonyl}-3-pyridin-3-yl-4,5-dihydro-1H-pyrazol-5-yl)phenol;
   2-{3-pyrazin-2-yl-1-[(5-pyridin-2-yl-2-thienyl)carbonyl]-4,5-dihydro-1H-pyrazol-5-yl}phenol;
   2-(1-{[5-(phenylsulfonyl)-2-thienyl]sulfonyl}-3-pyridin-3-yl-4,5-dihydro-1H-pyrazol-5-yl)phenol;
   N-[(3-{[5-(2-hydroxyphenyl)-3-pyridin-3-yl-4,5-dihydro-1H-pyrazol-1-yl]carbonyl}-2-furyl)methyl]-5-methyl-2-furamide;
   5-fluoro-2-{3-pyridin-3-yl-1-[(5-pyridin-2-yl-2-thienyl)carbonyl]-4,5-dihydro-1H-pyrazol-5-yl}phenol;
   4-{[5-(2-hydroxyphenyl)-3-pyridin-3-yl-4,5-dihydro-1H-pyrazol-1-yl]carbonyl}-1-(4-methoxyphenyl)pyrrolidin-2-one;
   2-(1-{[5-(4-hydroxyphenyl)isoxazol-3-yl]carbonyl}-3-pyridin-3-yl-4,5-dihydro-1H-pyrazol-5-yl)phenol;
   2-(1-{[2-(1-methyl-1H-pyrazol-4-yl)-1,3-thiazol-5-yl]carbonyl}-3-pyridin-3-yl-4,5-dihydro-1H-pyrazol-5-yl)phenol;
   2-{1-[5-(phenylethynyl)-2-furoyl]-3-pyridin-3-yl-4,5-dihydro-1H-pyrazol-5-yl}phenol;
   5-(2-hydroxyphenyl)-N-[(1R,2S)-2-phenylcyclopropyl]-3-pyridin-3-yl-4,5-dihydro-1H-pyrazole-1-carboxamide;
   4-(5-{[5-(2-hydroxyphenyl)-3-pyridin-3-yl-4,5-dihydro-1H-pyrazol-1-yl]carbonyl}-1,3-thiazol-2-yl)benzamide;
   2-{1-[(5-{2-[(ethylamino)methyl]phenyl}-2-thienyl)carbonyl]-3-pyridin-3-yl-4,5-dihydro-1H-pyrazol-5-yl}phenol;
   4-(5-{[5-(2-hydroxyphenyl)-3-pyridin-3-yl-4,5-dihydro-1H-pyrazol-1-yl]carbonyl}-1,3-thiazol-2-yl)benzonitrile;
   2-{1-[5-(4-methoxyphenyl)-2-furoyl]-3-pyridin-3-yl-4,5-dihydro-1H-pyrazol-5-yl}phenol;
   2-(1-{[5-(4-methoxyphenyl)isoxazol-3-yl]carbonyl}-3-pyridin-3-yl-4,5-dihydro-1H-pyrazol-5-yl)phenol;

2-{1-[3-(cyclopentyloxy)-4-methoxybenzoyl]-3-pyridin-3-yl-4,5-dihydro-1H-pyrazol-5-yl}phenol;
2-[3-pyridin-3-yl-1-({5-[2-(pyrrolidin-1-ylmethyl)phenyl]-2-thienyl}carbonyl)-4,5-dihydro-1H-pyrazol-5-yl]phenol;
2-{1-[3-(benzyloxy)-4-methoxybenzoyl]-3-pyridin-3-yl-4,5-dihydro-1H-pyrazol-5-yl}phenol;
2-{3-pyridin-2-yl-1-[(5-pyridin-2-yl-2-thienyl)carbonyl]-4,5-dihydro-1H-pyrazol-5-yl}phenol;
2-(1-{[5-(1,3-oxazol-5-yl)-2-thienyl]sulfonyl}-3-pyridin-3-yl-4,5-dihydro-1H-pyrazol-5-yl)phenol;
1-(4-fluorobenzyl)-4-{[5-(2-hydroxyphenyl)-3-pyridin-3-yl-4,5-dihydro-1H-pyrazol-1-yl]carbonyl}pyrrolidin-2-one;
tert-butyl 4-[(5-{[5-(2-hydroxyphenyl)-3-pyridin-3-yl-4,5-dihydro-1H-pyrazol-1-yl]carbonyl}-2-thienyl)methyl]piperazine-1-carboxylate;
2-{1-[5-(2-fluorophenyl)-2-furoyl]-3-pyridin-3-yl-4,5-dihydro-1H-pyrazol-5-yl}phenol;
2-(1-{[5-(3,4-dimethoxyphenyl)isoxazol-3-yl]carbonyl}-3-pyridin-3-yl-4,5-dihydro-1H-pyrazol-5-yl)phenol;
2-(1-{[3-(2-chlorophenyl)-1H-pyrazol-5-yl]carbonyl}-3-pyridin-3-yl-4,5-dihydro-1H-pyrazol-5-yl)phenol;
2-(1-{5-[(3-methoxyphenoxy)methyl]-2-furoyl}-3-pyridin-3-yl-4,5-dihydro-1H-pyrazol-5-yl)phenol;
2-[1-({5-[1-(2-morpholin-4-ylethyl)-1H-pyrazol-4-yl]-2-thienyl}carbonyl)-3-pyridin-3-yl-4,5-dihydro-1H-pyrazol-5-yl]phenol;
2-(1-{[5-(1,3-benzodioxol-5-yl)isoxazol-3-yl]carbonyl}-3-pyridin-3-yl-4,5-dihydro-1H-pyrazol-5-yl)phenol;
2-{1-[(5-methyl-1-phenyl-1H-pyrazol-4-yl)carbonyl]-3-pyridin-3-yl-4,5-dihydro-1H-pyrazol-5-yl}phenol;
2-(1-{[2,5-dimethyl-1-(pyridin-4-ylmethyl)-1H-pyrrol-3-yl]-carbonyl}-3-pyridin-3-yl-4,5-dihydro-1H-pyrazol-5-yl)phenol;
2-(1-{[1-(phenylsulfonyl)-1H-indol-3-yl]carbonyl}-3-pyridin-3-yl-4,5-dihydro-1H-pyrazol-5-yl)phenol;
2-{1-[3-(1H-pyrazol-1-yl)benzoyl]-3-pyridin-3-yl-4,5-dihydro-1H-pyrazol-5-yl}phenol;
2-[1-({1-[2-(aminomethyl)phenyl]-1H-pyrazol-4-yl}carbonyl)-3-pyridin-3-yl-4,5-dihydro-1H-pyrazol-5-yl]phenol;
3-{1-[4-(1H-benzimidazol-1-ylmethyl)benzoyl]-3-pyridin-3-yl-4,5-dihydro-1H-pyrazol-5-yl}phenol;
N,N-dibenzyl-5-{[5-(2-hydroxyphenyl)-3-pyridin-3-yl-4,5-dihydro-1H-pyrazol-1-yl]carbonyl}-1-methyl-1H-pyrrole-2-sulfonamide;
2-{1-[5-(4-chlorophenyl)-2-methyl-3-furoyl]-3-pyridin-3-yl-4,5-dihydro-1H-pyrazol-5-yl}phenol;
2-{1-[2-methyl-5-(piperidin-1-ylsulfonyl)-3-furoyl]-3-pyridin-3-yl-4,5-dihydro-1H-pyrazol-5-yl}phenol;
2-(1-{[5-(1H-pyrazol-4-yl)-2-thienyl]carbonyl}-3-pyridin-3-yl-4,5-dihydro-1H-pyrazol-5-yl)phenol;
2-{1-[5-methyl-4-(pyrrolidin-1-ylmethyl)-2-furoyl]-3-pyridin-3-yl-4,5-dihydro-1H-pyrazol-5-yl}phenol;
2-{1-[(5-phenyl-1,3-oxazol-4-yl)carbonyl]-3-pyridin-3-yl-4,5-dihydro-1H-pyrazol-5-yl}phenol;
2-(1-{[4-(4-chlorophenyl)-2-thienyl]carbonyl}-3-pyridin-3-yl-4,5-dihydro-1H-pyrazol-5-yl)phenol;
2-{1-[5-(morpholin-4-ylmethyl)-2-furoyl]-3-pyridin-3-yl-4,5-dihydro-1H-pyrazol-5-yl}phenol;
4-(5-{[5-(2-hydroxyphenyl)-3-pyridin-3-yl-4,5-dihydro-1H-pyrazol-1-yl]carbonyl}-2-thienyl)benzoic acid;
3-(5-{[5-(2-hydroxyphenyl)-3-pyridin-3-yl-4,5-dihydro-1H-pyrazol-1-yl]carbonyl}-2-thienyl)benzonitrile;
2-{1-[5-methyl-4-(morpholin-4-ylmethyl)-2-furoyl]-3-pyridin-3-yl-4,5-dihydro-1H-pyrazol-5-yl}phenol;
2-(1-{[5-(2-methylphenyl)-2-thienyl]carbonyl}-3-pyridin-3-yl-4,5-dihydro-1H-pyrazol-5-yl)phenol;
2-{1-[5-(4-fluorophenyl)-2-methyl-3-furoyl]-3-pyridin-3-yl-4,5-dihydro-1H-pyrazol-5-yl}phenol;
2-[3-pyridin-3-yl-1-({5-[4-(pyrrolidin-1-ylmethyl)phenyl]-2-thienyl}carbonyl)-4,5-dihydro-1H-pyrazol-5-yl]phenol;
2-[3-pyridin-3-yl-1-(4-pyridin-2-ylbenzoyl)-4,5-dihydro-1H-pyrazol-5-yl]phenol;
2-(4-{[5-(2-hydroxyphenyl)-3-pyridin-3-yl-4,5-dihydro-1H-pyrazol-1-yl]carbonyl}-1H-pyrazol-1-yl)benzonitrile;
3-{1-[2-methyl-5-(piperidin-1-ylsulfonyl)-3-furoyl]-3-pyridin-3-yl-4,5-dihydro-1H-pyrazol-5-yl}phenol;
2-(1-{[5-(3-methoxyphenyl)isoxazol-3-yl]carbonyl}-3-pyridin-3-yl-4,5-dihydro-1H-pyrazol-5-yl)phenol;
2-{1-[2-methyl-5-(morpholin-4-ylmethyl)-3-furoyl]-3-pyridin-3-yl-4,5-dihydro-1H-pyrazol-5-yl}phenol;
N-[(5-{[5-(2-hydroxyphenyl)-3-pyridin-3-yl-4,5-dihydro-1H-pyrazol-1-yl]carbonyl}-2-furyl)methyl]-2-methyl-3-furamide;
2-{1-[(5-{4-[(4-ethylpiperazin-1-yl)methyl]-phenyl}-2-thienyl)carbonyl]-3-pyridin-3-yl-4,5-dihydro-1H-pyrazol-5-yl}phenol;
2-[1-(5-phenyl-2-furoyl)-3-pyridin-3-yl-4,5-dihydro-1H-pyrazol-5-yl]phenol;
2-{3-pyridin-3-yl-1-[(2-pyridin-4-yl-1,3-thiazol-4-yl)carbonyl]-4,5-dihydro-1H-pyrazol-5-yl}phenol;
2-{1-[5-(4-nitrophenyl)-2-furoyl]-3-pyridin-3-yl-4,5-dihydro-1H-pyrazol-5-yl}phenol;
2-{3-pyridin-3-yl-1-[(2-pyridin-2-yl-1,3-thiazol-5-yl)carbonyl]-4,5-dihydro-1H-pyrazol-5-yl}phenol;
2-{3-pyridin-3-yl-1-[3-(1H-tetrazol-1-yl)benzoyl]-4,5-dihydro-1H-pyrazol-5-yl}phenol;
2-{1-[(5-phenyl-2-thienyl)carbonyl]-3-pyridin-3-yl-4,5-dihydro-1H-pyrazol-5-yl}phenol;
2-(3-pyridin-3-yl-1-{[5-(1H-tetrazol-1-yl)-1H-pyrazol-4-yl]-carbonyl}-4,5-dihydro-1H-pyrazol-5-yl)phenol;
2-(1-{[3-(3,4-dimethoxyphenyl)-1H-pyrazol-5-yl]-carbonyl}-3-pyridin-3-yl-4,5-dihydro-1H-pyrazol-5-yl)phenol;
2-(1-{[5-(4-chlorophenyl)-1H-pyrrol-2-yl]-carbonyl}-3-pyridin-3-yl-4,5-dihydro-1H-pyrazol-5-yl)phenol;
2-{1-[2-methyl-5-(pyrrolidin-1-ylsulfonyl)-3-furoyl]-3-pyridin-3-yl-4,5-dihydro-1H-pyrazol-5-yl}phenol;
2-[1-(2,2'-bithien-5-ylcarbonyl)-3-pyridin-3-yl-4,5-dihydro-1H-pyrazol-5-yl]phenol;
2-{1-[(5-methyl-3-phenylisoxazol-4-yl)carbonyl]-3-pyridin-3-yl-4,5-dihydro-1H-pyrazol-5-yl}phenol;
2-{3-pyridin-3-yl-1-[(5-pyridin-2-yl-2-thienyl)carbonyl]-4,5-dihydro-1H-pyrazol-5-yl}phenol;
4-{[5-(2-hydroxyphenyl)-3-pyridin-3-yl-4,5-dihydro-1H-pyrazol-1-yl]-carbonyl}-1-(3-methoxyphenyl)pyrrolidin-2-one;
2-{1-[(5-methyl-2-phenyl-1,3-oxazol-4-yl)acetyl]-3-pyridin-3-yl-4,5-dihydro-1H-pyrazol-5-yl}phenol;
2-[1-({5-[4-(piperazin-1-ylmethyl)phenyl]-2-thienyl}carbonyl)-3-pyridin-3-yl-4,5-dihydro-1H-pyrazol-5-yl]-phenol;
2-{1-[(5-{2-[(isopropylamino)methyl]-phenyl}-2-thienyl)carbonyl]-3-pyridin-3-yl-4,5-dihydro-1H-pyrazol-5-yl}phenol;
2-(3-pyridin-3-yl-1-{[5-(2-thienyl)pyridin-3-yl]carbonyl}-4,5-dihydro-1H-pyrazol-5-yl)phenol;
2-{3-pyridin-3-yl-1-[(1-pyridin-2-yl-1H-pyrazol-4-yl)carbonyl]-4,5-dihydro-1H-pyrazol-5-yl}phenol;

2-{3-pyridin-3-yl-1-[(5-pyridin-4-yl-2-thienyl)carbonyl]-4,5-dihydro-1H-pyrazol-5-yl}phenol;
2-{3-pyridin-3-yl-1-[4-(1H-pyrrol-1-yl)benzoyl]-4,5-dihydro-1H-pyrazol-5-yl}phenol;
5-(2-hydroxyphenyl)-N-(2-phenoxyphenyl)-3-pyridin-3-yl-4,5-dihydro-1H-pyrazole-1-carboxamide;
3-fluoro-2-{3-pyridin-3-yl-1-[(5-pyridin-2-yl-2-thienyl)carbonyl]-4,5-dihydro-1H-pyrazol-5-yl}phenol;
2-(1-{5-[(benzylsulfanyl)methyl]-2-furoyl}-3-pyridin-3-yl-4,5-dihydro-1H-pyrazol-5-yl)phenol;
2-{1-[5-methyl-4-(piperidin-1-ylmethyl)-2-furoyl]-3-pyridin-3-yl-4,5-dihydro-1H-pyrazol-5-yl}phenol;
2-[3-pyridin-3-yl-1-(3-pyridin-2-ylbenzoyl)-4,5-dihydro-1H-pyrazol-5-yl]phenol;
2-{1-[(4-methyl-2-pyrazin-2-yl-1,3-thiazol-5-yl)carbonyl]-3-pyridin-3-yl-4,5-dihydro-1H-pyrazol-5-yl}phenol;
2-(1-{[5-(4-methylphenyl)isoxazol-3-yl]carbonyl}-3-pyridin-3-yl-4,5-dihydro-1H-pyrazol-5-yl)phenol;
2-[1-({5-[4-(morpholin-4-ylmethyl)phenyl]-2-thienyl}carbonyl)-3-pyridin-3-yl-4,5-dihydro-1H-pyrazol-5-yl]phenol;
2-{1-[(2'-fluorobiphenyl-3-yl)carbonyl]-3-pyridin-3-yl-4,5-dihydro-1H-pyrazol-5-yl}phenol;
2-(1-{[5-(4-methylphenyl)-1H-pyrrol-2-yl]carbonyl}-3-pyridin-3-yl-4,5-dihydro-1H-pyrazol-5-yl)phenol;
2-(1-{[2-(3-chlorophenyl)-1,3-thiazol-4-yl]carbonyl}-3-pyridin-3-yl-4,5-dihydro-1H-pyrazol-5-yl)phenol;
2-{1-[(2-phenyl-1,3-thiazol-4-yl)carbonyl]-3-pyridin-3-yl-4,5-dihydro-1H-pyrazol-5-yl}phenol;
2-(1,3-benzoxazol-2-ylamino)-5-{2-[5-(2-hydroxyphenyl)-3-pyridin-3-yl-4,5-dihydro-1H-pyrazol-1-yl]-2-oxoethyl}-1,5-dihydro-4H-imidazol-4-one;
2-{1-[(2,4-diphenyl-1,3-thiazol-5-yl)acetyl]-3-pyridin-3-yl-4,5-dihydro-1H-pyrazol-5-yl}phenol;
2-[1-({5-[2-(hydroxymethyl)phenyl]-2-thienyl}carbonyl)-3-pyridin-3-yl-4,5-dihydro-1H-pyrazol-5-yl]phenol;
2-(3-pyridin-3-yl-1-{[5-(2-pyridin-2-ylethyl)-2-thienyl]carbonyl}-4,5-dihydro-1H-pyrazol-5-yl)phenol;
2-{1-[(5-amino-1-phenyl-1H-pyrazol-4-yl)carbonyl]-3-pyridin-3-yl-4,5-dihydro-1H-pyrazol-5-yl}phenol;
2-(1-{[5-(2-methyl-1,3-thiazol-4-yl)isoxazol-3-yl]carbonyl}-3-pyridin-3-yl-4,5-dihydro-1H-pyrazol-5-yl)phenol;
2-{1-[(5-phenyl-1H-pyrrol-2-yl)carbonyl]-3-pyridin-3-yl-4,5-dihydro-1H-pyrazol-5-yl}phenol;
2-(1-{[2-(2,3-dihydro-1-benzofuran-5-yl)-1,3-thiazol-4-yl]carbonyl}-3-pyridin-3-yl-4,5-dihydro-1H-pyrazol-5-yl)phenol;
2-(5-{[5-(2-hydroxyphenyl)-3-pyridin-3-yl-4,5-dihydro-1H-pyrazol-1-yl]carbonyl}-2-thienyl)benzaldehyde;
2-[3-pyridin-3-yl-1-({5-[3-(pyrrolidin-1-ylmethyl)phenyl]-2-thienyl}carbonyl)-4,5-dihydro-1H-pyrazol-5-yl]phenol;
N-(4-{[5-(2-hydroxyphenyl)-3-pyridin-3-yl-4,5-dihydro-1H-pyrazol-1-yl]carbonyl}phenyl)-1-phenylmethanesulfonamide;
2-(1-{[5-(6-methoxypyridin-3-yl)-2-thienyl]carbonyl}-3-pyridin-3-yl-4,5-dihydro-1H-pyrazol-5-yl)phenol;
2-{1-[5-phenylisoxazol-3-yl)carbonyl]-3-pyridin-3-yl-4,5-dihydro-1H-pyrazol-5-yl}phenol;
2-{1-[(4-methyl-2-pyridin-3-yl-1,3-thiazol-5-yl)carbonyl]-3-pyridin-3-yl-4,5-dihydro-1H-pyrazol-5-yl}phenol;
2-{1-[(4-methyl-2-phenyl-1,3-thiazol-5-yl)carbonyl]-3-pyridin-3-yl-4,5-dihydro-1H-pyrazol-5-yl}phenol;

2-[1-(2-methyl-5-phenyl-3-furoyl)-3-pyridin-3-yl-4,5-dihydro-1H-pyrazol-5-yl]phenol;
2-(1-{[3-(2,3-dihydro-1,4-benzodioxin-6-yl)-1H-pyrazol-5-yl]carbonyl}-3-pyridin-3-yl-4,5-dihydro-1H-pyrazol-5-yl)phenol;
2-fluoro-6-{3-pyridin-3-yl-1-[(5-pyridin-2-yl-2-thienyl)carbonyl]-4,5-dihydro-1H-pyrazol-5-yl}phenol;
1-(2,4-dimethylphenyl)-4-{[5-(2-hydroxyphenyl)-3-pyridin-3-yl-4,5-dihydro-1H-pyrazol-1-yl]carbonyl}pyrrolidin-2-one;
2-(3-pyridin-3-yl-1-{[3-(2-thienyl)-1H-pyrazol-5-yl]carbonyl}-4,5-dihydro-1H-pyrazol-5-yl)phenol;
2-(1-{[1-(4-methoxyphenyl)cyclopentyl]carbonyl}-3-pyridin-3-yl-4,5-dihydro-1H-pyrazol-5-yl)phenol;
1-(2-furylmethyl)-4-{[5-(2-hydroxyphenyl)-3-pyridin-3-yl-4,5-dihydro-1H-pyrazol-1-yl]carbonyl}pyrrolidin-2-one;
2-(1-{[1-(4-fluorophenyl)cyclopentyl]carbonyl}-3-pyridin-3-yl-4,5-dihydro-1H-pyrazol-5-yl)phenol;
2-(3-pyridin-3-yl-1-{[(1S,2R)-2-pyridin-2-ylcyclopropyl]carbonyl}-4,5-dihydro-1H-pyrazol-5-yl)phenol;
2-(1-{[2-(4-methylphenyl)-1,3-thiazol-4-yl]carbonyl}-3-pyridin-3-yl-4,5-dihydro-1H-pyrazol-5-yl)phenol;
2-(1-{5-[(4-fluorophenoxy)methyl]-2-furoyl}-3-pyridin-3-yl-4,5-dihydro-1H-pyrazol-5-yl)phenol;
2-(1-{[5-(2-chlorophenyl)-2-thienyl]carbonyl}-3-pyridin-3-yl-4,5-dihydro-1H-pyrazol-5-yl)phenol;
2-{3-pyridin-3-yl-1-[(5-pyridin-2-yl-2-thienyl)sulfonyl]-4,5-dihydro-1H-pyrazol-5-yl}phenol;
2-{1-[5-(1H-pyrazol-1-ylmethyl)-2-furoyl]-3-pyridin-3-yl-4,5-dihydro-1H-pyrazol-5-yl}phenol;
2-(3-pyridin-3-yl-1-{[2-(2-thienyl)-1,3-thiazol-4-yl]carbonyl}-4,5-dihydro-1H-pyrazol-5-yl)phenol;
2-(3-pyridin-3-yl-1-{[(1S,2S)-2-pyridin-4-ylcyclopropyl]carbonyl}-4,5-dihydro-1H-pyrazol-5-yl)phenol;
2-(1-{[5-(3-hydroxyphenyl)isoxazol-3-yl]carbonyl}-3-pyridin-3-yl-4,5-dihydro-1H-pyrazol-5-yl)phenol;
2-(1-{[5-(6-morpholin-4-ylpyridin-3-yl)-2-thienyl]carbonyl}-3-pyridin-3-yl-4,5-dihydro-1H-pyrazol-5-yl)phenol;
2-{1-[3-methyl-5-(morpholin-4-ylmethyl)-2-furoyl]-3-pyridin-3-yl-4,5-dihydro-1H-pyrazol-5-yl}phenol;
2-(1-{[5-(2-methyl-1,3-thiazol-4-yl)-2-thienyl]carbonyl}-3-pyridin-3-yl-4,5-dihydro-1H-pyrazol-5-yl)phenol;
4-(5-{[5-(2-hydroxyphenyl)-3-pyridin-3-yl-4,5-dihydro-1H-pyrazol-1-yl]carbonyl}-2-thienyl)benzonitrile;
N-[(5-{[5-(2-hydroxyphenyl)-3-pyridin-3-yl-4,5-dihydro-1H-pyrazol-1-yl]carbonyl}-2-thienyl)methyl]pyridine-2-carboxamide;
2-(3-pyridin-3-yl-1-{[5-(pyrrolidin-1-ylmethyl)-2-thienyl]carbonyl}-4,5-dihydro-1H-pyrazol-5-yl)phenol;
2-(1-{[5-(4-chlorophenyl)isoxazol-3-yl]carbonyl}-3-pyridin-3-yl-4,5-dihydro-1H-pyrazol-5-yl)phenol;
2-{3-pyridin-3-yl-1-[(5-pyrimidin-5-yl-2-thienyl)carbonyl]-4,5-dihydro-1H-pyrazol-5-yl}phenol;
2-(1-{[5-(2-furyl)isoxazol-3-yl]carbonyl}-3-pyridin-3-yl-4,5-dihydro-1H-pyrazol-5-yl)phenol;
2-{1-[(1-benzyl-5-methyl-1H-1,2,3-triazol-4-yl)carbonyl]-3-pyridin-3-yl-4,5-dihydro-1H-pyrazol-5-yl}phenol;
4-{[5-(3-hydroxyphenyl)-3-pyridin-3-yl-4,5-dihydro-1H-pyrazol-1-yl]carbonyl}-2,5-dimethyl-N-(2-thienylmethyl)furan-3-sulfonamide;
2-(1-{[5-(3-chlorophenyl)-2-thienyl]carbonyl}-3-pyridin-3-yl-4,5-dihydro-1H-pyrazol-5-yl)phenol;

2-(1-{[2-(4-methoxyphenyl)-1,3-thiazol-4-yl]carbonyl}-3-pyridin-3-yl-4,5-dihydro-1H-pyrazol-5-yl)phenol;
3-fluoro-2-{1-[(3-phenyl-1H-pyrazol-5-yl)carbonyl]-3-pyridin-3-yl-4,5-dihydro-1H-pyrazol-5-yl}phenol;
2-{1-[5-(4-chlorophenyl)-2-furoyl]-3-pyridin-3-yl-4,5-dihydro-1H-pyrazol-5-yl}phenol;
2-{1-[2-methyl-5-(morpholin-4-ylsulfonyl)-3-furoyl]-3-pyridin-3-yl-4,5-dihydro-1H-pyrazol-5-yl}phenol;
N-biphenyl-2-yl-5-(2-hydroxyphenyl)-3-pyridin-3-yl-4,5-dihydro-1H-pyrazole-1-carboxamide;
2-{1-[2-methyl-5-(4-methylphenyl)-3-furoyl]-3-pyridin-3-yl-4,5-dihydro-1H-pyrazol-5-yl}phenol;
2-{5-[(5-phenyl-3-pyridin-3-yl-4,5-dihydro-1H-pyrazol-1-yl)carbonyl]-2-thienyl}pyridine;
4-{[5-(2-hydroxyphenyl)-3-pyridin-3-yl-4,5-dihydro-1H-pyrazol-1-yl]carbonyl}-1-(2-methylphenyl)pyrrolidin-2-one;
2-(3-pyridin-3-yl-1-{[5-(pyridin-2-ylethynyl)-2-thienyl]carbonyl}-4,5-dihydro-1H-pyrazol-5-yl)phenol;
3-{[5-(2-hydroxyphenyl)-3-pyridin-3-yl-4,5-dihydro-1H-pyrazol-1-yl]carbonyl}-1-phenylpyrrolidin-2-one;
2-{1-[5-morpholin-4-ylethyl)-2-furoyl]-3-pyridin-3-yl-4,5-dihydro-1H-pyrazol-5-yl}phenol;
2-{1-[(5-{2-[(methylamino)methyl]phenyl}-2-thienyl)carbonyl]-3-pyridin-3-yl-4,5-dihydro-1H-pyrazol-5-yl}phenol;
2-{3-pyridin-3-yl-1-[(2-pyridin-3-yl-1,3-thiazol-4-yl)carbonyl]-4,5-dihydro-1H-pyrazol-5-yl}phenol;
N-[(4-{[5-(2-hydroxyphenyl)-3-pyridin-3-yl-4,5-dihydro-1H-pyrazol-1-yl]carbonyl}-2-furyl)methyl]-5-methyl-3-furamide;
2-{1-[(5-phenylisoxazol-4-yl)carbonyl]-3-pyridin-3-yl-4,5-dihydro-1H-pyrazol-5-yl}phenol;
2-{1-[5-(3-methoxyphenyl)-2-furoyl]-3-pyridin-3-yl-4,5-dihydro-1H-pyrazol-5-yl}phenol;
4-fluoro-2-{3-pyridin-3-yl-1-[(5-pyridin-2-yl-2-thienyl)carbonyl]-4,5-dihydro-1H-pyrazol-5-yl}phenol;
2-(5-{[5-(2-hydroxyphenyl)-3-pyridin-3-yl-4,5-dihydro-1H-pyrazol-1-yl]carbonyl}-2-thienyl)benzonitrile;
2-[1-({2-[(4-methoxyphenyl)amino]-1,3-thiazol-4-yl}acetyl)-3-pyridin-3-yl-4,5-dihydro-1H-pyrazol-5-yl]phenol;
3-chloro-2-{3-pyridin-3-yl-1-[(5-pyridin-2-yl-2-thienyl)carbonyl]-4,5-dihydro-1H-pyrazol-5-yl}phenol;
2-(1-{[5-(1-propyl-1H-pyrazol-4-yl)-2-thienyl]carbonyl}-3-pyridin-3-yl-4,5-dihydro-1H-pyrazol-5-yl)phenol;
2-{3-pyridin-3-yl-1-[5-(pyrrolidin-1-ylmethyl)-2-furoyl]-4,5-dihydro-1H-pyrazol-5-yl}phenol;
2-(1-{[1-benzyl-2-(methylsulfanyl)-1H-imidazol-5-yl]carbonyl}-3-pyridin-3-yl-4,5-dihydro-1H-pyrazol-5-yl)phenol;
2-[3-pyridin-3-yl-1-(5-pyridin-2-yl-2-furoyl)-4,5-dihydro-1H-pyrazol-5-yl]phenol;
2-{1-[(6-morpholin-4-ylpyridin-3-yl)sulfonyl]-3-pyridin-3-yl-4,5-dihydro-1H-pyrazol-5-yl}phenol;
2-(1-{[3-(4-fluorophenyl)-5-methylisoxazol-4-yl]carbonyl}-3-pyridin-3-yl-4,5-dihydro-1H-pyrazol-5-yl)phenol;
2-{3-pyridin-3-yl-1-[(5-pyridin-3-yl-2-thienyl)carbonyl]-4,5-dihydro-1H-pyrazol-5-yl}phenol;
2-(1-{[5-(2-hydroxyphenyl)isoxazol-3-yl]carbonyl}-3-pyridin-3-yl-4,5-dihydro-1H-pyrazol-5-yl)phenol;
2-(1-{[5-(4-methylphenyl)-2-thienyl]carbonyl}-3-pyridin-3-yl-4,5-dihydro-1H-pyrazol-5-yl)phenol;
2-{1-[5-(4-methylphenyl)-2-furoyl]-3-pyridin-3-yl-4,5-dihydro-1H-pyrazol-5-yl}phenol;
2-{1-[(3-phenyl-1H-pyrazol-5-yl)carbonyl]-3-pyridin-3-yl-4,5-dihydro-1H-pyrazol-5-yl}phenol;
2-(3-pyridin-3-yl-1-{[5-(1,2,3-thiadiazol-4-yl)-2-thienyl]sulfonyl}-4,5-dihydro-1H-pyrazol-5-yl)phenol;
2-(1-{[2,5-dimethyl-1-(2-thienylmethyl)-1H-pyrrol-3-yl]carbonyl}-3-pyridin-3-yl-4,5-dihydro-1H-pyrazol-5-yl)phenol;
2-[1-({5-[2-(aminomethyl)phenyl]-2-thienyl}carbonyl)-3-pyridin-3-yl-4,5-dihydro-1H-pyrazol-5-yl]-3-fluorophenol;
3-methoxy-2-{3-pyridin-3-yl-1-[(5-pyridin-2-yl-2-thienyl)carbonyl]-4,5-dihydro-1H-pyrazol-5-yl}phenol;
2-(1-{[2-(benzylamino)-1,3-thiazol-5-yl]carbonyl}-3-pyridin-3-yl-4,5-dihydro-1H-pyrazol-5-yl)phenol;
4-{[5-(2-hydroxyphenyl)-3-pyridin-3-yl-4,5-dihydro-1H-pyrazol-1-yl]carbonyl}-1-phenylpyrrolidin-2-one;
2-(1-{[3-(2-furyl)-1H-pyrazol-5-yl]carbonyl}-3-pyridin-3-yl-4,5-dihydro-1H-pyrazol-5-yl)phenol;
3-{3-pyridin-3-yl-1-[(5-pyridin-2-yl-2-thienyl)carbonyl]-4,5-dihydro-1H-pyrazol-5-yl}phenol;
2-{1-[(3-phenylisoxazol-5-yl)carbonyl]-3-pyridin-3-yl-4,5-dihydro-1H-pyrazol-5-yl}phenol;
2-(1-{[3-(3-methylphenyl)-1H-pyrazol-5-yl]carbonyl}-3-pyridin-3-yl-4,5-dihydro-1H-pyrazol-5-yl)phenol;
2-(1-{[5-(4-chlorophenyl)-2-thienyl]-carbonyl}-3-pyridin-3-yl-4,5-dihydro-1H-pyrazol-5-yl)phenol;
2-(3-pyridin-3-yl-1-{5-[3-(trifluoromethyl)phenyl]-2-furoyl}-4,5-dihydro-1H-pyrazol-5-yl)phenol;
3-(3-pyridin-3-yl-1-{5-[3-(trifluoromethyl)phenyl]-2-furoyl}-4,5-dihydro-1H-pyrazol-5-yl)phenol;
2-[1-({5-[4-(aminomethyl)phenyl]-2-thienyl}carbonyl)-3-pyridin-3-yl-4,5-dihydro-1H-pyrazol-5-yl]phenol;
2-[1-({5-[4-(hydroxymethyl)phenyl]-2-thienyl}carbonyl)-3-pyridin-3-yl-4,5-dihydro-1H-pyrazol-5-yl]phenol;
2-[1-({5-[4-(aminomethyl)phenyl]-2-thienyl}carbonyl)-3-pyridin-3-yl-4,5-dihydro-1H-pyrazol-5-yl]phenol;
2-[1-({5-[4-(aminomethyl)-2-methylphenyl]-2-thienyl}carbonyl)-3-pyridin-3-yl-4,5-dihydro-1H-pyrazol-5-yl]phenol;
2-(5-{[5-(2-hydroxyphenyl)-3-pyridin-3-yl-4,5-dihydro-1H-pyrazol-1-yl]carbonyl}-2-thienyl)benzoic acid;
2-[1-({5-[2-(aminomethyl)phenyl]-1H-pyrazol-3-yl}carbonyl)-3-pyridin-3-yl-4,5-dihydro-1H-pyrazol-5-yl]phenol;
2-[1-({2-[2-(aminomethyl)phenyl]-1,3-thiazol-5-yl}carbonyl)-3-pyridin-3-yl-4,5-dihydro-1H-pyrazol-5-yl]phenol;
3-fluoro-4-(5-{[5-(2-hydroxyphenyl)-3-pyridin-3-yl-4,5-dihydro-1H-pyrazol-1-yl]carbonyl}-2-thienyl)benzonitrile;
2-[1-({5-[2-(aminomethyl)phenyl]-2-thienyl}carbonyl)-3-(6-aminopyridin-3-yl)-4,5-dihydro-1H-pyrazol-5-yl]phenol;
2-(5-{[5-(2-hydroxyphenyl)-3-pyridin-3-yl-4,5-dihydro-1H-pyrazol-1-yl]carbonyl}-2-thienyl)benzamide;
2-[1-({1-[2-(aminomethyl)phenyl]-1H-imidazol-4-yl}carbonyl)-3-pyridin-3-yl-4,5-dihydro-1H-pyrazol-5-yl]phenol;
2-[1-({5-[2-(aminomethyl)phenyl]-2-thienyl}carbonyl)-3-pyrazin-2-yl-4,5-dihydro-1H-pyrazol-5-yl]phenol;
2-(1-{[5-(6-piperazin-1-ylpyridin-3-yl)-2-thienyl]carbonyl}-3-pyridin-3-yl-4,5-dihydro-1H-pyrazol-5-yl)phenol;
2-(1-{[5-(2-isopropylphenyl)-2-thienyl]carbonyl}-3-pyridin-3-yl-4,5-dihydro-1H-pyrazol-5-yl)phenol;

5-(2-hydroxyphenyl)-N-[2-methoxy-5-(1-methyl-1-phenylethyl)phenyl]-3-pyridin-3-yl-4,5-dihydro-1H-pyrazole-1-carboxamide;
5-(2-hydroxyphenyl)-N-[2-(phenoxymethyl)phenyl]-3-pyridin-3-yl-4,5-dihydro-1H-pyrazole-1-carboxamide;
N-(3-{[ethyl(phenyl)amino]sulfonyl}-4-methylphenyl)-5-(2-hydroxyphenyl)-3-pyridin-3-yl-4,5-dihydro-1H-pyrazole-1-carboxamide;
N-[3-(4-bromo-1-methyl-1H-pyrazol-3-yl)phenyl]-5-(2-hydroxyphenyl)-3-pyridin-3-yl-4,5-dihydro-1H-pyrazole-1-carboxamide;
N-(2-benzylphenyl)-5-(2-hydroxyphenyl)-3-pyridin-3-yl-4,5-dihydro-1H-pyrazole-1-carboxamide;
5-(2-hydroxyphenyl)-N-(6-phenoxypyridin-3-yl)-3-pyridin-3-yl-4,5-dihydro-1H-pyrazole-1-carboxamide;
5-(2-hydroxyphenyl)-N-[4-(1H-imidazol-1-yl)phenyl]-3-pyridin-3-yl-4,5-dihydro-1H-pyrazole-1-carboxamide;
2-[1-({5-[2-(aminomethyl)phenyl]-2-thienyl}carbonyl)-3-(5-aminopyridin-3-yl)-4,5-dihydro-1H-pyrazol-5-yl]phenol;
5-(2-hydroxyphenyl)-N-(4-methyl-2-phenylpyrimidin-5-yl)-3-pyridin-3-yl-4,5-dihydro-1H-pyrazole-1-carboxamide;
N-[5-(1,1-dimethylpropyl)-2-phenoxyphenyl]-5-(2-hydroxyphenyl)-3-pyridin-3-yl-4,5-dihydro-1H-pyrazole-1-carboxamide;
5-(2-hydroxyphenyl)-N-(4-methoxybiphenyl-3-yl)-3-pyridin-3-yl-4,5-dihydro-1H-pyrazole-1-carboxamide;
2-[1-({5-[4-(2-amino-1,1-dimethylethyl)phenyl]-2-thienyl}carbonyl)-3-pyridin-3-yl-4,5-dihydro-1H-pyrazol-5-yl]phenol;
2-[1-({2-[2-(aminomethyl)phenyl]-1H-imidazol-5-yl}carbonyl)-3-pyridin-3-yl-4,5-dihydro-1H-pyrazol-5-yl]phenol;
4-(5-{[5-(2-hydroxyphenyl)-3-pyridin-3-yl-4,5-dihydro-1H-pyrazol-1-yl]carbonyl}-2-thienyl)isoindolin-1-one;
N-[3-(2-chloro-6-fluorophenyl)-5-methylisoxazol-4-yl]-5-(2-hydroxyphenyl)-3-pyridin-3-yl-4,5-dihydro-1H-pyrazole-1-carboxamide;
5-(2-hydroxyphenyl)-N-[3-(2-methyl-1,3-thiazol-4-yl)phenyl]-3-pyridin-3-yl-4,5-dihydro-1H-pyrazole-1-carboxamide;
3-fluoro-2-(3-pyridin-3-yl-1-{[5-(2H-tetrazol-5-yl)-2-thienyl]carbonyl}-4,5-dihydro-1H-pyrazol-5-yl)phenol;
3-fluoro-2-{1-[(1-phenyl-1H-imidazol-4-yl)carbonyl]-3-pyridin-3-yl-4,5-dihydro-1H-pyrazol-5-yl}phenol;
N-[4-(1,1-dioxido-1,2-thiazinan-2-yl)phenyl]-5-(2-hydroxyphenyl)-3-pyridin-3-yl-4,5-dihydro-1H-pyrazole-1-carboxamide;
N-[2-(2,3-dimethylphenoxy)pyridin-3-yl]-5-(2-hydroxyphenyl)-3-pyridin-3-yl-4,5-dihydro-1H-pyrazole-1-carboxamide;
5-(2-hydroxyphenyl)-3-pyridin-3-yl-N-{6-[3-(trifluoromethyl)phenoxy]pyridin-3-yl}-4,5-dihydro-1H-pyrazole-1-carboxamide;
2-[1-({5-[2-(2-aminoethyl)phenyl]-2-thienyl}carbonyl)-3-pyridin-3-yl-4,5-dihydro-1H-pyrazol-5-yl]phenol;
3-fluoro-2-(3-pyridin-3-yl-1-{[5-(1,2,3,4-tetrahydroisoquinolin-6-yl)-2-thienyl]carbonyl}-4,5-dihydro-1H-pyrazol-5-yl)phenol;
5-(2-hydroxyphenyl)-N-(3-methyl-1-phenyl-1H-pyrazol-5-yl)-3-pyridin-3-yl-4,5-dihydro-1H-pyrazole-1-carboxamide;
N-(4'-fluorobiphenyl-2-yl)-5-(2-hydroxyphenyl)-3-pyridin-3-yl-4,5-dihydro-1H-pyrazole-1-carboxamide;
5-(2-hydroxyphenyl)-N-[3-(1,3-oxazol-5-yl)phenyl]-3-pyridin-3-yl-4,5-dihydro-1H-pyrazole-1-carboxamide;
N-[4-(4-chlorophenoxy)phenyl]-5-(2-hydroxyphenyl)-3-pyridin-3-yl-4,5-dihydro-1H-pyrazole-1-carboxamide;
5-(2-hydroxyphenyl)-N-[4-(1,3-oxazol-5-yl)phenyl]-3-pyridin-3-yl-4,5-dihydro-1H-pyrazole-1-carboxamide;
(4S)-1-(2,4-dimethylphenyl)-4-{[5-(2-fluoro-6-hydroxyphenyl)-3-pyridin-3-yl-4,5-dihydro-1H-pyrazol-1-yl]carbonyl}pyrrolidin-2-one;
5-(2-hydroxyphenyl)-N-{4-[(4-methoxyphenyl)amino]phenyl}-3-pyridin-3-yl-4,5-dihydro-1H-pyrazole-1-carboxamide;
2-[1-({5-[2-(aminomethyl)-4-fluorophenyl]-2-thienyl}carbonyl)-3-pyridin-3-yl-4,5-dihydro-1H-pyrazol-5-yl]phenol;
2-[1-({5-[2-(aminomethyl)phenyl]-2-thienyl}carbonyl)-3-(6-aminopyridin-2-yl)-4,5-dihydro-1H-pyrazol-5-yl]phenol;
5-(2-hydroxyphenyl)-N-(4-{[(5-methyl-1,3,4-thiadiazol-2-yl)amino]sulfonyl}phenyl)-3-pyridin-3-yl-4,5-dihydro-1H-pyrazole-1-carboxamide;
2-[1-({5-[2-(aminomethyl)-4-methoxyphenyl]-2-thienyl}carbonyl)-3-pyridin-3-yl-4,5-dihydro-1H-pyrazol-5-yl]phenol;
N-[1-(4-chlorobenzyl)-5-oxopyrrolidin-3-yl]-5-(2-hydroxyphenyl)-3-pyridin-3-yl-4,5-dihydro-1H-pyrazole-1-carboxamide;
3-fluoro-2-(1-{[5-(1-methyl-1H-pyrazol-4-yl)-2-thienyl]carbonyl}-3-pyridin-3-yl-4,5-dihydro-1H-pyrazol-5-yl)phenol;
5-(2-hydroxyphenyl)-N-[4-(phenoxymethyl)-1,3-thiazol-2-yl]-3-pyridin-3-yl-4,5-dihydro-1H-pyrazole-1-carboxamide;
N-[3-(1,3-benzothiazol-2-yl)-2-thienyl]-5-(2-hydroxyphenyl)-3-pyridin-3-yl-4,5-dihydro-1H-pyrazole-1-carboxamide;
5-(2-hydroxyphenyl)-3-pyridin-3-yl-N-[4-(1H-pyrrol-1-yl)phenyl]-4,5-dihydro-1H-pyrazole-1-carboxamide;
N-(4-cyclohexylphenyl)-5-(2-hydroxyphenyl)-3-pyridin-3-yl-4,5-dihydro-1H-pyrazole-1-carboxamide;
N-[(3S)-1-benzylpyrrolidin-3-yl]-5-(2-hydroxyphenyl)-3-pyridin-3-yl-4,5-dihydro-1H-pyrazole-1-carboxamide;
2-(3-pyridin-3-yl-1-{[5-(1,2,3,4-tetrahydroisoquinolin-8-yl)-2-thienyl]carbonyl}-4,5-dihydro-1H-pyrazol-5-yl)phenol;
N-(4-benzylphenyl)-5-(2-hydroxyphenyl)-3-pyridin-3-yl-4,5-dihydro-1H-pyrazole-1-carboxamide;
N-(5-cyclobutyl-1H-pyrazol-3-yl)-5-(2-hydroxyphenyl)-3-pyridin-3-yl-4,5-dihydro-1H-pyrazole-1-carboxamide;
5-(2-hydroxyphenyl)-N-[2-(1H-pyrazol-1-yl)phenyl]-3-pyridin-3-yl-4,5-dihydro-1H-pyrazole-1-carboxamide;
5-(2-hydroxyphenyl)-N-(6-morpholin-4-ylpyridin-3-yl)-3-pyridin-3-yl-4,5-dihydro-1H-pyrazole-1-carboxamide;
3-fluoro-2-[3-pyridin-3-yl-1-({5-[3-(pyrrolidin-1-ylmethyl)phenyl]-2-thienyl}carbonyl)-4,5-dihydro-1H-pyrazol-5-yl]phenol;
N-[3-(benzyloxy)phenyl]-5-(2-hydroxyphenyl)-3-pyridin-3-yl-4,5-dihydro-1H-pyrazole-1-carboxamide;
N-(2-{[cyclohexyl(methyl)amino]sulfonyl}phenyl)-5-(2-hydroxyphenyl)-3-pyridin-3-yl-4,5-dihydro-1H-pyrazole-1-carboxamide;
2-(3-pyridin-3-yl-1-{[5-(1,2,3,4-tetrahydroisoquinolin-6-yl)-2-thienyl]carbonyl}-4,5-dihydro-1H-pyrazol-5-yl)phenol;

N-{4-[(2-chlorobenzyl)oxy]phenyl}-5-(2-hydroxyphenyl)-3-pyridin-3-yl-4,5-dihydro-1H-pyrazole-1-carboxamide;
5-(2-hydroxyphenyl)-N-(4'-methoxybiphenyl-2-yl)-3-pyridin-3-yl-4,5-dihydro-1H-pyrazole-1-carboxamide;
5-(2-hydroxyphenyl)-N-(2-phenylquinolin-4-yl)-3-pyridin-3-yl-4,5-dihydro-1H-pyrazole-1-carboxamide;
N-(3-benzoylphenyl)-5-(2-hydroxyphenyl)-3-pyridin-3-yl-4,5-dihydro-1H-pyrazole-1-carboxamide;
5-(2-hydroxyphenyl)-N-[4-(4-methylphenoxy)phenyl]-3-pyridin-3-yl-4,5-dihydro-1H-pyrazole-1-carboxamide;
5-(2-hydroxyphenyl)-N-{2-oxo-1-[4-(trifluoromethyl)benzyl]-1,2-dihydropyridin-3-yl}-3-pyridin-3-yl-4,5-dihydro-1H-pyrazole-1-carboxamide;
N-[4-(2,5-dimethoxybenzoyl)phenyl]-5-(2-hydroxyphenyl)-3-pyridin-3-yl-4,5-dihydro-1H-pyrazole-1-carboxamide;
2-(1-{[5-(4-bromophenyl)isoxazol-3-yl]carbonyl}-3-pyridin-3-yl-4,5-dihydro-1H-pyrazol-5-yl)phenol;
N-[2-(benzyloxy)phenyl]-5-(2-hydroxyphenyl)-3-pyridin-3-yl-4,5-dihydro-1H-pyrazole-1-carboxamide;
5-(2-hydroxyphenyl)-N-[1-phenyl-5-(trifluoromethyl)-1H-pyrazol-4-yl]-3-pyridin-3-yl-4,5-dihydro-1H-pyrazole-1-carboxamide;
5-(2-hydroxyphenyl)-N-{2-[(7-methyl-2,3-dihydro-1H-inden-4-yl)oxy]pyridin-3-yl}-3-pyridin-3-yl-4,5-dihydro-1H-pyrazole-1-carboxamide;
N-(2'-fluorobiphenyl-3-yl)-5-(2-hydroxyphenyl)-3-pyridin-3-yl-4,5-dihydro-1H-pyrazole-1-carboxamide;
2-{3-[5-(hydroxymethyl)pyridin-3-yl]-1-[(5-pyridin-2-yl-2-thienyl)carbonyl]-4,5-dihydro-1H-pyrazol-5-yl}phenol;
3-fluoro-2-{3-pyridin-3-yl-1-[(2-pyridin-2-yl-1H-imidazol-5-yl)carbonyl]-4,5-dihydro-1H-pyrazol-5-yl}phenol;
2-[1-({5-[4-(aminomethyl)-2-fluorophenyl]-2-thienyl}carbonyl)-3-pyridin-3-yl-4,5-dihydro-1H-pyrazol-5-yl]phenol;
N-[2-(2,4-difluorophenoxy)pyridin-3-yl]-5-(2-hydroxyphenyl)-3-pyridin-3-yl-4,5-dihydro-1H-pyrazole-1-carboxamide;
N-[1-(3,4-dichlorobenzyl)-6-oxo-1,6-dihydropyridin-3-yl]-5-(2-hydroxyphenyl)-3-pyridin-3-yl-4,5-dihydro-1H-pyrazole-1-carboxamide;
3-fluoro-2-{1-[(1-phenyl-1H-pyrazol-4-yl)carbonyl]-3-pyridin-3-yl-4,5-dihydro-1H-pyrazol-5-yl}phenol;
2-[1-({5-[2-(aminomethyl)phenyl]-2-thienyl}carbonyl)-3-(5-methylpyridin-3-yl)-4,5-dihydro-1H-pyrazol-5-yl]phenol;
2-[1-({5-[4-(aminomethyl)phenyl]-2-thienyl}carbonyl)-3-pyridin-3-yl-4,5-dihydro-1H-pyrazol-5-yl]-3-fluorophenol;
2-[1-({5-[2-(aminomethyl)phenyl]-2-thienyl}carbonyl)-3-(5-aminopyridin-3-yl)-4,5-dihydro-1H-pyrazol-5-yl]-3-fluorophenol;
3-fluoro-2-(3-pyridin-3-yl-1-{[5-(1,2,3,4-tetrahydroisoquinolin-5-yl)-2-thienyl]carbonyl}-4,5-dihydro-1H-pyrazol-5-yl)phenol;
N-{1-[3,5-bis(trifluoromethyl)benzyl]-2-oxo-1,2-dihydropyridin-3-yl}-5-(2-hydroxyphenyl)-3-pyridin-3-yl-4,5-dihydro-1H-pyrazole-1-carboxamide;
N-{4-[(4-chlorobenzyl)oxy]phenyl}-5-(2-hydroxyphenyl)-3-pyridin-3-yl-4,5-dihydro-1H-pyrazole-1-carboxamide;
N-(1,5-dimethyl-3-oxo-2-phenyl-2,3-dihydro-1H-pyrazol-4-yl)-5-(2-hydroxyphenyl)-3-pyridin-3-yl-4,5-dihydro-1H-pyrazole-1-carboxamide;
N-[2-(4-chlorobenzoyl)phenyl]-5-(2-hydroxyphenyl)-3-pyridin-3-yl-4,5-dihydro-1H-pyrazole-1-carboxamide;
N-[1-(2,4-dichlorobenzyl)-2-oxo-1,2-dihydropyridin-3-yl]-5-(2-hydroxyphenyl)-3-pyridin-3-yl-4,5-dihydro-1H-pyrazole-1-carboxamide;
5-(2-hydroxyphenyl)-N-(4-methylbiphenyl-3-yl)-3-pyridin-3-yl-4,5-dihydro-1H-pyrazole-1-carboxamide;
3-fluoro-2-{3-pyridin-3-yl-1-[(2-pyridin-2-yl-1,3-thiazol-4-yl)carbonyl]-4,5-dihydro-1H-pyrazol-5-yl}phenol;
N-(1-benzyl-3-tert-butyl-1H-pyrazol-5-yl)-5-(2-hydroxyphenyl)-3-pyridin-3-yl-4,5-dihydro-1H-pyrazole-1-carboxamide;
5-(2-hydroxyphenyl)-N-(2-phenoxypyridin-3-yl)-3-pyridin-3-yl-4,5-dihydro-1H-pyrazole-1-carboxamide;
3-fluoro-2-(3-pyridin-3-yl-1-{[5-(1,2,3,4-tetrahydroisoquinolin-8-yl)-2-thienyl]carbonyl}-4,5-dihydro-1H-pyrazol-5-yl)phenol;
N-(4-benzoylphenyl)-5-(2-hydroxyphenyl)-3-pyridin-3-yl-4,5-dihydro-1H-pyrazole-1-carboxamide;
2-{3-(5-aminopyridin-3-yl)-1-[(5-pyridin-2-yl-2-thienyl)carbonyl]-4,5-dihydro-1H-pyrazol-5-yl}phenol;
5-(2-hydroxyphenyl)-N-[3-(1H-pyrazol-1-yl)phenyl]-3-pyridin-3-yl-4,5-dihydro-1H-pyrazole-1-carboxamide;
5-(2-hydroxyphenyl)-N-(4'-methylbiphenyl-4-yl)-3-pyridin-3-yl-4,5-dihydro-1H-pyrazole-1-carboxamide;
N-[2-(4-chlorophenoxy)-5-(trifluoromethyl)phenyl]-5-(2-hydroxyphenyl)-3-pyridin-3-yl-4,5-dihydro-1H-pyrazole-1-carboxamide;
N-{5-chloro-6-oxo-1-[3-(trifluoromethyl)benzyl]-1,6-dihydropyridin-3-yl}-5-(2-hydroxyphenyl)-3-pyridin-3-yl-4,5-dihydro-1H-pyrazole-1-carboxamide;
5-(2-hydroxyphenyl)-N-(4-{[(5-methylisoxazol-3-yl)amino]sulfonyl}phenyl)-3-pyridin-3-yl-4,5-dihydro-1H-pyrazole-1-carboxamide;
5-(2-hydroxyphenyl)-N-(5-phenyl-1,3,4-thiadiazol-2-yl)-3-pyridin-3-yl-4,5-dihydro-1H-pyrazole-1-carboxamide;
N-[4-(4-fluorophenoxy)phenyl]-5-(2-hydroxyphenyl)-3-pyridin-3-yl-4,5-dihydro-1H-pyrazole-1-carboxamide;
N-[5-chloro-1-(4-chlorobenzyl)-6-oxo-1,6-dihydropyridin-3-yl-]-5-(2-hydroxyphenyl)-3-pyridin-3-yl-4,5-dihydro-1H-pyrazole-1-carboxamide;
5-(2-hydroxyphenyl)-3-pyridin-3-yl-N-[4-(1H-1,2,4-triazol-1-yl)phenyl]-4,5-dihydro-1H-pyrazole-1-carboxamide;
5-(2-hydroxyphenyl)-N-[2-(phenylsulfanyl)pyridin-3-yl]-3-pyridin-3-yl-4,5-dihydro-1H-pyrazole-1-carboxamide;
3-fluoro-2-(1-{[5-(3-{[(2-hydroxyethyl)amino]methyl}phenyl)-2-thienyl]carbonyl}-3-pyridin-3-yl-4,5-dihydro-1H-pyrazol-5-yl)phenol;
5-(2-hydroxyphenyl)-N-[1-methyl-3-(2-thienyl)-1H-pyrazol-5-yl]-3-pyridin-3-yl-4,5-dihydro-1H-pyrazole-1-carboxamide;
N-{5-[(dibenzylamino)sulfonyl]-1-methyl-1H-pyrrol-2-yl}-5-(2-hydroxyphenyl)-3-pyridin-3-yl-4,5-dihydro-1H-pyrazole-1-carboxamide;
5-(2-hydroxyphenyl)-3-pyridin-3-yl-N-{4-[(pyrimidin-2-ylamino)sulfonyl]phenyl}-4,5-dihydro-1H-pyrazole-1-carboxamide;
3-fluoro-2-{3-pyridin-3-yl-1-[(1-pyridin-2-yl-1H-pyrazol-4-yl)carbonyl]-4,5-dihydro-1H-pyrazol-5-yl}phenol;
N-(1-benzylpiperidin-4-yl)-5-(2-hydroxyphenyl)-3-pyridin-3-yl-4,5-dihydro-1H-pyrazole-1-carboxamide;

3-fluoro-2-{1-[(2-phenyl-1H-imidazol-5-yl)carbonyl]-3-pyridin-3-yl-4,5-dihydro-1H-pyrazol-5-yl}phenol;
benzyl 2-({[5-(2-hydroxyphenyl)-3-pyridin-3-yl-4,5-dihydro-1H-pyrazol-1-yl]carbonyl}amino)benzoate;
5-(2-hydroxyphenyl)-N-[4-(phenylsulfonyl)-3-thienyl]-3-pyridin-3-yl-4,5-dihydro-1H-pyrazole-1-carboxamide;
N-[5-fluoro-2-(1H-imidazol-1-yl)phenyl]-5-(2-hydroxyphenyl)-3-pyridin-3-yl-4,5-dihydro-1H-pyrazole-1-carboxamide;
2-[1-({5-[2-(aminomethyl)-4-(dimethylamino)phenyl]-2-thienyl}carbonyl)-3-pyridin-3-yl-4,5-dihydro-1H-pyrazol-5-yl]-3-fluorophenol;
5-(2-hydroxyphenyl)-N-(4-phenoxyphenyl)-3-pyridin-3-yl-4,5-dihydro-1H-pyrazole-1-carboxamide;
2-{3-(5-methylpyridin-3-yl)-1-[(5-pyridin-2-yl-2-thienyl)carbonyl]-4,5-dihydro-1H-pyrazol-5-yl}phenol;
5-(2-hydroxyphenyl)-N-(1-phenylcyclopentyl)-3-pyridin-3-yl-4,5-dihydro-1H-pyrazole-1-carboxamide;
5-(2-hydroxyphenyl)-3-pyridin-3-yl-N-{4-[(1,3-thiazol-2-ylamino)sulfonyl]-phenyl}-4,5-dihydro-1H-pyrazole-1-carboxamide;
5-(2-hydroxyphenyl)-N-(5-methyl-3-phenylisoxazol-4-yl)-3-pyridin-3-yl-4,5-dihydro-1H-pyrazole-1-carboxamide;
3-fluoro-2-{1-[(5-{3-[(4-methylpiperazin-1-yl)methyl]phenyl}-2-thienyl)carbonyl]-3-pyridin-3-yl-4,5-dihydro-1H-pyrazol-5-yl}phenol;
3-fluoro-2-{1-[(5-{3-[(methylamino)methyl]-phenyl}-2-thienyl)carbonyl]-3-pyridin-3-yl-4,5-dihydro-1H-pyrazol-5-yl}phenol;
5-(2-hydroxyphenyl)-N-[4-(1H-pyrazol-1-yl)phenyl]-3-pyridin-3-yl-4,5-dihydro-1H-pyrazole-1-carboxamide;
5-(2-hydroxyphenyl)-N-(2-phenyl-1,3-thiazol-4-yl)-3-pyridin-3-yl-4,5-dihydro-1H-pyrazole-1-carboxamide;
N-[2-(2,4-dichlorophenoxy)phenyl]-5-(2-hydroxyphenyl)-3-pyridin-3-yl-4,5-dihydro-1H-pyrazole-1-carboxamide;
2-(1-{[5-2,3-dihydro-1H-isoindol-5-yl)-2-thienyl]carbonyl}-3-pyridin-3-yl-4,5-dihydro-1H-pyrazol-5-yl)phenol;
N-[3-(benzyloxy)-4-methoxyphenyl]-5-(2-hydroxyphenyl)-3-pyridin-3-yl-4,5-dihydro-1H-pyrazole-1-carboxamide;
5-(2-hydroxyphenyl)-N-[4-(4-methylpiperazin-1-yl)phenyl]-3-pyridin-3-yl-4,5-dihydro-1H-pyrazole-1-carboxamide;
N-[5-chloro-1-(3-chlorobenzyl)-6-oxo-1,6-dihydropyridin-3-yl]-5-(2-hydroxyphenyl)-3-pyridin-3-yl-4,5-dihydro-1H-pyrazole-1-carboxamide;
N-[1-(3,4-difluorobenzyl)-6-oxo-1,6-dihydropyridin-3-yl]-5-(2-hydroxyphenyl)-3-pyridin-3-yl-4,5-dihydro-1H-pyrazole-1-carboxamide;
5-(2-hydroxyphenyl)-N-[4-(4-methoxyphenyl)-3-methylisoxazol-5-yl]-3-pyridin-3-yl-4,5-dihydro-1H-pyrazole-1-carboxamide;
N-{4-[3,5-bis(trifluoromethyl)phenoxy]phenyl}-5-(2-hydroxyphenyl)-3-pyridin-3-yl-4,5-dihydro-1H-pyrazole-1-carboxamide;
5-(2-hydroxyphenyl)-N-[3-(4-methylpiperazin-1-yl)phenyl]-3-pyridin-3-yl-4,5-dihydro-1H-pyrazole-1-carboxamide;
5-(2-hydroxyphenyl)-N-{4-[(4-nitrophenyl)sulfanyl]phenyl}-3-pyridin-3-yl-4,5-dihydro-1H-pyrazole-1-carboxamide;
5-(2-hydroxyphenyl)-3-pyridin-3-yl-N-(1-pyrimidin-2-ylpiperidin-4-yl)-4,5-dihydro-1H-pyrazole-1-carboxamide;
3-fluoro-2-{1-[(5-{2-[(methylamino)methyl]phenyl}-2-thienyl)carbonyl]-3-pyridin-3-yl-4,5-dihydro-1H-pyrazol-5-yl}phenol;
N-(5-cyclohexyl-2-methoxyphenyl)-5-(2-hydroxyphenyl)-3-pyridin-3-yl-4,5-dihydro-1H-pyrazole-1-carboxamide;
N-(1-benzyl-1H-benzimidazol-2-yl)-5-(2-hydroxyphenyl)-3-pyridin-3-yl-4,5-dihydro-1H-pyrazole-1-carboxamide;
N-biphenyl-4-yl-5-(2-hydroxyphenyl)-3-pyridin-3-yl-4,5-dihydro-1H-pyrazole-1-carboxamide;
5-(2-hydroxyphenyl)-N-(1-phenylcyclohexyl)-3-pyridin-3-yl-4,5-dihydro-1H-pyrazole-1-carboxamide;
2-(1-{[5-(2,3-dihydro-1H-isoindol-4-yl)-2-thienyl]carbonyl}-3-pyridin-3-yl-4,5-dihydro-1H-pyrazol-5-yl)phenol;
N-{2-[2-(5-bromo-2-methoxyphenyl)ethyl]-3-fluorophenyl}-5-(2-hydroxyphenyl)-3-pyridin-3-yl-4,5-dihydro-1H-pyrazole-1-carboxamide;
N-[1-(2-chlorobenzyl)-5-oxopyrrolidin-3-yl]-5-(2-hydroxyphenyl)-3-pyridin-3-yl-4,5-dihydro-1H-pyrazole-1-carboxamide;
2-(3-pyridin-3-yl-1-{[5-(1,2,3,4-tetrahydroisoquinolin-5-yl)-2-thienyl]carbonyl}-4,5-dihydro-1H-pyrazol-5-yl)phenol;
N-(4'-fluorobiphenyl-3-yl)-5-(2-hydroxyphenyl)-3-pyridin-3-yl-4,5-dihydro-1H-pyrazole-1-carboxamide;
N-{2-[(2-cyanophenyl)sulfanyl]phenyl}-5-(2-hydroxyphenyl)-3-pyridin-3-yl-4,5-dihydro-1H-pyrazole-1-carboxamide;
N-(1-benzyl-1H-pyrazol-4-yl)-5-(2-hydroxyphenyl)-3-pyridin-3-yl-4,5-dihydro-1H-pyrazole-1-carboxamide;
N-(1,3-diphenyl-1H-pyrazol-5-yl)-5-(2-hydroxyphenyl)-3-pyridin-3-yl-4,5-dihydro-1H-pyrazole-1-carboxamide;
2-[1-({5-[3-({[2-(dimethylamino)ethyl]amino}methyl)phenyl]-2-thienyl}carbonyl)-3-pyridin-3-yl-4,5-dihydro-1H-pyrazol-5-yl]-3-fluorophenol;
2-[1-({5-[2-(aminomethyl)-4-chlorophenyl]-2-thienyl}carbonyl)-3-pyridin-3-yl-4,5-dihydro-1H-pyrazol-5-yl]phenol;
N-[4-(4-chlorophenyl)-1,2,3-thiadiazol-5-yl]-5-(2-hydroxyphenyl)-3-pyridin-3-yl-4,5-dihydro-1H-pyrazole-1-carboxamide;
N-[1-(3,4-dichlorobenzyl)-2-oxo-1,2-dihydropyridin-3-yl]-5-(2-hydroxyphenyl)-3-pyridin-3-yl-4,5-dihydro-1H-pyrazole-1-carboxamide;
5-(2-hydroxyphenyl)-N-[2-(2-methylphenoxy)phenyl]-3-pyridin-3-yl-4,5-dihydro-1H-pyrazole-1-carboxamide;
N-[4-(benzyloxy)phenyl]-5-(2-hydroxyphenyl)-3-pyridin-3-yl-4,5-dihydro-1H-pyrazole-1-carboxamide;
N-[(1R,2R)-2-(benzyloxy)cyclopentyl]-5-(2-hydroxyphenyl)-3-pyridin-3-yl-4,5-dihydro-1H-pyrazole-1-carboxamide;
5-(2-hydroxyphenyl)-N-{6-oxo-1-[4-(trifluoromethyl)benzyl]-1,6-dihydropyridin-3-yl}-3-pyridin-3-yl-4,5-dihydro-1H-pyrazole-1-carboxamide;
N-[1-(2-chloro-6-fluorobenzyl)-2-oxo-1,2-dihydropyridin-3-yl]-5-(2-hydroxyphenyl)-3-pyridin-3-yl-4,5-dihydro-1H-pyrazole-1-carboxamide;
N-(4-benzoyl-2-nitrophenyl)-5-(2-hydroxyphenyl)-3-pyridin-3-yl-4,5-dihydro-1H-pyrazole-1-carboxamide;
N-[1-(4-chlorophenyl)cyclohexyl]-5-(2-hydroxyphenyl)-3-pyridin-3-yl-4,5-dihydro-1H-pyrazole-1-carboxamide;

5-(2-hydroxyphenyl)-3-pyridin-3-yl-N-[4'-(trifluoromethyl)biphenyl-2-yl]-4,5-dihydro-1H-pyrazole-1-carboxamide;
5-(2-hydroxyphenyl)-N-[4-(4-methoxyphenyl)-1,2,3-thiadiazol-5-yl]-3-pyridin-3-yl-4,5-dihydro-1H-pyrazole-1-carboxamide;
2-{3-(5-aminopyridin-3-yl)-1-[(5-pyridin-2-yl-2-thienyl)carbonyl]-4,5-dihydro-1H-pyrazol-5-yl}-3-fluorophenol;
2-[1-({5-[4-(aminomethyl)-2-chlorophenyl]-2-thienyl}carbonyl)-3-pyridin-3-yl-4,5-dihydro-1H-pyrazol-5-yl]phenol;
2-[1-({5-[2-(aminomethyl)phenyl]-2-thienyl}carbonyl)-3-(5-fluoropyridin-3-yl)-4,5-dihydro-1H-pyrazol-5-yl]phenol;
5-(2-hydroxyphenyl)-N-(5-methyl-1-phenyl-1H-pyrazol-4-yl)-3-pyridin-3-yl-4,5-dihydro-1H-pyrazole-1-carboxamide;
N-[2-(1,3-dioxo-1,3-dihydro-2H-isoindol-2-yl)phenyl]-5-(2-hydroxyphenyl)-3-pyridin-3-yl-4,5-dihydro-1H-pyrazole-1-carboxamide;
5-(2-hydroxyphenyl)-N-(1-methyl-3-phenyl-1H-pyrazol-5-yl)-3-pyridin-3-yl-4,5-dihydro-1H-pyrazole-1-carboxamide;
5-(2-hydroxyphenyl)-N-{6-oxo-1-[3-(trifluoromethyl)benzyl]-1,6-dihydropyridin-3-yl}-3-pyridin-3-yl-4,5-dihydro-1H-pyrazole-1-carboxamide;
2-(3-pyridin-3-yl-1-{[5-(1,2,3,4-tetrahydroisoquinolin-7-yl)-2-thienyl]carbonyl}-4,5-dihydro-1H-pyrazol-5-yl)phenol;
2-[1-({2-[2-(aminomethyl)phenyl]-1,3-thiazol-4-yl}carbonyl)-3-pyridin-3-yl-4,5-dihydro-1H-pyrazol-5-yl]phenol;
N-(5-{5-(2-hydroxyphenyl)-1-[(5-pyridin-2-yl-2-thienyl)carbonyl]-4,5-dihydro-1H-pyrazol-3-yl}pyridin-3-yl)acetamide;
5-(2-hydroxyphenyl)-N-[2-(phenylsulfonyl)phenyl]-3-pyridin-3-yl-4,5-dihydro-1H-pyrazole-1-carboxamide;
2-[1-({5-[3-(aminomethyl)pyridin-4-yl]-2-thienyl}carbonyl)-3-pyridin-3-yl-4,5-dihydro-1H-pyrazol-5-yl]phenol;
N-[(3R)-1-benzylpyrrolidin-3-yl]-5-(2-hydroxyphenyl)-3-pyridin-3-yl-4,5-dihydro-1H-pyrazole-1-carboxamide;
5-(2-hydroxyphenyl)-N-{4-[(3-oxo-2,3-dihydro-4H-1,4-benzoxazin-4-yl)methyl]phenyl}-3-pyridin-3-yl-4,5-dihydro-1H-pyrazole-1-carboxamide;
N-{5-chloro-2-oxo-1-[4-(trifluoromethyl)benzyl]-1,2-dihydropyridin-3-yl}-5-(2-hydroxyphenyl)-3-pyridin-3-yl-4,5-dihydro-1H pyrazole-1-carboxamide;
5-(2-hydroxyphenyl)-N-[2-(4-methylphenyl)quinolin-4-yl]-3-pyridin-3-yl-4,5-dihydro-1H-pyrazole-1-carboxamide;
N-[3-(cyclopentyloxy)-4-methoxyphenyl]-5-(2-hydroxyphenyl)-3-pyridin-3-yl-4,5-dihydro-1H-pyrazole-1-carboxamide;
5-(2-hydroxyphenyl)-N-[6-(1H-pyrazol-1-yl)pyridin-3-yl]-3-pyridin-3-yl-4,5-dihydro-1H-pyrazole-1-carboxamide;
5-(2-hydroxyphenyl)-N-(4-morpholin-4-ylphenyl)-3-pyridin-3-yl-4,5-dihydro-1H-pyrazole-1-carboxamide;
3-fluoro-2-(3-pyridin-3-yl-1-{[5-(1,2,3,4-tetrahydroisoquinolin-7-yl)-2-thienyl]carbonyl}-4,5-dihydro-1H-pyrazol-5-yl)phenol;
2-[1-({5-[2-(aminomethyl)phenyl]-2-thienyl}carbonyl)-3-pyridin-3-yl-4,5-dihydro-1H-pyrazol-5-yl]-3-chlorophenol;
(1S,2R,5S)-2-isopropyl-5-methylcyclohexyl 2-({[5-(2-hydroxyphenyl)-3-pyridin-3-yl-4,5-dihydro-1H-pyrazol-1-yl]carbonyl}amino)benzoate;
3-fluoro-2-{3-[5-(hydroxymethyl)pyridin-3-yl]-1-[(1-phenyl-1H-imidazol-4-yl)carbonyl]-4,5-dihydro-1H-pyrazol-5-yl}phenol;
3-fluoro-2-(3-pyridin-3-yl-1-{[1-(1,2,3,4-tetrahydroisoquinolin-6-yl)-1H-imidazol-4-yl]carbonyl}-4,5-dihydro-1H-pyrazol-5-yl)phenol;
3-fluoro-2-(3-[5-(hydroxymethyl)pyridin-3-yl]-1-{[1-(1,2,3,4-tetrahydroisoquinolin-6-yl)-1H-imidazol-4-yl]carbonyl}-4,5-dihydro-1H-pyrazol-5-yl)phenol;
2-[1-({1-[2-(aminomethyl)phenyl]-1H-imidazol-4-yl}carbonyl)-3-pyridin-3-yl-4,5-dihydro-1H-pyrazol-5-yl]-3-fluorophenol;
2-{1-({1-[2-(aminomethyl)phenyl]-1H-imidazol-4-yl}carbonyl)-3-[5-(hydroxymethyl)pyridin-3-yl]-4,5-dihydro-1H-pyrazol-5-yl}-3-fluorophenol;
2-(1-{[5-(2,3-dihydro-1H-isoindol-5-yl)-2-thienyl]carbonyl}-3-pyridin-3-yl-4,5-dihydro-1H-pyrazol-5-yl)-3-fluorophenol;
2-(1-{[5-(2,3-dihydro-1H-isoindol-4-yl)-2-thienyl]carbonyl}-3-pyridin-3-yl-4,5-dihydro-1H-pyrazol-5-yl)-3-fluorophenol;
3-fluoro-2-{1-[(1-phenyl-1H-pyrazol-3-yl)carbonyl]-3-pyridin-3-yl-4,5-dihydro-1H-pyrazol-5-yl}phenol;
3-fluoro-2-{3-pyridin-3-yl-1-[(1-pyridin-2-yl-1H-pyrazol-3-yl)carbonyl]-4,5-dihydro-1H-pyrazol-5-yl}phenol;
2-[1-({1-[2-(aminomethyl)phenyl]-1H-pyrazol-3-yl}carbonyl)-3-pyridin-3-yl-4,5-dihydro-1H-pyrazol-5-yl]-3-fluorophenol;
2-{1-{[5-(2,3-dihydro-1H-isoindol-5-yl)-2-thienyl]carbonyl}-3-[5-(hydroxymethyl)pyridin-3-yl]-4,5-dihydro-1H-pyrazol-5-yl}-3-fluorophenol;
2-{1-{[5-(2,3-dihydro-1H-isoindol-4-yl)-2-thienyl]carbonyl}-3-[5-(hydroxymethyl)pyridin-3-yl]-4,5-dihydro-1H-pyrazol-5-yl}-3-fluorophenol;
3-fluoro-2-(3-[5-(hydroxymethyl)pyridin-3-yl]-1-{[5-(1,2,3,4-tetrahydroisoquinolin-6-yl)-2-thienyl]carbonyl}-4,5-dihydro-1H-pyrazol-5-yl)phenol;
3-fluoro-2-(3-[5-(hydroxymethyl)pyridin-3-yl]-1-{[5-(1,2,3,4-tetrahydroisoquinolin-8-yl)-2-thienyl]carbonyl}-4,5-dihydro-1H-pyrazol-5-yl)phenol;
3-fluoro-2-(3-[5-(hydroxymethyl)pyridin-3-yl]-1-{[5-(1,2,3,4-tetrahydroisoquinolin-5-yl)-2-thienyl]carbonyl}-4,5-dihydro-1H-pyrazol-5-yl)phenol;
3-fluoro-2-[1-({5-[2-(methoxymethyl)phenyl]-2-thienyl}carbonyl)-3-pyridin-3-yl-4,5-dihydro-1H-pyrazol-5-yl]phenol;
2-{1-[(5-{2-[(2-aminoethoxy)methyl]-phenyl}-2-thienyl)carbonyl]-3-pyridin-3-yl-4,5-dihydro-1H-pyrazol-5-yl}-3-fluorophenol;
2-(1-{[5-(2-{[2-(dimethylamino)ethoxy]methyl}phenyl)-2-thienyl]carbonyl}-3-pyridin-3-yl-4,5-dihydro-1H-pyrazol-5-yl)-3-fluorophenol;
3-fluoro-2-{1-[(5-{2-[(2-methoxyethoxy)methyl]phenyl}-2-thienyl)carbonyl]-3-pyridin-3-yl-4,5-dihydro-1H-pyrazol-5-yl}phenol;
3-fluoro-2-[3-[5-(hydroxymethyl)pyridin-3-yl]-1-({5-[2-(methoxymethyl)phenyl]-2-thienyl}carbonyl)-4,5-dihydro-1H-pyrazol-5-yl]phenol;
2-{1-[(5-{2-[(2-aminoethoxy)methyl]-phenyl}-2-thienyl)carbonyl]-3-[5-(hydroxymethyl)pyridin-3-yl]-4,5-dihydro-1H-pyrazol-5-yl}-3-fluorophenol;

2-{1-{[5-(2-{[2-(dimethylamino)ethoxy]methyl}phenyl)-2-thienyl]carbonyl}-3-[5-(hydroxymethyl)pyridin-3-yl]-4,5-dihydro-1H-pyrazol-5-yl}-3-fluorophenol;

3-fluoro-2-{3-[5-(hydroxymethyl)pyridin-3-yl]-1-[(5-{2-[(2-methoxyethoxy)methyl]-phenyl}-2-thienyl)carbonyl]-4,5-dihydro-1H-pyrazol-5-yl}phenol;

5-{5-(2-fluoro-6-hydroxyphenyl)-1-[(5-pyridin-2-yl-2-thienyl)carbonyl]-4,5-dihydro-1H-pyrazol-3-yl}nicotinic acid;

5-{5-(2-fluoro-6-hydroxyphenyl)-1-[(5-pyridin-2-yl-2-thienyl)carbonyl]-4,5-dihydro-1H-pyrazol-3-yl}-N-methylnicotinamide;

5-{5-(2-fluoro-6-hydroxyphenyl)-1-[(5-pyridin-2-yl-2-thienyl)carbonyl]-4,5-dihydro-1H-pyrazol-3-yl}nicotinamide;

2-{3-[5-(aminomethyl)pyridin-3-yl]-1-[(5-pyridin-2-yl-2-thienyl)carbonyl]-4,5-dihydro-1H-pyrazol-5-yl}-3-fluorophenol;

3-fluoro-2-{3-{5-[(methylamino)methyl]pyridin-3-yl}-1-[(5-pyridin-2-yl-2-thienyl)carbonyl]-4,5-dihydro-1H-pyrazol-5-yl}phenol;

2-{3-{5-[(dimethylamino)methyl]pyridin-3-yl}-1-[(5-pyridin-2-yl-2-thienyl)carbonyl]-4,5-dihydro-1H-pyrazol-5-yl}-3-fluorophenol;

3-fluoro-2-{3-[5-(methoxymethyl)pyridin-3-yl]-1-[(5-pyridin-2-yl-2-thienyl)carbonyl]-4,5-dihydro-1H-pyrazol-5-yl}phenol;

2-{3-{5-[(2-aminoethoxy)methyl]pyridin-3-yl}-1-[(5-pyridin-2-yl-2-thienyl)carbonyl]-4,5-dihydro-1H-pyrazol-5-yl}-3-fluorophenol;

3-fluoro-2-{3-{5-[(2-methoxyethoxy)methyl]pyridin-3-yl}-1-[(5-pyridin-2-yl-2-thienyl)carbonyl]-4,5-dihydro-1H-pyrazol-5-yl}phenol;

2-{3-(5-aminopyridin-3-yl)-1-[(5-{2-[(methylamino)methyl]-phenyl}-2-thienyl)carbonyl]-4,5-dihydro-1H-pyrazol-5-yl}-3-fluorophenol; or 3-fluoro-2-{3-[5-(hydroxymethyl)pyridin-3-yl]-1-[(5-{2-[(methylamino)methyl]-phenyl}-2-thienyl)carbonyl]-4,5-dihydro-1H-pyrazol-5-yl}phenol.

31. A pharmaceutical composition comprising at least one chemical entity according to claim 1 and a pharmaceutically acceptable carrier.

32. The pharmaceutical composition according to claim 31, formulated for administration to a human patient.

33. At least one chemical entity of claim 13 wherein $R^2$ is 2-hydroxyphenyl, which group optionally is additionally substituted with one or two substituents selected from —F, —Cl, $C_{1-4}$ aliphatic, $C_{1-4}$ fluoroaliphatic, —O($C_{1-4}$ aliphatic), and —O($C_{1-4}$ fluoroaliphatic).

34. At least one chemical entity of claim 1 wherein $L_2$ is selected from the group consisting of —$(CR^bR^c)_n$—, —O—, —C($R^b$)($R^c$)—O—, —O—C($R^b$)($R^c$)—, —N($R^a$)—, —C($R^b$)($R^c$)—N($R^a$)—, —N($R^a$)—C($R^b$)($R^c$)—, —$SO_2$—, —$SO_2$—N($R^a$)—C($R^b$)($R^c$)—, —N($R^a$)—$SO_2$—C($R^b$)($R^c$)—, —C≡C—, —C($R^b$)($R^c$)—N($R^a$)—C(O)—, and —C($R^b$)($R^c$)—S—C($R^b$)($R^c$)—.

35. At least one chemical entity of claim 1 wherein $L_2$ is selected from the group consisting of —$(CH_2)_n$—, —O—, —$CH_2$—O—, —O—$CH_2$—, —NH—, —$CH_2$—NH—, —NH—$CH_2$—, —$SO_2$—, —$SO_2NHCH_2$—, —NH—$SO_2$—$CH_2$—, —C≡C—, —$CH_2$—NH—C(O)—, and —$CH_2$—S—$CH_2$—.

36. At least one chemical entity of claim 1 wherein $L_2$ is selected from the group consisting of —$(CH_2)_n$—, —O—, —NH—$CH_2$—, —$CH_2$—NH—, and —$SO_2$—.

37. At least one chemical entity of claim 1 wherein $L_2$ is —$(CH_2)_n$— and n is 0.

\* \* \* \* \*

UNITED STATES PATENT AND TRADEMARK OFFICE
CERTIFICATE OF CORRECTION

| | |
|---|---|
| PATENT NO. | : 7,795,249 B2 |
| APPLICATION NO. | : 12/002883 |
| DATED | : September 14, 2010 |
| INVENTOR(S) | : Ruth S. Adams et al. |

It is certified that error appears in the above-identified patent and that said Letters Patent is hereby corrected as shown below:

Please make the following corrections to the claims:

CLAIMS

In Column 228, Claim 1, Line 61, please delete, "-$SO_2$-,-$C(R^f)$=$C(R^f)$-,-$NR^aC(O)$-,-$C(O)NR^a$-, -$SO_2$-$NR^a$,-$NR^aSO_2$-, and $NR^aC(O)NR^a$-;" and replace with -- -$SO_2$-, -$NR^a$-, -$C(R^f)$=$C(R^f)$-, - C≡C-, -$NR^aC(O)$-, -$C(O)NR^a$-, -$SO_2$-$NR^a$, -$NR^aSO_2$-, and $NR^aC(O)NR^a$-; --

Signed and Sealed this
Twenty-fifth Day of September, 2012

David J. Kappos
*Director of the United States Patent and Trademark Office*